US010285348B2

(12) United States Patent
Kelliher et al.

(10) Patent No.: US 10,285,348 B2
(45) Date of Patent: May 14, 2019

(54) SIMULTANEOUS GENE EDITING AND HAPLOID INDUCTION

(71) Applicant: Syngenta Participations AG, Basel (CH)

(72) Inventors: Timothy Kelliher, Research Trianlge Park, NC (US); Qiudeng Que, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/901,464

(22) Filed: Feb. 21, 2018

(65) Prior Publication Data

US 2018/0273963 A1 Sep. 27, 2018

Related U.S. Application Data

(63) Continuation of application No. PCT/US2017/064512, filed on Dec. 4, 2017.

(60) Provisional application No. 62/429,260, filed on Dec. 2, 2016.

(51) Int. Cl.

| | |
|---|---|
| ***C12N 15/82*** | (2006.01) |
| ***A01H 1/08*** | (2006.01) |
| ***C07K 14/415*** | (2006.01) |
| ***C12Q 1/6895*** | (2018.01) |

(52) U.S. Cl.

CPC ............ *A01H 1/08* (2013.01); *C07K 14/415* (2013.01); *C12N 15/8213* (2013.01); *C12N 15/8216* (2013.01); *C12N 15/8241* (2013.01); *C12N 15/8287* (2013.01); *C12Q 1/6895* (2013.01); *C12Y 301/01032* (2013.01)

(58) Field of Classification Search

CPC ............ C12N 15/8218; C12N 15/8216; C12N 15/8213; C12N 9/22; C12N 2310/20; C12N 15/102; A01H 1/08; C12Y 301/01032

See application file for complete search history.

(56) References Cited

U.S. PATENT DOCUMENTS

| | | | | |
|---|---|---|---|---|
| 7,135,615 | B2 * | 11/2006 | Kato | A01H 1/08 800/276 |
| 9,677,082 | B2 | 6/2017 | Chintamanani et al. | |
| 2009/0297495 | A1 * | 12/2009 | Kerovuo | C11C 1/045 424/94.6 |
| 2015/0307889 | A1 * | 10/2015 | Petolino | C12N 15/8213 800/275 |
| 2017/0240912 | A1 | 8/2017 | Chintamanani et al. | |

FOREIGN PATENT DOCUMENTS

| | | | |
|---|---|---|---|
| WO | 2016/075255 | A1 | 5/2016 |
| WO | 2017/004375 | A1 | 1/2017 |
| WO | 2017/087682 | A1 | 5/2017 |
| WO | 2018/015956 | A1 | 1/2018 |
| WO | 2018/015957 | A1 | 1/2018 |
| WO | 2018/052919 | A1 | 3/2018 |

OTHER PUBLICATIONS

Huang, Shihshieh, et al. "Cloning of an *Arabidopsis patatin*-like gene, Sturdy, by activation T-DNA tagging." Plant Physiology 125.2 (2001): 573-584. (Year: 2001).*

Rietz, Steffen, et al. "Roles of *Arabidopsis patatin*-related phospholipases a in root development are related to auxin responses and phosphate deficiency." Molecular Plant 3.3 (2010): 524-538.( (Year: 2010).*

Scherer, Günther FE, et al. "Patatin-related phospholipase A: nomenclature, subfamilies and functions in plants." Trends in plant science 15.12 (2010): 693-700 (Year: 2010).*

Nair et al., "Dissection of a Major QTL qhir1 Conferring Maternal Haploid Induction Ability in Maize", Theor. Appl. Genet., Feb. 4, 2017, published oline with open access at Springerlink.com.

Kelliher et al., "Matrilineal, A Sperm-Specific Phospholipase, Triggers Maize Hapliod Induction", Feb. 2, 2017, Nature, vol. 542, pp. 105-122.

Gilles et al., "Loss of Pollen-Specific Phospolipase Not Like DAD triggers gynogenesis in Maize", The Embo Journal, Feb. 9, 2017, pp. 1-11.

Liu et al., "A 4bp Insertion at ZmPLA1 Encoding a Putative Phospholipase a Generates Haploid Induction in Maize", Molecular Pant, Jan. 31, 2017.

Gilles et al., "Loss of Pollen-Specific Phospholipase Not Like DAD triggers gynogenesis in Maize", The EMBO Journal, pp. 1-11, 2017.

Lui et al., "A 4bp Insertion at ZmPLA1 Encoding a Putative Phospholipase A Generates Haploid Induction in Maize", Accepted Manuscript, Molecular Plant, pp. 1-8, Jan. 31, 2017.

Nair et al., "Dissection of a Major QTL qhirl Conferring Maternal Haploid Induction Ability in Maize", Theoretical Applied Genetics, Dec. 8, 2016.

* cited by examiner

*Primary Examiner* — Weihua Fan

(74) *Attorney, Agent, or Firm* — Christopher Leming

(57) ABSTRACT

The presently disclosed subject matter relates to using a haploid inducing line (whether existing or created) and transforming the haploid line so that it encodes cellular machinery capable of editing genes. The transformed haploid inducing line is used as a parent in a cross between two plants. During pollination, the parental gametes fuse to form an embryo; and the gene editing machinery is also delivered to the embryo at this time. During embryonic development, one set of parental chromosomes are lost, and the gene editing machinery operates on the remaining set of chromosomes. Thus, at least one haploid progeny with edited genes is produced from the cross.

12 Claims, 24 Drawing Sheets

Specification includes a Sequence Listing.

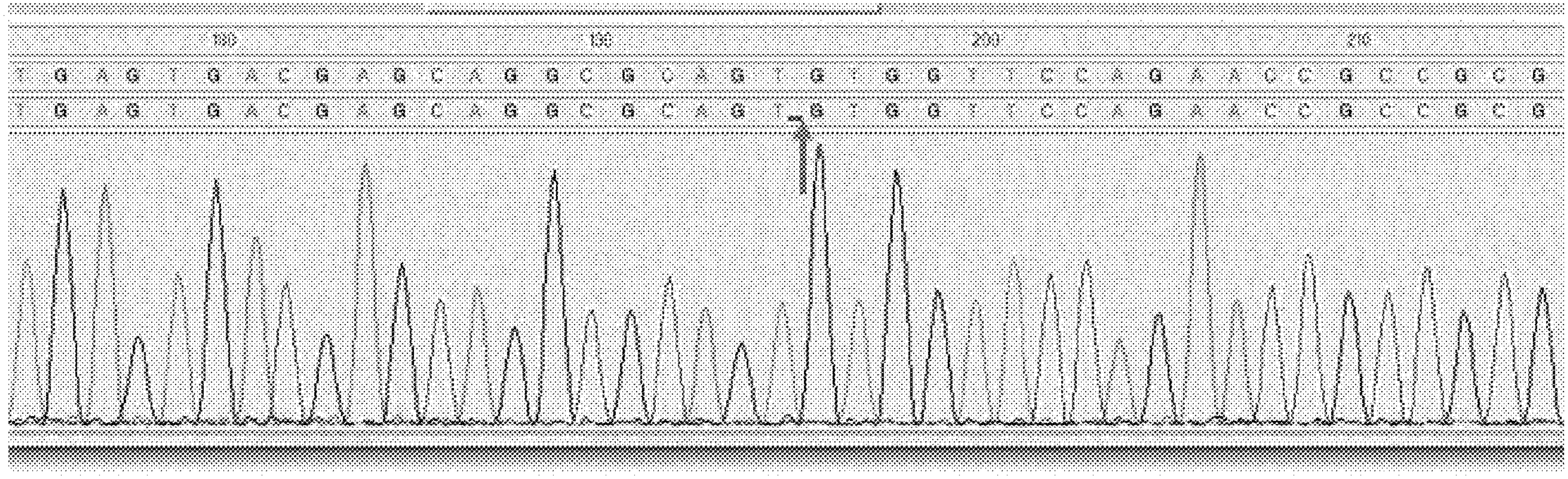

```
  1  CTCATCGAGT GTTCNCCGCA ATGCGCTGTT GCTGATTCTC AAGTGCGTGT GGGTGCAGGT
 61  GGAGAGCAGA AGAAGGCCGG CCGGCAGCGG CGGAGGAGGA GGGCGAGGCA GGCAGCGGCA
121  GGCGAAGGCG CGGGAGGGGA CGATGCGGCG AAGAAACGCC GGCTGAGTGA CGAGCAGGCG
181  CAGTTCCTGG AGATGAGCTT CAGGAAGGAA CGTAAACTGG AAACGCCCCG CAAGGTGCAG
241  CTCGCCGCGG AGCTGGGCCT GGACACCAAG CAGGTCGCGG TGTGGTTCCA GAACCGCCGC
301  GCCCGCTACA AGAGCAAGCT CATCGAGGAG GAGTTCTCCA AGCTCCGCGC GGCACACGAC
361  GCCGTCGTCG TCCACAACTG CCACCTCGAG GCCGAGGTAC AGTGCAACAG TCCGGCTGCC
```

FIG. 16

SIMULTANEOUS GENE EDITING AND HAPLOID INDUCTION

This application claims the benefit under 35 U.S.C. § 365(c) of International Application No. PCT/US2017/064512, filed Dec. 4, 2017 and designating the U.S., which claims the benefit of U.S. Provisional Application 62/429,260, filed Dec. 2, 2016, all of which are incorporated herein by reference in their entirety.

FIELD OF THE INVENTION

This invention is related to the field of plant biotechnology, specifically agriculture biotechnology and gene editing, as well as plant breeding. The presently disclosed subject matter relates to using a haploid inducing line (whether existing or created) and transforming the haploid inducing line so that it contains DNA coding for cellular machinery capable of editing genes.

SEQUENCE LISTING

This application is accompanied by a sequence listing entitled 81189_ST25.txt, created Dec. 4, 2017, which is approximately 334 kilobytes in size. This sequence listing is incorporated herein by reference in its entirety. This sequence listing is submitted herewith via EFS-Web, and is in compliance with 37 C.F.R. § 1.824(a)(2)-(6) and (b).

BACKGROUND

Targeted mutagenesis (also known as "gene editing") is a very important technology to crop breeding. There are numerous methods to edit specific gene targets now, including CRISPR, TALEN, meganucleases, and zinc fingers. One method to introduce editing machinery into plants is to use *Agrobacterium* or biolistic transformation of plant tissue. In transformation, DNA coding for the editing machinery (e.g., CAS9 and guide RNA) is introduced into plant callus, seed or embryonic tissue. Stably-transformed plants ("events") are then recovered, optionally with the help of a selectable marker. But because tissue culture is genotype-dependent, this route will not work for all crops, or even all varieties of the crops for which it does work. These are known as transformation-recalcitrant crops or varieties. These crops or varieties may be valued for their performance but it is a challenge for biotechnology that they cannot be transformed and thus cannot be directly edited via transformation. For recalcitrant varieties, one of two alternative approaches could be used to introduce desirable mutations. First, one could introduce the edits via trait introgression. This route is expensive, laborious, and time-consuming. It also means impurity of the final product because of genetic linkage—that is, there will be a linked block surrounding the introgressed edits, containing genes and alleles from the transformable donor line. This linkage can be an issue if any of those genes or alleles impact the performance of the transformation-recalcitrant line (may also be referred to as an "elite line"). Secondly, one could introduce the editing machinery transiently to the growing plant without tissue culture, such as floral dipping for *Arabidopsis* transformation. The challenge is ensuring edits end up in cells that contribute to the germ-line, so they are passed on to progeny seed. There are few established or routine methods to do this in crops.

Here we show a new method to transiently introduce editing machinery during haploid induction. Haploid induction ("HI") is a class of plant phenomena characterized by loss of one parent's set of chromosomes (the chromosomes from the haploid inducer parent) from the embryo at some time during or after fertilization, often during early embryo development. Haploid induction is also known as gynogenesis if the inducer line is used as the male in the cross, or androgenesis if the inducer line is used as the female in the cross. Haploid induction has been observed in numerous plant species, such as sorghum, barley, wheat, maize, *Arabidopsis*, and many other species.

Commonly, during haploid induction, both parent lines used in the induction cross are both diploids, so their gametes (egg cells and sperm cells) are haploids. Haploid induction is frequently a medium to low penetrance trait of the inducer line, so the resulting progeny, depending on the species or situation, may be either diploid (if no genome loss takes place) or haploids (if genome loss does indeed take place). If the parent line that is crossed to the haploid inducer is not diploid, but rather a tetraploid, hexaploid, or other plant of higher ploidy, the term haploid induction is something of a misnomer, because the "haploid" progeny produced will have a gametic chromosome number, and thus would not really be haploids, but rather diploids (if the parent is tetraploid) or triploids (if the parent is hexaploid) and so on. Therefore, as used herein, "haploids" possess half the number of chromosomes of either parent; thus haploids of diploid organisms (e.g., maize) exhibit monoploidy; haploids of tetraploid organisms (e.g., ryegrasses) exhibit diploidy; haploids of hexaploid organisms (e.g., wheat) exhibit triploidy.

Haploid induction can occur during self-pollination or intercros sing of two lines within the same species, or it can occur during wide crosses, where it can be viewed as a hybridization barrier, preventing the formation of interspecific hybrids. In maize, the most commonly employed method of inducing haploids is through the use of an intraspecific haploid inducer male line, which is primarily triggered by rearrangements of, mutations in, and/or recombinations, insertion, or deletions within a region of chromosome 1, specifically the MATRILINEAL (MATL) gene, also known as NOT LIKE DAD1 (NLD1) and PHOSPHOLIPASE A1 (PLA1) (with the notable exception of the ig type haploid induction, which is a result of a mutation in the INDETERMINATE GAMETOPHYTE1 gene on chromosome 3). In wheat, the most common method of inducting haploids is by wide cross to maize pollen—regardless of parent genotype or lineage, this works with almost any wheat crossed by almost any maize pollen.

HI maize lines contain a quantitative trait locus ("QTL") on Chromosome 1 responsible for at least 66% of the variation in haploid induction. The QTL causes haploid induction at different rates when it is introgressed into various backgrounds. All maize haploid inducer lines used in the seed industry are derivatives of the founding HI line, known as Stock6, and all have the haploid inducer chromosome 1 QTL mutation.

In maize, haploid seed or embryos are specifically produced by making crosses between a haploid inducer male (i.e., "haploid inducer pollen") and virtually any ear that one chooses—the ear could be of any inbred, hybrid, or other germplasm. Haploids are produced when the haploid inducer pollen DNA is not fully transmitted and/or maintained through the first cell divisions of the embryos. The resulting phenotype is not fully penetrant, with some ovules containing haploid embryos, and others containing diploid embryos, aneuploid embryos, chimeric embryos, or aborted embryos. The haploid kernels have embryos that contain only the maternal DNA plus normal triploid endosperm. After haploid induction, haploid embryos or seed are typically segregated from diploid and aneuploid siblings using a phenotypic or genetic marker screen and grown or cultured into haploid plants. These plants are then converted either naturally or via chemical manipulation (e.g., using an anti-microtubule agent such as colchicine) into doubled haploid ("DH") plants which then produce inbred seed.

Plant breeding is facilitated by the use of doubled haploid (DH) plants. The production of DH plants enables plant breeders to obtain inbred lines without multi-generational inbreeding, thus decreasing the time required to produce homozygous plants. DH plants provide an invaluable tool to plant breeders, particularly for generating inbred lines, QTL mapping, cytoplasmic conversions, trait introgression, and F2 screening for high throughput trait improvement. A great deal of time is spared as homozygous lines are essentially generated in one generation, negating the need for multi-generational single-seed decent (conventional inbreeding). In particular, because DH plants are entirely homozygous, they are very amenable to quantitative genetics studies. The production of haploid seed is critical for the doubled haploid breeding process. Haploid seed are produced on maternal germplasm when fertilized with pollen from a gynogenetic inducer, such as Stock 6 and Stock 6-derivative lines.

Here, we describe a novel method in which the in vivo haploid induction process can be co-opted to transiently introduce editing machinery into any germplasm by including it in the haploid inducer parent, either stably integrated as a transgene, or transiently expressed. Simultaneous editing plus haploid induction can be done in almost any crop via wide cross or de novo haploid induction for instance via CENH3 mutation (i.e., CENH3-modified haploid inducer; see, e.g., WO 2017/004375, incorporated herein by reference in its entirety) or via lipid spray (see P.C.T. Patent Application No. PCT/US2016/62548, incorporated herein by reference in its entirety). We show examples of HI in maize, both field corn and sweet corn, using a haploid inducer male as the editing donor line. Further, we show examples of HI in *Arabidopsis* using CENH3-modified haploid inducer lines.

We also show examples of HI in wheat using maize pollen as the editing donor line in a wide cross. In wheat, rice, barley, *brassica*, and other crops, the route to haploid induction would be to use a pollen donor that induces haploids via wide cross. For example, one could use corn pollen on wheat, millet pollen on wheat, barley pollen on other barley species, or any other wide crossing method. In those cases of gynogenetic haploid induction it would be preferable for the male line to contain the editing machinery, because it is the male (pollen-derived) DNA that is eliminated in the haploid induction process. In cases of androgenic haploid induction, for instance in the ig1 system in maize or via altered CENH3 in any crop (which can work via either the male or the female), the editing machinery would be optimally present in the female parent, because the female chromosomes are eliminated in the haploid induction process.

In simultaneous editing plus haploid induction, the goal is to rapidly and cost-effectively edit crops and elite lines ("editing destination lines") without tissue culture. The line that receives the edits could be elite germplasm, and the editing machinery itself would be eliminated during the haploid induction process. At the same time, edited doubled haploid lines are produced.

SUMMARY

Tissue culture recalcitrance is a major challenge to rapid elite line editing across crops. Using haploid inducing lines to deliver the targeted mutagenesis machinery to elite lines and simultaneously induce haploids represents the surmounting of this major obstacle. Next-generation breeding programs may come to depend on this process.

The editing machinery is delivered via the inducer line. The editing machinery is most often DNA-binding proteins combined in some cases with RNA and in some cases also with DNA. The DNA, RNA, and proteins that make up the editing machinery are encoded by and are present in the inducer line because they have been stably inserted in the inducer, for example, via bombardment or *agrobacterium* mediated transformation. In other examples, the editing machinery is transiently introduced (through exogenous application) or transiently expressed in the gametophyte prior to fertilization. After fertilization, edits are made by the editing machinery in the non-inducer target genes prior to or during elimination of the inducer chromosomes. The result is a haploid embryo or plant or seed that contains the chromosome set only from the non-inducer parent, where that chromosome set contains DNA sequences that have been edited. These edited haploids can be identified, grown, and their chromosomes doubled, preferably by colchicine or other mitotic inhibitor. This line can then be directly used in downstream breeding programs.

In one embodiment, the invention provides a method of editing a plant's genomic DNA. This is done by taking a first plant—which is a haploid inducing plant and which also has encoded into its DNA the machinery necessary for accomplishing the editing (for example, a Cas9 enzyme and a guide RNA)—and using that first plant's pollen to pollinate a second plant. The second plant is the plant to be edited. From that pollination event, progeny (e.g., embryos or seeds) are produced; at least one of which will be a haploid seed. This haploid seed will only contain the chromosomes of the second plant; the first plant's chromosomes have vanished (having been eliminated, lost or degraded), but before doing so, the first plant's chromosomes permitted the gene-editing machinery to be expressed. Alternately, and without wishing to be bound by theory, the first plant delivers the already-expressed editing machinery upon pollination via the pollen tube. Or, in the case that the haploid inducer line is the female in the cross, the haploid inducing plant's egg cell contains the editing machinery that is present and perhaps already being expressed, upon fertilization with the "wild type" or non-haploid inducing pollen grain. Through any of these routes, the haploid progeny obtained by the cross will also have had its genome edited.

In one aspect, the editing machinery is any DNA modification enzyme, but is preferably a site-directed nuclease. The site-directed nuclease is preferably CRISPR-based, but could also be a meganuclease, a transcription-activator like effector nuclease (TALEN), or a zinc finger nuclease. The nuclease used in this invention could be Cas9, Cfp1, dCas9-FokI, chimeric FEN1-FokI. In one aspect, the DNA modification enzyme is a site-directed base editing enzyme such as Cas9-cytidine deaminase or Cas9-adeninie deaminase, wherein the Cas9 can have one or both of its nuclease activity inactivated, i.e. chimeric Cas9 nickase (nCas9) or deactivated Cas9 (dCas9) fused to cytidine deaminase or adenine deaminase. The optional guide RNA targets the genome at the specific site intended to be edited. In one aspect, the optional guide RNA comprises an 18-21 nucleotide sequence with homology to any of SEQ ID NOs: 2, 4, 8, 21, 23, 25, 29, 32, and 33.

Once the edited haploid progeny is obtained, it may optionally have its chromosomes doubled by a chromosome doubling agent (for example colchicine, pronamide, dithipyr, trifluralin, or another known anti-microtubule agent).

In one embodiment, the first plant is a monocot or a dicot. Aspects of the first plant include maize, wheat, rice, barley, oats, triticale, sorghum, pearl millet, teosinte, bamboo, sugar cane, asparagus, onion, and garlic. In one embodiment, the second plant is a monocot or a dicot. Aspects of the second plant include maize, wheat, rice, barley, oats, triticale, sorghum, pearl millet, teosinte, bamboo, sugar cane, asparagus, onion, and garlic. In one embodiment, the first plant is a monocot or a dicot of a different species than the second plant. For example, in one aspect, the first plant is maize and the second plant is wheat. In another aspect, the first plant is wheat and the second plant is maize. In another embodiment, the first plant is a maize plant selected and/or derived from the lines Stock 6, RWK, RWS, UH400, AX5707RS, NP2222-matl, or any of the several other known HI lines. In yet another embodiment, the first plant comprises a mutation in a CENH3 gene, an ig1 gene, or another mutation conferring paternal-haploid inducing systems. In another embodiment, the first plant is a rice plant with the MATL gene modified or knocked out which makes it a haploid inducer line.

In another embodiment, the first plant is not necessarily a haploid inducer, yet the first plant comprises the genes necessary for encoding the gene editing machinery. In this embodiment, haploid induction is produced by administering a compound during, immediately before, or immediately following pollination. In one aspect, the composition comprises a lipid or a phospholipase inhibitor. In another aspect, the composition comprises methyl alpha-linolenoyl fluorophosphonate (MALFP), linoleic acid ethyl ester (LLAEE), linoleic acid (LLA), corn oil, distearoyl-phosphatidyl choline (DSPC), methyl arachidonyl fluorophosphonate (MAFP), Palmityl trifluoromethylketone (PACOCF3), Arachidonyl trifluoromethylketone (AACOCF3), Manoalide, Linolenic acid ethyl ester (LNAEE), Linolenic acid ethyl ester (LNAEE), Oleic acid methyl ester (OAME), Oleic acid ethyl ester (OAEE), Palmitic acid ethyl ester (PAEE), Palmitoleic acid ethyl ester (PLAEE), Linseed oil, corn oil, alpha-Linolenic acid (aLNA), gamma-Linolenic acid (gLNA), Oleic acid, Arachidonic acid, Stearic Acid, 9(Z)-11(E)-conjugated Linoleic acid, or 2-oleoyl-1-palmitoyl-sn-glycero-3-phospho-ethanolamine.

BRIEF DESCRIPTION OF THE SEQUENCES IN THE SEQUENCE LISTING

SEQ ID NO: 1 is a nucleotide sequence for vector 23396.

SEQ ID NO: 2 is the nucleotide sequence encoding the gRNA sequence for editing VLHP1 in maize.

SEQ ID NO: 3 is a nucleotide sequence for vector 23399.

SEQ ID NO: 4 is the gRNA sequence for editing GW2-2 in maize.

SEQ ID NO: 5 is the nucleotide sequence for vector 22808, comprising a TALEN construct.

SEQ ID NO: 6 is the target sequence for the TALEN of 22808.

SEQ ID NO: 7 is the nucleotide sequence for vector 23123 comprising a Cas9 construct.

SEQ ID NO: 8 is the gRNA for editing MATL in maize.

SEQ ID NO: 9 is nucleotide sequence for the relevant portion of MATL in NP2222.

SEQ ID NO: 10 is nucleotide sequence for the relevant portion of MATL in Stock6.

SEQ ID NO: 11 is nucleotide sequence for the relevant portion of MATL in USR01350333-3 Allele 1.

SEQ ID NO: 12 is nucleotide sequence for the relevant portion of MATL in USR01350333-3 Allele 2.

SEQ ID NO: 13 is nucleotide sequence for the relevant portion of MATL in USR01350344-2 Allele 1.

SEQ ID NO: 14 is nucleotide sequence for the relevant portion of MATL in USR01350344-2 Allele 2.

SEQ ID NO: 15 is nucleotide sequence for the relevant portion of MATL in USR01350343-1 Allele 1.

SEQ ID NO: 16 is nucleotide sequence for the relevant portion of MATL in USR01350328-1 Allele 1.

SEQ ID NO: 17 is nucleotide sequence for the relevant portion of MATL in USR01350337-2 Allele 1.

SEQ ID NO: 18 is nucleotide sequence for the relevant portion of MATL in USR01350337-2 Allele 2.

SEQ ID NO: 19 is the nucleotide sequence of cDNA wildtype MATL.

SEQ ID NO: 20 is the nucleotide sequence for vector 23397.

SEQ ID NO: 21 is the gRNA sequence for editing VLHP2 in maize.

SEQ ID NO: 22 is the nucleotide sequence for vector 23398.

SEQ ID NO: 23 is the gRNA sequence for editing GW2-1 in maize.

SEQ ID NO: 24 is the nucleotide sequence for vector 23763.

SEQ ID NO: 25 is the gRNA sequence for VLHP1 in wheat.

SEQ ID NO: 26 is the wheat VLHP target sequence for TaVLHP2.

SEQ ID NO: 27 is the wheat VLHP target sequence for TaVLHP3.

SEQ ID NO: 28 is the target sequence in ZmVLHP2-03 for editing.

SEQ ID NO: 29 is the edited sequence in ZmVLHP2-03.

SEQ ID NO: 30 is the repair donor template sequence for creating E149L mutation in ZmPYL-D.

SEQ ID NO: 31 is the nucleotide sequence for vector 23136.

SEQ ID NO: 32 is the gRNA of vector 23136.

SEQ ID NO: 33 is the nucleotide sequence of rice PLA gene Os03g27610.

SEQ ID NO: 34 is the nucleotide sequence for vector 24038.

SEQ ID NO: 35 is the nucleotide sequence for vector 24039.

SEQ ID NO: 36 is the nucleotide sequence for vector 24079.

SEQ ID NO: 37 is the nucleotide sequence for vector 24091.

SEQ ID NO: 38 is the nucleotide sequence for vector 24094.

SEQ ID NOs: 39 through 97 are primers and probes used in the identified PCR Taqman assays.

SEQ ID NO: 98 is the nucleotide sequence for vector 24075.

SEQ ID NO: 99 is a portion of the edited GW2-02 target site in haploid sweet corn line JSER82A063, shown in FIG. 13.

SEQ ID NO: 100 is the reverse complement of SEQ ID NO: 99 shown in FIG. 13.

SEQ ID NO: 101 is a portion of the edited TaVLHP1-4B target site in haploid wheat line JSWER30A22, shown in FIG. 16.

SEQ ID NO: 102 is the nucleotide sequence of the gRNA used in editing the *Arabidopsis* GL1 gene.

SEQ ID NO: 103 is the relevant portion of the wildtype *Arabidopsis* GL1 gene.

SEQ ID NO: 104 is the relevant portion of the edited GL1 gene (by single nucleotide deletion) in individual 135.

SEQ ID NO: 105 is the relevant portion of the edited GL1 gene (by single nucleotide insertion) in individual 135.

SEQ ID NO: 106 is the relevant portion of the unedited GL1 gene in individual 1033-A3 (product of cross between USR01424135 and Ler-425).

SEQ ID NO: 107 is the relevant portion of the edited GL1 gene (by single nucleotide insertion) in individual 1033-C3 (product of cross between USR01424135 and Ler-427).

SEQ ID NO: 108 is the relevant portion of the edited GL1 gene (by single nucleotide insertion) in individual 1033-E4 (product of cross between USR01424135 and Ler-437).

SEQ ID NO: 109 is the relevant portion of the edited GL1 gene (by deletion of three nucleotides) in individual 1041-H12.

SEQ ID NO: 110 is the relevant portion of the edited GL1 gene (by single nucleotide insertion) in individual 1042-E5 (product of cross between USR01424136 and Ler-25).

SEQ ID NO: 111 is the relevant portion of the edited GL1 gene (by single nucleotide deletion) in individual 1042-G12 (product of cross between USR01424136 and Ler-83).

SEQ ID NO: 112 is the relevant portion of the edited GL1 gene (by deletion of two nucleotides) in individual 1042-G10 (product of cross between USR01424136 and Ler-67).

SEQ ID NO: 113 is the relevant portion of the edited GL1 gene (by deletion of two nucleotides) in individual 1045-E3 (product of cross between USR01424136 and Ler-261).

SEQ ID NO: 114 is the relevant portion of the edited GL1 gene (by single nucleotide insertion) in individual 1045-D3 (product of cross between USR01424136 and Ler-260).

SEQ ID NO: 115 is the relevant portion of the edited GL1 gene (by single nucleotide insertion) in individual 1046-D11 (product of cross between USR01431609 and Ler-111).

SEQ ID NO: 116 is the relevant portion of the edited GL1 gene (by single nucleotide insertion) in individual 1046-G12 (product of cross between USR01431609 and Ler-122).

SEQ ID NO: 117 is the relevant portion of the edited GL1 gene (by deletion of sixteen nucleotides and insertion of eight nucleotides) in individual 1045-F2 (product of cross between USR01424136 and Ler-254).

BRIEF DESCRIPTION OF THE FIGURES

FIG. 16 shows sequencing confirmation of TaVLHP1-4B target site editing in haploid wheat line JSWER30A22. Lower panel showing 97 bp of TaVLHP1-4B sequence was deleted immediately downstream of the predicted Cas9 cleavage site. The 97 bp deleted sequences were marked by 2 arrows. The underlined sequence matches the gRNA sequence of SEQ ID NO: 25. The entire sequence is represented by SEQ ID NO: 101.

DEFINITIONS

Figure 1:
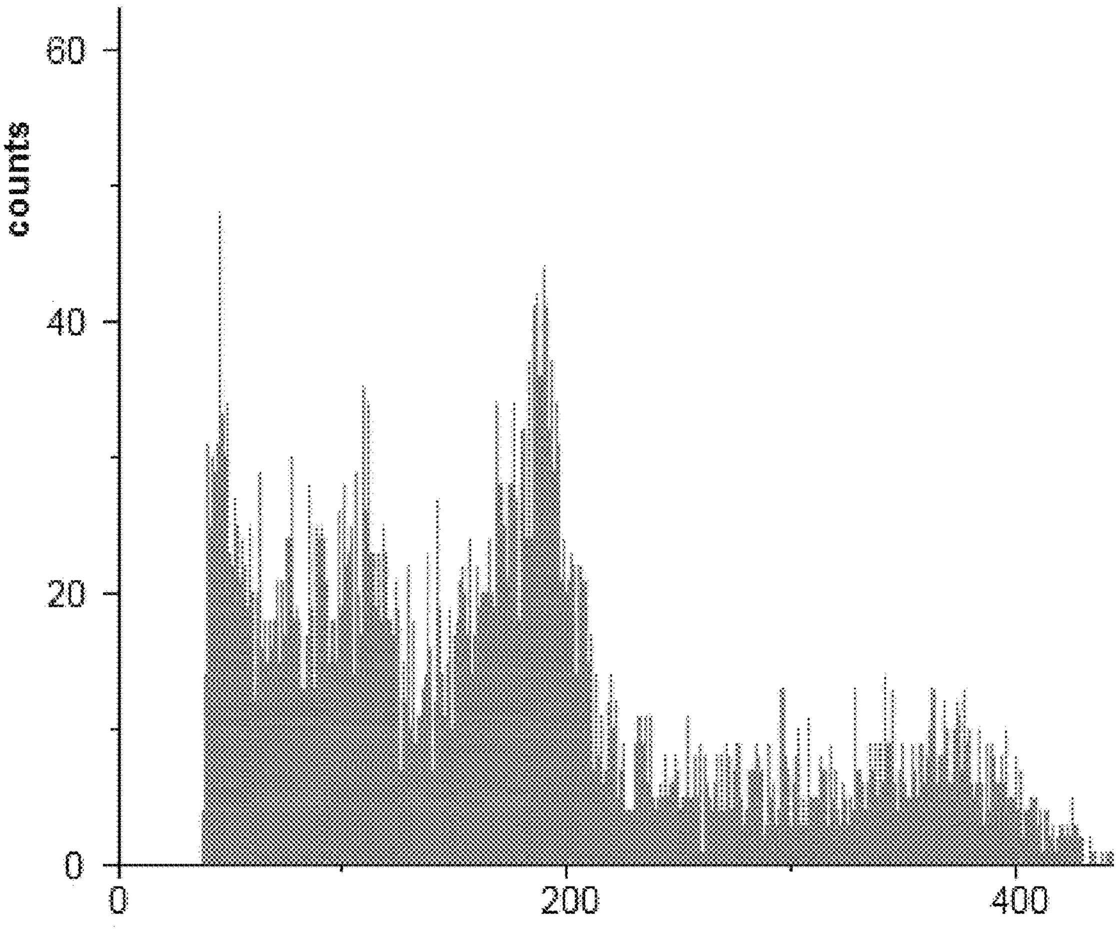
FIG. 1 shows the ploidy analysis (flow cytometry) data for USR01350334-3: DIPLOID (major peak at 200, secondary peak at 400).
Figure 2:
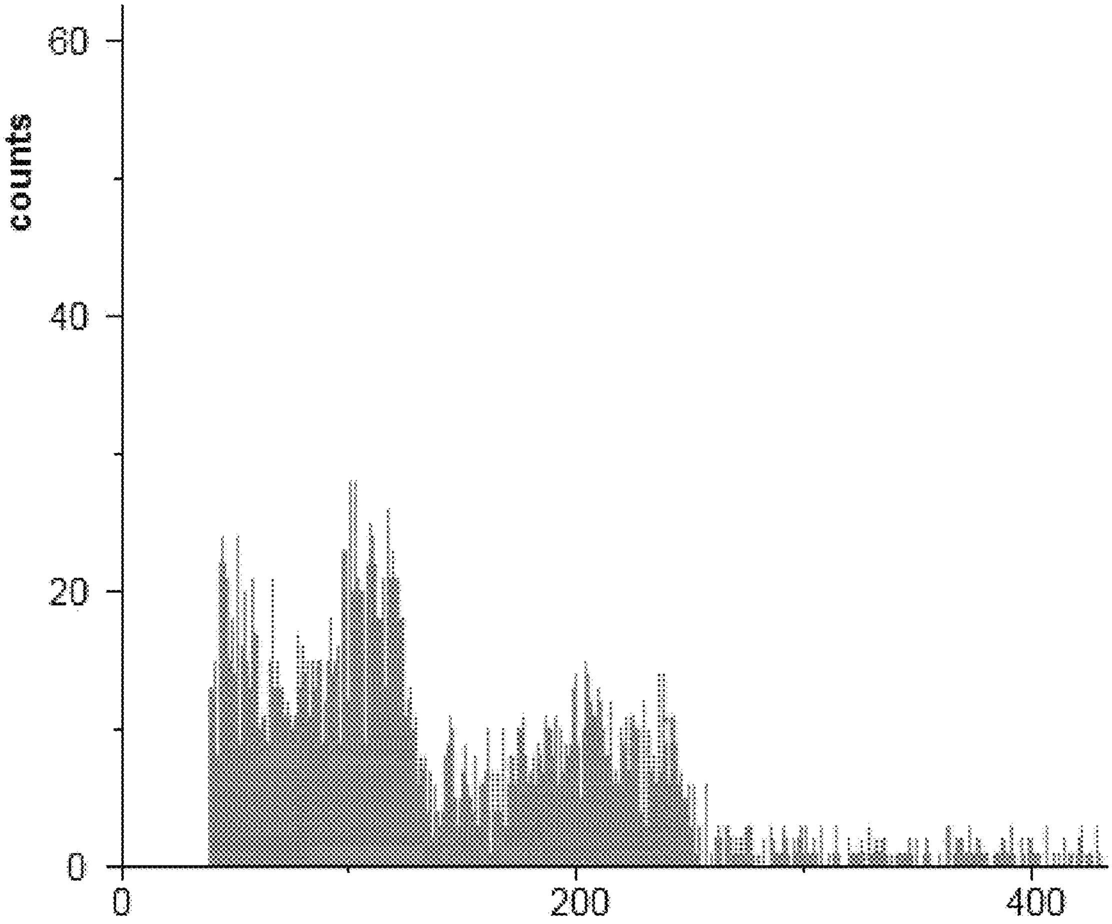
FIG. 2 shows the ploidy analysis (flow cytometry) data for USR01350333-3: HAPLOID (major peak at 100, secondary peak at 200).
Figure 3:
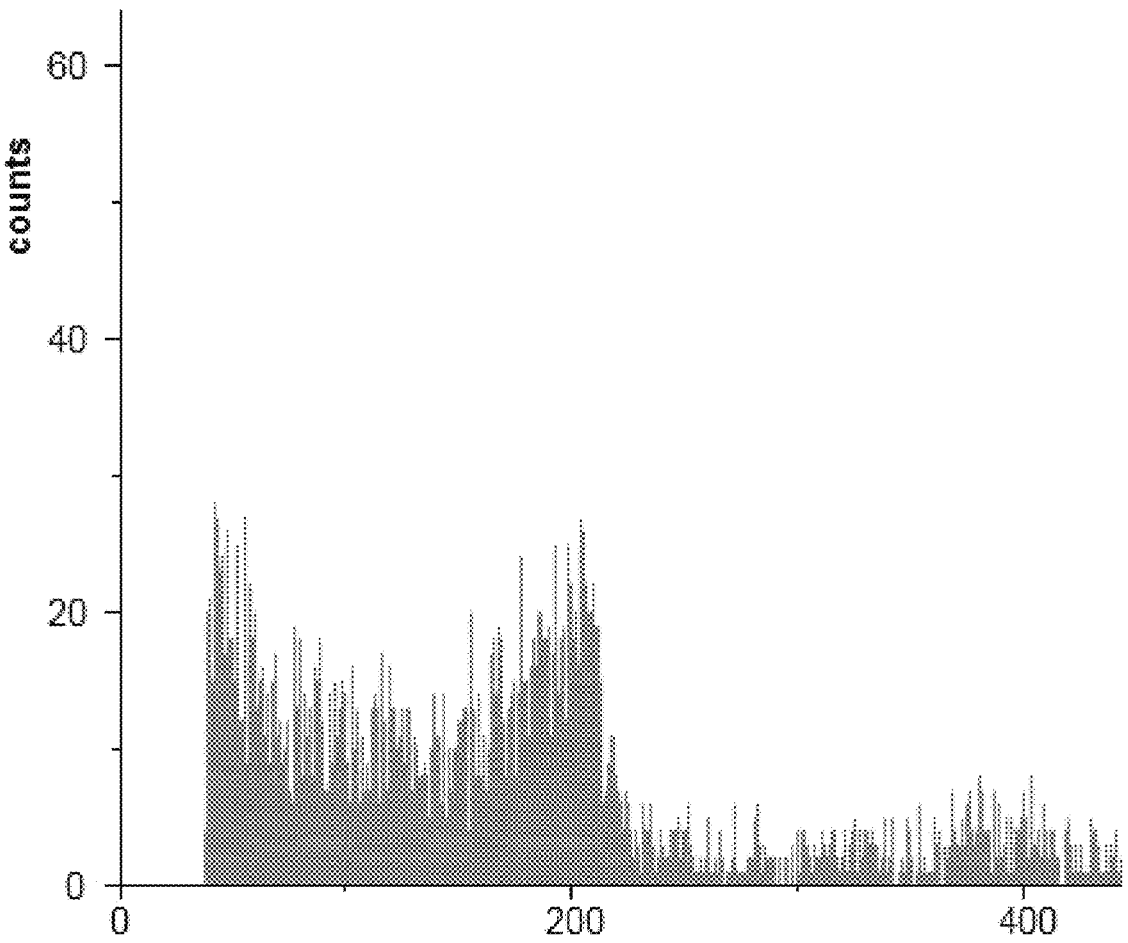
FIG. 3 shows the ploidy analysis (flow cytometry) data for USR01350333-10: DIPLOID (major peak at 200, secondary peak at 400).
Figure 4:
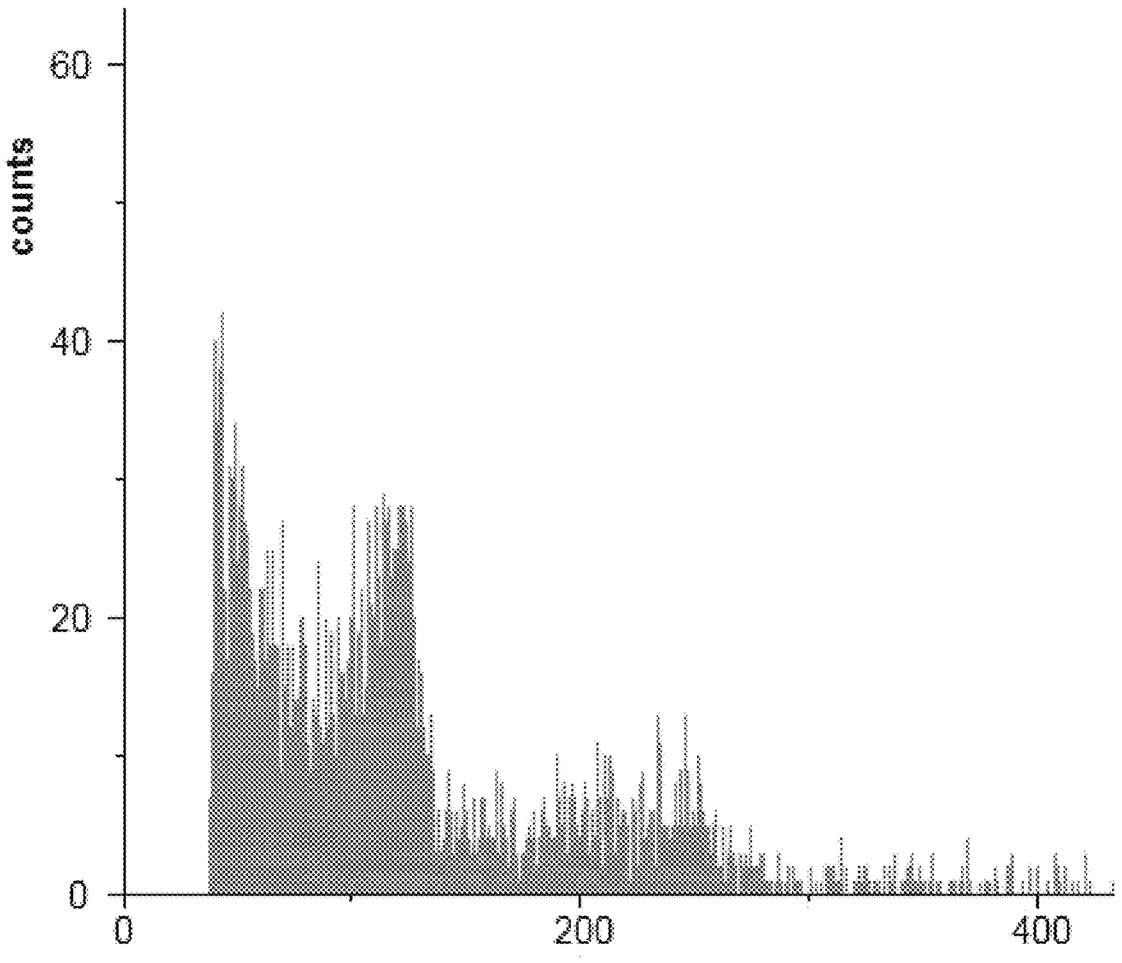
FIG. 4 shows the ploidy analysis (flow cytometry) data for USR01350344-2: HAPLOID (major peak at 100, secondary peak at 200).
Figure 5:
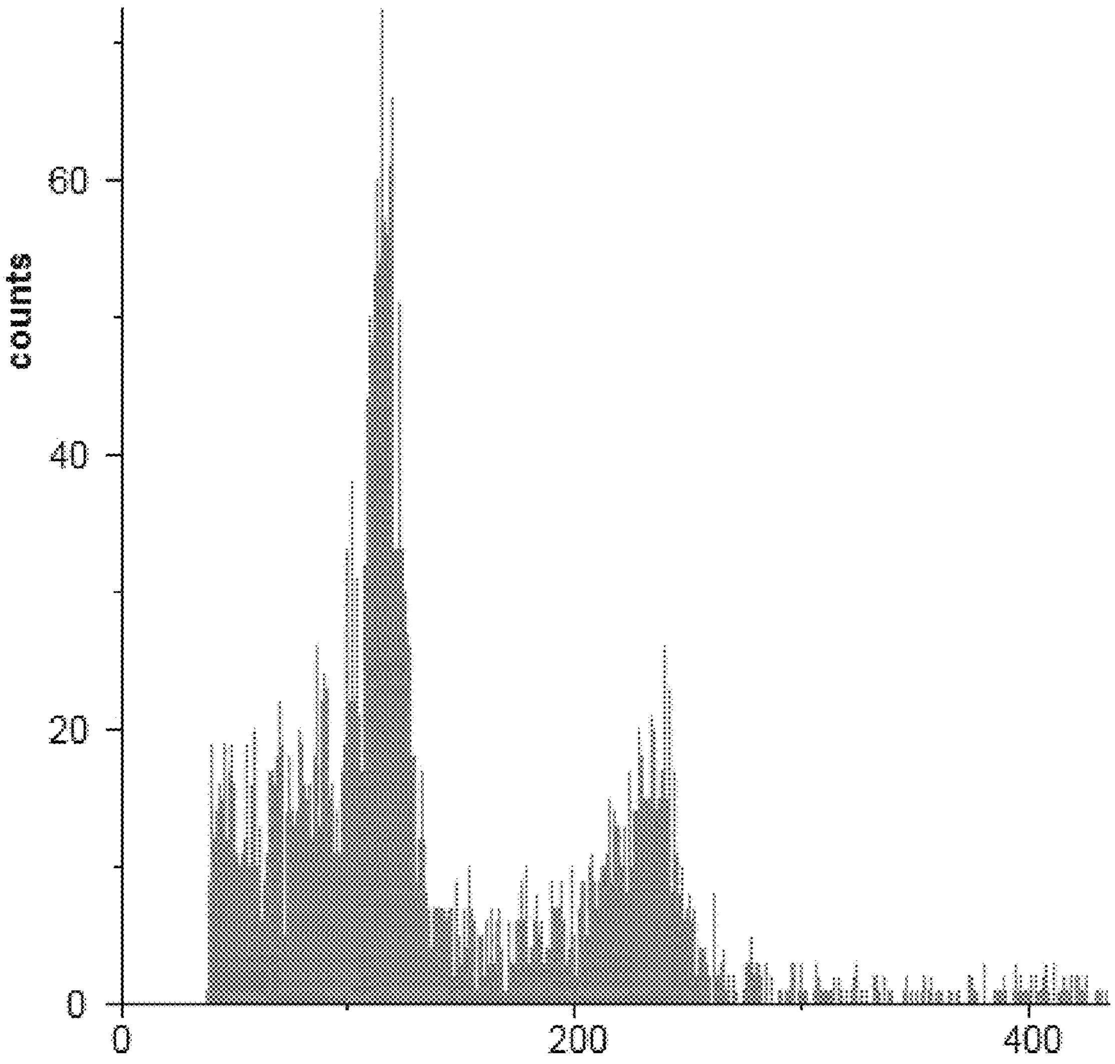
FIG. 5 shows the ploidy analysis (flow cytometry) data for USR01350343-1: HAPLOID (major peak at 100, secondary peak at 200).
Figure 6:
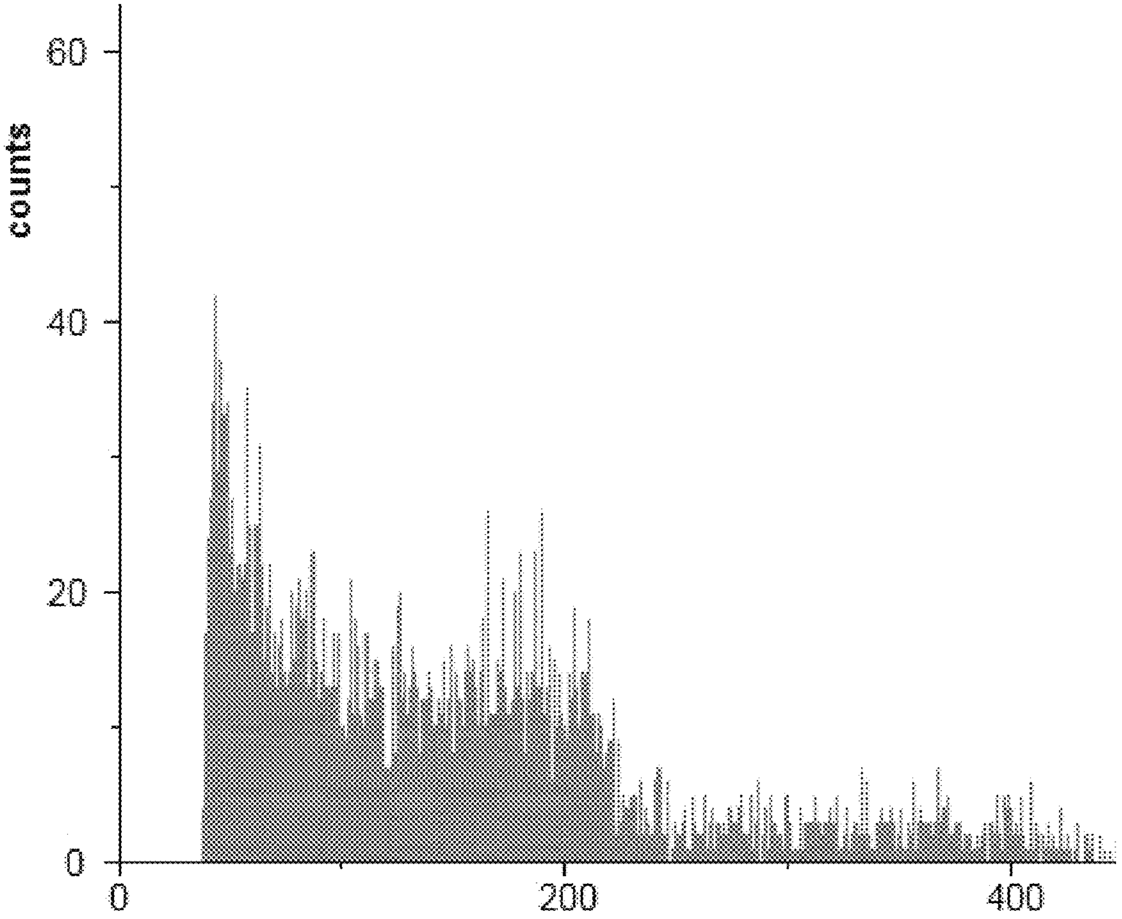
FIG. 6 shows the ploidy analysis (flow cytometry) data for USR01350341-1: DIPLOID (major peak at 200, secondary peak at 400).
Figure 7:
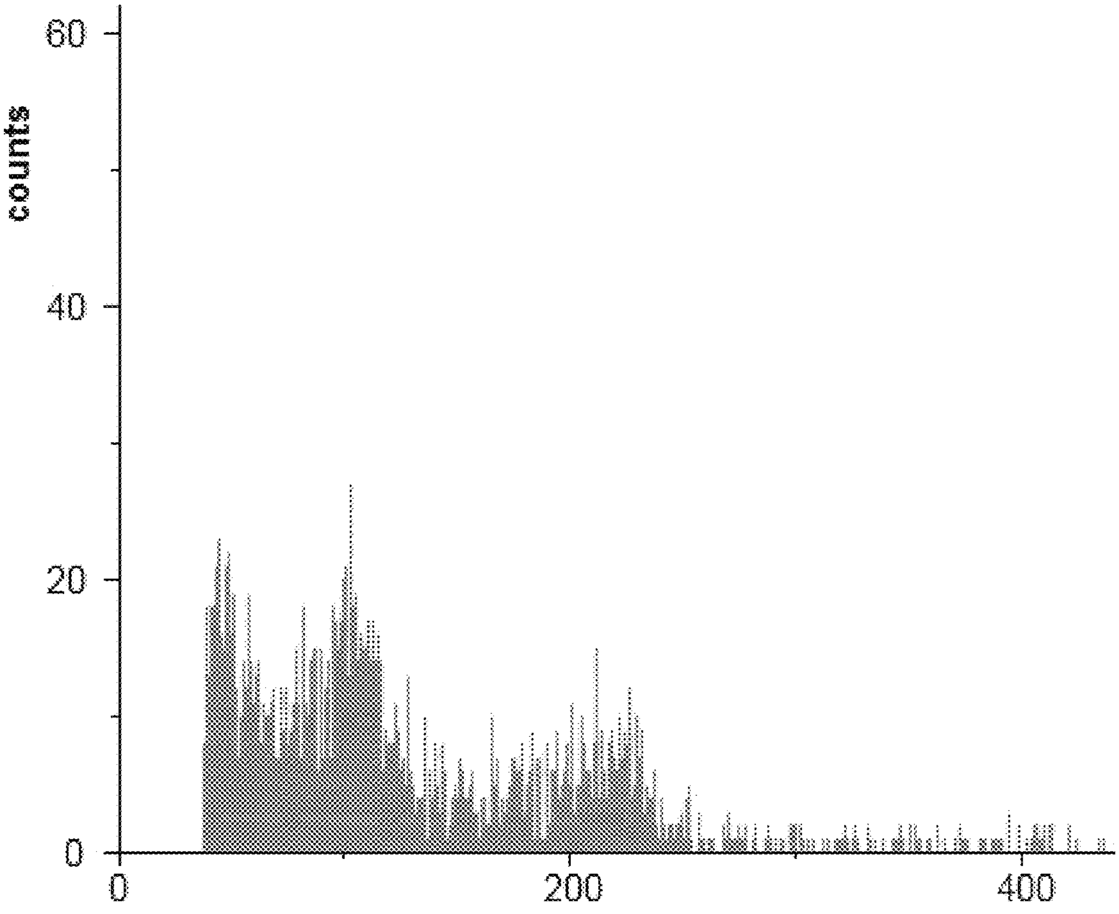
FIG. 7 shows the ploidy analysis (flow cytometry) data for USR01350328-1: HAPLOID (major peak at 100, secondary peak at 200).
Figure 8:
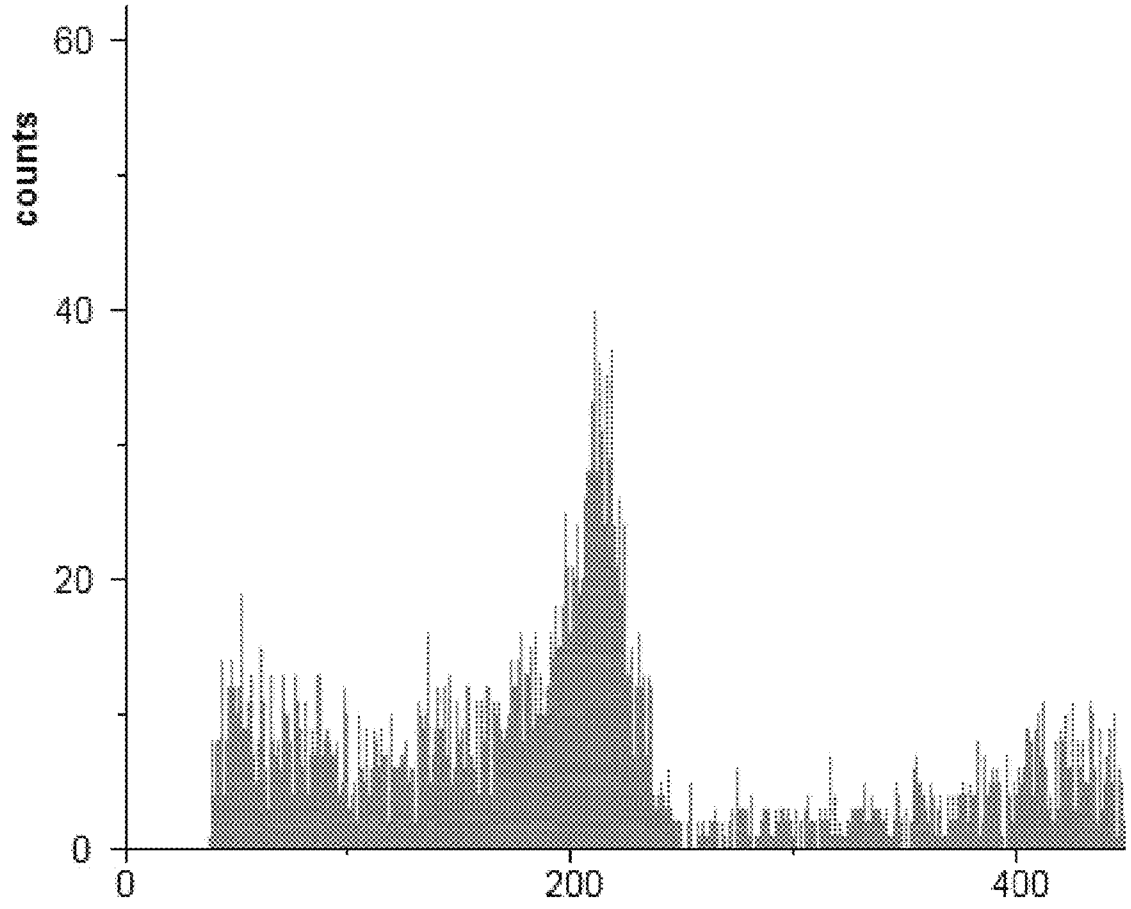
FIG. 8 shows the ploidy analysis (flow cytometry) data for USR01350321-3: DIPLOID (major peak at 200, secondary peak at 400).

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques and/or substitutions of equivalent techniques that would be apparent to one of skill in the art. While the following terms are believed to be well understood by one of ordinary skill in the art, the following definitions are set forth to facilitate explanation of the presently disclosed subject matter.

Following long-standing patent law convention, the terms "a," "an," and "the" refer to "one or more" when used in this application, including the claims. For example, the phrase "a cell" refers to one or more cells, and in some embodiments can refer to a tissue and/or an organ. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to all whole number values between 1 and 100 as well as whole numbers greater than 100.

Unless otherwise indicated, all numbers expressing quantities of ingredients, reaction conditions, and so forth used in the specification and claims are to be understood as being modified in all instances by the term "about." The term "about," as used herein when referring to a measurable value such as an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods and/or employ the discloses compositions, nucleic acids, polypeptides, etc. Accordingly, unless indicated to the contrary, the numerical parameters set forth in this specification and attached claims are approximations that can vary depending upon the desired properties sought to be obtained by the presently disclosed subject matter.

As used herein, the term "allele" refers to a variant or an alternative sequence form at a genetic locus. In diploids, a single allele is inherited by a progeny individual separately from each parent at each locus. The two alleles of a given locus present in a diploid organism occupy corresponding places on a pair of homologous chromosomes, although one of ordinary skill in the art understands that the alleles in any particular individual do not necessarily represent all of the alleles that are present in the species.

As used herein, the term "and/or" when used in the context of a list of entities, refers to the entities being present singly or in combination. Thus, for example, the phrase "A, B, C, and/or D" includes A, B, C, and D individually, but also includes any and all combinations and subcombinations of A, B, C, and D (e.g., AB, AC, AD, BC, BD, CD, ABC, ABD, and BCD). In some embodiments, one of more of the elements to which the "and/or" refers can also individually be present in single or multiple occurrences in the combinations(s) and/or subcombination(s).

As used herein, the phrase "associated with" refers to a recognizable and/or assayable relationship between two entities. For example, the phrase "associated with HI" refers to a trait, locus, gene, allele, marker, phenotype, etc., or the expression thereof, the presence or absence of which can influence an extent and/or degree at which a plant or its progeny exhibits HI. As such, a marker is "associated with" a trait when it is linked to it and when the presence of the marker is an indicator of whether and/or to what extent the desired trait or trait form will occur in a plant/germplasm comprising the marker. Similarly, a marker is "associated with" an allele when it is linked to it and when the presence of the marker is an indicator of whether the allele is present in a plant/germplasm comprising the marker. For example, "a marker associated with HI" refers to a marker whose presence or absence can be used to predict whether and/or to what extent a plant will display haploid induction.

The term "comprising," which is synonymous with "including," "containing," and "characterized by," is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting of" excludes any element, step, or ingredient not specifically recited. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of the related disclosure or claim to the specified materials and/or steps, plus those that do not materially affect the basic and novel characteristic(s) of the disclosed and/or claimed subject matter.

With respect to the terms "comprising," "consisting essentially of," and "consisting of," where one of these three terms is used herein, the presently disclosed and claimed subject matter can include in some embodiments the use of either of the other two terms. For example, if a subject matter relates in some embodiments to nucleic acids that encode polypeptides comprising amino acid sequences that are at least 95% identical to a SEQ ID NO: 9 or 19. It is understood that the disclosed subject matter thus also encompasses nucleic acids that encode polypeptides that in some embodiments consist essentially of amino acid sequences that are at least 95% identical to that SEQ ID NO: 9 or 19 as well as nucleic acids that encode polypeptides that in some embodiments consist of amino acid sequences that are at least 95% identical to that SEQ ID NO: 9 or 19. Similarly, it is also understood that in some embodiments the methods for the disclosed subject matter comprise the steps that are disclosed herein, in some embodiments the methods for the presently disclosed subject matter consist essentially of the steps that are disclosed, and in some embodiments the methods for the presently disclosed subject matter consist of the steps that are disclosed herein.

As used herein, the term "de novo haploid induction" refers to the triggering of haploid induction by the introduction of a spontaneous haploid inducing agent. Such introduction can be achieved by topical spray, hand-pollination, mutagenesis, or transgenic methods. The terms "de novo haploid induction," "de novo HI," and "haploid induction de novo" are used interchangeably throughout this specification.

As used herein, the term "gene" refers to a hereditary unit including a sequence of DNA that occupies a specific location on a chromosome and that contains the genetic instruction for a particular characteristic or trait in an organism.

A "genetic map" is a description of genetic linkage relationships among loci on one or more chromosomes within a given species, generally depicted in a diagrammatic or tabular form.

As used herein, a plant referred to as "haploid" has a reduced number of chromosomes (n) in the haploid plant, and its chromosome set is equal to that of the gamete. In a haploid organism, only half of the normal number of chromosomes are present. Thus haploids of diploid organisms (e.g., maize) exhibit monoploidy; haploids of tetraploid organisms (e.g., ryegrasses) exhibit diploidy; haploids of hexaploid organisms (e.g., wheat) exhibit triploidy; etc. As used herein, a plant referred to as "doubled haploid" is developed by doubling the haploid set of chromosomes. A plant or seed that is obtained from a doubled haploid plant that is selfed to any number of generations may still be identified as a doubled haploid plant. A doubled haploid plant is considered a homozygous plant. A plant is considered to be doubled haploid if it is fertile, even if the entire vegetative part of the plant does not consist of the cells with the doubled set of chromosomes; that is, a plant will be considered doubled haploid if it contains viable gametes, even if it is chimeric in vegetative tissues.

As used herein, the term "human-induced mutation" refers to any mutation that occurs as a result of either direct or indirect human action. This term includes, but is not limited to, mutations obtained by any method of targeted mutagenesis.

As used herein, "introduced" means delivered, expressed, applied, transported, transferred, permeated, or other like term to indicate the delivery, whether of nucleic acid or protein or combination thereof, of a desired object to an object. For example, nucleic acids encoding a site directed nuclease and optionally at least one guide RNA may be introduced into a haploid embryo upon haploid induction. Likewise, extant editing machinery (comprising a site directed nuclease protein and optionally at least one guide RNA) may be introduced to a haploid embryo upon application of appropriate cell-penetrating peptides.

As used herein, the terms "marker probe" and "probe" refer to a nucleotide sequence or nucleic acid molecule that can be used to detect the presence or absence of a sequence within a larger sequence, e.g., a nucleic acid probe that is complementary to all of or a portion of the marker or marker locus, through nucleic acid hybridization. Marker probes comprising about 8, 10, 15, 20, 30, 40, 50, 60, 70, 80, 90, 100 or more contiguous nucleotides can be used for nucleic acid hybridization.

As used herein, the term "molecular marker" can be used to refer to a genetic marker, as defined above, or an encoded product thereof (e.g., a protein) used as a point of reference when identifying the presence/absence of a HI-associated locus. A molecular marker can be derived from genomic nucleotide sequences or from expressed nucleotide sequences (e.g., from an RNA, a cDNA, etc.). The term also refers to nucleotide sequences complementary to or flanking the marker sequences, such as nucleotide sequences used as probes and/or primers capable of amplifying the marker sequence. Nucleotide sequences are "complementary" when they specifically hybridize in solution (e.g., according to Watson-Crick base pairing rules). This term also refers to the genetic markers that indicate a trait by the absence of the nucleotide sequences complementary to or flanking the marker sequences, such as nucleotide sequences used as probes and/or primers capable of amplifying the marker sequence.

As used herein, the terms "nucleotide sequence," "polynucleotide," "nucleic acid sequence," "nucleic acid molecule," and "nucleic acid fragment" refer to a polymer of RNA or DNA that is single- or double-stranded, optionally containing synthetic, non-natural, and/or altered nucleotide bases. A "nucleotide" is a monomeric unit from which DNA or RNA polymers are constructed and consists of a purine or pyrimidine base, a pentose, and a phosphoric acid group. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

As used herein, the term "nucleotide sequence identity" refers to the presence of identical nucleotides at corresponding positions of two polynucleotides. Polynucleotides have "identical" sequences if the sequence of nucleotides in the two polynucleotides is the same when aligned for maximum correspondence (e.g., in a comparison window). Sequence comparison between two or more polynucleotides is generally performed by comparing portions of the two sequences over a comparison window to identify and compare local regions of sequence similarity. The comparison window is generally from about 20 to 200 contiguous nucleotides. The "percentage of sequence identity" for polynucleotides, such as about 50, 55, 60, 65, 70, 75, 80, 85, 90, 95, 98, 99 or 100 percent sequence identity, can be determined by comparing two optimally aligned sequences over a comparison window, wherein the portion of the polynucleotide sequence in the comparison window can include additions or deletions (i.e., gaps) as compared to the reference sequence for optimal alignment of the two sequences. In some embodiments, the percentage is calculated by: (a) determining the number of positions at which the identical nucleic acid base occurs in both sequences; (b) dividing the number of matched positions by the total number of positions in the window of comparison; and (c) multiplying the result by 100. Optimal alignment of sequences for comparison can also be conducted by computerized implementations of known algorithms, or by visual inspection. Readily available sequence comparison and multiple sequence alignment algorithms are, respectively, the Basic Local Alignment Search Tool (BLAST) and ClustalW/ClustalW2/Clustal Omega programs available on the Internet (e.g., the website of the EMBL-EBI). Other suitable programs include, but are not limited to, GAP, BestFit, Plot Similarity, and FASTA, which are part of the Accelrys GCG Package available from Accelrys, Inc. of San Diego, Calif., United States of America. See also Smith & Waterman, 1981; Needleman & Wunsch, 1970; Pearson & Lipman, 1988; Ausubel et al., 1988; and Sambrook & Russell, 2001.

One example of an algorithm that is suitable for determining percent sequence identity and sequence similarity is the BLAST algorithm, which is described in Altschul et al., 1990. In some embodiments, a percentage of sequence identity refers to sequence identity over the full length of one of the gDNA, cDNA, or the predicted protein sequences in the largest ORF of SEQ ID No: 1 being compared. In some embodiments, a calculation to determine a percentage of nucleic acid sequence identity does not include in the calculation any nucleotide positions in which either of the compared nucleic acids includes an "N" (i.e., where any nucleotide could be present at that position).

The term "open reading frame" (ORF) refers to a nucleic acid sequence that encodes a polypeptide. In some embodiments, an ORF comprises a translation initiation codon (i.e., start codon), a translation termination (i.e., stop codon), and the nucleic acid sequence there between that encodes the amino acids present in the polypeptide. The terms "initiation codon" and "termination codon" refer to a unit of three adjacent nucleotides (i.e., a codon) in a coding sequence that specifies initiation and chain termination, respectively, of protein synthesis (mRNA translation).

Patatin-like phospholipase A2α may also be known as PLA, pPLA, pPLAIIA pPLAIIα, PLA2alpha, or PLA2, or other similar variation. Patatin-like phospholipase AIIα is also referred to as MATRILINEAL (MATL). These terms are used interchangeably throughout. A MATRILINEAL gene comprising a four basepair frameshift mutation is referred to as matrilineal (matl).

As used herein, the terms "phenotype," "phenotypic trait" or "trait" refer to one or more traits of a plant or plant cell. The phenotype can be observable to the naked eye, or by any other means of evaluation known in the art, e.g., microscopy, biochemical analysis, or an electromechanical assay. In some cases, a phenotype is directly controlled by a single gene or genetic locus (i.e., corresponds to a "single gene trait"). In the case of haploid induction use of color markers, such as R Navajo, and other markers including transgenes visualized by the presences or absences of color within the seed evidence if the seed is an induced haploid seed. The use of R Navajo as a color marker and the use of transgenes is well known in the art as means to detect induction of haploid seed on the female plant. In other cases, a phenotype is the result of interactions among several genes, which in some embodiments also results from an interaction of the plant and/or plant cell with its environment.

As used herein, the term "plant" can refer to a whole plant, any part thereof, or a cell or tissue culture derived from a plant. Thus, the term "plant" can refer to any of: whole plants, plant components or organs (e.g., leaves, stems, roots, etc.), plant tissues, seeds and/or plant cells.

A plant cell is a cell of a plant, taken from a plant, or derived through culture from a cell taken from a plant. Thus, the term "plant cell" includes without limitation cells within seeds, suspension cultures, embryos, meristematic regions, callus tissue, leaves, shoots, gametophytes, sporophytes, pollen, and microspores. The phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, calli, and the like.

As used herein, the term "primer" refers to an oligonucleotide which is capable of annealing to a nucleic acid target (in some embodiments, annealing specifically to a nucleic acid target) allowing a DNA polymerase and/or reverse transcriptase to attach thereto, thereby serving as a point of initiation of DNA synthesis when placed under conditions in which synthesis of a primer extension product is induced (e.g., in the presence of nucleotides and an agent for polymerization such as DNA polymerase and at a suitable temperature and pH). In some embodiments, one or more pluralities of primers are employed to amplify plant nucleic acids (e.g., using the polymerase chain reaction; PCR).

As used herein, the term "probe" refers to a nucleic acid (e.g., a single stranded nucleic acid or a strand of a double stranded or higher order nucleic acid, or a subsequence thereof) that can form a hydrogen-bonded duplex with a complementary sequence in a target nucleic acid sequence. Typically, a probe is of sufficient length to form a stable and sequence-specific duplex molecule with its complement, and as such can be employed in some embodiments to detect a sequence of interest present in a plurality of nucleic acids.

As used herein, the terms "progeny" and "progeny plant" refer to a plant generated from vegetative or sexual reproduction from one or more parent plants. In gynogenesis-mediated haploid induction, the haploid embryo on the female parent comprises female chromosomes to the exclusion of male chromosomes—thus it is not a progeny of the male haploid-inducing line. The haploid corn seed typically still has normal triploid endosperm that contains the male genome. The edited haploid progeny and subsequent edited doubled haploid plants and subsequent seed is not the only desired progeny. There is also the seed from the haploid inducer line itself, often carrying the Cas9 transgene, and subsequent plant and seed progeny of the haploid inducing plant. Both the haploid seed and the haploid inducer (self-pollination-derived) seed can be progeny. A progeny plant can be obtained by cloning or selfing a single parent plant, or by crossing two or more parental plants. For instance, a progeny plant can be obtained by cloning or selfing of a parent plant or by crossing two parental plants and include selfings as well as the $F_1$ or $F_2$ or still further generations. An $F_1$ is a first-generation progeny produced from parents at least one of which is used for the first time as donor of a trait, while progeny of second generation ($F_2$) or subsequent generations ($F_3$, $F_4$, and the like) are specimens produced from selfings, intercrosses, backcrosses, and/or other crosses of $F_1$s, $F_2$s, and the like. An $F_1$ can thus be (and in some embodiments is) a hybrid resulting from a cross between two true breeding parents (i.e., parents that are true-breeding are each homozygous for a trait of interest or an allele thereof), while an $F_2$ can be (and in some embodiments is) a progeny resulting from self-pollination of the $F_1$ hybrids.

As used herein, the phrase "recombination" refers to an exchange of DNA fragments between two DNA molecules or chromatids of paired chromosomes (a "crossover") over in a region of similar or identical nucleotide sequences. A "recombination event" is herein understood to refer in some embodiments to a meiotic crossover.

As used herein, the term "reference sequence" refers to a defined nucleotide sequence used as a basis for nucleotide sequence comparison. In some embodiments, any of SEQ ID NOs: 2, 4, 8, 21, 23, 25, 29, 32, and 33 can serve as a reference sequence for comparing to other sequences obtained from plants.

As used herein, the term "regenerate," and grammatical variants thereof, refers to the production of a plant from tissue culture.

As used herein, the phrase "stringent hybridization conditions" refers to conditions under which a polynucleotide hybridizes to its target subsequence, typically in a complex mixture of nucleic acids, but to essentially no other sequences. Stringent conditions are sequence-dependent and can be different under different circumstances.

Longer sequences typically hybridize specifically at higher temperatures. An extensive guide to the hybridization of nucleic acids is found in Sambrook & Russell, 2001. Generally, stringent conditions are selected to be about 5-10° C. lower than the thermal melting point ($T_m$) for the specific sequence at a defined ionic strength pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Exemplary stringent conditions are those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides).

Stringent conditions can also be achieved with the addition of destabilizing agents such as formamide. Additional exemplary stringent hybridization conditions include 50% formamide, 5×SSC, and 1% SDS incubating at 42° C.; or SSC, 1% SDS, incubating at 65° C.; with one or more washes in 0.2×SSC and 0.1% SDS at 65° C. For PCR, a temperature of about 36° C. is typical for low stringency amplification, although annealing temperatures can vary between about 32° C. and 48° C. (or higher) depending on primer length. Additional guidelines for determining hybridization parameters are provided in numerous references (see e.g., Ausubel et al., 1999).

As used herein, the term "trait" refers to a phenotype of interest, a gene that contributes to a phenotype of interest, as well as a nucleic acid sequence associated with a gene that contributes to a phenotype of interest. For example, a "HI trait" refers to a haploid induction phenotype as well as a gene (e.g., matl in maize or Os03g27610 in rice) that contributes to a haploid induction and a nucleic acid sequence (e.g., a HI-associated gene product) that is associated with the presence or absence of the haploid induction phenotype.

As used herein, the term "transgene" refers to a nucleic acid molecule introduced into an organism or one or more of its ancestors by some form of artificial transfer technique. The artificial transfer technique thus creates a "transgenic organism" or a "transgenic cell." It is understood that the artificial transfer technique can occur in an ancestor organism (or a cell therein and/or that can develop into the ancestor organism) and yet any progeny individual that has the artificially transferred nucleic acid molecule or a fragment thereof is still considered transgenic even if one or more natural and/or assisted breedings result in the artificially transferred nucleic acid molecule being present in the progeny individual.

As used herein, the term "targeted mutagenesis" or "mutagenesis strategy" refers to any method of mutagenesis that results in the intentional mutagenesis of a chosen gene. Targeted mutagenesis includes the methods CRISPR, TILLING, TALEN, and other methods not yet discovered but which may be used to achieve the same outcome.

As used herein, haploid induction rate ("HIR") means the number of surviving haploid kernels over the total number of kernels after an ear is pollinated with haploid inducer pollen.

Particular problems plague that haploid induction: increased embryo abortion rates and increased fertilization failure rates (reduced seed set rates). For these reasons, there exists a need to successfully determine the cause of HI, and to use that knowledge to determine methods of stably or increasingly creating haploid plants while simultaneously reducing fertilization failure and embryo abortions.

It is specifically contemplated that one could mutagenize a promoter to potentially improve the utility of the elements for the expression of transgenes in plants. The mutagenesis of these elements can be carried out at random and the mutagenized promoter sequences screened for activity in a trial-by-error procedure. Alternatively, particular sequences which provide the promoter with desirable expression characteristics, or the promoter with expression enhancement activity, could be identified and these or similar sequences introduced into the promoter via mutation. It is further contemplated that one could mutagenize these sequences in order to enhance their expression of transgenes in a particular species. The means for mutagenizing a DNA segment encoding a promoter sequence of the current invention are well-known to those of skill in the art. As indicated, modifications to promoter or other regulatory element may be made by random, or site-specific mutagenesis procedures. The promoter and other regulatory element may be modified by altering their structure through the addition or deletion of one or more nucleotides from the sequence which encodes the corresponding unmodified sequences.

Mutagenesis may be performed in accordance with any of the techniques known in the art, such as, and not limited to, synthesizing an oligonucleotide having one or more mutations within the sequence of a particular regulatory sequence. In particular, site-specific mutagenesis is a technique useful in the preparation of promoter mutants, through specific mutagenesis of the underlying DNA. RNA-guided endonucleases ("RGEN," e.g., CRISPR/Cas9) may also be used. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered.

Where a clone comprising a promoter has been isolated in accordance with the instant invention, one may wish to delimit the essential promoter regions within the clone. One efficient, targeted means for preparing mutagenized promoters relies upon the identification of putative regulatory elements within the promoter sequence. This can be initiated by comparison with promoter sequences known to be expressed in similar tissue specific or developmentally unique patterns. Sequences which are shared among promoters with similar expression patterns are likely candidates for the binding of transcription factors and are thus likely elements which confer expression patterns. Confirmation of these putative regulatory elements can be achieved by deletion analysis of each putative regulatory sequence followed by functional analysis of each deletion construct by assay of a reporter gene which is functionally attached to each construct. As such, once a starting promoter sequence is provided, any of a number of different deletion mutants of the starting promoter could be readily prepared.

The invention disclosed herein provides polynucleotide molecules comprising regulatory element fragments that may be used in constructing novel chimeric regulatory elements. Novel combinations comprising fragments of these polynucleotide molecules and at least one other regulatory element or fragment can be constructed and tested in plants and are considered to be within the scope of this invention. Thus the design, construction, and use of chimeric regulatory elements is one embodiment of this invention. Promoters of the present invention include homologues of cis elements known to affect gene regulation that show homology with the promoter sequences of the present invention.

Functional equivalent fragments of one of the transcription regulating nucleic acids described herein comprise at least 50, 100, 150, 200, 250, 300, 350, 400, 450, 500, 550, 600, 650, 700, 750, 800, 850, 900, 950, or 1000 base pairs of a transcription regulating nucleic acid. Equivalent fragments of transcription regulating nucleic acids, which are obtained by deleting the region encoding the 5'-untranslated region of the mRNA, would then only provide the (untranscribed) promoter region. The 5'-untranslated region can be easily determined by methods known in the art (such as 5'-RACE analysis). Accordingly, some of the transcription regulating nucleic acids, described herein, are equivalent fragments of other sequences.

As indicated above, deletion mutants of the promoter of the invention also could be randomly prepared and then assayed. Following this strategy, a series of constructs are prepared, each containing a different portion of the promoter (a subclone), and these constructs are then screened for activity. A suitable means for screening for activity is to attach a deleted promoter or intron construct which contains a deleted segment to a selectable or screenable marker, and to isolate only those cells expressing the marker gene. In this way, a number of different, deleted promoter constructs are identified which still retain the desired, or even enhanced, activity. The smallest segment which is required for activity is thereby identified through comparison of the selected constructs. This segment may then be used for the construction of vectors for the expression of exogenous genes.

An expression cassette as described herein may comprise further regulatory elements. The term in this context is to be understood in the broad meaning comprising all sequences which may influence construction or function of the expression cassette. Regulatory elements may, for example, modify transcription and/or translation in prokaryotic or eukaryotic organisms. The expression cassette described herein may be downstream (in 3' direction) of the nucleic acid sequence to be expressed and optionally contain additional regulatory elements, such as transcriptional or translational enhancers. Each additional regulatory element may be operably liked to the nucleic acid sequence to be expressed (or the transcription regulating nucleotide sequence). Additional regulatory elements may comprise additional promoters, minimal promoters, promoter elements, or transposon elements which may modify or enhance the expression regulating properties. The expression cassette may also contain one or more introns, one or more exons and one or more terminators.

Furthermore, it is contemplated that promoters combining elements from more than one promoter may be useful. For example, U.S. Pat. No. 5,491,288 discloses combining a Cauliflower Mosaic Virus promoter with a histone promoter. Thus, the elements from the promoters disclosed herein may be combined with elements from other promoters. Promoters which are useful for plant transgene expression include those that are inducible, viral, synthetic, constitutive (Odell Nature 313: 810-812 (1985)), temporally regulated, spatially regulated, tissue specific, and spatial temporally regulated. Using the regulatory elements described herein, numerous agronomic genes can be expressed in transformed plants. More particularly, plants can be genetically engineered to express various phenotypes of agronomic interest.

DETAILED DESCRIPTION

One embodiment of the invention provides a method of editing plant genomic DNA, comprising: (i) obtaining a first plant, wherein the first plant is a haploid inducer line of the plant, and wherein said first plant is capable of expressing a DNA modification enzyme and optionally a guide nucleic acid; (ii) obtaining a second plant, wherein the second plant comprises the plant genomic DNA which is to be edited; (iii) pollinating the second plant with pollen from the first plant; and (iv) selecting at least one haploid progeny produced by the pollination of step (c) wherein the haploid progeny comprises the genome of the second plant but not the first plant, and the genome of the haploid progeny has been modified by the DNA modification enzyme and optional guide nucleic acid delivered by the first plant.

In one aspect of the method, the DNA modification enzyme is a site-directed nuclease selected from the group consisting of meganucleases (MNs), zinc-finger nucleases (ZFNs), transcription-activator like effector nucleases (TALENs), Cas9 nuclease, Cfp1 nuclease, dCas9-FokI, dCpf1-FokI, chimeric Cas9-cytidine deaminase, chimeric Cas9-adenine deaminase, chimeric FEN1-FokI, and Mega-TALs, a nickase Cas9 (nCas9), chimeric dCas9 non-FokI nuclease and dCpf1 non-FokI nuclease; and further wherein the guide nucleic acid is a guide RNA.

In another aspect of the method, the edited haploid progeny is treated with a chromosome doubling agent, thereby creating an edited doubled haploid progeny. For example, the chromosome doubling agent is colchicine, pronamide, dithipyr, trifluralin, or another known anti-microtubule agent.

In another aspect of the method, the first plant is a monocot or a dicot. For example, the first plant is a monocot selected from the group consisting of maize, wheat, rice, barley, oats, triticale, sorghum, pearl millet, teosinte, bamboo, sugar cane, asparagus, onion, and garlic. In another aspect, the second plant is a monocot or a dicot. For example the second plant is a monocot selected from the group consisting of maize, wheat, rice, barley, oats, triticale, sorghum, pearl millet, teosinte, bamboo, sugar cane, asparagus, onion, and garlic.

In another aspect of the method, the optional guide RNA is an 18-21 nucleotide sequence and is homologous to a sequence selected from the group consisting of SEQ ID NOs: 2, 4, 8, 21, 23, 25, 29, 32, and 33. In another aspect, the first plant expresses a marker gene. For example, the marker gene is selected from the group consisting of GUS, PMI, PAT, GFP, RFP, CFP, B1, C1, R-nj, anthocyanin pigments, and any other marker gene.

In another aspect of the method, the first plant is a maize plant selected and/or derived from the lines Stock 6, RWK, RWS, UH400, AX5707RS, NP2222-matl, or any of the several other known HI lines.

In one embodiment, the first plant and the second plant are different species. In one aspect, first plant is a wheat plant and the second plant is a maize plant. In another aspect, the first plant is a maize plant and the second plant is a wheat plant.

One object of the invention is a gene-edited plant produced by the method provided.

In another embodiment, the invention provides a method of editing plant genomic DNA, comprising: (i) obtaining a first plant, wherein said first plant is capable of expressing a DNA modification enzyme and optionally a guide nucleic acid; (ii) obtaining a second plant, wherein the second plant comprises the plant genomic DNA which is to be edited; (iii) pollinating the second plant with pollen from the first plant; (iv) applying a composition comprising a lipid or a phospholipase inhibitor immediately preceding, during, or following the pollination of step (iii); and (v) selecting at least one haploid progeny produced by the pollination of step (iii) wherein the haploid progeny comprises the genome of the second plant but not the first plant, and the genome of the haploid progeny has been modified by the DNA modification enzyme and optional guide nucleic acid delivered by the first plant. In one aspect, the composition comprises methyl alpha-linolenoyl fluorophosphonate (MALFP), linoleic acid ethyl ester (LLAEE), linoleic acid (LLA), corn oil, distearoyl-phosphatidyl choline (DSPC), methyl arachidonyl fluorophosphonate (MAFP), Palmityl trifluoromethylketone (PACOCF3), Arachidonyl trifluoromethylketone (AACOCF3), Manoalide, Linolenic acid ethyl ester (LNAEE), Linolenic acid ethyl ester (LNAEE), Oleic acid methyl ester (OAME), Oleic acid ethyl ester (OAEE), Palmitic acid ethyl ester (PAEE), Palmitoleic acid ethyl ester (PLAEE), Linseed oil, corn oil, alpha-Linolenic acid (aLNA), gamma-Linolenic acid (gLNA), Oleic acid, Arachidonic acid, Stearic Acid, 9(Z)-11(E)-conjugated Linoleic acid, or 2-oleoyl-1-palmitoyl-sn-glycero-3-phospho-ethanolamine.

In another embodiment, the invention provides a method of editing plant genomic DNA, comprising: (i) obtaining a first plant, wherein said first plant is capable of expressing a DNA modification enzyme and optionally a guide nucleic acid; (ii) obtaining a second plant, wherein the second plant comprises the plant genomic DNA which is to be edited; (iii) crossing the first plant with the second plant; and (iv) selecting at least one haploid progeny produced by the crossing of step (iii) wherein the haploid progeny comprises the genome of the second plant but not the first plant, and the genome of the haploid progeny has been modified by the DNA modification enzyme and optional guide nucleic acid delivered by the first plant. In one aspect, the first plant acts as the female parent in the cross of step (iii). In another aspect, the first plant comprises a mutation in a CENH3 gene, an ig1 gene, or another mutation conferring paternal-haploid inducing systems.

EXAMPLES

I. Producing New Haploid Inducer Lines Comprising the Editing Machinery.

We transformed a transformable line of maize called NP2222 with a TALEN construct, and separately transformed this line with a Cas9 and guide RNA construct. The TALEN construct (pBSC22808 (SEQ ID NO: 5), with TALENs targeting cleavage within target sequence, 5'-TCCAGGGTCAACGTGGAGACAGGGAGGTACGAACCGGTGACTGGCGAAGGAAGCA-3', SEQ ID NO: 6; TALEN recognition sequence underlined) and the Cas9 construct (pBSC23123 (SEQ ID NO: 7) with guide RNA sequence of xZmPLAIIA, 5'-GGGTCAACGTGGAGACAGGG-3', SEQ ID NO: 8) were designed to target mutations into the fourth exon of maize gene called MATRILINEAL (MATL; GRAMENE ID: GRMZM2G471240). This gene, when mutated at the target site by the TALEN or by the Cas9 and guide RNA, is knocked out, resulting in a loss of function of the protein product. We previously established that lines that are homozygous for loss of function mutations in MATL are haploid inducer lines, meaning that when they are used as pollen donors in crosses, they induce the formation of haploids on the resulting ears (see P.C.T. Patent Application No. PCT/US2016/62548, filed Nov. 17, 2016, incorporated herein by reference in its entirety).

We produced several events and self-pollinated them to make T1 seed. We grew up T1 individuals from event MZET152408A042A. We recovered five T1 progeny that retained two copies of the Cas9 and guide RNA editing machinery stably transformed, and were also homozygous mutant for the MATL gene. See Table 1.

TABLE 1

New HI lines comprising the genome editing machinery.

| New HI Line Individual ID | wt MATL Presence | Cas9 Presence | Mutation in MATL |
|---|---|---|---|
| USR01283349 | − | + | 13 bp deletion, homozygous |
| USR01283378 | − | + | 13 bp deletion, homozygous |
| USR01283388 | − | + | 8 bp deletion, homozygous |
| USR01283391 | − | + | 8 bp deletion, homozygous |
| USR01283398 | − | + | 13 bp deletion, homozygous |

The MATL mutations are detected using a TaqMan assay, which amplifies the wildtype copy of MATL (referred to herein as MATL or wt-MATL; these terms are used interchangeably throughout). When both copies of MATL are mutated, this assays reads negative (i.e., "−"). The Cas9 and guide RNA editing machinery were stably inserted via Construct 23123 (SEQ ID NO: 7). We sequenced the mutations in MATL via PCR and subcloning. Four colonies of each PCR product was sequenced, and all of the colonies for a given individual had the same sequence, indicating these plants are all homozygous mutant for the MATL allele (also referred to herein as matl when referencing the 4 basepair insertion in MATRILINEAL found in Stock6 and other Stock6-derived lines, or μMATL when referencing any other human-induced mutation in MATRILINEAL;). There were two plants that had 8 bp deletions, and three plants that had 13 bp deletions.

II. Using the New HI Lines as Male Parents and Progeny Analysis.

We crossed the above new HI plants as male pollen donors to a female tester line, which contained a recessive color marker but were wild type for the MATL gene. The male haploid inducer line is homozygous wild type for the same color marker. This female line was thus a non-haploid inducer and were homozygous wild-type for the MATL gene but homozygous mutant for the color marker. We recovered seeds from the crosses, and germinated seedlings therefrom.

Progeny seedlings were subjected to several assays. Progeny seedlings were scored as diploids if they do not exhibit the color marker (because the recessive marker is complemented by the male inducer DNA). Progeny seedlings were scored as putative haploids if they do exhibit the color marker because the recessive marker is not complemented. Of the 2656 seeds planted, we used the color assay and identified 90 seedlings as putative haploids.

We further analyzed the 90 putative haploids for presence of the wildtype MATL gene using a Taqman marker assay. Of these, 82 were positive for MATL, meaning they were not edited by the editing machinery provided by the male parent. The remaining 8 putative haploid seedlings were negative for wildtype MATL using the Taqman marker, indicating that they may have been edited by the editing machinery provided by the male parent.

We performed ploidy analysis via Flow Cytometry on these 8 putative, edited haploid seedlings using leaf tissue in a ploidy analyzer. See FIGS. 1-8. We found that four of them were true haploids, while the others were actually diploids. As we discuss below, we ran PCR and sequenced the mutations in the MATL gene in these four true haploids as well as for plant USR01350337-2 which, according to the MATL Taqman assay, was not edited by the genome editing machinery.

The finding that there were four diploids among the 90 putative haploids was not unexpected—the seedling assay is not perfect and there are occasional false positives. We tested the 90 haploids for the presence of the Cas9 construct (Construct 23123), and found it was missing in 86 out of 90, including the four true haploids above. In contrast, the four edited diploids that we found during the ploidy analysis all had the Cas9 construct present, confirming their status as hybrid diploids that were falsely identified by the haploid seedling assay as being haploids.

We then used the leaf tissue to isolate genomic DNA and ran a PCR reaction to sequence the MATL gene in those four true haploid, putative edited individuals, specifically focusing on the sequence flanking the guide RNA target mutagenesis site. This was to determine the nature of the edits that may or may not have occurred there. We sub-cloned the PCR fragment using commercially-available TOPO Blunt IV kit, and sequenced at least four colonies each (forward and reverse sequencing). See Table 2, below, for comparisons of the edited alleles and the reference wt-MATL allele.

TABLE 2

Comparing the Edited Alleles against wt-MATL.

| Individual ID | Allele Type | Sequence (corresponds to 1126-1166 of SEQ ID NO: 19) | SEQ ID NO: |
|---|---|---|---|
| NP2222 | wt-MATL | AGGGTCAACGTGGA GACAGGGAGGTACG AACCGGTGACTGG | 9 |
| Stock6 | mat1 | AGGGTCAACGTGGA GACAGGCGAGGAGG TACGAACCGGTGAC TGG | 10 |
| USR01350333-3 Allele 1 | edited | AGGGTCAACGTGGA GACAAGGGAGGTAC GAACCGGTGACTGG | 11 |
| USR01350333-3 Allele 2 | PCR contamination | AGGGTCAACGTGGA :::::::::::::G AACCGGTGACTGG | 12 |
| USR01350344-2 Allele 1 | edited | AGGGTCAACGTGGA GAC:GGGAGGTACG AACCGGTGACTGG | 13 |
| USR01350344-2 Allele 2 | PCR contamination | AGGGTCAACGTGGA :::::::::::::G AACCGGTGACTGG | 14 |
| USR01350343-1 Allele 1 | edited | AGGGTCAACGTGGA GACAAGGGAGGTAC GAACCGGTGACTGG | 15 |
| USR01350328-1 Allele 1 | edited | AGGGTCAACGTGGA GAC:GGGAGGTACG AACCGGTGACTGG | 16 |
| USR01350337-2 Allele 1 | not edited | AGGGTCAACGTGGA GACAGGGAGGTACG AACCGGTGACTGG | 17 |
| USR01350337-2 Allele 2 | PCR contamination | AGGGTCAACGTGGA :::::::::::::G AACCGGTGACTGG | 18 |

Individual USR01350333-3 produced an edited MATL allele with an insertion of alanine at basepair 1143 of the cDNA sequence (underlined in Table 2). This would be sufficient to cause a frameshift in the coding sequence, which would produce a premature STOP codon. What we previously thought was Edited Allele #2 of USR01350333-3 (a 13 basepair deletion of GACAAGGGAGGTAC) was actually the result of PCR contamination. After resequencing, we confirmed that this plant only has one edited allele, and it was found in 6 out of 6 colonies.

This alleles is novel in that it is not in either the male or the female parent plant of this individual. The male parent ID for this individual was USR01283391, and that plant was found to be homozygous for an 8 bp deletion.

Individual USR01350344-2 provides a deletion of A (a deletion of basepair 1143 of the wild type cDNA sequence). This mutation would be sufficient to cause a frame-shift in the coding sequence, and produce a premature STOP codon. After resequencing and discovering the PCR contamination, we confirmed this was found in 6 out of 6 colonies. Previously identified as Edited Allele #2 of USR01350344-2, this was identified as PCR contamination.

Individual USR01350343-1 provides an insertion of A at basepair 1143 of the cDNA sequence. This would be sufficient to cause a frame-shift in the coding sequence, and produce a premature STOP codon. This was found in 4 out of 4 colonies.

Individual USR01350328-1 provides a deletion of A (a deletion of basepair 1143 from the wild type cDNA sequence). This mutation would be sufficient to cause a frame-shift in the coding sequence, and produce a premature STOP codon. It was found in 4 out of 4 colonies.

Individual USR01350337-2 had no change: its sequence was 100% identical to that of wt-MATL.

In summary, we found that 4 out of 86 confirmed haploids had mutations in the MATL gene. We have confirmed that these plants are haploids and do not contain any Cas9 DNA. It is clear that the Cas9 transgene has been eliminated along with the rest of the male-derived DNA during embryogenesis, and that edits have occurred to the female (egg cell-derived) genome in the process of embryogenesis.

We know that the edits are novel and occurred in the female genome in the process of embryogenesis because the haploid inducer line typically makes maternal haploids and we have confirmed that these are indeed haploids. One might try to argue that there is a chance that these are actually paternal haploids, and that the edits we are seeing are actually edits that were already present in the paternal DNA. However, we can prove that this is not the case. First, the mutations do not match those of the paternal parent. This can clearly be seen in Table 3 and 4 (shown below). The edited haploid plant USR01350343-1 was homozygous for an insertion of a single nucleotide (an "A"), but the male parent plant had a deletion of 13 nucleotides. Similarly, plant USR01350328-1 was homozygous for a deletion of an A, but the male parent had a deletion of 13 nucleotides. These examples, taken together, prove that during the haploid induction process, it is possible to have editing of the maternal genome occur, resulting in the formation of edited maternal haploids. According to these and based on the assay detecting MATL presence and the confirmation via ploidy analysis, and using the Cas9 transgene on the male side under control of the maize ubiquitin promoter, the rate of editing during the haploid induction process is about 4/86, or 4.65%.

Furthermore, the rate of editing during haploid induction may be very different when using different haploid inducer lines or using wide crosses. It appears that both haploid induction in maize using MATL mutant lines and wide crosses in barley, wheat, or other crops all work via similar mechanisms: fertilization is followed by genome elimination. It also appears that the time period between fertilization and genome elimination is long enough for the editing machinery to edit the target gene in the genome of the line to which the inducer line has been hybridized (the target germplasm). It is noted that the choice of promoter driving expression of the stably transformed editing proteins system may have a large impact on the rate of editing in haploids. We used a constitutive sugarcane promoter (prSoUbi4) but other promoters driving high or specific expression in the embryo sac, the egg cell, in the pollen, or in sperm cells might be more effective, particularly in the case of wide crosses, in which the male DNA is eliminated in a much more robust and rapid fashion than in intraspecific haploid inducer systems like the maize haploid inducer system or CENH3 type haploid inducer systems. In other words, during a wide cross, for instance when crossing maize pollen on to wheat ears, which is done in order to induce wheat maternal haploids, it might work best to have the editing machinery in the maize pollen driven by a promoter that has strong pollen or sperm cell expression, perhaps in addition to zygote expression, so that abundant editing machinery (RNA and protein) is delivered and present in the zygote cell and during the subsequent two, four, or eight cell embryo stage, even if the male DNA is eliminated or lost very quickly.

TABLE 3

Haploid Progeny Produced

| Individual Progeny ID code | wt MATL Presence | Ploidy Analysis | Cas9 Presence | Allele 1 |
|---|---|---|---|---|
| USR01350333-3 | – | Haploid | – | insertion of A |
| USR01350344-2 | – | Haploid | – | deletion of A |
| USR01350343-1 | – | Haploid | – | insertion of an A |
| USR01350328-1 | – | Haploid | – | deletion of A |
| USR01350337-2 | + | Haploid | – | no mutation |
| USR01350334-3 | – | Diploid | + | |
| USR01350333-10 | – | Diploid | + | |
| USR01350341-1 | – | Diploid | + | |
| USR01350321-3 | – | Diploid | + | |

TABLE 4

Male Parent Information and Their Progeny

| Male Parent ID | wt MATL Presence | Sequencing (# colonies) | Cas9 Presence | Progeny ID |
|---|---|---|---|---|
| USR01283391 | – | deletion of 8 nt (4) | + | USR01350333-3 and USR01350333-10 |
| USR01283349 | – | deletion of 13 nt (4) | + | USR01350344-2, USR01350328-1 and USR01350321-3 |
| USR01283378 | – | deletion of 13 nt (4) | + | USR01350343-1 and USR01350341-1 |
| USR01283398 | – | deletion of 13 nt (4) | + | USR01350337-2 |
| USR01283388 | – | deletion of 8 nt (4) | + | USR01350334-3 |

III. Simultaneous Haploid Induction and Editing in Elite Maize Inbred Lines.

A transformable haploid inducer line, NP2222-HI, RWK, RWS, or UH400 or Stock6 or any other haploid inducer line, all of which already have the mutant versions of MATL, is stably transformed with construct expressing genome modification system such as Cas9+ guide RNA (Cong, L. et al. 2013. Multiplex genome engineering using CRISPR/Cas systems. *Science* 339, 819-823), dCas9-FokI+ guide RNA (Tsai, S. Q. et al. 2014, Dimeric CRISPR RNA-guided FokI nucleases for highly specific genome editing. *Nature Biotechnol.* 32, 569-576), TALEN (Li et al., 2012, High-efficiency TALEN-based gene editing produces disease-resistant rice. Nature Biotech. 30, 390-392), engineered meganuclease (Gao et al., 2010, Heritable targeted mutagenesis in maize using a designed endonuclease. *Plant Journal.* 61:176-187), zinc finger nuclease (Shukla et al. 2009. Precise genome modification in the crop species *Zea mays* using zinc-finger nucleases. Nature 459, 437-441), dCas9-cytidine deaminase (Komor et al. 2016, Programmable editing of a target base in genomic DNA without double-stranded DNA cleavage. Nature doi:10.1038/nature17946) or any other genome modification system. The transgenic haploid inducer line also expressing the editing machinery is then used as pollen donor to create mutations and haploids in target lines via outcrossing. Haploid embryos or seeds are then recovered, identified as haploids, and tested for the edits at the target site (whatever target site is chosen by virtue of the TALEN construct design or the Cas9 guide RNA design). Haploids containing the desired edits is chromosomally doubled using standard procedures using standard means such as colchicine, trifluralin or other chromosome doubling agent. Identification of the induced haploids can be simplified by using a color marker as is typically done in corn doubled haploid production—this color marker can display in the resulting embryos, seeds, seedlings, or adult plant. Presence of mutations at the target site can be checked by sequence analysis (DNA sequencing), by marker analysis, or by phenotype. Because there is only one copy of the DNA to mutate in haploid plants, recessive phenotypes should display so that could be another way to identify the haploids that were edited.

A. Mutagenesis of VLHP Targets in Elite Maize Inbred Line with Transgenic Editing Locus Generated Directly in a Haploid Inducer Line.

VLHP1 and VLHP2 are homeodomain-leucine zipper I-class homeobox genes and members of a class of proteins that is unique to plants. The HD domain is involved in DNA binding whereas the Zip domain is involved in protein homo- and hetero-dimerization. HD-Zip I proteins are generally involved in responses related to abiotic stress, abscisic acid (ABA), blue light, de-etiolation and embryogenesis (Elhiti and Stasolla, 2009. Structure and function of homodomain-leucine zipper (HD-Zip) proteins. *Plant Signal Behav.* 4: 86-88). VLHP1 and VLHP2 are in the same gene family as Grassy Tillersl (GT1). GT1 promotes lateral bud dormancy and suppresses elongation of lateral ear branches in maize.

Figure 9:
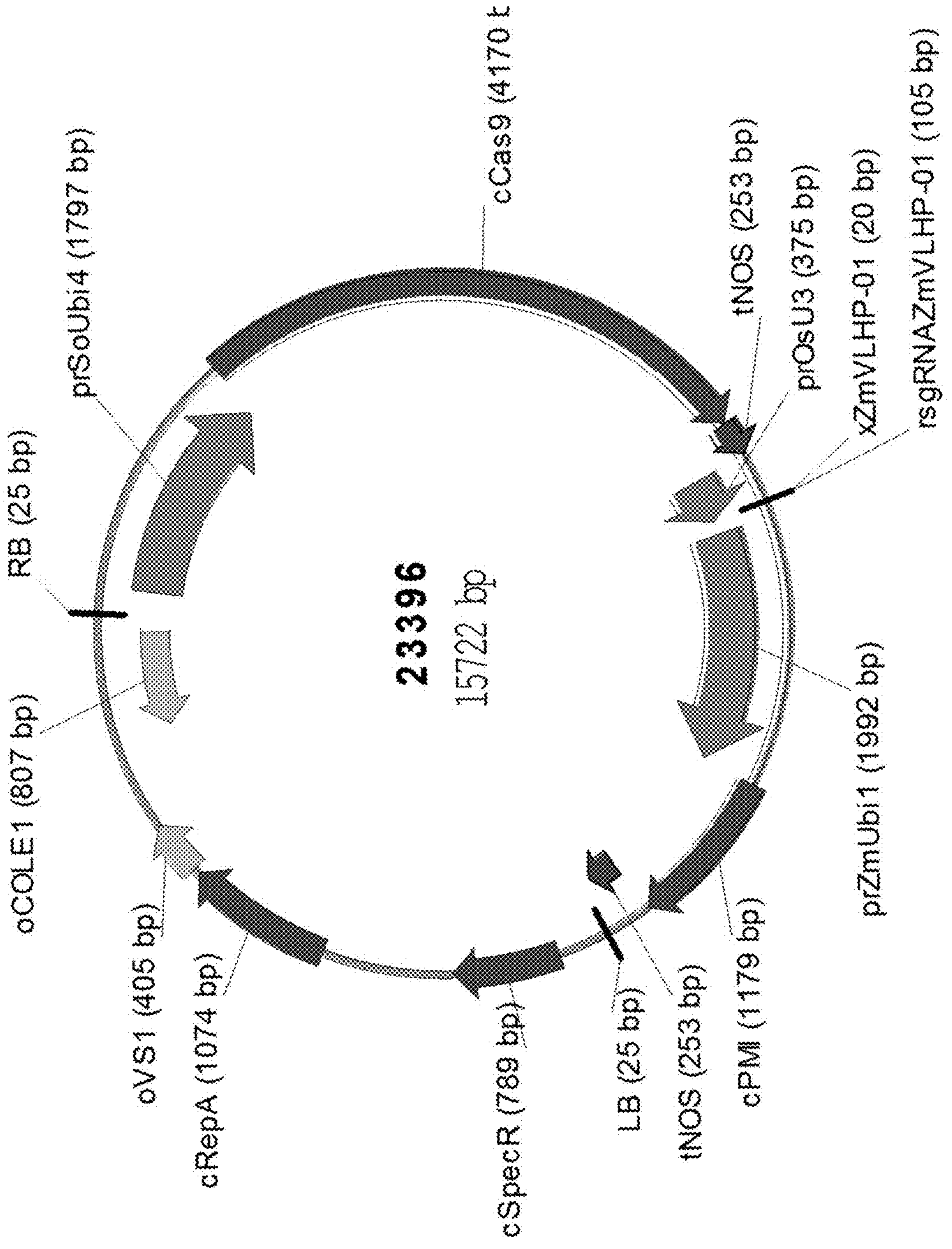
FIG. 9 is a schematic drawing of vector 23396 (SEQ ID NO: 1) used for *Agrobacterium*-mediated transformation of maize immature embryos to generate targeted mutations in ZmVLHP1 genes. xZmVLHP-01: guide RNA (gRNA) sequence (5'-GCAGGAGGCGTCGAGCAGCG-3', SEQ ID NO: 2); rsgRNAZmVLHP-01: single guide RNA (sgRNA) comprising of gRNA, tracRNA and PolIII termination sequences. cPMI: PMI selectable marker gene; cCas9: Cas9 nuclease gene; RB: T-DNA right border; LB: T-DNA left border; tNOS: Nopaline synthetase terminator. cSpec: Spectinomycin resistance gene.

In this example, vector 23396 (SEQ ID NO: 1; see also FIG. 9) for expressing Cas9 and single guide RNA (sgRNA) was made to target maize VLHP1 (GRMZM2G104204) and its homolog VLHP2 (GRMZM2G062244) genes. Vector 23396 expresses a sgRNA with 20-nucleotide targeting sequence xZmVLHP-01 (5'-GCAGGAGGCGTCGAGCAGCG-3', SEQ ID NO: 2). xZmVLHP-01 targets both VLHP1 and VLHP2 genes at the second exon. Vector 23396 was introduced into a transformable haploid inducer line NP2222-HI using *Agrobacterium*-mediated transformation with mannose selection. NP2222-HI was derived from crossing of transformable maize inbred line NP2222 with Stock 6 derivative line RWKS to introgress the haploid induction (HI) locus. NP2222-HI has an average haploid induction rate of about 9.2%.

NP2222-HI transformants from vector 23396 were assayed for modification of genomic VLHP target sequences (5'-GCAGGAGGCGTCGAGCA/GCG-3'; SEQ ID NO: 2). The slash ("/") represents the Cas9 cleavage position. Target locus editing activity was determined using quantitative PCR Taqman method as described before (WO2016106121, incorporated herein by reference). Transgenic lines with high target site modification activities—i.e., both VLHP1 and VLHP2 genes were modified, and preferably containing single copy transgene—were selected for further studies and used for crossing or progeny production.

Pollen from T0 transformants of 23396 is used directly to pollinate ears of elite inbred line ID5829 or other maize lines including sweet corn lines to induce production of haploid embryos. Alternatively, T0 transformants of 23396 in NP2222-HI background are selfed to produce progeny lines carrying homozygous transgene and pollen from the progeny plants are used to pollinate other corn lines to induce haploid embryo formation. The induced haploid embryos are extracted from kernels and placed on embryo rescue media for direct germination or allowed to mature to form seeds. Tissues from the induced haploid embryos and the resulting plants are assayed to determine if editing has occurred in the VLHP target sequences. If the induced haploid embryos or plants contain desired mutations, chromosome doubling treatment is applied to produce doubled haploid lines from them. For example, using embryo rescue method, embryos are extracted from elite line ID5829 ears pollinated with transgenic haploid inducer line carrying 23396 editing locus at 18-22 days after pollination ("DAP," extraction between 10-25 DAP is theoretically possible). DNA is isolated from germinated haploid seedlings and used for assay. Colchicine treatment is applied to seedling for chromosome doubling. Alternatively, chromosome doubling agent can be applied to the isolated embryos during germination. DNA is extracted from germinated seedlings and used for determining that mutation has occurred at the xZmVLHP-01 target sequence.

Alternate methods are available. One could allow the seed to mature and select haploids later by another phenotype. One could let the seed dry down and at a later date germinate the seeds to determine haploids without a marker (e.g., using plant size rather than a gene conferring a color marker), at which point one would test for edits and apply chromosome doubling agents where appropriate. This method may have its advantages in that embryo screening and/or rescue is avoided.

B. Mutagenesis of GW2 Targets in Elite Maize Inbred Line with Transgenic Editing Locus Introduced Directly in a Haploid Inducer Line.

A mutation in DA2, an E3-ubiquitin ligase gene, in rice resulted in larger seeds (Song et al., 2007). Rice DA2 has 2 maize homologs, GW2-1 (GRMZM2G170088) and GW2-2 (GRMZM2G007288). The maize genes are 94% identical at the protein level and 90% identical at the DNA level. GRMZM2G170088 has a large 177 bp insert (59 aa) in comparison with GRMZM2G007288.

Figure 10:
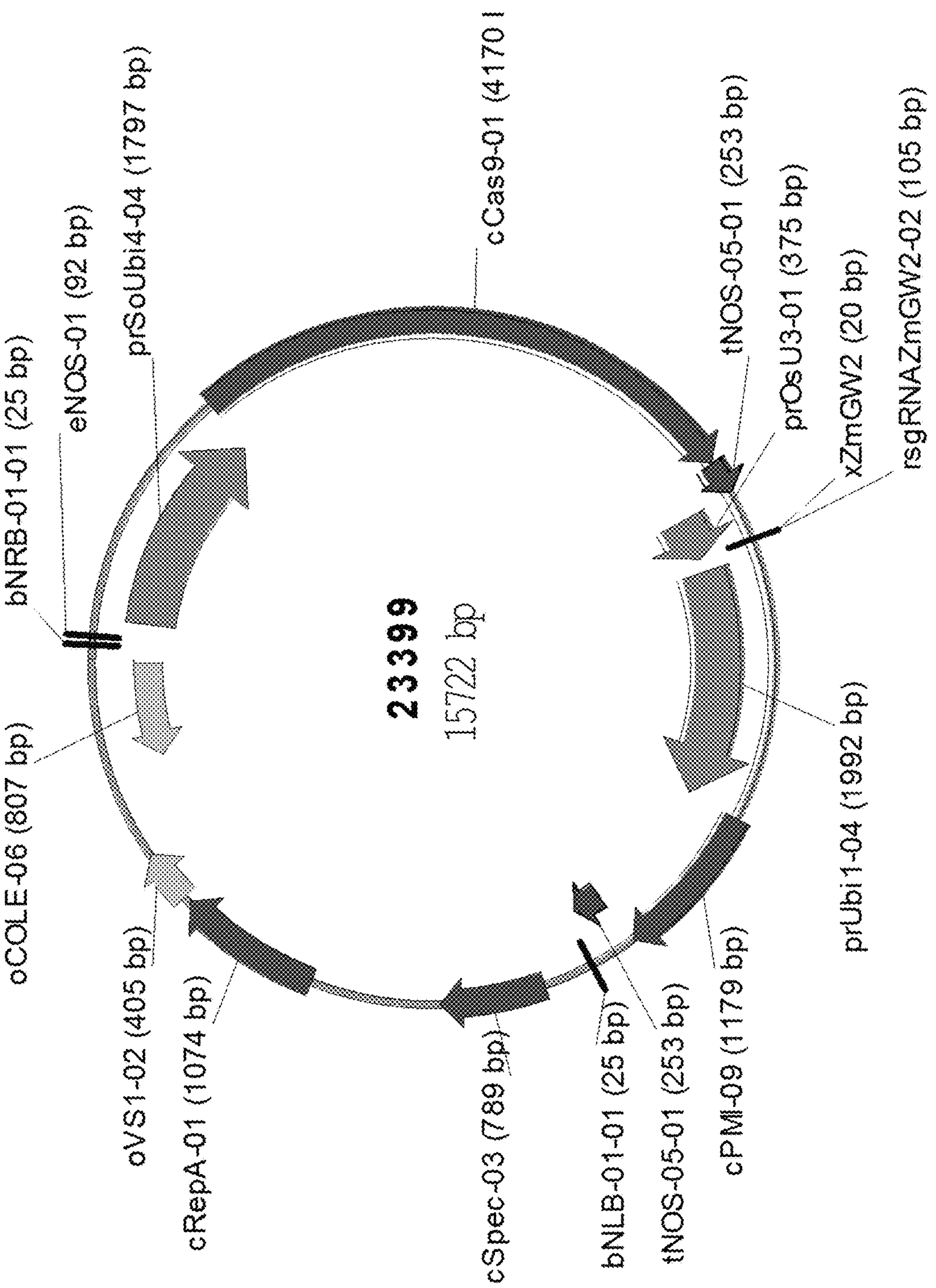
FIG. 10 is a schematic drawing of vector 23399 (SEQ ID NO: 3) used for *Agrobacterium*-mediated transformation of maize immature embryos to generate targeted mutations in ZmGW2 genes. xZmGW2-02: guide RNA (gRNA) sequence (5'-AAGCTCGCGCCCTGCTACCC-3', SEQ ID NO: 4); rsgRNAZmGW2-02: single guide RNA (sgRNA) comprising of gRNA, tracrRNA and PolIII termination sequences. cPMI-09: PMI selectable marker gene; cCas9-01: Cas9 nuclease gene; RB: T-DNA right border; LB: T-DNA left border; tNOS: Nopaline synthetase terminator. cSpec: Spectinomycin resistance gene.

In this example, vector 23399 (SEQ ID NO: 3, see also FIG. 10) was made for expression of Cas9 and sgRNA to target both maize GW2-1 (GRMZM2G170088) and its homolog GW2-2 (GRMZM2G007288) genes. Both GW2-1 and GW2-2 genes contain target sequence xZmGW2-02 (5'-AAGCTCGCGCCCTGCTACCC-3', SEQ ID NO: 4) in exon 1 and this sequence was used to design sgRNA expressed from vector 23399. Binary vector 23399 expresses single guide RNA (sgRNA) with 20-nucleotide targeting sequence xZmGW2-02 fused to single guide RNA scaffold comprising of both crRNA and tracrRNA. Vector 23399 was introduced into a transformable haploid inducer line NP2222-HI using *Agrobacterium*-mediated transformation with mannose selection. NP2222-HI was derived from crossing of transformable maize inbred line NP2222 with Stock 6 derivative line RWKS to introgress the haploid induction (HI) locus.

NP2222-HI transformants of vector 23399 were assayed for modification of genomic GW2-2 target sequences (5'-AAGCTCGCGCCCTGCTA/CCC-3', SEQ ID NO: 4; the slash ("/") indicates the Cas9 cleavage position). Target sequence editing activity was determined using quantitative PCR Taqman method as described before (WO2016106121). Transgenic lines with high target site modification activities—i.e. both GW2-1 and GW2-2 genes were modified, and preferably containing single copy transgene—were selected for further studies and used for crossing or progeny production.

Pollen from T0 transformants of 23399 is used directly to pollinate ears of elite inbred line ID5829 or other maize line including sweet corn lines to induce production of haploid embryos. Alternatively, T0 transformants of 23399 in NP2222-HI background are selfed to produce progeny lines carrying homozygous transgene and pollen from the progeny plants are used to pollinate other corn lines to induce haploid embryo formation. The induced haploid embryos are extracted from kernels and placed on embryo rescue media for direct germination or allowed to mature to form seeds. Tissues from the induced haploid embryos and the resulting plants are assayed to determine if editing has occurred in the maize GW2 target sequences. If the induced haploid embryos or plants contain desired mutations, chromosome doubling treatment is applied to produce doubled haploid lines from them. For example, using embryo rescue method, embryos are extracted from elite line ID5829 ears pollinated with transgenic haploid inducer line carrying 23396 editing locus at 18-22 days after pollination. DNA is isolated from germinated haploid seedlings and used for assay. Colchicine treatment is applied to seedling for chromosome doubling. Alternatively, chromosome doubling agent can be applied to the isolated embryos during germination. DNA is extracted from germinated seedlings and used for determining if mutation has occurred at the xZmGW2-02 target sequence. Alternately, one could allow the seed to mature and select haploids later by another phenotype. One could even let the seed dry down and at a later date germinate the seeds to determine haploids without a marker (e.g., using plant size rather than a gene conferring a color marker), at which point one would test for edits and apply chromosome doubling agents where appropriate. This method may have its advantages in that embryo screening and/or rescue is avoided.

IV. Simultaneous Haploid Induction and Editing in Corn, Rice, Sunflower, or any Other Crop Via Chemical-Based Haploid Induction Any line of corn, rice, wheat, tomato, sunflower, barley, or any other crop is transformable with the editing construct (Cas9 plus guide RNAs designed to mutate a particular target site) and then optionally make the editing construct either heterozygous or homozygous (via self-pollination of the transformed event), and then using lipid or oil applications during outcrossing (pollination onto target lines) in order to induce de novo haploids and simultaneously edit the target sites in the target genomes. These lipid applications have the ability to induce haploids when applied to pollen, silks, flowers, or tassels of any plant—regardless of male parent. In particular, the male parent is not required to have any mutations in the MATL gene (i.e., it can be homozygous wild type for the MATRILINEAL gene). These lipid applications induce haploids de novo, without any genetic requirement on behalf of either parent. See P.C.T. Patent Application No. PCT/US2016/62548, incorporated herein by reference in its entirety. The mechanism of de novo haploid induction via lipid spray apparently works the same way as it does in matl mutant (genetic haploid inducer) lines: via chromosome elimination post-fertilization. Haploid progeny are isolated and checked for the induced mutations (caused via the editing process) and then doubled to make edited, doubled haploid plants.

V. Mutagenesis of Target Sequences in Elite Field Corn and Sweet Corn Inbred Lines with Transgenic Editing Locus Introgressed into a Haploid Inducer Line.

Transgenic locus expressing genome editing machinery can also be generated in conventional transformable maize line without haploid inducing activity such as A188, Hi-II or NP2222 and then introgressed into haploid inducer line such as NP2222-HI, RWK, RWKS, RWS, or UH400 or Stock6 or any other haploid inducer line.

In this example, maize inbred line NP2222 is transformed with VLHP Cas9-sgRNA vectors (23396 and 23397) and GW2 Cas9-sgRNA vectors (23398 and 23399). Vectors 23396 and 23399 have been described in previous examples (Example IIIA and Example IIIB). Vector 23397 (SEQ ID NO: 20) is identical to 23396 except the gRNA-coding sequence xZmVLHP-01 (5'-GCAGGAGGCGTCGAGCAGCG-3', SEQ ID NO: 2) is replaced with xZmVLHP-02 (5'-GCTGGAGCTGAGCTTCCGGG-3', SEQ ID NO: 21). Vector 23398 (SEQ ID NO: 23) is identical to 23399 except the gRNA-coding sequence xZmGW2-02 (5'-AAGCTCGCGCCCTGCTACCC-3', SEQ ID NO: 4) in 23399 is replaced by xZmGW2-01 (5'-GAGCGGTTCACGCGGCCGCA-3', SEQ ID NO: 23). These vectors were introduced into *Agrobacterium* strain LBA4404 (pVGW7). The resulting *Agrobacterium* strain containing vector 23396, 23397, 23398, or 23399 was used to transform immature embryos of transformable elite inbred line NP2222. Calli were induced from infected immature embryos and selected on mannose media to recover transgenic calli. Transgenic calli were placed on regeneration and rooting media to recover transgenic plants expressing the CRISPR-Cas9 editing machinery. Transgenic plants were assayed for transgene copy number and moved to greenhouse for seed production.

Single copy transformants of vector 23396 (MZET154902A004A, MZET154902B006A), 23397 (MZET154903B009A, MZET154903B012A), 23398 (MZET154904B005A, MZET154904B014A) and 23399 (MZET154905A002A, MZET154905A010A) were identified and backcrossed with non-transgenic NP2222. Ears of transgenic progeny plants containing T-DNA insert of each of the above vectors were pollinated with pollen of haploid inducer line RWKS to produce F1 progeny. F1 progeny containing transgenic locus and haploid induction locus were identified by genotyping assays and self-pollinated to produce F2 progeny seeds. F2 progeny seeds were planted and seedling plants assayed to identify plants homozygous for transgenic Cas9-sgRNA locus (assay #2540) and haploid induction locus (assay #2827) with qPCR Taqman assays.

Lines homozygous for the haploid induction locus and preferably homozygous transgenic 23396, 23397, 23398, and 23399 Cas9-sgRNA editing locus were used to pollinate ears from target elite field corn line ID5829 and sweet corn lines (SWC726 or SWC412F) for haploid induction. Induced haploid embryos were isolated from pollinated ID5829, SWC412F, SWC726 ears and geminated on embryo rescue media. Alternatively, pollinated ears were allowed to mature and kernels with haploid embryos were germinated. Leaf samples were collected and analyzed with Taqman assay to identify plants containing mutations in VLHP and GW2 genes but absence of genetic components from induction line such as transgenic Cas9-sgRNA or other non-transgenic marker gene sequences. Identified haploid plants with targeted GW2 or VLHP gene mutations were treated with colchicine for chromosome doubling to recover doubled haploid plants for seed production. Alternatively, extracted haploid embryos can be treated with chromosome doubling agent such as colchicine and the resulting plants are analyzed for ploidy level and presence of targeted mutations in GW2 or VLHP genes. Plants with targeted GW2 and VLHP gene mutations are grown to maturity for seed production and further progeny evaluation.

For example, edited haploid lines (JSER82A056 and JSER82A063) were identified from crosses between sweet corn line SWC412F ears pollinated with haploid inducer containing 23399 Cas9-sgRNA transgene. Line JSER82A056 has both GW2-01 and GW2-02 target genes mutated, whereas line JSER82A063 only has GW2-02 gene mutated (See Table 5). Neither of these lines contain Cas9 transgene (assay #2540 for Cas9 or #1750 for PMI selectable marker gene) or haploid inducer gene (assay #2827) as the male genome has been eliminated from the haploids.

Figure 11:
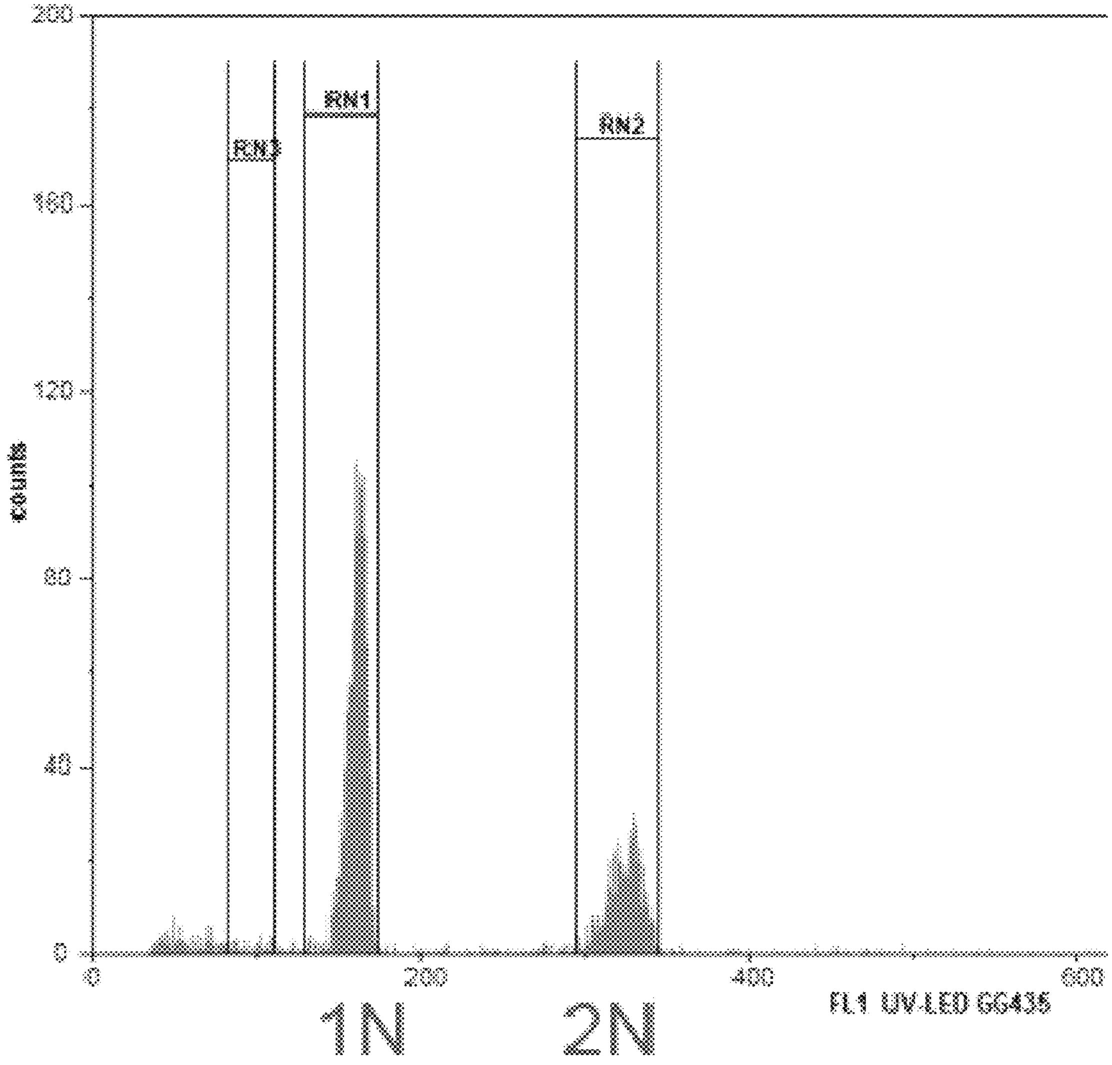
FIG. 11 shows ploidy assay of edited haploid sweet corn line JSER82A056 and FIG. 12 shows the same for edited haploid sweet corn line JSER82A063. These lines were obtained through crossing with RWKS haploid induction line carrying transgene locus of CRISPR-Cas9 expression vector 23399.
Figure 12:
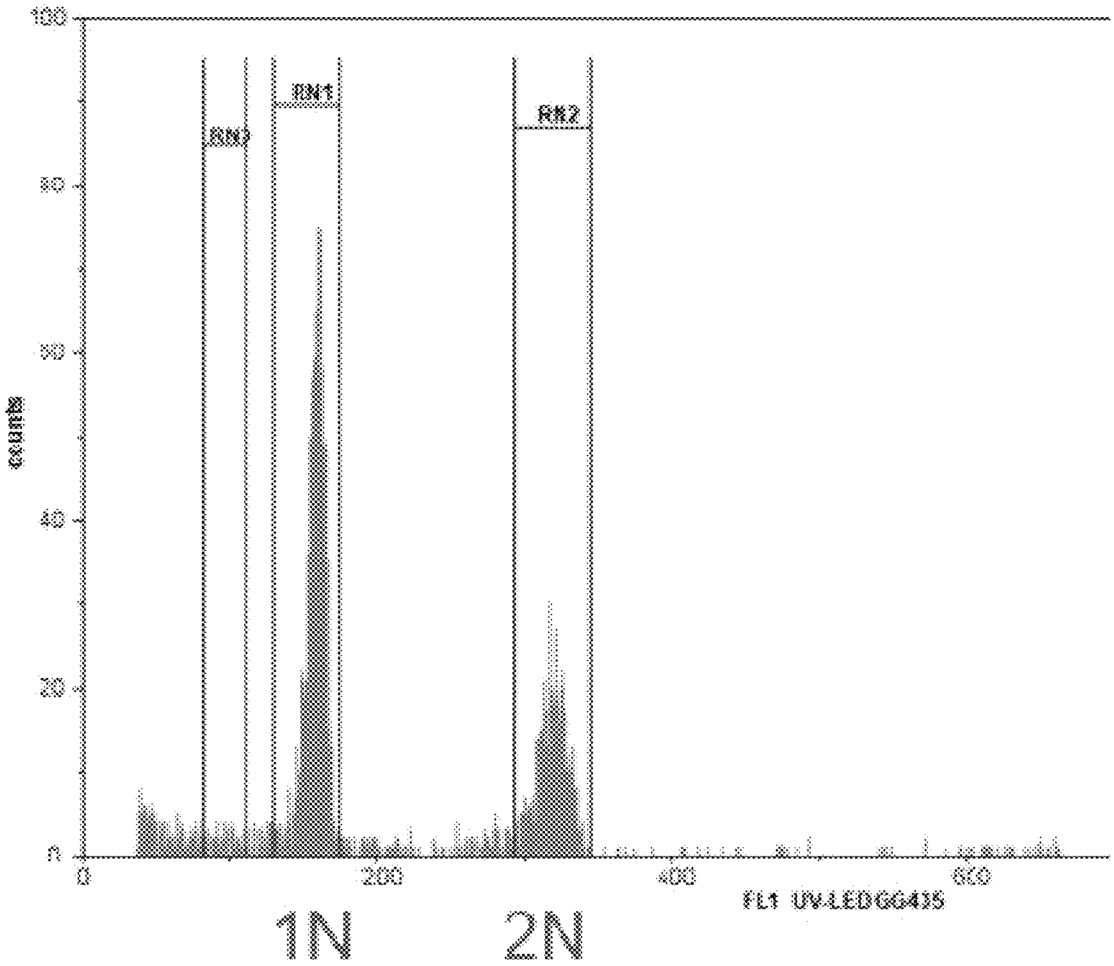

Ploidy level analysis confirmed that both lines are haploids (FIGS. 11 and 12). Note that wildtype ("WY") genes in the haploids have a copy number of "2" and mutant will be "0" since the copy call is relative to the endogenous ADH gene copy number. Therefore, haploid lines carrying WT unedited GW2-01 or GW2-02 genes will have a copy call of "2." WT haploid inducer locus will have copy call of "2" for assay #2826 and "0" for assay #2827 (haploid inducer variant). If a corn plant line is a diploid between sweet corn and transgenic inducer, it will be heterozygous for the haploid inducer gene and thus have copy call of "1" for both assay #2826 and assay #2827.

Similar to examples above in introducing transgenic editing locus into Stock6 induction line, transgenic editing locus can be introduced into these lines used for wide crosses to induce haploid induction and targeted sequence mutation. Transgenic lines expressing editing machinery can be generated in any line of corn, wheat, barley, rye, pearl millet, rice, brassica, lettuce, tomato, or any other crop by direct transformation or out-crossing. Preferably the transgenic locus is made homozygous and then the line is used as pollen donor in a wide cross with other compatible recipient crops to induce haploids to produce desired edits. The process of post-fertilization genome elimination in wide crosses is basically the same as the process in the maize MATL mutant system, although in some cases the foreign pollen-derived DNA and editing machinery may be eliminated slightly earlier in embryo development, which is why this method is preferably practiced using a promoter that drives expression of the editing machinery in the pollen, sperm cells, and/or zygote cell, so that the editing RNA and protein is present and able to edit the target genome even though the male DNA is eliminated rather quickly after fertilization.

TABLE 5

Progeny zygosity analysis from crosses. Taqman analysis results showing the lines do not contain transgene or haploid inducer locus from pollen donor, but have edits in GW2-01 and/or GW2-02 targets.

| | | Allele: | | | | | |
|---|---|---|---|---|---|---|---|
| | | cCas9-01 | cPMI-09 | CRISPR target in GW2-01 (23399) | CRISPR target in GW2-02 (23399) | pPLAIIa WT allele | RWK (Haploid Inducer) allele of pPLAIIa |
| | | Assay ID: | | | | | |
| Plant ID | Construct ID | 2540 Copy# level | 1750 Copy# level | 3065 Copy# level | 3095 Copy# level | 2826 Copy# level | 2827 Copy# level |
| 1-copy control | | + | 1 | ND | ND | 1 | 1 |
| wild type control | | 0 | 0 | 2 | 2 | 2 | 0 |
| JSER82A056 | 23399 | 0 | 0 | 0 | 0 | 2 | 0 |
| JSER82A063 | 23399 | 0 | 0 | 1 or 2 | 0 | 2 | 0 |
| JSER85A021 | 23399 | 0 | 0 | 0 | >2 | 2 | 0 |
| JSER85A022 | 23399 | 0 | 0 | 0 | >2 | 2 | 0 |
| JSER85A024 | 23399 | 0 | 0 | 0 | >2 | 2 | 0 |
| JSER85A027 | 23399 | 0 | 0 | 0 | >2 | 2 | 0 |
| JSER85A037 | 23399 | 0 | 0 | 0 | >2 | 2 | 0 |
| JSER85A039 | 23399 | 0 | 0 | 0 | >2 | 2 | 0 |
| JSER85A044 | 23399 | 0 | 0 | 0 | >2 | 2 | 0 |
| JSER85A055 | 23399 | 0 | 0 | 0 | >2 | 2 | 0 |

Figure 13:
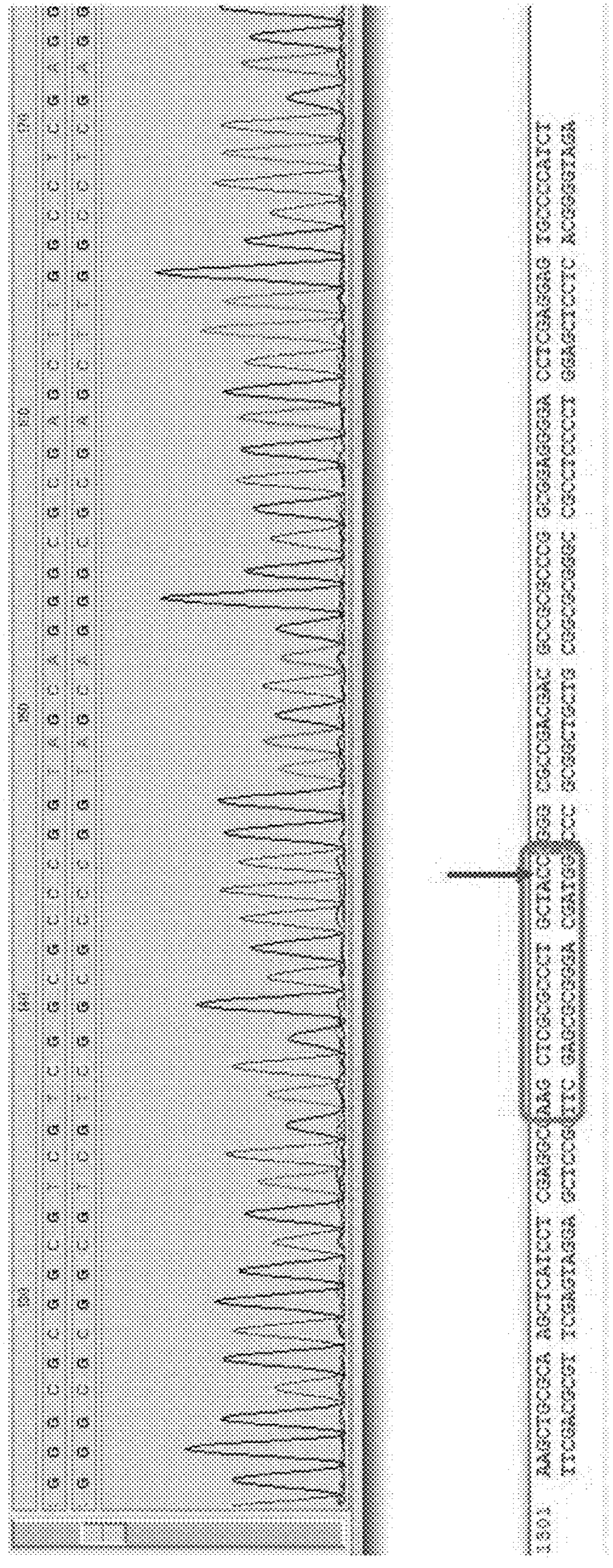
FIG. 13 shows sequencing confirmation of GW2-02 target site editing in haploid sweet corn line JSER82A063. A single base C next to the predicted Cas9 cleavage site was deleted. The sequence presented within the box is identical to SEQ ID NO: 4. The top-line sequence presented at the bottom of the figure is represented by SEQ ID NO: 99. The bottom-line sequence is represented by SEQ ID NO: 100 and is the reverse complement of SEQ ID NO: 99.

To further confirm target-specific editing in these haploid lines, GW2-02 target region was amplified from JSER82A063 by PCR and the PCR product was sequenced. A single base C was deleted in JSER82A063 in comparison with the WT sequence precisely at the Cas9 cleavage site (FIG. 13). These results clearly demonstrated that editing machinery brought into the egg cell from the male gametophyte can edit the female genome before the male genome is eliminated after double fertilization to form haploid embryo. Candidate edited haploid lines without transgene were treated with injection of 0.125% colchicine in 0.5% DMSO or seedling drenching in 0.06% colchicine solution (Eder and Chalyk, 2002, In vivo haploid induction in maize. Theor. Appl. Genetics 104:703-708). Treated lines were planted in soil and grown in greenhouse for progeny seed production.

VI. Simultaneous Haploid Induction and Editing in Wheat and Other Monocots Via Wide Cross.

Haploid induction is also achieved using interspecific or intergeneric wide crosses (Kasha and Kao, 1970, High frequency haploid production in barley (*Hordeum vulgare* L.). Nature 225:874-886). For example, wheat haploids can be obtained by pollination with various intergeneric crosses with maize (Suenaga and Nakajima 1989), pearl millet (Inagaki and Mujeeb-Kazi 1995), teosinte (Ushiyama et al. 1991), *H. bulbosum* (Barclay 1975), and sorghum (Ohkawa et al. 1992). Barley haploids are obtained by pollination with *Hordeum bulbosum* pollen. Tobacco haploids can be obtained by crossing with *N. africana* pollen. Many other examples exist in other crops.

To demonstrate feasibility of simultaneous haploid induction and editing via wide crosses, maize transgenic lines expressing Cas9 and sgRNA targeting wheat VLHP gene sequences were generated. Vector 23763 (SEQ ID NO: 24) contains expression cassettes for Cas9 and sgRNA containing protospacer sequence xTaVLHP1 (5'-GACGAGCAGGCGCAGTTCC-3', SEQ ID NO: 25) for guiding Cas9-mediated cleavage of TaVLHP1 target sites in wheat. The wheat genome has three xTaVLHP1 targets in total (TaVLHP1-4A, TaVLHP1-4B and TaVLHP1-4D), with each one in its three sub-genomes. The guide sequence in 23397 (SEQ ID NO: 20), xZmVLHP (5'-GCTGGAGCTGAGCTTCCGGG-3', SEQ ID NO: 21) will also direct cleavage of wheat VLHP target sequences, xTaVLHP2-1A (5'-GCTGGAGCTGAGCTTCCGGG-3', SEQ ID NO: 26) or xTaVLHP2-1B (5'-TCTGGAGCTGAGCTTCCGGG-3', SEQ ID NO: 27). There are three VLHP2A genes containing xTaVLHP2-1A and 3 VLHP2B genes containing xTaVLHP2-1B sequences in the Chinese Spring wheat genome. Vectors 23397 and 23763 were transformed into maize inbred line NP2222 using *Agrobacterium*-mediated transformation to generate transgenic lines expressing Cas9 and sgRNA. Transgenic maize lines were grown in greenhouse and selfed to produce T1 plants.

Pollen collected from transgenic maize T0 or progeny T1 plants carrying T-DNA of vector 23397 or 23763 were used to pollinate emasculated spring wheat line AC-Nanda. At one to two days before anthesis, wheat florets were emasculated and two days later are pollinated with fresh maize pollen carrying the editing machinery. For convenience, spikelets from a Syngenta elite cytoplasmic male sterile ("CMS") wheat line (16A300292) were also directly used as female donors to induce haploid embryo formation with transgenic maize pollen expressing 23397 or 23763 Cas9-sgRNA. Embryos were extracted from pollinated florets at 14-20 days after pollination for embryo rescue to recover haploid plantlets from the wheat×maize haploid induction system. Excised embryos were cultured on either full strength MS (Murashige and Skoog 1962) or ½ MS or B5 basal medium containing various modifications of organic supplements and grown in vitro for 3-5 weeks at 20-25° C. and 16-hour day length.

Figure 14:
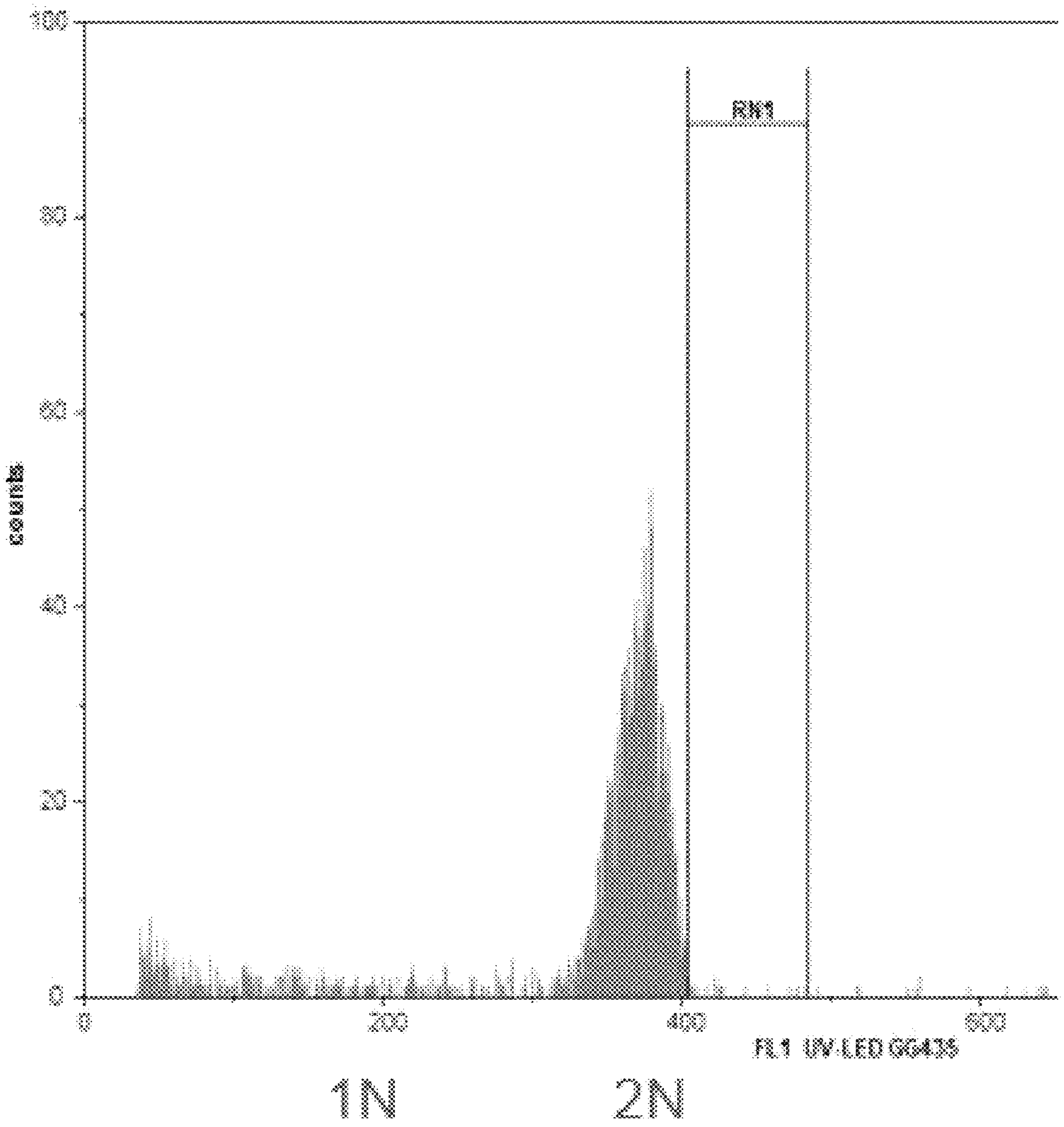
FIG. 14 shows ploidy analysis of wild type control.
Figure 15:
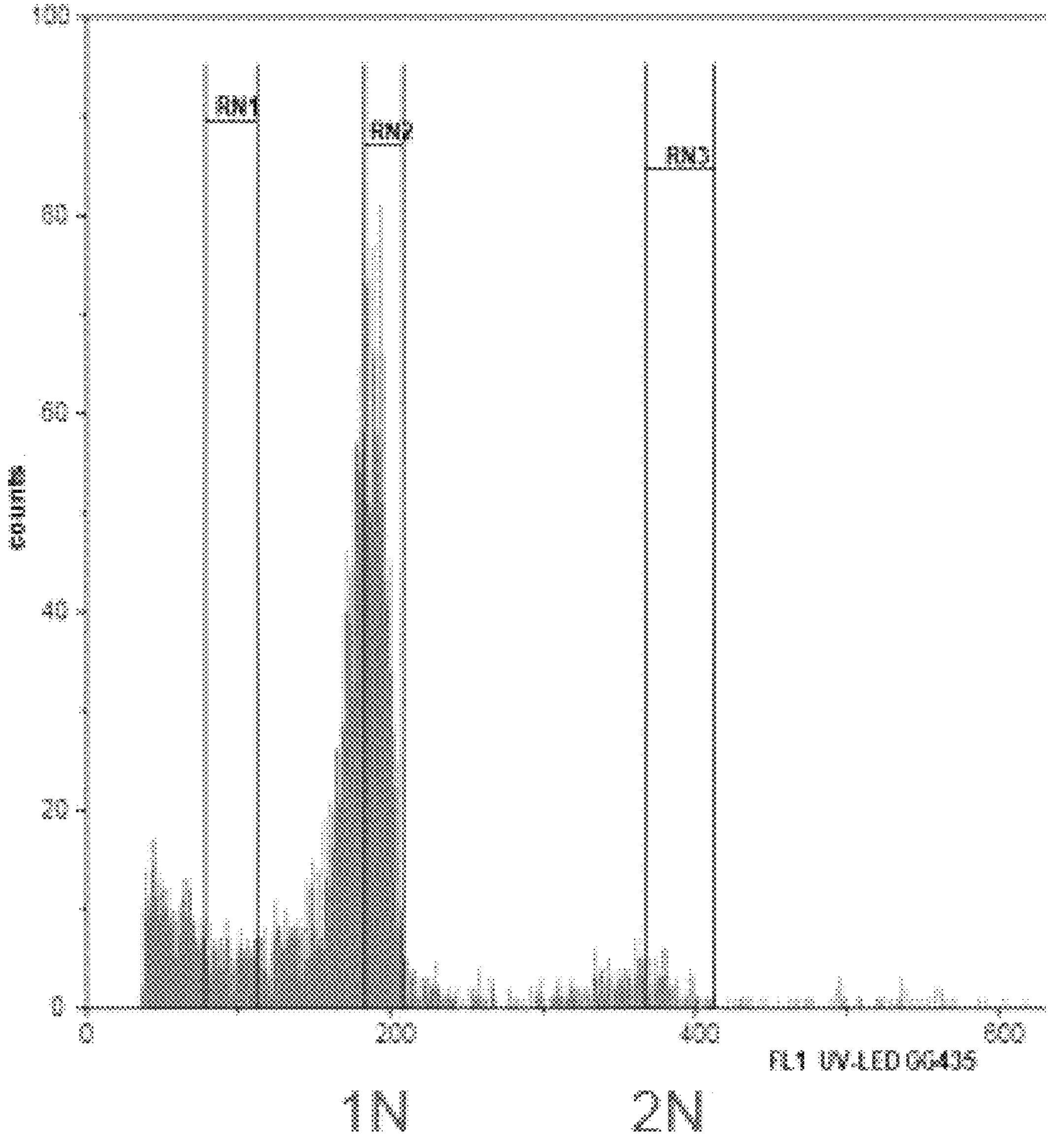
FIG. 15 shows ploidy analysis of edited haploid wheat line JSWER30A22.

For example, pollen of T1 progeny from transgenic maize line MZET164902A044A containing vector 23763 was used to pollinate spikes of CMS line 16A300292 to induce wheat haploids. Haploid embryos were rescued and the resulting wheat haploid seedling were sampled for qPCR analysis to determine the copy number of VLHP target sequences (See Table 6). One of the haploid lines (JSWER30A22) was found to contain mutation in TaVLHP1-4B gene, but not in its orthologs TaVLHP1-4A and TaVLHP1-4D in the A and D sub-genomes. Ploidy level analysis confirmed that JSWER30A22 is a true haploid (See FIGS. 14 and 15). The mutation within the TaVLHP1-4B target region was further characterized by sequencing and was found to contain 97 bp deletion starting from the predicted Cas9 cleavage site (FIG. 16). We also identified another line JSW16A07 with "0" copy in TaVLHP1-4A gene (assay #3252), suggesting targeted editing in the target sequence. However, the deletion in this target gene is probably quite large in deleting the primer binding site(s) since we were not able to recover PCR product for sequencing. Haploid seedlings with an edited target site were transplanted to soil after 3-5 weeks in vitro culture. The transplanted seedlings were hardened for one week in a growth chamber under the same environmental regime. Colchicine was added after shoots had formed. However, the chromosome doubling treatment can be done earlier at embryo rescue in vitro culture stage or later after transplanting. When whole wheat seedlings are treated for doubling, roots of the haploid seedling are trimmed leaving a zone of 2-3 cm and then submerged in a 0.1% colchicine solution with 2% dimethyl sulfoxide (DMSO) and ca. 0.05% Tween-20 at 20° C. for 5 hours. After this treatment, the roots are washed to remove residual colchicine and potted in peat soil. Plant tissue samples can be removed from haploid seedlings for mutation detection to identify plants containing mutations in TaVLHP target gene sequences but with the maize chromosomes including sequences encoding the transgenic editing machinery completely eliminated. Since JSWER30A22 is from a CMS line, the plant is pollinated with a restorer to produce progeny seeds.

TABLE 6

Taqman analysis for wheat progeny from wide crosses. Line JSW30A22 is edited.

| | | Allele: | | | | |
|---|---|---|---|---|---|---|
| | | TAV_4A | TAV_4B | TAV_4D Assay ID: | PMI | CAS9 |
| Plant ID | Construct ID | 3252 Copy# level | 3253 Copy# level | 3254 Copy# level | 1750 Copy# level | 2540 Copy# level |
| WT, AC-Nanda | N/A | >2 | 2 | >2 | 0 | 0 |
| WT, AC-Nanda | N/A | 2 | 2 | 2 | 0 | 0 |
| WT, CMS | N/A | 2 | 2 | 2 | 0 | 0 |
| WT, CMS | N/A | 2 | 2 | 2 | 0 | 0 |
| JSW29A01 | 23763 | 2 | 2 | 2 | 0 | 0 |
| JSW29A02 | 23763 | 2 | 2 | 2 | 0 | 0 |
| JSW29A03 | 23763 | 2 | 2 | 2 | 0 | 0 |
| JSW29A04 | 23763 | 2 | 2 | 2 | 0 | 0 |
| JSW29A05 | 23763 | 1 or 2 | 2 | 2 | 0 | 0 |
| JSW29A06 | 23763 | 2 | 2 | 2 | 0 | 0 |
| JSW29A07 | 23763 | 2 | 2 | 2 | 0 | 0 |
| JSW29A08 | 23763 | 2 | 2 | 2 | 0 | 0 |
| JSW29A09 | 23763 | 2 | 2 | 2 | 0 | 0 |
| JSW29A10 | 23763 | 2 | 2 | 2 | 0 | 0 |
| JSW29A11 | 23763 | 2 | 2 | 2 | 0 | 0 |
| JSW29A12 | 23763 | 2 | 2 | 2 | 0 | 0 |
| JSW29A13 | 23763 | 2 | 2 | 2 | 0 | 0 |
| JSW29A14 | 23763 | 2 | 2 | 2 | 0 | 0 |
| JSW29A15 | 23763 | 2 | 2 | 2 | 0 | 0 |
| JSW29A16 | 23763 | 2 | 2 | 2 | 0 | 0 |
| JSW30A01 | 23763 | 2 | 2 | 2 | 0 | 0 |
| JSW30A02 | 23763 | 2 | 1 or 2 | 2 | 0 | 0 |
| JSW30A03 | 23763 | 2 | 2 | 2 | 0 | 0 |
| JSW30A04 | 23763 | 2 | 2 | 2 | 0 | 0 |
| JSW30A05 | 23763 | 2 | 2 | 2 | 0 | 0 |
| JSW30A06 | 23763 | 2 | 2 | 2 | 0 | 0 |
| JSW30A07 | 23763 | 2 | 2 | 2 | 0 | 0 |
| JSW30A08 | 23763 | 2 | 2 | 2 | 0 | 0 |
| JSW30A09 | 23763 | 2 | 2 | 2 | 0 | 0 |
| JSW30A10 | 23763 | 2 | 2 | 2 | 0 | 0 |
| JSW30A11 | 23763 | 2 | 2 | 2 | 0 | 0 |
| JSW30A12 | 23763 | 2 | 2 | 2 | 0 | 0 |

TABLE 6-continued

Taqman analysis for wheat progeny from wide crosses. Line JSW30A22 is edited.

| | | Allele: | | | | |
|---|---|---|---|---|---|---|
| | | TAV_4A | TAV_4B | TAV_4D Assay ID: | PMI | CAS9 |
| Plant ID | Construct ID | 3252 Copy# level | 3253 Copy# level | 3254 Copy# level | 1750 Copy# level | 2540 Copy# level |
| JSW30A13 | 23763 | 2 | 2 | 2 | 0 | 0 |
| JSW30A14 | 23763 | 2 | 2 | 2 | 0 | 0 |
| JSW30A15 | 23763 | 2 | 2 | 2 | 0 | 0 |
| JSW30A16 | 23763 | 2 | 2 | 2 | 0 | 0 |
| JSW30A17 | 23763 | 2 | 2 | 2 | 0 | 0 |
| JSW30A18 | 23763 | 2 | 2 | 2 | 0 | 0 |
| JSW30A19 | 23763 | >2 | 2 | 2 | 0 | 0 |
| JSW30A20 | 23763 | 2 | 2 | 2 | 0 | 0 |
| JSW30A21 | 23763 | 2 | 2 | 2 | 0 | 0 |
| JSW30A22 | 23763 | 2 | 0 | 2 | 0 | 0 |
| JSW30A23 | 23763 | 2 | 2 | 1 or 2 | 0 | 0 |
| JSW30A24 | 23763 | 2 | 2 | 2 | 0 | 0 |
| JSW30A25 | 23763 | 2 | 2 | 2 | 0 | 0 |
| JSW30A26 | 23763 | 2 | 2 | 2 | 0 | 0 |
| JSW30A27 | 23763 | 2 | 2 | 2 | 0 | 0 |
| JSW30A28 | 23763 | 2 | 2 | 2 | 0 | 0 |
| JSW30A29 | 23763 | 2 | 2 | 2 | 0 | 0 |
| JSW30A30 | 23763 | 2 | 1 or 2 | 1 or 2 | 0 | 0 |
| JSW30A31 | 23763 | 2 | 2 | 2 | 0 | 0 |

To further demonstrate feasibility of simultaneous haploid induction and editing via wide crosses, maize transgenic lines expressing Cas9 from five promoters that have high and/or specific expression in pollen, along with sgRNA targeting wheat VLHP gene sequences, were generated. These five vectors were 24038 (SEQ ID NO: 34), 24039 (SEQ ID NO: 35), 24079 (SEQ ID NO: 36), 24091 (SEQ ID NO: 37), and 24094 (SEQ ID NO: 38). All five of these vectors utilized the same sgRNA containing protospacer sequence xTaVLHP2 (5'-GCTGGAGCTGAGCTTC-CGGG-3', SEQ ID NO: 21) for guiding Cas9-mediated cleavage of TaVLHP2 target sites in wheat. The wheat genome has three xTaVLHP2 targets in total (TaVLHP2-2A, TaVLHP2-2B and TaVLHP2-2D), with each one in its three sub-genomes. The guide sequence in these five constructs also directs cleavage of wheat VLHP target sequences, xTaVLHP2 (5'-GCTGGAGCTGAGCTTCCGGG-3', SEQ ID NO: 26) or xTaVLHP3 (5'-TCTGGAGCTGAGCTTC-CGGG-3', SEQ ID NO: 27). There are three TaVLHP2 genes containing xTaVLHP2 and 3 TaVLHP3 genes containing xTaVLHP2-1B sequences in the Chinese Spring wheat genome.

Vector 24038 (SEQ ID NO: 34) contains expression cassettes for Cas9 under control of a pollen-preferred high expression promoter prZmGRMZM5G876285 and terminator tZmGRMZM5G876285 from the maize prf3 (profilin homolog3) gene, which has an extremely high native expression at the RNA and protein level in pollen and which has evidence of high sperm cell expression.

Vector 24039 (SEQ ID NO: 35) contains expression cassettes for Cas9 under control of a pollen-preferred high expression promoter prZmGRMZM2G020852 and terminator tZmGRMZM2G020852 from the maize EXPB2 (BETA EXPANSIN2) gene, which has an extremely high native expression at the RNA and protein level in pollen and which has evidence of sperm cell expression.

Vector 24079 (SEQ ID NO: 36) contains expression cassettes for Cas9 under control of a pollen-preferred high expression promoter prZmGRMZM2G146551 and terminator tZmGRMZM2G146551 from the maize EXPB1 (BETA EXPANSIN1) gene, which has an extremely high native expression at the RNA and protein level in pollen and which has evidence of sperm cell expression.

Vector 24091 (SEQ ID NO: 37) contains expression cassettes for Cas9 under control of a pollen-preferred promoter prZmGRMZM2G471240 and terminator tZmGMRMZM2G471240 from the maize MATL (MATRILINEAL) gene, which shows evidence of pollen and possibly sperm cell expression at the RNA and protein level.

Vector 24094 (SEQ ID NO: 38) contains expression cassettes for Cas9 under control of a pollen-preferred promoter prZmGRMZM2G471240 and terminator tZmGMRMZM2G471240 from the maize MATL (MATRILINEAL) gene, which shows evidence of pollen and possibly sperm cell expression at the RNA and protein level. This construct additionally has an N-terminal fusion of AmCyan fluorescent protein on the Cas9 molecule for imaging and visualization of the Cas9 localization in pollen.

These five vectors (24038, 24039, 24079, 24091, and 24094) were transformed into maize inbred line NP2222 using *Agrobacterium*-mediated transformation to generate transgenic lines expressing Cas9 and sgRNA.

Figure 17:
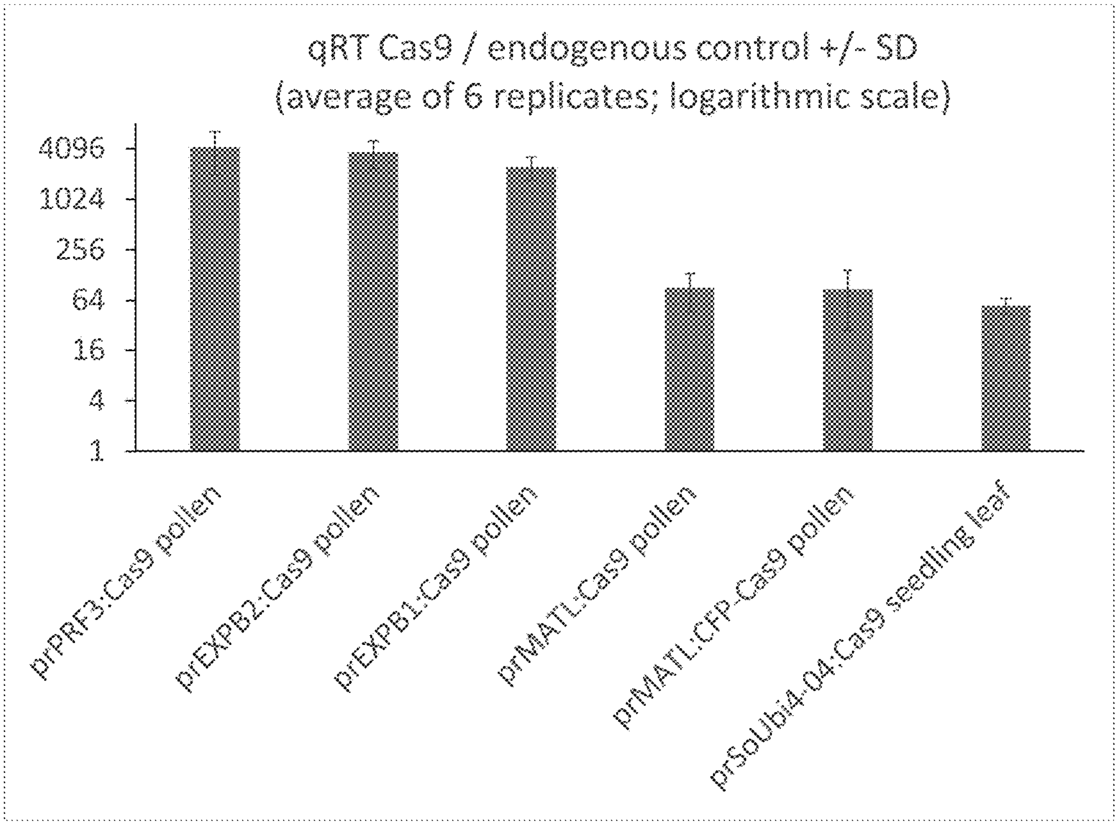
FIG. 17 shows pollen expression as measured by pollen collected from transgenic maize T0 plants carrying T-DNA of vector 24038, 24039, 24079, 24091, and 24094, which were used to pollinate emasculated spring wheat line AC-Nanda. The expression was high in the pollen, averaging about 100 fold higher in plants carrying T-DNA vectors 24038, 24039, and 24079 compared to the sugar cane ubiquitin promoter used in many of the corn and wheat examples. The expression was also higher in pollen from plants containing vactors 24038, 24039, and 24079 when compared to the pollen carrying the MATRILINEAL promoter constructs (24094 and 24091).
Figure 18:
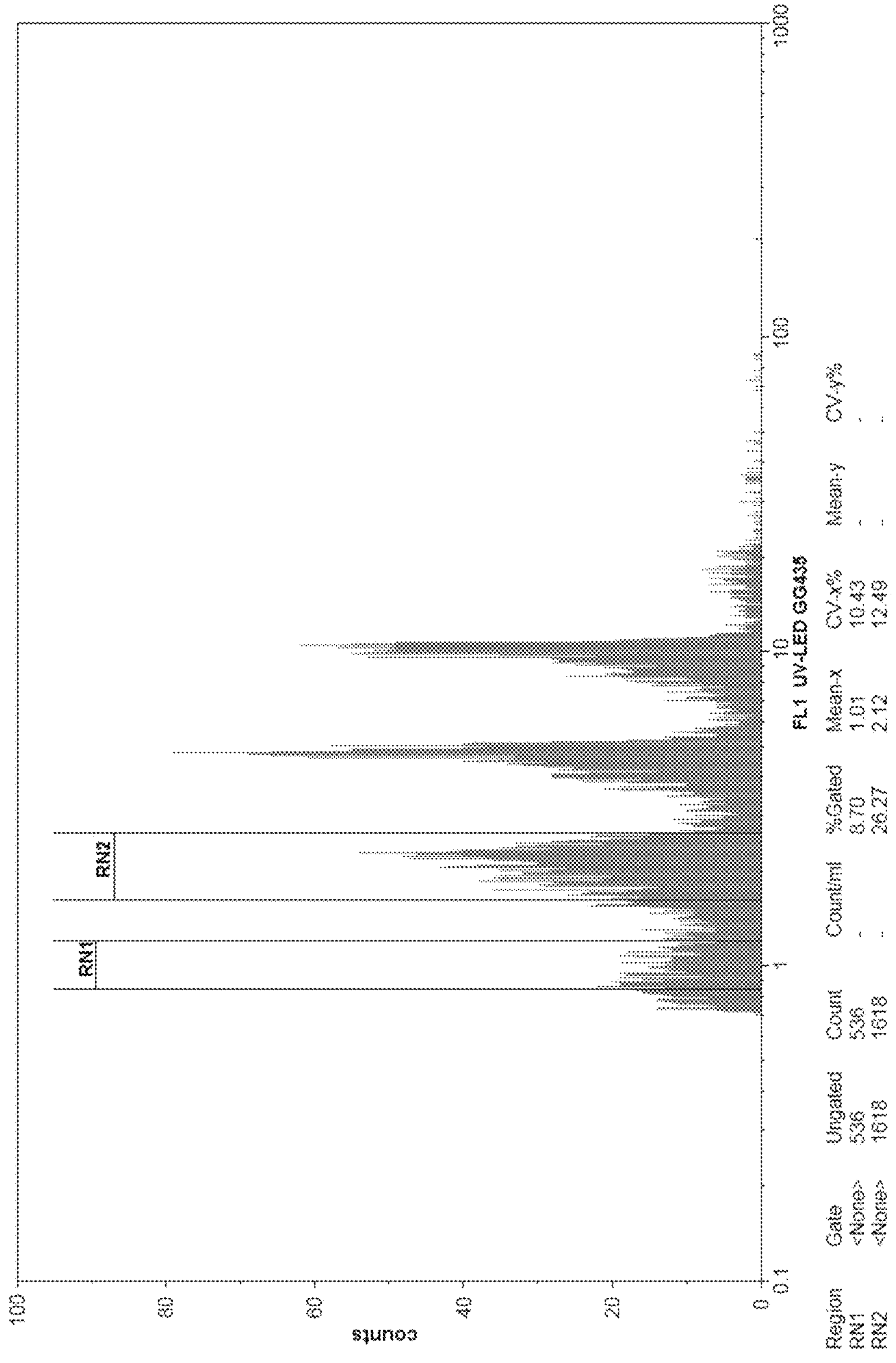
FIG. 18 shows the ploidy analysis histogram of a diploid control (parent USR01424135). The first peak is located at the "2" position on the logarithmic X-axis. Because this is leaf tissue from *Arabidopsis*, we see multiple peaks indicating the normal level of endoreduplication.
Figure 19:
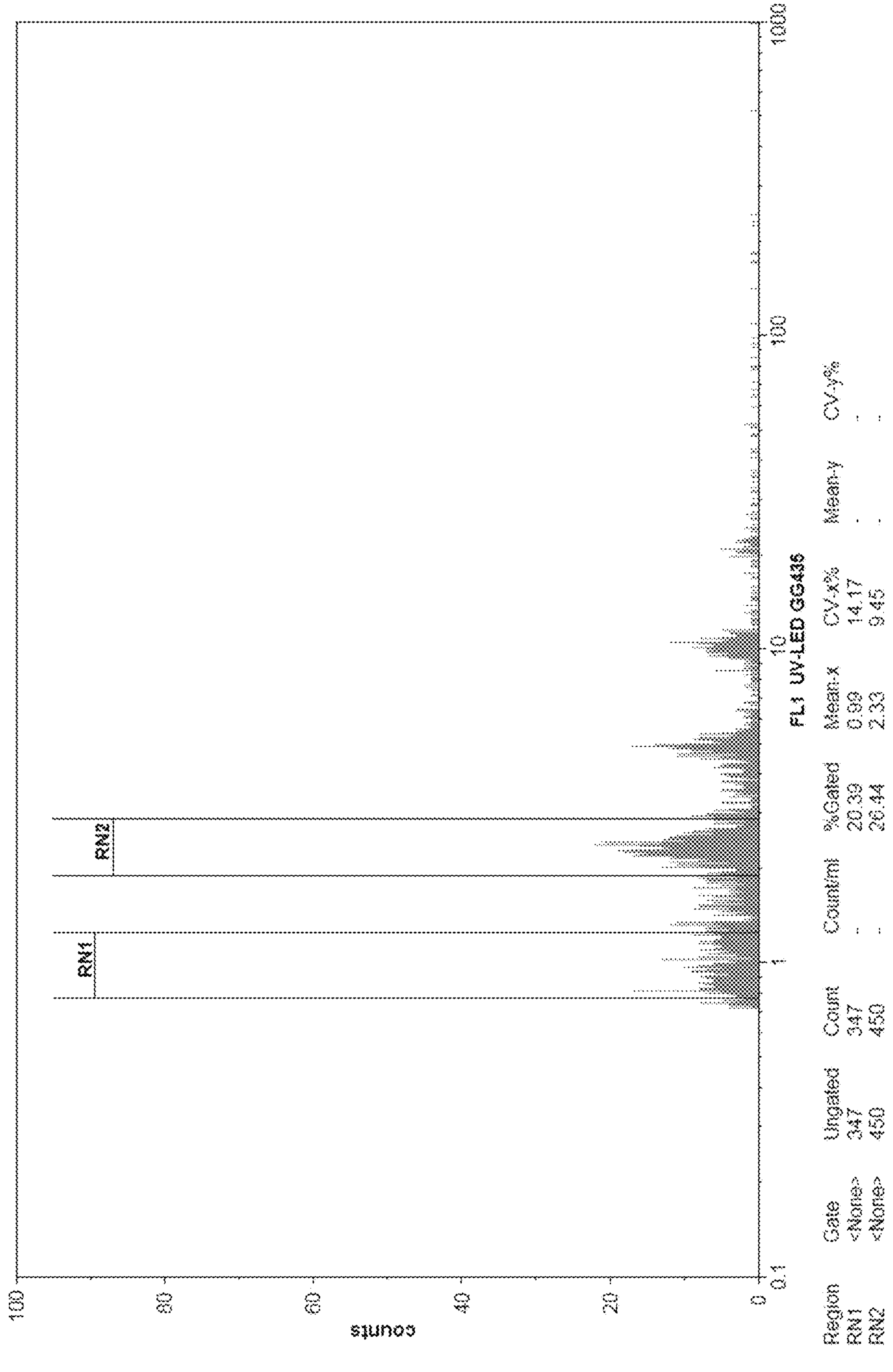
FIG. 19 shows the ploidy analysis histogram of a diploid control (parent USR01431603). The first peak is located at the "2" position on the logarithmic X-axis. Because this is leaf tissue from *Arabidopsis*, we see multiple peaks indicating the normal level of endoreduplication.
Figure 20:
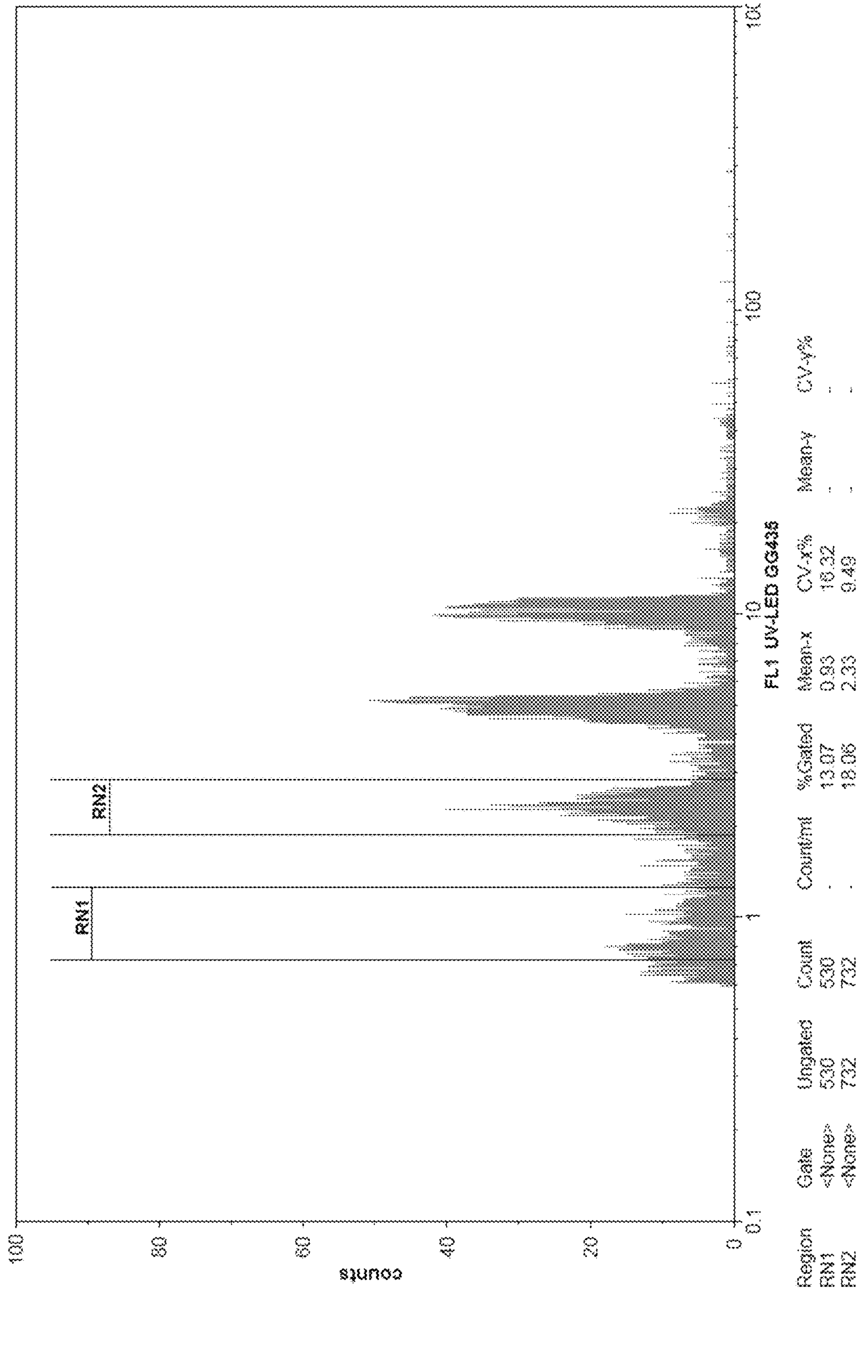
FIG. 20 shows the ploidy analysis histogram of a diploid control (parent USR01431609). The first peak is located at the "2" position on the logarithmic X-axis. Because this is leaf tissue from *Arabidopsis*, we see multiple peaks indicating the normal level of endoreduplication.
Figure 21:
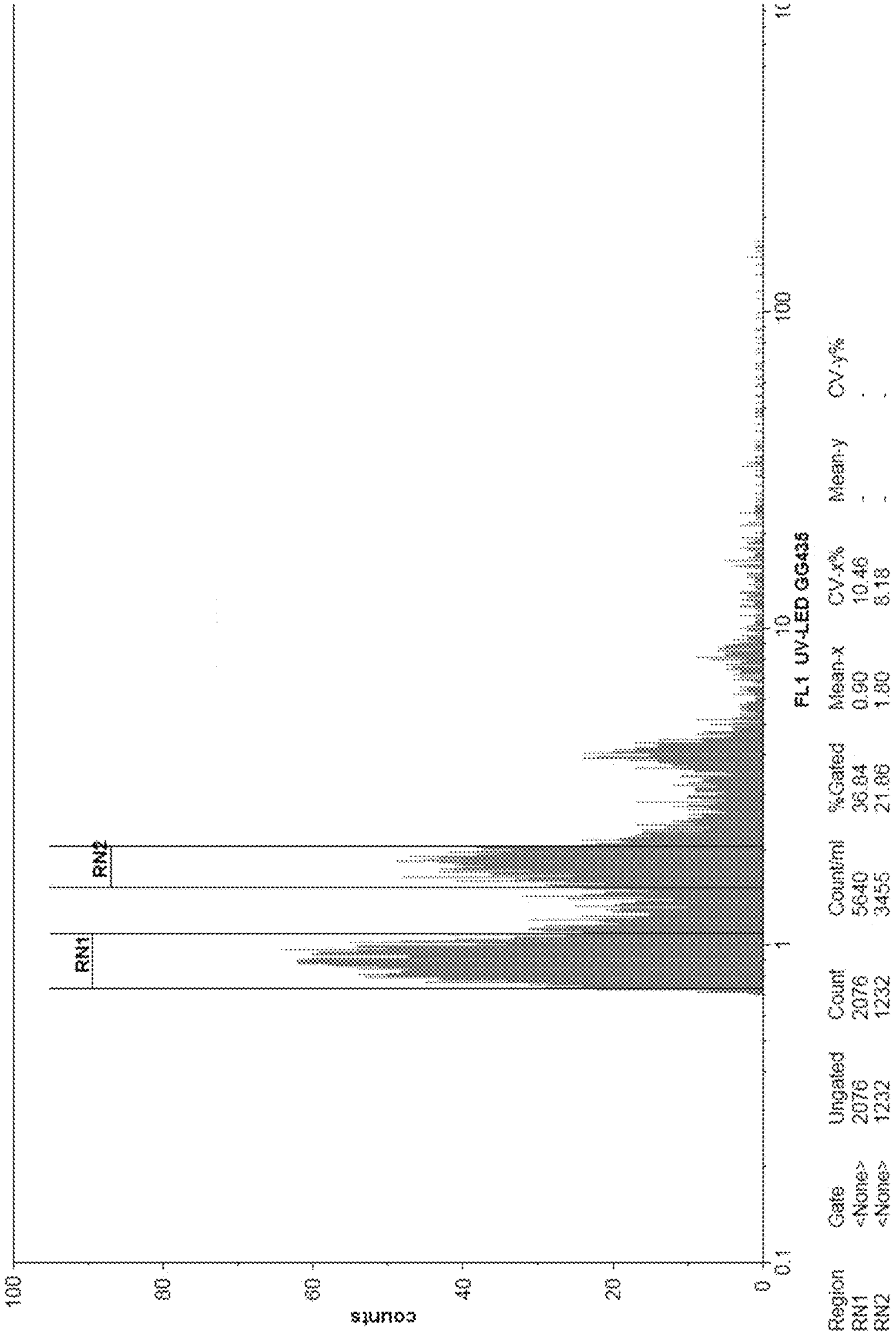
FIG. 21 shows the ploidy analysis histogram of an edited haploid from plate 1033, well C3 (USR01424135 X Ler-427). The first peak is located at the "1" position on the logarithmic X-axis, indicating it is a haploid. Because this is leaf tissue from *Arabidopsis*, we see multiple peaks indicating the normal level of endoreduplication.
Figure 22:
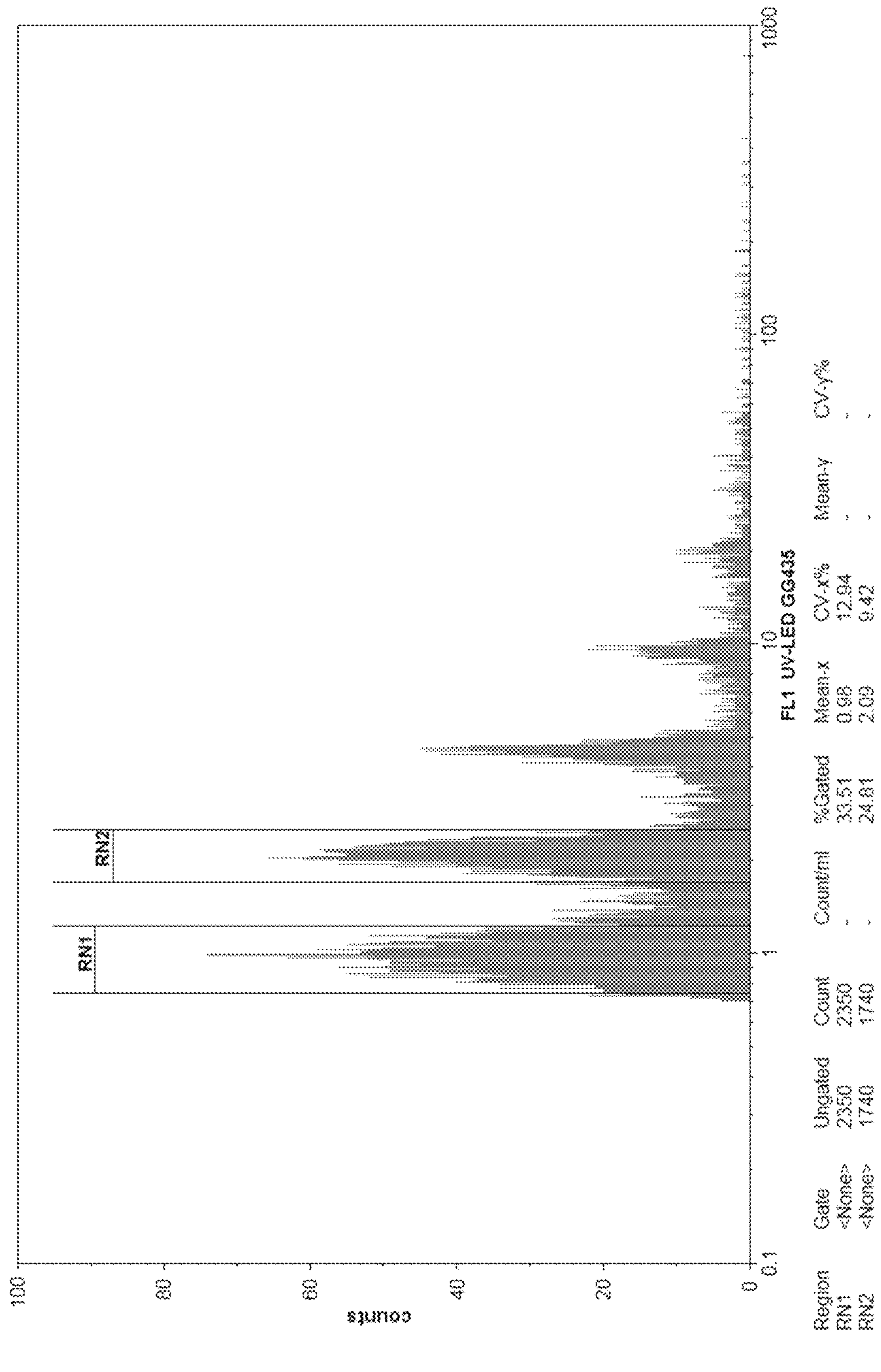
FIG. 22 shows the ploidy analysis histogram of an edited haploid from plate 1033, well E4 (USR01424135 X Ler-437). The first peak is located at the "1" position on the logarithmic X-axis, indicating it is a haploid. Because this is leaf tissue from *Arabidopsis*, we see multiple peaks indicating the normal level of endoreduplication.
Figure 23:
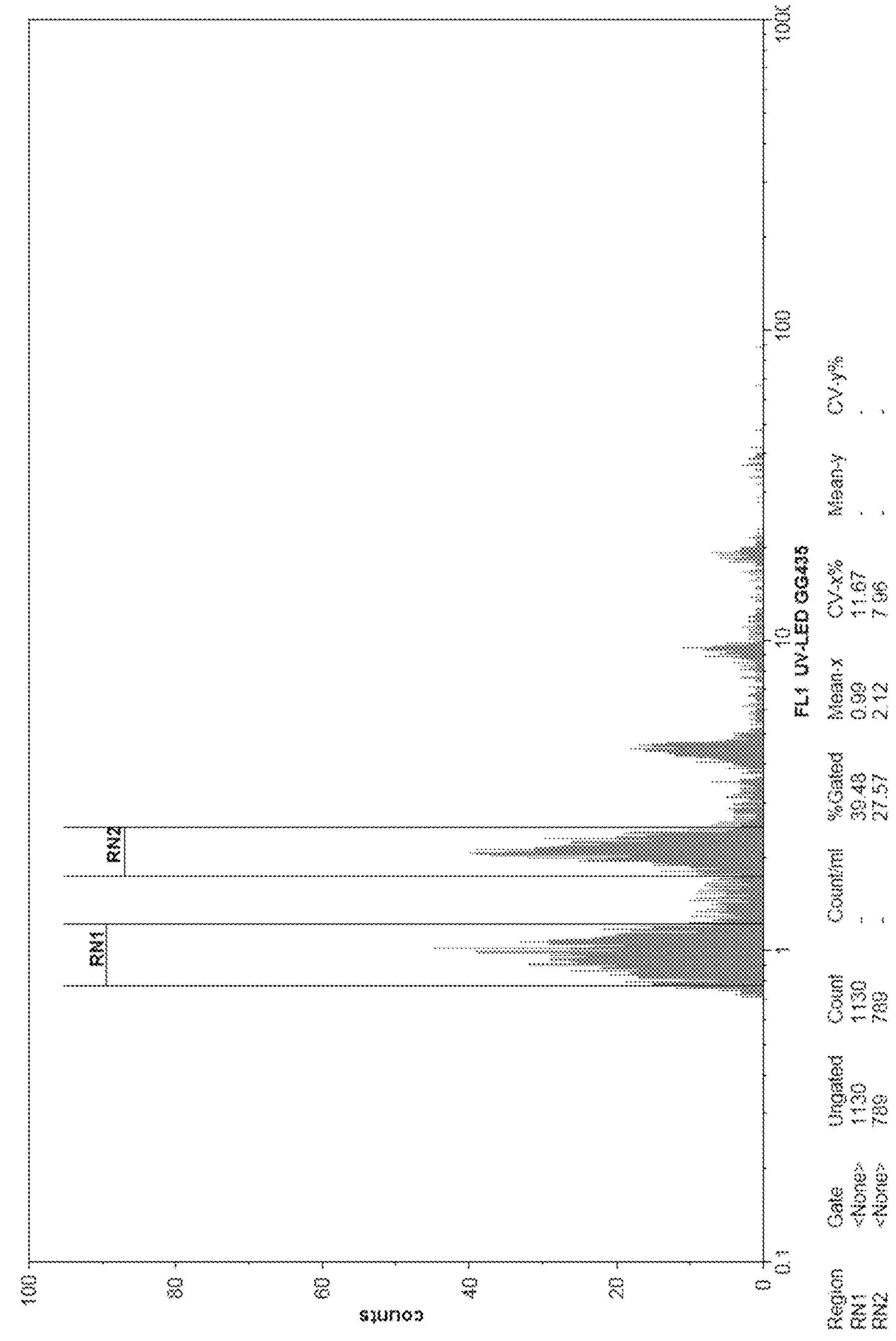
FIG. 23 shows the ploidy analysis histogram of an edited haploid from plate 1046, well H12 (USR01431609 X Ler-123). The first peak is located at the "1" position on the logarithmic X-axis, indicating it is a haploid. Because this is leaf tissue from *Arabidopsis*, we see multiple peaks indicating the normal level of endoreduplication.

Transgenic maize lines were grown in greenhouse and single and two-copy transgenic plants were outcrossed onto spring wheat and a CMS wheat line. Pollen collected from transgenic maize T0 plants carrying T-DNAs of one of the vectors 24038, 24039, 24079, 24091, and 24094 were used to pollinate emasculated spring wheat line AC-Nanda. Pollen was also used for a qRT experiment, in which the expression of the Cas9 was measured at the RNA level and compared to Cas9 expression in leaf samples when the Cas9 was driven by a sugar cane ubiquitin promoter used in many of the corn and wheat examples given above. As you can see in FIG. 17, the expression was high in the pollen, averaging about 100 fold higher in plants carrying the T-DNA vectors 24038, 24039, and 24079 compared to the Ubiquitin promoter. The expression was also higher in pollen from plants containing vectors 24038, 24039, and 24079 when compared to the pollen carrying the MATRILINEAL promoter constructs (24094 and 24091), which is known to have lower native gene expression. All five of these promoters have expression patterns that are restricted to pollen. As an indication that the promoters were working properly, we observed no T0 expression of Cas9 in callus seedling leaves, and there was no editing of the VLHP target sites in the T0 maize leaves (without wishing to be bound by theory, editing may happen at the maize target sites, in all likelihood, at the mature pollen stage, when the Cas9 is expressed for the first time).

At one to two days before anthesis, wheat florets were emasculated from the CMS line and the AC Nanda line. Two days later the florets were pollinated with fresh maize pollen carrying the editing machinery, Cas9-sgRNA, from either construct 24038, 24039, 24091, or 24094 (T0 plants transformed with construct 24079 were delayed, and not crossed to wheat in this manner). Wheat embryos were extracted from pollinated florets at 14-20 days after pollination for embryo rescue to recover haploid plantlets from the wheat× maize haploid induction system. Excised embryos were cultured on either full strength MS (Murashige and Skoog 1962) or ½ MS or B5 basal medium containing various modifications of organic supplements and grown in vitro for 1-5 weeks at 20-25° C. and 16-hour day length. For example, pollen of T0 progeny from transgenic maize line MZKE172601A100A containing vector 24039 was used to pollinate spikes of CMS line 16A300292 to induce wheat haploids. Haploid embryos were rescued and the resulting wheat haploid seedlings were sampled for qPCR analysis to determine the copy number of VLHP target sequences (Table 7). In this analysis, we tested for the Cas9 transgene using assay #2540. All wheat embryos rescued and tested lacked this transgene and gave scores of "0" for Cas9, because they do not have any corn DNA in the developing embryo and therefore do not have the transgene. The corn DNA is totally eliminated, kicked out or fails to be fully delivered in the first place during the haploid induction process, taking place during and/or after fertilization). In addition to Cas9, we test for assays #3332 and #3333, which give non-specific amplification of both VLHP2-2A and -2D alleles. These assays typically read as "2" or ">2" in haploid wheat, and the majority of the haploids we produced using the transgenic maize pollen scored 2 or >2 for these assays. We used these assays to look for putative edited haploids, by looking for scores of 0 or 1. A call of "1" might indicate that one of the two alleles, either VLHP2-2A, or -2D, was edited. Finally, we tested for assay 3255 in AC Nanda haploids, which detects VLHP2-2B specifically. The CMS line does not amplify this assay, even when it is wild-type, so we did not use it for the CMS haploids. The unedited haploids give a score of a "2," while putative edited haploids are found because they have a score of "0." A score of "1" might indicate a faulty reading or a chimeric, partially-edited sample.

As an example, one of the AC Nanda haploid plants 440-A5 was found to contain mutation in TaVLHP2-2B gene, but not in its orthologs TaVLHP2-2A and TaVLHP2-2D in the A and D sub-genomes (Table 7). The Taqman data also showed that it lacked the Cas9 transgene. The mutation within the TaVLHP2-2B target region was further characterized by sequencing, but although we were able to amplify the A and D alleles, we could no longer amplify the B allele, suggesting that there is a larger edit present, likely a large deletion, that results in the PCR product no longer amplifying.

As another example, one of the CMS haploid plants 450-D11 was found to contain mutation in either the TaVLHP2-2D or -2A homologues, according to the score of "1" for both assays 3332 and 3333. (Table 7). The taqman data showed that it lacked the Cas9 transgene. The TaVLHP2-2A, 2B and 2D target regions were further characterized by sequencing, but although we were able to amplify the A and B alleles, we could no longer amplify the D allele, suggesting that there is a larger edit present that led to PCR failure.

Considering the 2295 wheat haploids produced from crosses to maize pollen carrying one of the following five preferred-pollen expression constructs (24038, 24039, 24091, and 24094), we found 15 haploids that gave Taqman assay data that indicated possible editing at either the VLHP2-2A, VLHP2-2D, or VLHP2-2B target sites. After sequencing, seven of those haploids were found to have wild-type sequences at the target sites, and were called false positives due to Taqman error. These errors are thought to be either due to the fact that assays #3332 and #3333 gave non-specific amplification of both VLHP-2A and -2D alleles, leading to some missed calls, or due to low DNA quantity.

Of the remaining 8 putative edited haploids, six were AC Nanda (440-B3, 440-D3, 440-A5, 447-G8, 456-G9, 459-A2) where the editing transgene was from construct 24038. Four of those (440-B3, 440-D3, 440-A5, and 456-G9) contained edits in VLHP2-2B. These were found because they had a Taqman score of "0" for assay 3255. These plants lacked Cas9 (score of "0") but had wild-type "2" scores for VLHP2-2A or VLHP2-2D (assays #3332 and #3333) indicating they were not edited that those sites. These six plants were confirmed to be haploids by ploidy analysis. We attempted to sequence the edited alleles, but while the PCR and sequencing reactions worked well for 2A and 2D, we were not able to obtain a PCR product for 2B. We repeated the PCR several times using a range of reaction conditions but could not amplify the 2B homeologs from these haploid plants. This may indicate that the editing caused a large change in the 2B gene in these plants that may end up deleting the primer annealing site. We expect that many of the CMS plants also have edits at the VLHP2-2B target site, but we did not have an assay to detect the VLHP2-2B allele from the CMS line.

Considering AC Nanda alone, we calculate an overall editing rate at that allele of 0.7% for all constructs, but a particularly high editing rate of 1.4% for construct 24038.

In addition to these four edited haploids with scores of "0" for 3255, several other plants gave scores of "0 or 1" or "1" for 3255, which indicates possible chimerism (partial editing in certain cell lineages of the embryo or plantlet), but we did not follow up on those plants. For AC Nanda homolog VLHP2-2A, plant 447-G8 contained an edit which we were also not able to sequence because the PCR reaction failed, even though 2B and 2D did amplify and contained wild-type sequence. We repeated the PCR several times using a range of reaction conditions but could not amplify the 2A homolog. Similarly, for VLHP2-2D, plant 459-A2 contained an edit which we were not able to sequence because the PCR reaction failed. We repeated the PCR several times using a range of reaction conditions but could not amplify the 2D homolog. We also found putative edits in 447-H12 and 440-G6, but upon sequencing we found that these were false positives.

For the CMS haploids, plant 450-D11 gave scores of "1" for both assay #3332 and 3333 (Table 7). Upon sequencing, we found that the 2A homolog had wild-type sequence, but we could not PCR-amplify the 2D homolog, suggesting that a large edit had occurred. We repeated the PCR several times using a range of reaction conditions but could not amplify the 2D homolog. For plant 452-B11, the Taqman score was "0" for #3332 (VLHP2-2A), and we could not amplify that allele for sequencing, even though the 2D and 2B PCR products and sequences were normal. We repeated the PCR several times using a range of reaction conditions but could not amplify the 2A homolog. We also found five plants that had putative edits according to the Taqman data for assays 3332 and 3333, but PCR-sequencing showed these to be false positives; the sequence was wild-type (unedited).

In total, we found two edited CMS haploids and six edited AC Nanda haploids. There may be many more edited haploids that we were not able to detect because we did not have assays for the 2B gene for the CMS plants, nor for the VLHP3 gene target sites of the guide RNA in these five constructs.

The sequencing data from these edited haploids are consistent with the concept of a large deletion, inversion or rearrangement around the guide RNA target site, and extending far enough away to possibly include removal of one of the primer binding sites. This type of large change is not uncommon during editing by Cas9, especially in tissues where DNA repair via non-homologous end-joining is slower or inhibited—which may be the case in the just-fertilized zygote or early haploid wheat embryo.

TABLE 7

Sequencing data from edited wheat haploids.

| CMS | Con- | | TAV_2A 3332 | | TAV_2D 3333 | | TAV32_2B 3255 | | PMI 1750 | | Cas9 2540 | | |
|---|---|---|---|---|---|---|---|---|---|---|---|---|---|
| Plant ID | struct ID | copy # | Raw Copy # | Copy # level | Raw Copy # | Copy # level | Raw Copy # | Copy # level | Raw Copy # | Copy # level | Raw Copy # | Copy # level | Sequencing result |
| 427-A2 | WT | N/A | 2.44 | >2 | 2.38 | 2 | Not tested | | 0.00 | 0 | 0.00 | 0 | not sequenced |
| 427-B2 | WT | N/A | 1.99 | 2 | 1.99 | 2 | Not tested | | 0.00 | 0 | 0.00 | 0 | not sequenced |
| 427-C2 | WT | N/A | 2.02 | 2 | 2.07 | 2 | Not tested | | 0.00 | 0 | 0.00 | 0 | not sequenced |
| 427-D2 | WT | N/A | 2.31 | 2 | 2.16 | 2 | Not tested | | 0.00 | 0 | 0.00 | 0 | not sequenced |
| 427-A10 | 24091 | 2 | 2.07 | 2 | 1.66 | 2 | Not tested | | 0.00 | 0 | 0.00 | 0 | not sequenced |
| 427-B10 | 24091 | 2 | 1.95 | 2 | 1.84 | 2 | Not tested | | 0.00 | 0 | 0.00 | 0 | not sequenced |
| 427-C10 | 24091 | 2 | 1.93 | 2 | 2.28 | 2 | Not tested | | 0.00 | 0 | 0.00 | 0 | not sequenced |
| 427-D10 | 24091 | 2 | 2.59 | >2 | 2.48 | >2 | Not tested | | 0.00 | 0 | 0.00 | 0 | not sequenced |
| 427-E10 | 24091 | 2 | 1.90 | 2 | 1.78 | 2 | Not tested | | 0.00 | 0 | 0.00 | 0 | not sequenced |
| 427-F10 | 24091 | 2 | 2.03 | 2 | 1.96 | 2 | Not tested | | 0.00 | 0 | 0.00 | 0 | not sequenced |
| 427-G10 | 24091 | 2 | 2.08 | 2 | 2.25 | 2 | Not tested | | 0.00 | 0 | 0.00 | 0 | not sequenced |
| 427-H10 | 24091 | 2 | 0.58 | 1 | 0.81 | 1 | Not tested | | 0.00 | 0 | 0.00 | 0 | A and D were both WT |
| 427-A11 | 24091 | 2 | 1.57 | 1 or 2 | 1.93 | 2 | Not tested | | 0.00 | 0 | 0.00 | 0 | not sequenced |
| 427-B11 | 24091 | 2 | 1.41 | 1 or 2 | 1.63 | 2 | Not tested | | 0.00 | 0 | 0.00 | 0 | not sequenced |
| 427-C11 | 24091 | 2 | 1.06 | 1 | 1.21 | 1 | Not tested | | 0.01 | 0 | 0.01 | 0 | not sequenced |
| 427-D11 | 24091 | 2 | 1.98 | 2 | 2.03 | 2 | Not tested | | 0.00 | 0 | 0.00 | 0 | not sequenced |
| 427-E11 | 24091 | 2 | 1.94 | 2 | 1.94 | 2 | Not tested | | 0.00 | 0 | 0.00 | 0 | not sequenced |
| 427-F11 | 24091 | 2 | 1.84 | 2 | 1.84 | 2 | Not tested | | 0.00 | 0 | 0.00 | 0 | not sequenced |
| 427-G11 | 24091 | 2 | 1.54 | 1 or 2 | 1.76 | 2 | Not tested | | 0.00 | 0 | 0.00 | 0 | not sequenced |
| 427-H11 | 24091 | 2 | 1.75 | 2 | 1.76 | 2 | Not tested | | 0.00 | 0 | 0.00 | 0 | not sequenced |
| 427-A12 | 24091 | 2 | 1.99 | 2 | 2.15 | 2 | Not tested | | 0.00 | 0 | 0.00 | 0 | not sequenced |
| 427-B12 | 24091 | 2 | 0.72 | 1 | 1.26 | 1 | Not tested | | 0.00 | 0 | 0.00 | 0 | A and D were both WT |
| 427-C12 | 24091 | 2 | 1.69 | 2 | 1.50 | 1 or 2 | Not tested | | 0.00 | 0 | 0.01 | 0 | not sequenced |
| 427-D12 | 24091 | 1 | 2.34 | 2 | 2.03 | 2 | Not tested | | 0.00 | 0 | 0.00 | 0 | not sequenced |
| 427-E12 | 24091 | 1 | 1.98 | 2 | 2.04 | 2 | Not tested | | 0.00 | 0 | 0.00 | 0 | not sequenced |
| 427-F12 | 24091 | 1 | 1.89 | 2 | 1.97 | 2 | Not tested | | 0.00 | 0 | 0.00 | 0 | not sequenced |
| 427-G12 | 24091 | 1 | 1.56 | 1 or 2 | 1.77 | 2 | Not tested | | 0.00 | 0 | 0.00 | 0 | not sequenced |
| 427-H12 | 24091 | 1 | 1.57 | 1 or 2 | 2.36 | 2 | Not tested | | 0.00 | 0 | 0.00 | 0 | not sequenced |
| 428-A3 | 24091 | 1 | 2.12 | 2 | 1.75 | 2 | Not tested | | 0.00 | 0 | 0.00 | 0 | not sequenced |
| 428-B3 | 24091 | 1 | 2.69 | >2 | 1.89 | 2 | Not tested | | 0.00 | 0 | 0.00 | 0 | not sequenced |
| 428-C3 | 24091 | 1 | 2.09 | 2 | 2.44 | >2 | Not tested | | 0.00 | 0 | 0.00 | 0 | not sequenced |
| 428-D3 | 24091 | 1 | 2.05 | 2 | 2.39 | 2 | Not tested | | 0.00 | 0 | 0.00 | 0 | not sequenced |
| 428-E3 | 24091 | 1 | 2.48 | >2 | 2.87 | >2 | Not tested | | 0.00 | 0 | 0.00 | 0 | not sequenced |
| 428-F3 | 24091 | 1 | 2.33 | 2 | 2.76 | >2 | Not tested | | 0.00 | 0 | 0.00 | 0 | not sequenced |
| 428-G3 | 24091 | 1 | 2.84 | >2 | 0.22 | 0 | Not tested | | 0.00 | 0 | 0.00 | 0 | A and D were both WT |
| 428-H3 | 24091 | 1 | 2.83 | >2 | 2.60 | >2 | Not tested | | 0.00 | 0 | 0.00 | 0 | not sequenced |
| 450-A11 | 24094 | 1 | 1.97 | 2 | 2.24 | 2 | Not tested | | 0.00 | 0 | 0.00 | 0 | not sequenced |
| 450-B11 | 24094 | 1 | 2.13 | 2 | 2.04 | 2 | Not tested | | 0.00 | 0 | 0.00 | 0 | not sequenced |
| 450-C11 | 24094 | 1 | 2.15 | 2 | 2.18 | 2 | Not tested | | 0.00 | 0 | 0.00 | 0 | not sequenced |
| 450-D11 | 24094 | 1 | 1.04 | 1 | 0.99 | 1 | Not tested | | 0.00 | 0 | 0.00 | 0 | A & B were WT; D failed |
| 450-E11 | 24094 | 1 | 2.35 | 2 | 2.01 | 2 | Not tested | | 0.00 | 0 | 0.00 | 0 | not sequenced |
| 450-F11 | 24094 | 1 | 2.02 | 2 | 1.90 | 2 | Not tested | | 0.00 | 0 | 0.00 | 0 | not sequenced |
| 450-G11 | 24039 | 1 | 1.76 | 2 | 1.72 | 2 | Not tested | | 0.00 | 0 | 0.00 | 0 | not sequenced |
| 450-H11 | 24039 | 1 | 2.07 | 2 | 2.04 | 2 | Not tested | | 0.00 | 0 | 0.00 | 0 | not sequenced |
| 452-H4 | 24038 | 2 | 2.62 | >2 | 0.01 | 0 | Not tested | | 0.00 | 0 | 0.00 | 0 | A and D were both WT |
| 452-A11 | 24038 | 2 | 2.24 | 2 | 2.28 | 2 | Not tested | | 0.00 | 0 | 0.00 | 0 | not sequenced |
| 452-B11 | 24038 | 2 | 0.00 | 0 | 2.22 | 2 | Not tested | | 0.00 | 0 | 0.00 | 0 | B & D were WT; A failed |
| 452-C11 | 24038 | 2 | 2.55 | >2 | 2.22 | 2 | Not tested | | 0.00 | 0 | 0.00 | 0 | not sequenced |

TABLE 7-continued

Sequencing data from edited wheat haploids.

| | | | | | | | | | | | | |
|---|---|---|---|---|---|---|---|---|---|---|---|---|
| 452-D11 | 24038 | 2 | 0.82 | 1 | 1.26 | 1 | Not tested | | 0.00 | 0 | 0.00 | 0 | A and D were both WT |
| 452-E11 | 24038 | 2 | 2.43 | >2 | 2.36 | 2 | Not tested | | 0.00 | 0 | 0.00 | 0 | not sequenced |
| 452-F11 | 24038 | 2 | 2.12 | 2 | 2.21 | 2 | Not tested | | 0.00 | 0 | 0.00 | 0 | not sequenced |
| 452-G11 | 24038 | 2 | 2.38 | 2 | 1.99 | 2 | Not tested | | 0.00 | 0 | 0.00 | 0 | not sequenced |
| 452-H11 | 24038 | 2 | 1.82 | 2 | 1.83 | 2 | Not tested | | 0.00 | 0 | 0.00 | 0 | not sequenced |

| NANDA | con- | | TAV_2A 3332 | | TAV_2D 3333 | | TAV_2B 3255 | | PMI 1750 | | Cas9 2540 | | |
|---|---|---|---|---|---|---|---|---|---|---|---|---|---|
| Plant ID | struct ID | copy # | Raw Copy # | Copy # level | Raw Copy # | Copy # level | Raw Copy # | Copy # level | Raw Copy # | Copy # level | Raw Copy # | Copy # level | Sequencing result |
| 425-A2 | WT | N/A | 2.30 | 2 | 2.62 | >2 | 1.908 | 2 | 0.00 | 0 | 0.00 | 0 | not sequenced |
| 425-B2 | WT | N/A | 2.28 | 2 | 2.41 | >2 | 2.274 | 2 | 0.00 | 0 | 0.00 | 0 | not sequenced |
| 425-C2 | WT | N/A | 2.47 | >2 | 1.92 | 2 | 1.962 | 2 | 0.00 | 0 | 0.00 | 0 | not sequenced |
| 425-D2 | WT | N/A | 2.10 | 2 | 2.11 | 2 | 1.772 | 2 | 0.00 | 0 | 0.00 | 0 | not sequenced |
| 447-A12 | 24038 | 2 | 1.72 | 2 | 1.90 | 2 | 2.02 | 2 | 0.00 | 0 | 0.00 | 0 | not sequenced |
| 447-B12 | 24039 | 2 | 2.18 | 2 | 1.62 | 2 | 1.47 | 1 or 2 | 0.00 | 0 | 0.00 | 0 | not sequenced |
| 447-C12 | 24039 | 2 | 1.78 | 2 | 2.40 | 2 | 1.90 | 2 | 0.00 | 0 | 0.00 | 0 | not sequenced |
| 447-D12 | 24039 | 2 | 1.58 | 1 or 2 | 1.70 | 2 | 2.18 | 2 | 0.00 | 0 | 0.00 | 0 | not sequenced |
| 447-E12 | 24039 | 2 | 2.13 | 2 | 1.82 | 2 | 2.14 | 2 | 0.00 | 0 | 0.00 | 0 | not sequenced |
| 447-F12 | 24039 | 2 | 2.25 | 2 | 1.78 | 2 | 2.15 | 2 | 0.00 | 0 | 0.00 | 0 | not sequenced |
| 447-G12 | 24039 | 2 | 1.90 | 2 | 2.30 | 2 | 2.23 | 2 | 0.00 | 0 | 0.00 | 0 | not sequenced |
| 447-H12 | 24039 | 1 | 2.34 | 2 | 1.95 | 2 | 0.89 | 1 | 0.00 | 0 | 0.00 | 0 | A, B, and D were all WT |
| 440-A2 | 24039 | 1 | 1.72 | 2 | 1.71 | 2 | 1.24 | 1 | 0.00 | 0 | 0.00 | 0 | not sequenced |
| 440-B2 | 24039 | 1 | 2.30 | 2 | 2.56 | >2 | 1.77 | 2 | 0.00 | 0 | 0.00 | 0 | not sequenced |
| 440-C2 | 24039 | 1 | 3.05 | >2 | 1.85 | 2 | 2.01 | 2 | 0.00 | 0 | 0.00 | 0 | not sequenced |
| 440-D2 | 24039 | 1 | 1.66 | 2 | 1.70 | 2 | 1.44 | 1 or 2 | 0.00 | 0 | 0.00 | 0 | not sequenced |
| 440-E2 | 24039 | 1 | 2.23 | 2 | 1.91 | 2 | 2.04 | 2 | 0.00 | 0 | 0.00 | 0 | not sequenced |
| 440-F2 | 24039 | 1 | 2.63 | >2 | 2.07 | 2 | 2.28 | 2 | 0.00 | 0 | 0.00 | 0 | not sequenced |
| 440-G2 | 24038 | 11 | 1.91 | 2 | 1.87 | 2 | 2.10 | 2 | 0.00 | 0 | 0.00 | 0 | not sequenced |
| 440-H2 | 24038 | 1 | 1.85 | 2 | 1.80 | 2 | 1.97 | 2 | 0.00 | 0 | 0.00 | 0 | not sequenced |
| 440-A3 | 24038 | 1 | 2.52 | >2 | 2.05 | 2 | 1.99 | 2 | 0.00 | 0 | 0.00 | 0 | not sequenced |
| 440-B3 | 24038 | 1 | 2.16 | 2 | 2.19 | 2 | 0.00 | 0 | 0.00 | 0 | 0.00 | 0 | A & D were WT; B failed |
| 440-C3 | 24038 | 1 | 2.58 | >2 | 2.02 | 2 | 2.78 | >2 | 0.00 | 0 | 0.00 | 0 | not sequenced |
| 440-D3 | 24038 | 1 | 2.34 | 2 | 2.32 | 2 | 0.00 | 0 | 0.00 | 0 | 0.00 | 0 | A & D were WT; B failed |
| 440-E3 | 24038 | 1 | 2.49 | >2 | 2.23 | 2 | 2.47 | >2 | 0.00 | 0 | 0.00 | 0 | not sequenced |
| 440-F3 | 24038 | 1 | 2.08 | 2 | 2.10 | 2 | 2.17 | 2 | 0.00 | 0 | 0.00 | 0 | not sequenced |
| 440-F4 | 24038 | 1 | 1.73 | 2 | 1.47 | 1 or 2 | 1.41 | 1 or 2 | 0.00 | 0 | 0.00 | 0 | not sequenced |
| 440-G4 | 24038 | 1 | 1.53 | 1 or 2 | 2.02 | 2 | 1.99 | 2 | 0.00 | 0 | 0.00 | 0 | not sequenced |
| 440-H4 | 24038 | 1 | 2.22 | 2 | 1.90 | 2 | 0.00 | 0 | 0.00 | 0 | 0.00 | 0 | not sequenced |
| 440-A5 | 24038 | 1 | 2.22 | 2 | 1.90 | 2 | 0.00 | 0 | 0.00 | 0 | 0.00 | 0 | A & D were WT; B failed |
| 440-A6 | 24039 | 2 | 2.49 | >2 | 2.32 | 2 | 1.84 | 2 | 0.00 | 0 | 0.00 | 0 | not sequenced |
| 440-B6 | 24039 | 2 | 2.12 | 2 | 2.03 | 2 | 2.21 | 2 | 0.00 | 0 | 0.00 | 0 | not sequenced |
| 440-C6 | 24039 | 2 | 2.63 | >2 | 2.07 | 2 | 2.28 | 2 | 0.00 | 0 | 0.00 | 0 | not sequenced |
| 440-D6 | 24039 | 2 | 2.49 | >2 | 2.23 | 2 | 2.47 | >2 | 0.00 | 0 | 0.00 | 0 | not sequenced |
| 440-E6 | 24039 | 2 | 2.45 | >2 | 2.20 | 2 | 2.32 | 2 | 0.00 | 0 | 0.00 | 0 | not sequenced |
| 440-F6 | 24039 | 2 | 2.10 | 2 | 1.92 | 2 | 1.91 | 2 | 0.00 | 0 | 0.00 | 0 | not sequenced |
| 440-G6 | 24039 | 2 | 0.57 | 1 | 0.66 | 1 | 0.53 | 1 | 0.00 | 0 | 0.00 | 0 | A, B & D were all WT |
| 440-H6 | 24039 | 2 | 1.81 | 2 | 1.96 | 2 | 2.51 | >2 | 0.00 | 0 | 0.00 | 0 | not sequenced |
| 447-A8 | 24038 | 1 | 2.42 | >2 | 2.21 | 2 | 2.10 | 2 | 0.00 | 0 | 0.00 | 0 | not sequenced |
| 447-B8 | 24038 | 1 | 2.46 | >2 | 2.32 | 2 | 2.09 | 2 | 0.00 | 0 | 0.00 | 0 | not sequenced |
| 447-C8 | 24038 | 1 | 2.09 | 2 | 2.08 | 2 | 2.29 | 2 | 0.00 | 0 | 0.00 | 0 | not sequenced |
| 447-D8 | 24038 | 1 | 2.13 | 2 | 2.14 | 2 | 2.34 | 2 | 0.00 | 0 | 0.00 | 0 | not sequenced |
| 447-E8 | 24038 | 11 | 2.36 | 2 | 2.31 | 2 | 2.44 | >2 | 0.00 | 0 | 0.00 | 0 | not sequenced |
| 447-F8 | 24038 | 1 | 2.72 | >2 | 2.28 | 2 | 2.00 | 2 | 0.00 | 0 | 0.00 | 0 | not sequenced |
| 447-G8 | 24038 | 1 | 0.71 | 1 | 1.34 | 1 or 2 | 2.33 | 2 | 0.00 | 0 | 0.00 | 0 | B & D were WT; A failed |
| 447-H8 | 24038 | 1 | 2.25 | 2 | 2.29 | 2 | 2.01 | 2 | 0.00 | 0 | 0.00 | 0 | not sequenced |
| 456-A9 | 24038 | 2 | 2.19 | 2 | 1.59 | 1 or 2 | 2.03 | 2 | 0.00 | 0 | 0.00 | 0 | not sequenced |
| 456-B9 | 24038 | 2 | 2.13 | 2 | 2.11 | 2 | 2.02 | 2 | 0.00 | 0 | 0.00 | 0 | not sequenced |
| 456-C9 | 24038 | 2 | 2.16 | 2 | 1.85 | 2 | 1.45 | 1 or 2 | 0.00 | 0 | 0.00 | 0 | not sequenced |
| 456-D9 | 24038 | 2 | 2.56 | >2 | 2.18 | 2 | 1.76 | 2 | 0.00 | 0 | 0.00 | 0 | not sequenced |
| 456-E9 | 24038 | 2 | 2.29 | 2 | 2.03 | 2 | 1.65 | 2 | 0.00 | 0 | 0.00 | 0 | not sequenced |
| 456-F9 | 24038 | 2 | 2.24 | 2 | 2.02 | 2 | 2.05 | 2 | 0.00 | 0 | 0.00 | 0 | not sequenced |
| 456-G9 | 24038 | 2 | 2.49 | >2 | 2.03 | 2 | 0.00 | 0 | 0.00 | 0 | 0.00 | 0 | A & D were WT; B failed |
| 456-H9 | 24038 | 2 | 1.78 | 2 | 1.62 | 2 | 1.38 | 1 or 2 | 0.00 | 0 | 0.00 | 0 | not sequenced |
| 459-A2 | 24038 | 2 | 1.38 | 1 or 2 | 1.11 | 1 | 0.94 | 1 | 0.00 | 0 | 0.00 | 0 | A & B were WT; D failed |
| 459-B2 | 24038 | 2 | 1.86 | 2 | 1.91 | 2 | 2.12 | 2 | 0.00 | 0 | 0.00 | 0 | not sequenced |
| 459-C2 | 24038 | 2 | 1.94 | 2 | 2.09 | 2 | 1.42 | 1 or 2 | 0.00 | 0 | 0.00 | 0 | not sequenced |

TABLE 7-continued

| Sequencing data from edited wheat haploids. | | | | | | | | | | | | |
|---|---|---|---|---|---|---|---|---|---|---|---|---|
| 459-D2 | 24038 | 2 | 2.09 | 2 | 2.05 | 2 | 1.91 | 2 | 0.00 | 0 | 0.00 | 0 | not sequenced |
| 459-E2 | 24038 | 2 | 2.18 | 2 | 2.12 | 2 | 2.12 | 2 | 0.00 | 0 | 0.00 | 0 | not sequenced |

Overall, we found that the editing frequency (number of edited haploids identified divided by the total number of haploids) for construct 24038 was 0.79%; for construct 24039 it was 0%; for construct 24091 it was 0%, and for construct 24094 it was 0.75%. However, this editing rate is certainly an under-estimate because we did not have assays to detect edits at many of the guide RNA target sites. Additionally, because we used T0 pollen that was either 1 or 2 copy, we know that with the 1-copy pollen, only 50% of the fertilizing pollen grains will contain the Cas9, and so only half of the embryos have the opportunity to be edited; similarly, for 2 copy parents, assuming random segregation of the transgenes in the male meiosis, we would expect about 75% of the pollen to contain Cas9, so 25% of the embryos cannot be edited. It is reasonable to conclude that, when one is trying to use this simultaneous editing plus haploid induction technology with the editing machinery carried by the pollen, it may in some cases be more optimal to use a promoter that express specifically or highly in pollen and in sperm cells, so that the Cas9 can be expressed at a higher level. In cases where the gene target might impact development of the haploid inducer plant, having a pollen or sperm-preferred promoter that does not express in leaves might be useful because it would avoid editing the target gene in the haploid inducer plant during development—perhaps editing it for the first time in pollen.

Because the sperm cells fertilize the egg, they have the potential to deliver Cas9 RNA and protein (as well as the transgene DNA itself, integrated into one of the male chromosomes that will be eliminated). As we demonstrated in the wide-cross work in this example, it may work well to have the Cas9 and/or guide RNA under the control of a promoter that specifically or highly expresses in pollen, and in particular in sperm cells, when using a haploid inducer as the male to edit elite lines. We do not know exactly whether MATRILINEAL, EXPB1, EXPB2, and PRF3 express in the vegetative nucleus, the sperm cells, or both, and whether there might be any expression in a zygote cell type, but these were chosen because they are supposedly highly and/or specifically expressed in pollen. The PRF3 promoter has a DUO1 binding motif in the promoter, which may indicate it expresses in sperm cells. This is consistent with that promoter having higher editing frequency. The fact that we found many edited wheat haploids after the wide cross makes it clear that when there is high expression of Cas9 in pollen, using these or any other promoter, that expression can lead to editing in the wheat embryos after the wide cross. There is a strong possibility that these promoters, as well as other promoters that drive expression in pollen, or in particular in the sperm cells, might increase the efficiency of the editing process during corn haploid induction, or rice haploid induction.

Similarly, in the next example below, we show haploid editing in a dicot using a CENH3-modified-haploid inducer line, and we use constitutive promoter to drive the Cas9. But in an attempt to increase the efficiency of the haploid editing, we could opt to use a promoter that drives high and/or specific expression in egg cells, such as the EGG APPARATUS1 gene's promoter ("prEA1") (see, e.g., Gray-Mitsumune, M. and Matton, D. P., *The Egg apparatus* 1 *gene from maize is a member of a large gene family found in both monocots and dicots*, Planta 223(3):618-625 (February 2006)) or EGG CELL1 (EC1) (see, e.g., Sprunck S, et al., *Egg cell-secreted EC*1 *triggers sperm cell activation during double fertilization*. Science 2012; 338:1093-97; PMID: 23180860; http://dx.doi.org/10.1126/science.1223944).

As an example of this, one could use a sperm-cell expressed promoter, such as the *Arabidopsis* sperm-specific DUO1 promoter (see, e.g., Engel, et al., *Green Sperm. Identification of Male Gamete Promoters in Arabidopsis*, Plant Physiology August 2005, 138 (4) 2124-2133; DOI: 10.1104/pp. 104.054213), or homologs of DUO1 from other species (for instance, the maize genes GRMZM2G105137 and GRMZM2G046443 are both DUO1 homologs that share a similar pollen-specific expression pattern). If one used any of these to drive Cas9 expression in the sperm cells of a haploid inducer line like RWK, NP2222-HI, or an matl mutant, it might make a highly efficient haploid editor line for use in editing diverse elite maize or wheat germplasm, via intraspecific or wide cross, respectively.

Other suitable sperm-expressed promoters for this concept of driving high Cas9 expression in sperm cells would include the DUO1 homologs in wheat, rice, barley, tomato, sunflower, or other monocots or dicots. Other suitable promoters for this concept are shown in Table 8 below. These promoters, or their homologs in crop species—might be very useful for this concept. The principal at work is that gamete cell expression of the editing machinery can increase the rate or efficiency of this invention because it means that there will be abundant editing protein or RNA present or delivered to the embryo during fertilization so that editing can happen rapidly.

TABLE 8

Promoters List: promoters one can use in a transgene to drive high sperm cell expression of editing machinery to boost the efficiency of simultaneous editing and doubled-haploid induction ("SEDHI").

| Gene Name | Gene ID | Maize Ortholog | Rice Ortholog |
|---|---|---|---|
| DUO1 | At3G60460 | GRMZM2G105137, GRMZM2G046443 | LOC_Os04g46384 |
| MGH3 | At1G19890 | NA | NA |
| GEX1 | At5G55490 | GRMZM2G388045 | LOC_Os09g27040, LOC_Os07g47194 |
| GEX2 | At5G49150 | GRMZM2G036832 | LOC_Os09g25650 |
| GEX3 | At5G16020 | GRMZM2G458159 | LOC_Os01g42060 |
| HAP2/GSC1 | At4G11720 | GRMZM2G412911 | LOC_Os05g18730 |
| CycB1 | At4G37490 | NA | NA |
| DAZ1 | At2G17180 | GRMZM2G132057 | NA |
| DAZ2 | At4G35280 | NA | LOC_Os02g19180 |
| DAZ3 | At4G35700 | NA | NA |
| PCR11 | At1G68610 | NA | NA |
| DAN1 | At3G04620 | NA | NA |
| TIP1 | AT3G47440 | NA | LOC_Os04g46490 |
| MKKK20 | AT3G50310 | NA | NA |
| DAF1 | At3G62230 | NA | NA |
| DAW1 | At4G35560 | GRMZM2G176647 | NA |
| DAU2/DMP9 | At5G39650 | NA | NA |

VII. Simultaneous Haploid Induction and Editing in Dicots Via Wide Cross or Via Crosses to CENH3-Altered Lines or Other Haploid Inducing Lines.

In vivo haploid induction can also be achieved using interspecific or intergeneric wide crosses on dicot plant species, for example, in cotton (Turcotte et al. 1969, Semigametic production of haploids in pima cotton. Crop Sci.

9:653-655) and tobacco (Burke et al, 1979, Maternal haploids of *Nicotiana tabacum* L. Science 206:585; Wernsman et al. 1989, Androgenetic vs. gynogenetic doubled haploids of tobacco. Crop Sci. 29:1151-1155). Haploid *Arabidopsis* plants can be obtained by crossing with pollen from mutant CENH3 plant, or by crossing said plants as females to wild type pollen (Ravi and Chan, 2010, Haploid plants produced by centromere-mediated genome elimination. Nature 464: 615-618). Other candidate genes which may be modified to generate a haploid inducer and SEDHI editing line include KNL2 and CENPC (both of which may operate via centromere-mediated uniparental genome elimination) as well as MSI2 and sunflower PLA2. In this case, the haploid-inducing genome (be it the male or female in the cross) also contains the editing machinery, so that the editing can be achieved during the haploid induction process, with the result being an edited maternal or paternal haploid progeny plant without altered CENH3 or editing transgenes. See, e.g., WO 2017/004375, incorporated herein by reference in its entirety. Transgenic locus expressing editing machinery can be introduced into any dicot crops or their wild relatives of *Brassica*, tomato, pepper, lettuce, eggplant, soybean, sunflower, sugar beet, cotton, alfalfa, tobacco, and others. The transgenic lines expressing editing machinery are then used as pollen donors, or in the case of CENH3, either pollen donors or acceptors, in interspecific or intergeneric wide crosses for haploid induction and simultaneous genome editing. For example, *N. africana* transgenic CRISPR-Cas9 lines expressing sgRNA targeting tobacco gibberellin 20-oxidase are created through *Agrobacterium*-mediated transformation and used to pollinate emasculated tobacco flowers to induce haploid plants with their genome edited at the gibberellin 20-oxidase locus. Preferably, an easily transformable line with large number of pollen is used as pollen donor for haploid induction and to provide the editing machinery transiently. The recipient plant for haploid production has flowers that are easy to emasculate or is male sterile. More preferably, a color or other visual marker is present in the induction line or is included in the editing locus to easily differentiate haploid embryos or plants from diploids resulted from normal zygote development.

We exemplified this by utilizing an *Arabidopsis* haploid inducer line in the Columbia ecotype, and transforming it with a construct encoding expression of Cas9 and a single guide RNA targeting the GLABROUS1 gene (GL1) which, when knocked out, gives a trichome-less phenotype. We crossed the T0s as females by Landsberg *Erecta* (Ler) ecotype pollen, and recovered gll edited haploid progeny.

The haploid inducer materials were obtained from the Comai lab at UC Davis. These materials are typically utilized as paternal haploid inducer lines (causing androgenesis, when crossed as females to wild-type males) but can also act as maternal haploid inducers (causing gynogenesis, when crossed as males to wild-type females). These lines have been altered to become haploid inducers by replacing the native CENH3 gene with a *Zea Mays* CENH3 transgene as reported in (Maheshwari, et al, 2017, Centromere location in *Arabidopsis* is unaltered by extreme divergence in CENH3 protein sequence. Genome Research 27(3)).

In particular, both copies of the native AtCENH3 gene was knocked out and complemented with the stably inserted ZmCENH3 transgene, which did not impact normal plant development, and did not produce haploids upon self-pollination, but did produce about 10% haploids upon outcross. This is a modification to the original concept of CENH3-tailswap described in detail in (Ravi and Chan, 2010, Haploid plants produced by centromere-mediated genome elimination. Nature 464: 615-618) and many subsequent publications.

After we obtained the CENH3* lines from UC Davis, we grew them up, confirmed that they had the ZmCENH3 transgene and were homozygous "null" for the native AtCENH3 gene. We did this by designing a taqman qPCR assay for ZmCENH3 (assay #2298) and by using PCR and gel electrophoresis to test 183 seedlings for the zygosity of the AtCENH3 genotype by running PCR using the Xbal forward and reverse primers (SEQ NO TKX and TKY) and Reddy mix at 60° C. annealing temperature and cutting with the Xbal restriction enzyme overnight at 37° C. The wild-type allele would be cut by this enzyme and produce two bands (189 bp, 25 bp) while the mutant would remain at 215 bp. These tests showed that all of the seed that UC Davis sent were homozygous for the mutant allele Atcenh3-1, and that there were multiple copies of the ZmCENH3 transgene present.

Confident that these acquired seeds were indeed haploid inducers, we kept 100 plants and initiated floral dip transformation with binary vector 24075 (SEQ ID NO: 98) containing a sgRNA cassette targeting the *Arabidopsis* (GL1) gene (AT3G27920) at two target sites. The target sequences are 5'-GGAAAAGTTGTAGACTGAGA-3', and 5'-GCAGTGATGAACAATGACGG-3' (complementary strand). The disruption of the GL1 gene produces visible phenotypes of partially or completely glabrous plants (glabrous plants lack trichomes). The Cas9 gene (cCas9-05) in this vector was driven by the *Arabidopsis thaliana* elongation factor promoter. The vector also contains two selectable marker cassettes conferring Kan resistance and AmCyan florescence driven by the CMP-02 promoter and *Glycine max* UBI-01 promoter respectively. The vector was moved into the *agrobacterium* strain EHA101 and then floral dip transformed into the haploid inducer *Arabidopsis* plants.

The transformation protocol was as follows: In the morning we spread 24075 EHA101 RecA *Agrobacterium* obtained from plates to YPSpec100Kan50 plates. We cultured these in 28° C. dark for 24 hours. We prepared infiltration medium (4 L): ½ XMS salts (8.66 g), 1×Gamborg's B5 vitamins (4 ml), 5% (W/V) sucrose (200 g), 0.044 μM BAP (12.5 mg - - - 12.5 mlDMSO) 40 μL, followed by filter sterilization. We then added 250 μl 40 mg/ml AS (20 mg/L) and 25 μl SIlwet L-77(50 μl/L) to 500 ml Infiltration media. Using a loop to collect the *Agrobacterium* and put in 50 ml tube with ~10 ml o the filter sterilization, we suspended the *Agrobacterium* until it produced 1 L with an optical density 600 of 0.54. We dipped the inflorescence shoot in to the suspension medium for 20-30 seconds and used the lid to cover the tray. We repeated this for a second time with another suspension of OD600 of 0.552.

About 4 weeks after transformation, approximately 100,000 self-pollinated seeds were harvested and incubated at 4° C. for two days vernalization, and then the seeds were sterilized by soaking in 70% ethanol for 1 minute and then soaking in 50% (V/V) bleach with 0.05% (v/v) Triton X-100 for a further 10 minutes, then washing the seeds in four changes of sterile water. The seeds were then placed on kanamycin (50 μg/ml) plates for germination-screening/selection in a plant tissue culture room (23° C. day, 24° C. night, 16 hours lighting). 38 positive transformants were identified because they were resistant to the kanamycin selection, and they were grown into seedlings before being transferred onto soil and sampled to test for the presence of the Cas9 T-DNA (assay #3049) as well as the status of the two guide RNA cut sites (assays #3321 and #3322). 10 single copy and 15 2-copy events were identified that had both alleles of GL1 mutated and that had a trichomeless phenotype. These plants were prioritized because they had shown evidence of Cas9 activity (by virtue of the mutated GL1 and the glabrous phenotype), they had the Cas9 transgene and they had the ZmCENH3 transgene by qPCR assay. These plants were induced to flower for a long period of time by keeping them in the following growth conditions: 16 hours light, 23° C. Day 20° C. night temperature, not >60% relative humidity.

At the same time as these haploid inducer plants that were transformed with the Cas9 construct were being identified, we were sowing and growing a population of Landsberg *Erecta* (Ler) seed obtained from the *Arabidopsis* Biological Resource Center at Ohio State University (line #CS20). These are wild type seed and the sequence of the GL1 guide RNA target sites in CS20 match that of the guide RNA in our construct. We allowed both populations to flower and made about 2000 controlled crosses, using the wild-type Ler plants as the male pollen-donor, crossing onto the approximately 25 haploid inducers with the Cas9 construct, which was used as the female. We made up to 100 crosses per female, marking the crossed flowers with a black marker and removing flowers that we did not cross so as to limit the potential of harvesting self-pollinated siliques. In most cases, we emasculated the female flowers prior to pollination by removing the anthers with forceps, again to avoid contamination with self-pollinated seed, but in some cases this was not necessary because the anthers were young or mal-developed.

About 15 days we harvested the siliques which had developed a light brown color. Then we opened the siliques and planted the seeds in the soil. Then put them in the 6° C. (day and light), 8 hours day length, 200 umal/$m^2$s lighting, 60% relative humidity growth chamber for 4 days. Then we transferred them to 16 hours light, 23° C. Day, 20° C. night temperature, not >60% humidity growth chamber for 7-10 days. We observed a high frequency of aborted seed in almost all of the siliques, averaging about 40-50% of the total seeds. This number of aborted embryos is very consistent with the performance of this haploid inducer material in published reports. Without wishing to be constrained by this theory, it has been speculated that the aborted seed is most likely caused by partial or complete genome elimination in the endosperm leading to endosperm imbalance and failure. This is a natural phenomenon in CENH3-type haploid inducer lines during outcross and is likely not connected with the presence of the Cas9 transgene. These aborted embryos do not germinate. Because of the steady and reliable rate of embryo abortion in every outcrossed silique, we ended up using the absence of that phenotype to screen away siliques that were accidental self-pollinations. That way we germinated siliques that had been outcrossed.

In total we recovered approximately 2000 germinated progeny, the majority of which were outcrossed. We identified the edited haploids via a combination of qPCR marker assays and/or phenotypic screening. The markers that we used to detect the edited haploids were as follows.

First, we looked for a “0” score for the ZmCENH3 assay. This indicates that the plant is a haploid because the maternal genome has been lost, and so the ZmCENH3 transgene, which is present in multiple copies of the mother haploid inducer plant, has also been lost. The diploids, in contrast, will be hybrids between the maternal and paternal genome, and will have a “1” or “2” or higher Taqman score for this assay, depending on the copy number of the mother plant. The key is that all diploids will show evidence of this transgene, but paternal haploids, having only the Ler genome, will not and will thus be a “0.”

Second, we looked for a “0” score for the Cas9 assay, which indicates that it is non-transgenic. This can also be seen visually by using a fluorescent light and looking for the CFP fluorescent marker.

Third, we looked for a “0” score for one of the GL1 target site assays, which indicates that the plant has been edited. The diploid plants might show a “0,” “1” or “2” for those assays, but the haploids either showed a “2” or a “0.” The first of the two GL1 guide RNAs apparently had a much higher editing efficiency than the second, because assay 3321 had a high preponderance of “0”s and “1”s in the haploid inducer T0s, but 3322 had mostly “2”s.

Using these assays, we were able to identify unedited haploids (which were “0” for ZmCENH3 and Cas9, but had “2” scores for both GL1 target sites) and also edited haploids (which had a “0” for the ZmCENH3, Cas9 and GL1 (3321) assays). We were also able to identify diploid hybrids that had Cas9 (and often were edited at the GL1 sites) and diploid hybrids that did not have Cas9 (and often had one copy of GL1 edited (from the maternal parent) but not the other, and thus had a score of “1” for the GL1 assay. We were also able to identify several putative edited haploids because they had a score of “0” for the target site assay (3321), the ZmCENH3 (2298) and the Cas9 (3049). See Table 9 below for an example of progeny Taqman data from parent USR01424136 containing three putative edited haploids (plant 254 in well F2, plant 260 in well D3, and plant 261 in plant E3).

TABLE 9

Progeny analysis from parent USR01424136.

| PLATE 1045 | | AtGL1-1 cut site 3321 | | AtGL1-2 cut site 3322 | | ZmCENH3 2298 | | Cas9 3049 | | | |
|---|---|---|---|---|---|---|---|---|---|---|---|
| Well | HI parent was single copy Cas9 Plant ID | Raw Copy# | Copy# level | Raw Copy# | Copy# level | Raw Copy# | Copy# level | Raw Copy# | Copy# level | Putative Haploid | Putative Edited |
| E2 | USR01424136 X Ler-253 | 0.06 | 0 | 0.87 | 1 | 4.30 | >2 | 2.93 | >2 | | x |
| F2 | USR01424136 X Ler-254 | 0.00 | 0 | 0.32 | 0 or 1 | 0.00 | 0 | 0.00 | 0 | x | x |
| G2 | USR01424136 X Ler-255 | 1.32 | 1 or 2 | 2.06 | 2 | 3.16 | >2 | 0.00 | 0 | | |
| H2 | USR01424136 X Ler-256 | 0.02 | 0 | 0.99 | 1 | 2.51 | >2 | 2.99 | >2 | | x |
| A3 | USR01424136 X Ler-257 | 0.04 | 0 | 0.87 | 1 | 2.40 | 2 | 2.84 | >2 | | x |
| B3 | USR01424136 X Ler-258 | 0.03 | 0 | 1.64 | 2 | 2.99 | >2 | 3.17 | >2 | | x |
| C3 | USR01424136 X Ler-259 | 0.03 | 0 | 1.21 | 1 | 5.28 | >2 | 5.28 | >2 | | x |
| D3 | USR01424136 X Ler-260 | 0.06 | 0 | 2.01 | 2 | 0.00 | 0 | 0.00 | 0 | x | x |
| E3 | USR01424136 X Ler-261 | 0.00 | 0 | 2.01 | 2 | 0.01 | 0 | 0.00 | 0 | x | x |
| F3 | USR01424136 X Ler-262 | 2.04 | 2 | 2.10 | 2 | 0.00 | 0 | 0.00 | 0 | x | |

TABLE 9-continued

| Progeny analysis from parent USR01424136. | | | | | | | | | | | |
|---|---|---|---|---|---|---|---|---|---|---|---|
| PLATE 1045 | | AtGL1-1 cut site 3321 | | AtGL1-2 cut site 3322 | | ZmCENH3 2298 | | Cas9 3049 | | | |
| HI parent was single copy Cas9 Well | Plant ID | Raw Copy# | Copy# level | Raw Copy# | Copy# level | Raw Copy# | Copy# level | Raw Copy# | Copy# level | Putative Haploid | Putative Edited |
| G3 | USR01424136 X Ler-263 | 1.36 | 1 or 2 | 1.25 | 1 | 0.00 | 0 | 0.00 | 0 | x | |
| H3 | USR01424136 X Ler-264 | 1.75 | 2 | 1.71 | 2 | 0.00 | 0 | 0.00 | 0 | x | |
| A4 | USR01424136 X Ler-265 | 0.00 | 0 | 1.67 | 2 | 3.06 | >2 | 3.16 | >2 | | x |
| B4 | USR01424136 X Ler-266 | 1.66 | 2 | 2.32 | 2 | 0.00 | 0 | 0.00 | 0 | x | |
| C4 | USR01424136 X Ler-267 | 2.09 | 2 | 1.94 | 2 | 3.99 | >2 | 0.00 | 0 | | |
| D4 | USR01424136 X Ler-268 | 1.47 | 1 or 2 | 2.08 | 2 | 6.34 | >2 | 1.51 | 1 or 2 | | |
| E4 | USR01424136 X Ler-269 | 1.95 | 2 | 1.76 | 2 | 3.19 | >2 | 0.00 | 0 | | |
| F4 | USR01424136 X Ler-270 | 1.92 | 2 | 2.17 | 2 | 4.28 | >2 | 0.02 | 0 | | |
| G4 | USR01424136 X Ler-271 | 2.02 | 2 | 1.85 | 2 | 4.31 | >2 | 0.00 | 0 | | |
| H4 | USR01424136 X Ler-272 | 0.00 | 0 | 1.71 | 2 | 1.65 | 2 | 1.12 | 1 | | x |

Simply by germinating seeds and sampling for qPCR Taqman analysis, we were able to identify 8 putative edited haploids. Edited haploids were also identified by phenotypic visual screening, and then confirmed later by Taqman assay. We screened for the edited haploids by looking for trichomeless, or glabrous, plants, which indicated that they did not have any wild-type alleles for the GL1 gene, and by looking for a lack of cyan fluorescent protein ("CFP") expression in the embryo or seedling root. This indicated that they lacked the Cas9 T-DNA. We observed several of these plants, and submitted them for Taqman assays. For three such plants that we identified phenotypically, we were able to confirm that they were truly edited haploids by the Taqman assays. We were aware of the fact that it is possible that some of these glabrous plants that lack CFP were false positives, either because the CFP was silent or because of self-pollination of the fully-edited mother plant and production of null segregant, fully edited (and thus glabrous) progeny. The Taqman assays were able to detect and screen out these false positives, because they directly tested for the presence of not only the Cas9 transgene, but also the ZmCENH3 allele, which would certainly be present in any self-pollinated contaminating seed. We found several examples of self-pollinated seed that all came from one mother plant. The pollination notes for that mother indicated that there was highly abundant pollen that may have resulted in some self-pollination. We excluded these progeny from the total analysis.

Figure 24:
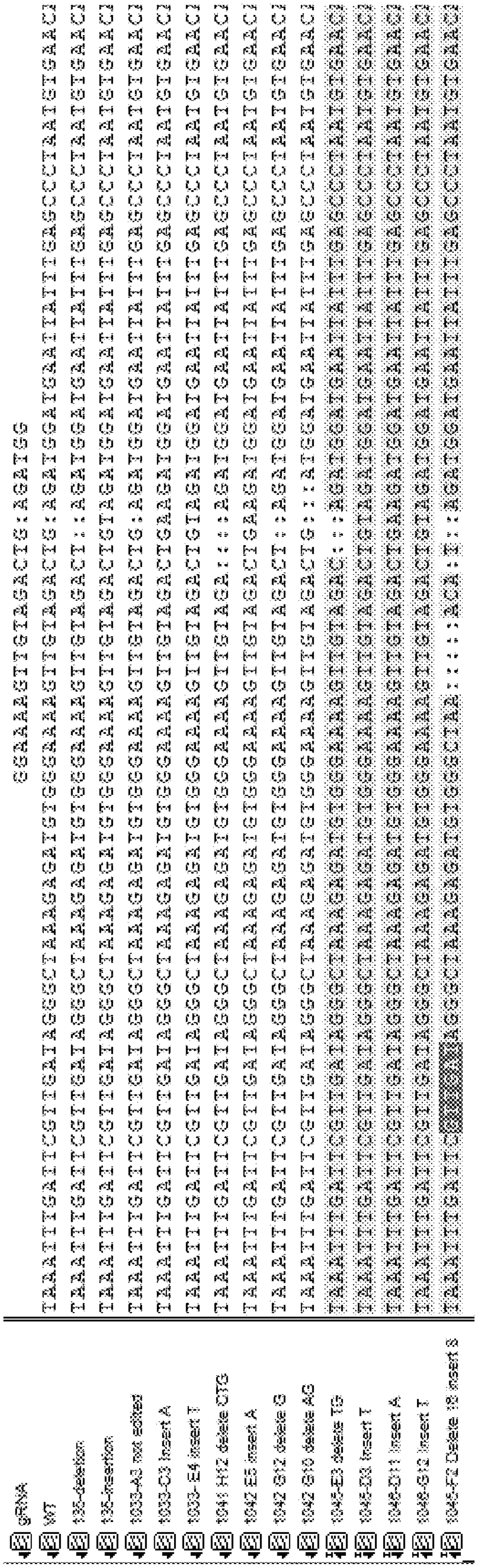
FIG. 24 shows the GL1 target site sequence mutations in the parent #USR01424135 and all of the sequenced edited haploids from outcrosses by Landsberg erecta pollen. It is clear that the precise edit made is different in the different haploids. From top to bottom, the sequences shown are represented by SEQ ID NOs: 102-117, respectively.

All of the putative edited haploids identified by Taqman assay were sequenced. We used PCR to amplify the edited alleles, and then subcloned and sequenced at least 8 colonies for each putative edited allele. See Table 10 for the sequence changes we found in the edited haploids at the first guide RNA (assay #3321) target site, as well as the Taqman data from the T0 parents. In total, we found 19 putative edited haploids, and we confirmed that the 3321 target sites had mutations in 11 of the 12 edited haploids that we attempted to sequence. Whether the other 7 would also have mutations will be confirmed upon sequencing. See the sequence alignment for these edits in FIG. 24.

TABLE 10

| Taqman and sequence data from 19 edited haploids. | | | | | | | | | | | | |
|---|---|---|---|---|---|---|---|---|---|---|---|---|
| | | | AtGL1-1 cut site 3321 | | AtGL1-2 cut site 3322 | | ZmCENH3 2298 | | Cas9 3049 | | Target | |
| Plate | Well | Plant ID | Raw Copy# | Copy# level | Raw Copy# | Copy# level | Raw Copy# | Copy# level | Raw Copy# | Copy# level | site mutation | PA confirm? |
| 1033 | A3 | USR01424135 X Ler-425 | 0.00 | 0 | 1.67 | 2 | 0.04 | 0 | 0.00 | 0 | wild type | Not done |
| 1033 | C3 | USR01424135 X Ler-427 | 0.21 | 0 | 2.43 | >2 | 0.01 | 0 | 0.00 | 0 | insert A | Yes |
| 1033 | E4 | USR01424135 X Ler-437 | 0.08 | 0 | 2.04 | 2 | 0.00 | 0 | 0.00 | 0 | insert T | Yes |
| 1042 | E5 | USR01424136 X Ler-25 | 0.16 | 0 | 2.95 | >2 | 0.00 | 0 | 0.00 | 0 | insert A | Not done |
| 1042 | G10 | USR01424136 X Ler-67 | 0.00 | 0 | 2.19 | 2 | 0.00 | 0 | 0.00 | 0 | delete AG | Not done |
| 1042 | G12 | USR01424136 X Ler-83 | 0.00 | 0 | 1.86 | 2 | 0.00 | 0 | 0.00 | 0 | delete G | Not done |
| 1043 | B11 | USR01424136 X Ler-154 | 0.16 | 0 | 1.59 | 1 or 2 | 0.01 | 0 | 0.00 | 0 | Not done | Not done |
| 1045 | F2 | USR01424136 X Ler-254 | 0.00 | 0 | 0.32 | 0 or 1 | 0.00 | 0 | 0.00 | 0 | delete 8nt* | Not done |
| 1045 | D3 | USR01424136 X Ler-260 | 0.06 | 0 | 2.01 | 2 | 0.00 | 0 | 0.00 | 0 | insert T | Not done |
| 1045 | E3 | USR01424136 X Ler-261 | 0.00 | 0 | 2.01 | 2 | 0.01 | 0 | 0.00 | 0 | delete TG | Not done |
| 1046 | D11 | USR01431609 X Ler-111 | 0.09 | 0 | 1.59 | 1 or 2 | 0.02 | 0 | 0.01 | 0 | insert A | Not done |
| 1046 | G12 | USR01431609 X Ler-122 | 0.02 | 0 | 1.62 | 2 | 0.00 | 0 | 0.00 | 0 | insert T | Not done |
| 1046 | H12 | USR01431609 X Ler-123 | 0.00 | 0 | 0.00 | 0 | 0.00 | 0 | 0.00 | 0 | delete CTG | Yes |
| 0583 | D12 | USR01431603 X Ler-80 | 0.00 | 0 | 1.50 | 1 or 2 | 0.00 | 0 | 0.00 | 0 | Not done | Not done |
| 0584 | A9 | USR01431603 X Ler-137 | 0.00 | 0 | 1.87 | 2 | 0.00 | 0 | 0.00 | 0 | Not done | Not done |
| 0584 | C11 | USR01431603 X Ler-155 | 0.05 | 0 | 2.06 | 2 | 0.00 | 0 | 0.17 | 0 | Not done | Not done |
| 0584 | G11 | USR01431603 X Ler-159 | 0.09 | 0 | 2.15 | 2 | 0.00 | 0 | 0.00 | 0 | Not done | Not done |
| 0584 | C12 | USR01431603 X Ler-163 | 0.00 | 0 | 1.35 | 1 or 2 | 0.00 | 0 | 0.11 | 0 | Not done | Not done |
| 0584 | F12 | USR01431603 X Ler-166 | 0.00 | 0 | 1.65 | 2 | 0.00 | 0 | 0.00 | 0 | Not done | Not done |
| 0585 | H7 | USR01431603 X Ler-212 | 0.06 | 0 | 2.05 | 2 | 0.00 | 0 | 0.01 | 0 | Not done | Not done |
| Female Parent | | USR01424135 | 0.03 | 0 | 1.42 | 1 or 2 | 4.46 | >2 | 2.98 | >2 | ΔG, +T chimera | Diploid |

TABLE 10-continued

Taqman and sequence data from 19 edited haploids.

| Plate | Well | Plant ID | AtGL1-1 cut site 3321 Raw Copy# | AtGL1-1 cut site 3321 Copy# level | AtGL1-2 cut site 3322 Raw Copy# | AtGL1-2 cut site 3322 Copy# level | ZmCENH3 2298 Raw Copy# | ZmCENH3 2298 Copy# level | Cas9 3049 Raw Copy# | Cas9 3049 Copy# level | Target site mutation | PA confirm? |
|---|---|---|---|---|---|---|---|---|---|---|---|---|
| T0 | | USR01424136 | 0.03 | 0 | 1.13 | 1 | 3.59 | >2 | 2.76 | >2 | Not done | Diploid |
| Plants | | USR01431603 | 0.14 | 0 | 1.25 | 1 | 2.48 | >2 | 3.42 | >2 | Not done | Diploid |
| | | USR01431609 | 0.18 | 0 | 1.1 | 1 | 4.75 | >2 | 5.57 | >2 | Not done | Diploid |

*delete 16 nt insert CTAAACAT

We further ran leaf samples from three edited haploid plants through ploidy analysis, along with three diploid controls (tissue sampled from the maternal parent plants), which showed that they were true haploids (FIGS. 18-23). This served to reconfirm their status as edited haploids.

In three parental lines where we were confident that there was no self-pollination contamination, we did not do any phenotypic pre-screening, but instead sampled all germinated progeny for Taqman analysis (Table 11). The three female parents for these progeny were USR01431603, USR01431609, and USR01431604. We found a haploid induction rate of about 9.7% calculated by dividing the number of progeny that lack the ZmCENH3 and Cas9 transgenes (59) by the total number of progeny sampled (605). Of the 59 haploids we found that 10 were edited. That means 16.9% of haploids, on average, were edited by the maternal Cas9, prior to elimination of the maternal genome. Without wishing to be constrained by this final number, this means that, using this system, as a percentage of total progeny, 9.7%*16.9%=1.64% of all germinated progeny were edited haploids.

TABLE 11

Haploid induction rate and editing rate data from three sets of progeny, each derived from a different SEDHI inducer female parent crossed by Landsberg erecta pollen.

| ID | Parent plant Cas9-05 | Parent plant cNpt2-10 | Total samples | Haploid number | Haploid rate | Edited Haploid | Edited Haploid rate |
|---|---|---|---|---|---|---|---|
| USR01431603 X Landsberg erecta | >2 | >2 | 230 | 36 | 15.65 | 7 | 19.44 |
| USR01431609X Landsberg erecta | >2 | >2 | 123 | 14 | 11.38 | 3 | 21.43 |
| USR01431604 X Landsberg erecta | 2 | 1 | 252 | 9 | 3.57 | 0 | 0.00 |

The rate of CENH3* type haploid editing or other paternal haploid editing (using a maternal haploid inducer line) might be increased through the use of a promoter that drives the expression of Cas9 and/or the guide RNA to a higher level in the egg cell before fertilization and/or in the zygote cell during or after fertilization. An example of such a promoter would the promoter for EA1 (EGG APPARATUS1) (GRMZM2G456746), although there are many other examples. One could also express the Cas9 in the context of an egg apparatus-specific enhancer (EASE), which is a 77-bp sequence that stimulates expression of adjoining genes in the egg cell or the very early zygote (see, e.g., Yang, et al. *An Egg Apparatus-Specific Enhancer of Arabidopsis, Identified by Enhancer Detection*, PLANT PHYSIOLOGY November 2005, 139 (3) 1421-1432; DOI: https://doi.org/10.1104/pp. 105.068262).

VIII. Simultaneous Haploid Induction and Editing by Directly Modifying a Target Base in Genomic DNA Sequence.

Targeted mutagenesis of DNA sequence can also be achieved through direct conversion of one DNA base to another without requiring double stranded breaks (DSBs). For example, cytidine deaminase APOBEC1, adenine deaminase, and other enhancing components like Uracil DNA glycosylase (UDG) can be fused to Cas9 (A840H) nickase or nuclease-inactivated dead Cas9 (dCa9) to direct editing of DNA sequence without introducing double strand DNA breaks (Komor et al. 2016. Programmable editing of a target base in genomic DNA without double-stranded DNA cleavage. Nature doi:10.1038/nature17946; Gaudelli et al. 2017. Programmable base editing of A:T to G:C in genomic DNA without DNA cleavage. Nature doi:10.1038/nature24644; Komor et al. 2017. Improved base excision repair inhibition and bacteriophage Mu Gam protein yields C:G-to-T:A base editors with higher efficiency and product purity. *Science Advances*, Vol. 3, no. 8, eaao4774, DOI: 10.1126/sciadv.aao4774). This kind of base editor machinery can also be delivered through haploid induction line to induce base editing in target sequences directly in other varieties. For example, a guide RNA sequence, xZmVLHP-03 (5'-AGGCGTCGAGCAGCGAGGTG-3', SEQ ID NO: 28) is designed to target the cytidine deaminase base editor system to convert ZmVLHP gene exon 2 genomic sequence 5'-AGGCGT<u>C</u>GAGCAGCGAGGTG-3' (SEQ ID NO: 28) into 5'-AGGCGT<u>T</u>GAGCAGCGAGGTG-3' (SEQ ID NO: 29), thus changing the arginine codon CGA into a stop codon (TGA) in the coding sequence and causing premature termination of the protein sequence and functional gene knockout. The C to T mutation is underlined. Similarly, chimeric nCas9- or dCas9-adenine deaminase base editing system can be used to mutate the coding region, splicing junction or promoter sequence of ZmVLHP or other genes to generate variants that have altered gene activity. Both cytidine and adenine deaminase are particularly useful for altering transcript splicing site since canonical splicing junction has 5'- . . . AG/GT . . . 3' sequence (or 5'- . . . AC/CT . . . 3' in the opposite strand).

IX. Simultaneous Haploid Induction and Editing by Allele Replacement with DNA Template Not only can in vivo haploid induction system be used to introduce protein, RNA or DNA for cleavage or conversion of target sequence, it can also be used to deliver DNA template for homology-dependent repair for precise sequence replacement in the target region in the form of transgenic DNA. The template DNA can be inserted into the inducer line genome carrying genome editing machinery such as CRISPR-Cas9 system, either in the same transgenic locus or different locus. When both Cas9-sgRNA and template DNA are present in the induced haploid embryos, cleavage of the target sequence will result in repair of the chromosomal break with the homologous transgenic DNA sequence as template. For example, for creating E149L mutation in ZmPYL-D gene (GRMZM2G048733_P02) (see WO16033230, incorporated herein by reference), DNA fragment containing donor sequence (5'-CCTTGGTGTTGCCGTCGGGGACGTCGACGACGAATGACAGGATGACGAGCGTCC CTGGCCGGCCGTCGATGACCT-3', SEQ ID NO: 30) is used as repair donor. It should be noted that additional homology sequences can be added to flank this core repair donor sequence. One or more copies of this repair donor sequence are inserted into Cas9-sgRNA expression vector 23136 (SEQ ID NO: 31) which expresses guide RNA 5'-GTCGGGGACGTCGACGACGA-3' (SEQ ID NO: 32) to form allele modification vector pBSC23136-AMD. It should be noted that the potential PAM site has been removed from the donor DNA sequences so that the integrated donor sequence will not be cleaved by the Cas9-sgRNA complex expressed from pBSC23136-AMD. pBSC23136-AMD is transformed into haploid inducer line NP2222-HI to generate transgenic editing line. Transgenic editing-haploid induction lines are selfed to produce progeny lines homozygous editing loci. These homozygous lines are used to pollinate target elite maize inbred lines to induce haploid formation and also introduce modified alleles by expressed Cas9-sgRNA using donor DNA present transiently before pollen donor chromosomes are eliminated.

X. Inducing Haploids and Simultaneous Gene Editing in Rice

A HI-rice line is obtained. For example, the rice MATL ortholog, Os03g27610 (SEQ ID NO: 33, is mutated to create a new rice HI line. This line is transformed with a vector comprising a site-directed mutagenesis system for editing the rice genome, for example the CRISPR/Cas9 system.

The rice HI line is crossed with a different rice line, preferably an elite line, to produce at least one progeny haploid embryo. During the cross to produce at least one progeny haploid embryo, the HI parent rice plant also causes the genome editing machinery, e.g., Cas9 plus a guide RNA, to be delivered to the embryo. At that point, the editing machinery operates to edit the genome of the haploid embryo, and thus an edited, haploid progeny plant is obtained.

XI. Taqman Assays and Conditions.

Several assays are mentioned by number or by target name. Provided below is a table of assays mentioned above and the sequences of the relevant primers and probes. Conditions for PCR are standard for all assays and are as follows: Denature at 98° C. for 2 minutes; followed by 35 cycles of (i) denature at 98° C. for 30 seconds, (ii) anneal at 60° C. for 30 seconds, (iii) extension at 72° C. for 1 minute; followed by final extension at 72° C. for 10 minutes with a hold at 4° C. until ready. Assays are carried out at these conditions unless otherwise noted below.

TABLE 11

Assay primers and probes.

| Target | Assay No. | Sequence | SEQ ID NO: |
|---|---|---|---|
| | Cas9-in corn 2540 | | |
| Forward Primer | FE09340 | TTGTGCTGCTCCACGAACA | 39 |
| Reverse Primer | FE09341 | GCCAGCCACTACGAGAAGCT | 40 |
| Probe | FE09342 | CTGCTTCTGCTCGTTGTCCTCCGG | 41 |
| | mat1 2827 | | |
| Forward Primer | FE10299 | GCGGATGCTGGCACAGC | 42 |
| Reverse Primer | FE10300 | GGCATTGCTTCCTTCTCCG | 43 |
| Probe | FE10301 | CAGGGAGCGAGGTAC | 44 |
| | PMI 1750 | | |
| Forward Primer | FE07390 | CTGGTGGCCAACGTGAAGTT | 45 |
| Reverse Primer | FE07391 | GCTTCACGGGCTGGGTC | 46 |
| Probe | FE07392 | AGGCCAAGCCCGCCAACCAG | 47 |
| | MATL-WT 2826 | | |
| Forward Primer | FE10297 | GCGGATGCTGGCACAGA | 48 |
| Reverse Primer | FE10298 | GCATTGCTTCCTTCGCCA | 49 |
| Probe | FE10299 | CAGGGAGGTACGAACC | 50 |
| | TAV_4A 3252 | | |
| Forward Primer | FE11306 | GCGGCGAAGAAGCGAA | 51 |
| Reverse Primer | FE11307 | GCGGCGTCTCCAGCTTC | 52 |
| Probe | FE11308 | CCAGGAACTGCG | 53 |

TABLE 11-continued

Assay primers and probes.

| Target Assay No. | | Sequence | SEQ ID NO: |
|---|---|---|---|
| | TAV_4B 3253 | | |
| Forward Primer | FE11309 | AAGAAACGCCGGCTGAGT | 54 |
| Reverse Primer | FE11310 | ACCTTGCGGGGCGTT | 55 |
| Probe | FE11308 | CCAGGAACTGCG | 56 |
| | TAV_4D 3254 | | |
| Forward Primer | FE11309 | AAGAAACGCCGGCTGAGT | 57 |
| Reverse Primer | FE11311 | CCTTGCGCGGCGTC | 58 |
| Probe | FE11308 | CCAGGAACTGCG | 59 |
| | GW2-01 3065 | | |
| Forward Primer | FE10799 | TGATCCTCGAGGCCAAGCT | 60 |
| Reverse Primer | FE10800 | AGGTCGAGGTCCCCTCCA | 61 |
| Probe | FE10801 | CCTGCTACCCGGGC | 62 |
| | GW2-02 3095 | | |
| Forward Primer | FE10991 | CGCGCCCTGCTACCC | 63 |
| Reverse Primer | FE10992 | GCGCGTGCTTACCAGGA | 64 |
| Probe | FE10993 | TCGAGGAGTGCCC | 65 |
| | TaVHLP2-2A 3332 | | |
| Forward Primer | FE11312 | CACCGATGAGCAGGCG | 66 |
| Reverse Primer | FE11313 | AGATACACCTTCCGGCCG | 67 |
| Probe | FE11314 | TTCCTCCCGGAAGC | 68 |
| | TaVHLP2-2D 3333 | | |
| Forward Primer | FE11312 | CACCGATGAGCAGGCG | 69 |
| Reverse Primer | FE11313 | AGATACACCTTCCGGCCAGT | 70 |
| Probe | FE11314 | CTCCTCCCGGAAGC | 71 |

TABLE 11-continued

Assay primers and probes.

| Target Assay No. | | Sequence | SEQ ID NO: |
|---|---|---|---|
| | 3049 | | |
| Forward Primer | FE10730 | CAAGTTTCTGGACAAGGAGATTCTC | 72 |
| Reverse Primer | FE10731 | AAGAATTCCCTTCTTAATAGCTGGAGA | 73 |
| Probe | FE10732 | CACGAGCACATTGCTAACCTTGCTGG | 74 |
| | TaVHLP2-2B 3255 | | |
| Forward Primer | FE11315 | TCACCGATGAGCAGGCA | 75 |
| Reverse Primer | FE11316 | ATACACCTTCCGGCCAGC | 76 |
| Probe | FE11317 | TTCCTCCCGGAAGC | 77 |
| | 3321 | | |
| Forward Primer | FE11540 | GATAGGGCTAAAGAGATGTGGGAA | 78 |
| Reverse Primer | FE11541 | CTTTGTTCACATTAGGGCTCAAATAA | 79 |
| Probe | FE11542 | TAGACTGAGATGGATG | 80 |
| | 3322 | | |
| Forward Primer | FE11543 | AAAACCACCGGAGAAGACGA | 81 |
| Reverse Primer | FE11544 | AGGTGTGGCGGCAGTGA | 82 |
| Probe | FE11545 | CACCGTCATTGTTC | 83 |
| | Cas9-in Arabidopsis 3049 | | |
| Forward Primer | FE10730 | CAAGTTTCTGGACAAGGAGATTCTC | 84 |
| Reverse Primer | FE10731 | AAGAATTCCCTTCTTAATAGCTGGAGA | 85 |
| Probe | FE10732 | CACGAGCACATTGCTAACCTTGCTGG | 86 |
| | ZmCENH3 2298 | | |
| Forward Primer | FE08737 | GCGACGCCGGAAAGG | 87 |
| Reverse Primer | FE08738 | TGGCGTGGTTTCGTCTTCTTA | 88 |
| Probe | FE08739 | AAGAGCGGCGTCTGGAGGTGACTCA | 89 |

TABLE 11-continued

Assay primers and probes.

| Target Assay No. | | Sequence | SEQ ID NO: |
|---|---|---|---|
| | GL1 3321 target site (PCR) | | |
| Forward Primer | 3321F | AACCGCATCGTCAG AAAAAC | 90 |
| Reverse Primer | 3321R | TCAACTTAACCGGC CAAATC | 91 |
| Annealing Temp. | 60° C. | | |
| | VLHP2-2A target site (PCR) | | |
| Forward Primer | FE4117 | CATCCCTTCTCTTC CCTCCTG | 92 |
| Reverse Primer | FE4118 | GCCAGTGTGAGTGT GTATGAGCA | 93 |
| Annealing Temp. | 61° C. | | |
| | VLHP2-2B target site (PCR) | | |
| Forward Primer | FE4120 | CATCGTTTTCTCCC CTCCTCA | 94 |
| Reverse Primer | FE4121 | ACTGATATGCACGG CGCCA | 95 |
| Annealing Temp. | 62° C. | | |
| | VLHP2-2D target site (PCR) | | |
| Forward Primer | FE4121 | TGCAGTAGCTTCAT TTTCACCG | 96 |
| Reverse Primer | FE4122 | AGGAATTGATATGT ACGCCCGT | 97 |
| Annealing Temp. | 61° C. | | |

What is claimed is:

1. A method of editing maize genomic DNA, comprising:

a) obtaining a first maize plant comprising a loss-of-function mutation in a wildtype patatin-like phospholipase A2α gene having a cDNA sequence as represented by SEQ ID NO: 19, wherein said first maize plant expresses a DNA modification enzyme and optionally at least one guide nucleic acid;

b) obtaining a second maize plant, wherein the second maize plant comprises the maize plant genomic DNA which is to be edited;

c) pollinating the second maize plant with pollen from the first maize plant; and d) selecting at least one haploid progeny produced by the pollination of step (c) wherein the haploid progeny comprises the genome of the second maize plant but not the first maize plant, and the genome of the haploid progeny has been modified by the DNA modification enzyme and optional at least one guide nucleic acid delivered by the first maize plant.

2. The method of claim 1, wherein the DNA modification enzyme is a site-directed nuclease selected from the group consisting of meganucleases (MNs), zinc-finger nucleases (ZFNs), transcription-activator like effector nucleases (TALENs), Cas9 nuclease, Cfp1 nuclease, dCas9-FokI, dCpf1-FokI, chimeric Cas9-cytidine deaminase, chimeric Cas9-adenine deaminase, chimeric FEN1-FokI, and Mega-TALs, a nickase Cas9 (nCas9), chimeric dCas9 non-FokI nuclease and dCpf1 non-FokI nuclease.

3. The method of claim 1, wherein the at least one guide nucleic acid is a guide RNA.

4. The method of claim 1, wherein the edited haploid progeny is treated with a chromosome doubling agent, thereby creating an edited doubled haploid progeny.

5. The method of claim 4, wherein the chromosome doubling agent is colchicine, pronamide, dithipyr, trifluralin, or another known anti-microtubule agent.

6. The method of claim 3, wherein the guide RNA is an 18-21 nucleotide sequence and is at least 90% identical to a sequence selected from the group consisting of SEQ ID NOs: 2, 4, 8, 21, 23, 25, 29, 32, and 33.

7. The method of claim 1, wherein the first maize plant expresses a marker gene.

8. The method of claim 7, wherein the marker gene is selected from the group consisting of GUS, PMI, PAT, GFP, RFP, CFP, B1, C1, R-nj, and anthocyanin pigments.

9. The method of claim 1, wherein the first maize plant is a transformable maize plant selected and/or derived from the group consisting of lines Stock 6, RWK, RWS, UH400, AX5707RS, and NP2222-matl.

10. The method of claim 1, wherein the loss-of-function mutation in the wildtype patatin-like phospholipase A2α gene is a knock-out mutation.

11. The method of claim 10, wherein the knock-out mutation is a frame-shift mutation in exon 1 or exon 4 of the wildtype patatin-like phospholipase A2α gene.

12. The method of claim 1, wherein the first maize plant comprises SEQ ID NO: 10, 11, 13, 15, or 16.

* * * * *

SEQUENCE LISTING

<160> NUMBER OF SEQ ID NOS: 117

<210> SEQ ID NO 1
<211> LENGTH: 15722
<212> TYPE: DNA
<213> ORGANISM: Artificial Sequence
<220> FEATURE:
<223> OTHER INFORMATION: vector 23396
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (304)..(2100)
<223> OTHER INFORMATION: prSoUbi4-04
<220> FEATURE:
<221> NAME/KEY: gene
<222> LOCATION: (2117)..(6286)
<223> OTHER INFORMATION: cCas9-01
<220> FEATURE:
<221> NAME/KEY: mutation
<222> LOCATION: (5606)..(5608)
<223> OTHER INFORMATION: L to V mutation
<220> FEATURE:
<221> NAME/KEY: mutation
<222> LOCATION: (5651)..(5653)
<223> OTHER INFORMATION: I to V mutation
<220> FEATURE:
<221> NAME/KEY: terminator
<222> LOCATION: (6292)..(6544)
<223> OTHER INFORMATION: tNOS-05-01
<220> FEATURE:
<221> NAME/KEY: promoter
<222> LOCATION: (6551)..(6925)
<223> OTHER INFORMATION: prOsU3-01
<220> FEATURE:
<221> NAME/KEY: misc_feature
<222> LOCATION: (6927)..(6946)
<223> OTHER INFORMATION: xZmVLHP
<220> FEATURE:
<221> NAME/KEY: misc_feature
<222> LOCATION: (6927)..(7032)
<223> OTHER INFORMATION: rsgRNAZmVLHP-01
<220> FEATURE:
<221> NAME/KEY: promoter
<222> LOCATION: (7042)..(9033)
<223> OTHER INFORMATION: prUbi1-04
<220> FEATURE:
<221> NAME/KEY: gene
<222> LOCATION: (9050)..(10228)
<223> OTHER INFORMATION: cPMI-09
<220> FEATURE:
<221> NAME/KEY: terminator
<222> LOCATION: (10251)..(10503)
<223> OTHER INFORMATION: tNOS-05-01
<220> FEATURE:
<221> NAME/KEY: misc_feature
<222> LOCATION: (10547)..(10676)
<223> OTHER INFORMATION: bNLB-03
<220> FEATURE:
<221> NAME/KEY: gene
<222> LOCATION: (10956)..(11744)
<223> OTHER INFORMATION: cSpec-03
<220> FEATURE:
<221> NAME/KEY: promoter
<222> LOCATION: (11839)..(11969)
<223> OTHER INFORMATION: prVirG-01
<220> FEATURE:
<221> NAME/KEY: gene
<222> LOCATION: (12706)..(13779)
<223> OTHER INFORMATION: cRepA-01

<400> SEQUENCE: 1
attcctgtgg ttggcatgca catacaaatg gacgaacgga taaacctttt cacgcccttt 60
taaatatccg attattctaa taaacgctct tttctcttag gtttacccgc caatatatcc 120
tgtcaaacac tgatagttta aactgaaggc gggaaacgac aatctgatca tgagcggaga 180
attaagggag tcacgttatg acccccgccg atgacgcggg acaagccgtt ttacgtttgg 240
aactgacaga accgcaacgc tgcaggaatt ggccgcagcg gccatttaaa caaagcttgg 300
taccattatg tggtctaggt aggttctata tataagaaaa cttgaaatgt tctaaaaaaa 360
aattcaagcc catgcatgat tgaagcaaac ggtatagcaa cggtgttaac ctgatctagt 420
gatctcttgc aatccttaac ggccacctac cgcaggtagc aaacggcgtc cccctcctcg 480
atatctccgc ggcgacctct ggctttttcc gcggaattgc gcggtgggga cggattccac 540
gagaccgcga cgcaaccgcc tctcgccgct gggccccaca ccgctcggtg ccgtagcctc 600
acgggactct ttctccctcc tcccccgtta taaattggct tcatcccctc cttgcctcat 660
ccatccaaat cccagtcccc aatcccatcc cttcgtagga gaaattcatc gaagctaagc 720
gaatcctcgc gatcctctca aggtactgcg agttttcgat ccccctctcg acccctcgta 780
tgtttgtgtt tgtcgtagcg tttgattagg tatgctttcc ctgtttgtgt tcgtcgtagc 840
gtttgattag gtatgctttc cctgttcgtg ttcatcgtag tgtttgatta ggtcgtgtga 900
ggcgatggcc tgctcgcgtc cttcgatctg tagtcgattt gcgggtcgtg gtgtagatct 960
gcgggctgtg atgaagttat ttggtgtgat ctgctcgcct gattctgcgg gttggctcga 1020
gtagatatga tggttggacc ggttggttcg tttaccgcgc tagggttggg ctgggatgat 1080
gttgcatgcg ccgttgcgcg tgatcccgca gcaggacttg cgtttgattg ccagatctcg 1140
ttacgattat gtgatttggt ttggactttt tagatctgta gcttctgctt atgtgccaga 1200
tgcgcctact gctcatatgc ctgatgataa tcataaatgg ctgtggaact aactagttga 1260
ttgcggagtc atgtatcagc tacaggtgta gggactagct acaggtgtag ggacttgcgt 1320

-continued ctaattgttt ggtcctttac tcatgttgca attatgcaat ttagtttaga ttgtttgttc 1380
cactcatcta ggctgtaaaa gggacactgc ttagattgct gtttaatctt tttagtagat 1440
tatattatat tggtaactta ttacccctat tacatgccat acgtgacttc tgctcatgcc 1500
tgatgataat catagatcac tgtggaatta attagttgat tgttgaatca tgtttcatgt 1560
acataccacg gcacaattgc ttagttcctt aacaaatgca aattttactg atccatgtat 1620
gatttgcgtg gttctctaat gtgaaatact atagctactt gttagtaaga atcaggttcg 1680
tatgcttaat gctgtatgtg ccttctgctc atgcctgatg ataatcatat atcactggaa 1740
ttaattagtt gatcgtttaa tcatatatca agtacatacc atgccacaat tttagtcac 1800
ttaacccatg cagattgaac tggtccctgc atgttttgct aaattgttct attctgatta 1860
gaccatatat catgtatttt tttttggtaa tggttctctt attttaaatg ctatatagtt 1920
ctggtacttg ttagaaagat ctgcttcata gtttagttgc ctatccctcg aattaggatg 1980
ctgagcagct gatcctatag ctttgtttca tgtatcaatt cttttgtgtt caacagtcag 2040
tttttgttag attcattgta acttatggtc gcttactctt ctggtcctca atgcttgcag 2100
gatcgcggcc gctcatatgg acaagaagta cagcatcggc ctggacatcg gcaccaacag 2160
cgtgggctgg gccgtgatca ccgacgagta caaggtgccg agcaagaagt tcaaggtgct 2220
gggcaacacc gacaggcaca gcatcaagaa gaacctgatc ggcgccctgc tgttcgacag 2280
cggcgagacc gccgaggcca ccaggctgaa gaggaccgcc aggaggaggt acaccaggag 2340
gaagaacagg atctgctacc tgcaggagat cttcagcaac gagatggcca aggtggacga 2400
cagcttcttc cacaggctgg aggagagctt cctggtggag gaggacaaga agcacgagag 2460
gcacccgatc ttcggcaaca tcgtggacga ggtggcctac cacgagaagt acccgaccat 2520
ctaccacctg aggaagaagc tggtggacag caccgacaag gccgacctga ggctgatcta 2580
cctggccctg gcccacatga tcaagttcag gggccacttc ctgatcgagg gcgacctgaa 2640
cccggacaac agcgacgtgg acaagctgtt catccagctg gtgcagacct acaaccagct 2700
gttcgaggag aacccgatca acgccagcgg cgtggacgcc aaggccatcc tgagcgccag 2760
gctgagcaag agcaggaggc tggagaacct gatcgcccag ctgccgggcg agaagaagaa 2820
cggcctgttc ggcaacctga tcgccctgag cctgggcctg accccgaact tcaagagcaa 2880
cttcgacctg gccgaggacg ccaagctgca gctgagcaag gacacctacg acgacgacct 2940
ggacaacctg ctggcccaga tcggcgacca gtacgccgac ctgttcctgg ccgccaagaa 3000
cctgagcgac gccatcctgc tgagcgacat cctgagggtg aacaccgaga tcaccaaggc 3060
cccgctgagc gccagcatga tcaagaggta cgacgagcac caccaggacc tgaccctgct 3120
gaaggccctg gtgaggcagc agctgccgga gaagtacaag gagatcttct tcgaccagag 3180
caagaacggc tacgccggct acatcgacgg cggcgccagc caggaggagt tctacaagtt 3240
catcaagccg atcctggaga agatggacgg caccgaggag ctgctggtga agctgaacag 3300
ggaggacctg ctgaggaagc agaggacctt cgacaacggc agcatcccgc accagatcca 3360
cctgggcgag ctgcacgcca tcctgaggag gcaggaggac ttctacccgt tcctgaagga 3420
caacagggag aagatcgaga agatcctgac cttccgcatc ccgtactacg tgggcccgct 3480
ggccaggggc aacagcaggt tcgcctggat gaccaggaag agcgaggaga ccatcacccc 3540
gtggaacttc gaggaggtgg tggacaaggg cgccagcgcc cagagcttca tcgagaggat 3600
gaccaacttc gacaagaacc tgccgaacga gaaggtgctg ccgaagcaca gcctgctgta 3660
cgagtacttc accgtgtaca acgagctgac caaggtgaag tacgtgaccg agggcatgag 3720

-continued

```
gaagccggcc ttcctgagcg gcgagcagaa gaaggccatc gtggacctgc tgttcaagac   3780
caacaggaag gtgaccgtga agcagctgaa ggaggactac ttcaagaaga tcgagtgctt   3840
cgacagcgtg gagatcagcg gcgtggagga caggttcaac gccagcctgg gcacctacca   3900
cgacctgctg aagatcatca aggacaagga cttcctggac aacgaggaga acgaggacat   3960
cctggaggac atcgtgctga ccctgaccct gttcgaggac agggagatga tcgaggagag   4020
gctgaagacc tacgcccacc tgttcgacga caaggtgatg aagcagctga agaggaggag   4080
gtacaccggc tggggcaggc tgagcaggaa gctgatcaac ggcatcaggg acaagcagag   4140
cggcaagacc atcctggact tcctgaagag cgacggcttc gccaacagga acttcatgca   4200
gctgatccac gacgacagcc tgaccttcaa ggaggacatc cagaaggccc aggtgagcgg   4260
ccagggcgac agcctgcacg agcacatcgc caacctggcc ggcagcccgg ccatcaagaa   4320
gggcatcctg cagaccgtga aggtggtgga cgagctggtg aaggtgatgg gcaggcacaa   4380
gccggagaac atcgtgatcg agatggccag ggagaaccag accacccaga agggccagaa   4440
gaacagcagg gagaggatga agaggatcga ggagggcatc aaggagctgg gcagccagat   4500
cctgaaggag cacccggtgg agaacaccca gctgcagaac gagaagctgt acctgtacta   4560
cctgcagaac ggcagggaca tgtacgtgga ccaggagctg gacatcaaca ggctgagcga   4620
ctacgacgtg gaccacatcg tgccgcagag cttcctgaag gacgacagca tcgacaacaa   4680
ggtgctgacc aggagcgaca agaacagggg caagagcgac aacgtgccga gcgaggaggt   4740
ggtgaagaag atgaaaaact actggaggca gctgctgaac gccaagctga tcacccagag   4800
gaagttcgac aacctgacca aggccgagag gggcggcctg agcgagctgg acaaggccgg   4860
cttcattaaa aggcagctgg tggagaccag gcagatcacc aagcacgtgg cccagatcct   4920
ggacagcagg atgaacacca agtacgacga gaacgacaag ctgatcaggg aggtgaaggt   4980
gatcaccctg aagagcaagc tggtgagcga cttcaggaag gacttccagt tctacaaggt   5040
gagggagatc aataattacc accacgccca cgacgcctac ctgaacgccg tggtgggcac   5100
cgccctgatt aaaaagtacc cgaagctgga gagcgagttc gtgtacggcg actacaaggt   5160
gtacgacgtg aggaagatga tcgccaagag cgagcaggag atcggcaagg ccaccgccaa   5220
gtacttcttc tacagcaaca tcatgaactt cttcaagacc gagatcaccc tggccaacgg   5280
cgagatcagg aagaggccgc tgatcgagac caacggcgag accggcgaga tcgtgtggga   5340
caagggcagg gacttcgcca ccgtgaggaa ggtgctgtcc atgccgcagg tgaacatcgt   5400
gaagaagacc gaggtgcaga ccggcggctt cagcaaggag agcatcctgc cgaagaggaa   5460
cagcgacaag ctgatcgcca ggaagaagga ctgggacccg aagaagtacg gcggcttcga   5520
cagcccgacc gtggcctaca gcgtgctggt ggtggccaag gtggagaagg gcaagagcaa   5580
gaagctgaag agcgtgaagg agctggtggg catcaccatc atggagagga gcagcttcga   5640
gaagaaccca gtggacttcc tggaggccaa gggctacaag gaggtgaaga aggacctgat   5700
cattaaactg ccgaagtaca gcctgttcga gctggagaac ggcaggaaga ggatgctggc   5760
cagcgccggc gagctgcaga agggcaacga gctggccctg ccgagcaagt acgtgaactt   5820
cctgtacctg gccagccact acgagaagct gaagggcagc ccggaggaca acgagcagaa   5880
gcagctgttc gtggagcagc acaagcacta cctggacgag atcatcgagc agatcagcga   5940
gttcagcaag agggtgatcc tggccgacgc caacctggac aaggtgctga gcgcctacaa   6000
caagcacagg gacaagccga tcagggagca ggccgagaac atcatccacc tgttcaccct   6060
```

-continued gaccaacctg ggcgccccgg ccgccttcaa gtacttcgac accaccatcg acaggaagag 6120
gtacaccagc accaaggagg tgctggacgc caccctgatc caccagagca tcaccggcct 6180
gtacgagacc aggatcgacc tgagccagct gggcggcgac agcagcccgc cgaagaagaa 6240
gaggaaggtg agctggaagg acgccagcgg ctggagcagg atgtgaagct tgatcgttca 6300
aacatttggc aataaagttt cttaagattg aatcctgttg ccggtcttgc gatgattatc 6360
atataatttc tgttgaatta cgttaagcat gtaataatta acatgtaatg catgacgtta 6420
tttatgagat gggtttttat gattagagtc ccgcaattat acatttaata cgcgatagaa 6480
aacaaaatat agcgcgcaaa ctaggataaa ttatcgcgcg cggtgtcatc tatgttacta 6540
gatcttcgaa gggatcttta aacatacgaa cagatcactt aaagttcttc tgaagcaact 6600
taaagttatc aggcatgcat ggatcttgga ggaatcagat gtgcagtcag ggaccatagc 6660
acaggacagg cgtcttctac tggtgctacc agcaaatgct ggaagccggg aacactgggt 6720
acgttggaaa ccacgtgatg tggagtaaga taaactgtag gagaaaagca tttcgtagtg 6780
ggccatgaag cctttcagga catgtattgc agtatgggcc ggcccattac gcaattggac 6840
gacaacaaag actagtatta gtaccacctc ggctatccac atagatcaaa gctggtttaa 6900
aagagttgtg cagatgatcc gtggcagcag gaggcgtcga gcagcggttt tagagctaga 6960
aatagcaagt taaaataagg ctagtccgtt atcaacttga aaaagtggca ccgagtcggt 7020
gctttttttt tcggaccgcg cctgcagtgc agcgtgaccc ggtcgtgccc ctctctagag 7080
ataatgagca ttgcatgtct aagttataaa aaattaccac atattttttt tgtcacactt 7140
gtttgaagtg cagtttatct atctttatac atatatttaa actttactct acgaataata 7200
taatctatag tactacaata atatcagtgt tttagagaat catataaatg aacagttaga 7260
catggtctaa aggacaattg agtattttga caacaggact ctacagtttt atctttttag 7320
tgtgcatgtg ttctcctttt tttttgcaaa tagcttcacc tatataatac ttcatccatt 7380
ttattagtac atccatttag ggtttagggt taatggtttt tatagactaa tttttttagt 7440
acatctattt tattctattt tagcctctaa attaagaaaa ctaaaactct attttagttt 7500
ttttatttaa taatttagat ataaaataga ataaaataaa gtgactaaaa attaaacaaa 7560
taccctttaa gaaattaaaa aaactaagga aacatttttc ttgtttcgag tagataatgc 7620
cagcctgtta aacgccgtcg acgagtctaa cggacaccaa ccagcgaacc agcagcgtcg 7680
cgtcgggcca agcgaagcag acggcacggc atctctgtcg ctgcctctgg acccctctcg 7740
agagttccgc tccaccgttg gacttgctcc gctgtcggca tccagaaatt gcgtggcgga 7800
gcggcagacg tgagccggca cggcaggcgg cctcctcctc ctctcacggc accggcagct 7860
acgggggatt cctttcccac cgctccttcg ctttcccttc ctcgcccgcc gtaataaata 7920 gacacccct ccacaccctc tttccccaac ctcgtgttgt tcggagcgca cacacacaca 7980
accagatctc ccccaaatcc acccgtcggc acctccgctt caaggtacgc cgctcgtcct 8040
cccccccccc cctctctacc ttctctagat cggcgttccg gtccatggtt agggcccggt 8100
agttctactt ctgttcatgt ttgtgttaga tccgtgtttg tgttagatcc gtgctgctag 8160
cgttcgtaca cggatgcgac ctgtacgtca gacacgttct gattgctaac ttgccagtgt 8220
ttctctttgg ggaatcctgg gatggctcta gccgttccgc agacgggatc gatttcatga 8280
ttttttttgt ttcgttgcat agggtttggt ttgccctttt cctttatttc aatatatgcc 8340
gtgcacttgt ttgtcgggtc atcttttcat gctttttttt gtcttggttg tgatgatgtg 8400
gtctggttgg gcggtcgttc tagatcggag tagaattctg tttcaaacta cctggtggat 8460

-continued

```
ttattaattt tggatctgta tgtgtgtgcc atacatattc atagttacga attgaagatg   8520
atggatggaa atatcgatct aggataggta tacatgttga tgcgggtttt actgatgcat   8580
atacagagat gctttttgtt cgcttggttg tgatgatgtg gtgtggttgg gcggtcgttc   8640
attcgttcta gatcggagta gaatactgtt tcaaactacc tggtgtattt attaattttg   8700
gaactgtatg tgtgtgtcat acatcttcat agttacgagt ttaagatgga tggaaatatc   8760
gatctaggat aggtatacat gttgatgtgg gttttactga tgcatataca tgatggcata   8820
tgcagcatct attcatatgc tctaaccttg agtacctatc tattataata aacaagtatg   8880
ttttataatt attttgatct tgatatactt ggatgatggc atatgcagca gctatatgtg   8940
gattttttta gccctgcctt catacgctat ttatttgctt ggtactgttt cttttgtcga   9000
tgctcaccct gttgtttggt gttacttctg cagggatccg gcagcagcca tgcagaagct   9060
gatcaacagc gtgcagaact acgcctgggg cagcaagacc gccctgaccg agctgtacgg   9120
catggagaac cccagcagcc agcccatggc cgagctgtgg atgggcgccc accccaagag   9180
cagcagccgc gtgcagaacg ccgccggcga catcgtgagc ctgcgcgacg tgatcgagag   9240
cgacaagagc accctgctgg gcgaggccgt ggccaagcgc ttcggcgagc tgcccttcct   9300
gttcaaggtg ctgtgcgccg cccagcccct gagcatccag gtgcacccca acaagcacaa   9360
cagcgagatc ggcttcgcca aggagaacgc cgccggcatc cccatggacg ccgccgagcg   9420
caactacaag gaccccaacc acaagcccga gctggtgttc gccctgaccc ccttcctggc   9480
catgaacgcc ttccgcgagt tcagcgagat cgtgagcctg ctgcagcccg tggccggcgc   9540
ccaccccgcc atcgcccact tcctgcagca gcccgacgcc gagcgcctga gcgagctgtt   9600
cgccagcctg ctgaacatgc agggcgagga gaagagccgc gccctggcca tcctgaagag   9660
cgccctggac agccagcagg gcgagccctg gcagaccatc cgcctgatca gcgagttcta   9720
ccccgaggac agcggcctgt tcagccccct gctgctgaac gtggtgaagc tgaaccccgg   9780
cgaggccatg ttcctgttcg ccgagacccc ccacgcctac ctgcagggcg tggccctgga   9840
ggtgatggcc aacagcgaca acgtgctgcg cgccggcctg acccccaagt acatcgacat   9900
ccccgagctg gtggccaacg tgaagttcga ggccaagccc gccaaccagc tgctgaccca   9960
gcccgtgaag cagggcgccg agctggactt ccccatcccc gtggacgact tcgccttcag  10020
cctgcacgac ctgagcgaca aggagaccac catcagccag cagagcgccg ccatcctgtt  10080
ctgcgtggag ggcgacgcca ccctgtggaa gggcagccag cagctgcagc tgaagcccgg  10140
cgagagcgcc ttcatcgccg ccaacgagag ccccgtgacc gtgaagggcc acggccgcct  10200
ggcccgcgtg tacaacaagc tgtgatagga gctcgatccg tcgacctgca gatcgttcaa  10260
acatttggca ataaagtttc ttaagattga atcctgttgc cggtcttgcg atgattatca  10320
tataatttct gttgaattac gttaagcatg taataattaa catgtaatgc atgacgttat  10380
ttatgagatg ggtttttatg attagagtcc cgcaattata catttaatac gcgatagaaa  10440
acaaaatata gcgcgcaaac taggataaat tatcgcgcgc ggtgtcatct atgttactag  10500
atcggcgcgc cgcaattgaa gtttgggcgg ccagcatggc cgtatccgca atgtgttatt  10560
aagttgtcta agcgtcaatt tgtttacacc acaatatatc ctgccaccag ccagccaaca  10620
gctccccgac cggcagctcg gcacaaaatc accactcgat acaggcagcc catcagaatt  10680
aattctcatg tttgacagct tatcatcgac tgcacggtgc accaatgctt ctggcgtcag  10740
gcagccatcg gaagctgtgg tatggctgtg caggtcgtaa atcactgcat aattcgtgtc  10800
```

-continued gctcaaggcg cactcccgtt ctggataatg ttttttgcgc cgacatcata acggttctgg 10860
caaatattct gaaatgagct gttgacaatt aatcatccgg ctcgtataat gtgtggaatt 10920
gtgagcggat aacaatttca cacaggaaac agaccatgag ggaagcgttg atcgccgaag 10980
tatcgactca actatcagag gtagttggcg tcatcgagcg ccatctcgaa ccgacgttgc 11040
tggccgtaca tttgtacggc tccgcagtgg atggcggcct gaagccacac agtgatattg 11100
atttgctggt tacggtgacc gtaaggcttg atgaaacaac gcggcgagct ttgatcaacg 11160
accttttgga aacttcggct tcccctggag agagcgagat tctccgcgct gtagaagtca 11220
ccattgttgt gcacgacgac atcattccgt ggcgttatcc agctaagcgc gaactgcaat 11280
ttggagaatg gcagcgcaat gacattcttg caggtatctt cgagccagcc acgatcgaca 11340
ttgatctggc tatcttgctg acaaaagcaa gagaacatag cgttgccttg gtaggtccag 11400
cggcggagga actctttgat ccggttcctg aacaggatct atttgaggcg ctaaatgaaa 11460
ccttaacgct atggaactcg ccgcccgact gggctggcga tgagcgaaat gtagtgctta 11520
cgttgtcccg catttggtac agcgcagtaa ccggcaaaat cgcgccgaag gatgtcgctg 11580
ccgactgggc aatggagcgc ctgccggccc agtatcagcc cgtcatactt gaagctaggc 11640
aggcttatct tggacaagaa gatcgcttgg cctcgcgcgc agatcagttg gaagaatttg 11700
ttcactacgt gaaaggcgag atcaccaaag tagtcggcaa ataaagctct agtggatctc 11760
cgtacccggg gatctggctc gcggcggacg cacgacgccg gggcgagacc ataggcgatc 11820
tcctaaatca atagtagctg taacctcgaa gcgtttcact tgtaacaacg attgagaatt 11880
tttgtcataa aattgaaata cttggttcgc atttttgtca tccgcggtca gccgcaattc 11940
tgacgaactg cccatttagc tggagatgat tgtacatcct tcacgtgaaa atttctcaag 12000
cgctgtgaac aagggttcag attttagatt gaaaggtgag ccgttgaaac acgttcttct 12060
tgtcgatgac gacgtcgcta tgcggcatct tattattgaa taccttacga tccacgcctt 12120
caaagtgacc gcggtagccg acagcaccca gttcacaaga gtactctctt ccgcgacggt 12180
cgatgtcgtg gttgttgatc tagatttagg tcgtgaagat gggctcgagc taggagcaag 12240
tgattttatc gctaagccgt tcagtatcag agagtttcta gcacgcattc gggttgcctt 12300
gcgcgtgcgc cccaacgttg tccgctccaa agaccgacgg tctttttgtt ttactgactg 12360
gacacttaat ctcaggcaac gtcgcttgat gtccgaagct ggcggtgagg tgaaacttac 12420
ggcaggtgag ttcaatcttc tcctcgcgtt tttagagaaa ccccgcgacg ttctatcgcg 12480
cgagcaactt ctcattgcca gtcgagtacg cgacgaggag gtttatgaca ggagtataga 12540
tgttctcatt ttgaggctgc gccgcaaact tgaggcagat ccgtcaagcc ctcaactgat 12600
aaaaacagca agaggtgccg gttatttctt tgacgcggac gtgcaggttt cgcacggggg 12660
gacgatggca gcctgagcca attcccagat ccccgaggaa tcggcgtgag cggtcgcaaa 12720
ccatccggcc cggtacaaat cggcgcggcg ctgggtgatg acctggtgga gaagttgaag 12780
gccgcgcagg ccgcccagcg gcaacgcatc gaggcagaag cacgccccgg tgaatcgtgg 12840
caagcggccg ctgatcgaat ccgcaaagaa tcccggcaac cgccggcagc cggtgcgccg 12900
tcgattagga agccgcccaa gggcgacgag caaccagatt ttttcgttcc gatgctctat 12960
gacgtgggca cccgcgatag tcgcagcatc atggacgtgg ccgttttccg tctgtcgaag 13020
cgtgaccgac gagctggcga ggtgatccgc tacgagcttc cagacgggca cgtagaggtt 13080
tccgcagggc cggccggcat ggccagtgtg tgggattacg acctggtact gatggcggtt 13140
tcccatctaa ccgaatccat gaaccgatac cgggaaggga agggagacaa gcccggccgc 13200

```
gtgttccgtc cacacgttgc ggacgtactc aagttctgcc ggcgagccga tggcggaaag  13260
cagaaagacg acctggtaga aacctgcatt cggttaaaca ccacgcacgt tgccatgcag  13320
cgtacgaaga aggccaagaa cggccgcctg gtgacggtat ccgagggtga agccttgatt  13380
agccgctaca agatcgtaaa gagcgaaacc gggcggccgg agtacatcga gatcgagcta  13440
gctgattgga tgtaccgcga gatcacagaa ggcaagaacc cggacgtgct gacggttcac  13500
cccgattact ttttgatcga tcccggcatc ggccgttttc tctaccgcct ggcacgccgc  13560
gccgcaggca aggcagaagc cagatggttg ttcaagacga tctacgaacg cagtggcagc  13620
gccggagagt tcaagaagtt ctgtttcacc gtgcgcaagc tgatcgggtc aaatgacctg  13680
ccggagtacg atttgaagga ggaggcgggg caggctggcc cgatcctagt catgcgctac  13740
cgcaacctga tcgagggcga agcatccgcc ggttcctaat gtacggagca gatgctaggg  13800
caaattgccc tagcagggga aaaaggtcga aaaggtctct ttcctgtgga tagcacgtac  13860
attgggaacc caaagccgta cattgggaac cggaacccgt acattgggaa cccaaagccg  13920
tacattggga accggtcaca catgtaagtg actgatataa aagagaaaaa aggcgatttt  13980
tccgcctaaa actctttaaa acttattaaa actcttaaaa cccgcctggc ctgtgcataa  14040
ctgtctggcc agcgcacagc cgaagagctg caaaaagcgc ctacccttcg gtcgctgcgc  14100
tccctacgcc ccgccgcttc gcgtcggcct atcgcggccg ctggccgctc aaaaatggct  14160
ggcctacggc caggcaatct accagggcgc ggacaagccg cgccgtcgcc actcgaccgc  14220
cggcgctgag gtctgcctcg tgaagaaggt gttgctgact cataccaggc ctgaatcgcc  14280
ccatcatcca gccagaaagt gagggagcca cggttgatga gagctttgtt gtaggtggac  14340
cagttggtga ttttgaactt ttgctttgcc acggaacggt ctgcgttgtc gggaagatgc  14400
gtgatctgat ccttcaactc agcaaaagtt cgatttattc aacaaagccg ccgtcccgtc  14460
aagtcagcgt aatgctctgc cagtgttaca accaattaac caattctgat tagaaaaact  14520
catcgagcat caaatgaaac tgcaatttat tcatatcagg attatcaata ccatattttt  14580
gaaaaagccg tttctgtaat gaaggagaaa actcaccgag gcagttccat aggatggcaa  14640
gatcctggta tcggtctgcg attccgactc gtccaacatc aatacaacct attaatttcc  14700
cctcgtcaaa aataaggtta tcaagtgaga aatcaccatg agtgacgact gaatccggtg  14760
agaatggcaa aagctctgca ttaatgaatc ggccaacgcg cggggagagg cggtttgcgt  14820
attgggcgct cttccgcttc ctcgctcact gactcgctgc gctcggtcgt tcggctgcgg  14880
cgagcggtat cagctcactc aaaggcggta atacggttat ccacagaatc aggggataac  14940
gcaggaaaga acatgtgagc aaaaggccag caaaaggcca ggaaccgtaa aaaggccgcg  15000
ttgctggcgt ttttccatag gctccgcccc cctgacgagc atcacaaaaa tcgacgctca  15060
agtcagaggt ggcgaaaccc gacaggacta taaagatacc aggcgtttcc ccctggaagc  15120
tccctcgtgc gctctcctgt tccgaccctg ccgcttaccg gatacctgtc cgcctttctc  15180
ccttcgggaa gcgtggcgct ttctcatagc tcacgctgta ggtatctcag ttcggtgtag  15240
gtcgttcgct ccaagctggg ctgtgtgcac gaaccccccg ttcagcccga ccgctgcgcc  15300
ttatccggta actatcgtct tgagtccaac ccggtaagac acgacttatc gccactggca  15360
gcagccactg gtaacaggat tagcagagcg aggtatgtag gcggtgctac agagttcttg  15420
aagtggtggc ctaactacgg ctacactaga agaacagtat ttggtatctg cgctctgctg  15480
aagccagtta ccttcggaaa aagagttggt agctcttgat ccggcaaaca aaccaccgct  15540
```

ggtagcggtg gtttttttgt ttgcaagcag cagattacgc gcagaaaaaa aggatctcaa 15600
gaagatcctt tgatcttttc tacggggtct gacgctcagt ggaacgaaaa ctcacgttaa 15660
gggattttgg tcatgagatt atcaaaaagg atcttcacct agatcctttt gatccggaat 15720
ta 15722

<210> SEQ ID NO 2
<211> LENGTH: 20
<212> TYPE: DNA
<213> ORGANISM: Artificial Sequence
<220> FEATURE:
<223> OTHER INFORMATION: gRNA sequence for editing VLHP1

<400> SEQUENCE: 2
gcaggaggcg tcgagcagcg 20

<210> SEQ ID NO 3
<211> LENGTH: 15722
<212> TYPE: DNA
<213> ORGANISM: Artificial Sequence
<220> FEATURE:
<223> OTHER INFORMATION: vector 23399
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (304)..(2100)
<223> OTHER INFORMATION: prSoUbi4-04
<220> FEATURE:
<221> NAME/KEY: gene
<222> LOCATION: (2117)..(6286)
<223> OTHER INFORMATION: cCas9-01
<220> FEATURE:
<221> NAME/KEY: mutation
<222> LOCATION: (5606)..(5608)
<223> OTHER INFORMATION: L to V mutation
<220> FEATURE:
<221> NAME/KEY: mutation
<222> LOCATION: (5651)..(5653)
<223> OTHER INFORMATION: I to V mutation
<220> FEATURE:
<221> NAME/KEY: terminator
<222> LOCATION: (6292)..(6544)
<223> OTHER INFORMATION: tNOS-05-01
<220> FEATURE:
<221> NAME/KEY: promoter
<222> LOCATION: (6551)..(6925)
<223> OTHER INFORMATION: prOsU3-01
<220> FEATURE:
<221> NAME/KEY: misc_feature
<222> LOCATION: (6927)..(6946)
<223> OTHER INFORMATION: xZmGW2
<220> FEATURE:
<221> NAME/KEY: misc_feature
<222> LOCATION: (6927)..(7031)
<223> OTHER INFORMATION: rsgRNAZmGW2-02
<220> FEATURE:
<221> NAME/KEY: promoter
<222> LOCATION: (7042)..(9033)
<223> OTHER INFORMATION: prUbi1-04
<220> FEATURE:
<221> NAME/KEY: gene
<222> LOCATION: (9050)..(10228)
<223> OTHER INFORMATION: cPMI-09
<220> FEATURE:
<221> NAME/KEY: terminator
<222> LOCATION: (10251)..(10503)
<223> OTHER INFORMATION: tNOS-05-01
<220> FEATURE:
<221> NAME/KEY: misc_feature
<222> LOCATION: (10547)..(10676)
<223> OTHER INFORMATION: bNLB-03

-continued

<220> FEATURE:
<221> NAME/KEY: gene
<222> LOCATION: (10956)..(11744)
<223> OTHER INFORMATION: cSpec-03
<220> FEATURE:
<221> NAME/KEY: promoter
<222> LOCATION: (11839)..(11969)
<223> OTHER INFORMATION: prVirG-01
<220> FEATURE:
<221> NAME/KEY: gene
<222> LOCATION: (12706)..(13779)
<223> OTHER INFORMATION: cRepA-01
<220> FEATURE:
<221> NAME/KEY: misc_feature
<222> LOCATION: (13822)..(14226)
<223> OTHER INFORMATION: oVS1-02
<220> FEATURE:
<221> NAME/KEY: misc_feature
<222> LOCATION: (14904)..(15710)
<223> OTHER INFORMATION: oCOLE-06

<400> SEQUENCE: 3
attcctgtgg ttggcatgca catacaaatg gacgaacgga taaacctttt cacgcccttt 60
taaatatccg attattctaa taaacgctct tttctcttag gtttacccgc caatatatcc 120
tgtcaaacac tgatagttta aactgaaggc gggaaacgac aatctgatca tgagcggaga 180
attaagggag tcacgttatg acccccgccg atgacgcggg acaagccgtt ttacgtttgg 240
aactgacaga accgcaacgc tgcaggaatt ggccgcagcg gccatttaaa caaagcttgg 300
taccattatg tggtctaggt aggttctata tataagaaaa cttgaaatgt tctaaaaaaa 360
aattcaagcc catgcatgat tgaagcaaac ggtatagcaa cggtgttaac ctgatctagt 420
gatctcttgc aatccttaac ggccacctac cgcaggtagc aaacggcgtc cccctcctcg 480
atatctccgc ggcgacctct ggctttttcc gcggaattgc gcggtgggga cggattccac 540
gagaccgcga cgcaaccgcc tctcgccgct gggccccaca ccgctcggtg ccgtagcctc 600
acgggactct ttctccctcc tcccccgtta taaattggct tcatcccctc cttgcctcat 660
ccatccaaat cccagtcccc aatcccatcc cttcgtagga gaaattcatc gaagctaagc 720
gaatcctcgc gatcctctca aggtactgcg agttttcgat ccccctctcg acccctcgta 780
tgtttgtgtt tgtcgtagcg tttgattagg tatgctttcc ctgtttgtgt tcgtcgtagc 840
gtttgattag gtatgctttc cctgttcgtg ttcatcgtag tgtttgatta ggtcgtgtga 900
ggcgatggcc tgctcgcgtc cttcgatctg tagtcgattt gcgggtcgtg gtgtagatct 960
gcgggctgtg atgaagttat ttggtgtgat ctgctcgcct gattctgcgg gttggctcga 1020
gtagatatga tggttggacc ggttggttcg tttaccgcgc tagggttggg ctgggatgat 1080
gttgcatgcg ccgttgcgcg tgatcccgca gcaggacttg cgtttgattg ccagatctcg 1140
ttacgattat gtgatttggt ttggactttt tagatctgta gcttctgctt atgtgccaga 1200
tgcgcctact gctcatatgc ctgatgataa tcataaatgg ctgtggaact aactagttga 1260
ttgcggagtc atgtatcagc tacaggtgta gggactagct acaggtgtag ggacttgcgt 1320
ctaattgttt ggtcctttac tcatgttgca attatgcaat ttagtttaga ttgtttgttc 1380
cactcatcta ggctgtaaaa gggacactgc ttagattgct gtttaatctt tttagtagat 1440
tatattatat tggtaactta ttacccctat tacatgccat acgtgacttc tgctcatgcc 1500
tgatgataat catagatcac tgtggaatta attagttgat tgttgaatca tgtttcatgt 1560
acataccacg gcacaattgc ttagttcctt aacaaatgca aattttactg atccatgtat 1620
gatttgcgtg gttctctaat gtgaaatact atagctactt gttagtaaga atcaggttcg 1680

-continued

```
tatgcttaat gctgtatgtg ccttctgctc atgcctgatg ataatcatat atcactggaa   1740
ttaattagtt gatcgtttaa tcatatatca agtacatacc atgccacaat ttttagtcac   1800
ttaacccatg cagattgaac tggtccctgc atgttttgct aaattgttct attctgatta   1860
gaccatatat catgtatttt tttttggtaa tggttctctt attttaaatg ctatatagtt   1920
ctggtacttg ttagaaagat ctgcttcata gtttagttgc ctatccctcg aattaggatg   1980
ctgagcagct gatcctatag ctttgtttca tgtatcaatt cttttgtgtt caacagtcag   2040
tttttgttag attcattgta acttatggtc gcttactctt ctggtcctca atgcttgcag   2100
gatcgcggcc gctcatatgg acaagaagta cagcatcggc ctggacatcg gcaccaacag   2160
cgtgggctgg gccgtgatca ccgacgagta caaggtgccg agcaagaagt tcaaggtgct   2220
gggcaacacc gacaggcaca gcatcaagaa gaacctgatc ggcgccctgc tgttcgacag   2280
cggcgagacc gccgaggcca ccaggctgaa gaggaccgcc aggaggaggt acaccaggag   2340
gaagaacagg atctgctacc tgcaggagat cttcagcaac gagatggcca aggtggacga   2400
cagcttcttc cacaggctgg aggagagctt cctggtggag gaggacaaga agcacgagag   2460
gcacccgatc ttcggcaaca tcgtggacga ggtggcctac cacgagaagt acccgaccat   2520
ctaccacctg aggaagaagc tggtggacag caccgacaag gccgacctga ggctgatcta   2580
cctggccctg gcccacatga tcaagttcag gggccacttc ctgatcgagg gcgacctgaa   2640
cccggacaac agcgacgtgg acaagctgtt catccagctg gtgcagacct acaaccagct   2700
gttcgaggag aacccgatca acgccagcgg cgtggacgcc aaggccatcc tgagcgccag   2760
gctgagcaag agcaggaggc tggagaacct gatcgcccag ctgccgggcg agaagaagaa   2820
cggcctgttc ggcaacctga tcgccctgag cctgggcctg accccgaact tcaagagcaa   2880
cttcgacctg gccgaggacg ccaagctgca gctgagcaag gacacctacg acgacgacct   2940
ggacaacctg ctggcccaga tcggcgacca gtacgccgac ctgttcctgg ccgccaagaa   3000
cctgagcgac gccatcctgc tgagcgacat cctgagggtg aacaccgaga tcaccaaggc   3060
cccgctgagc gccagcatga tcaagaggta cgacgagcac caccaggacc tgaccctgct   3120
gaaggccctg gtgaggcagc agctgccgga gaagtacaag gagatcttct tcgaccagag   3180
caagaacggc tacgccggct acatcgacgg cggcgccagc caggaggagt tctacaagtt   3240
catcaagccg atcctggaga agatggacgg caccgaggag ctgctggtga agctgaacag   3300
ggaggacctg ctgaggaagc agaggacctt cgacaacggc agcatcccgc accagatcca   3360
cctgggcgag ctgcacgcca tcctgaggag gcaggaggac ttctacccgt tcctgaagga   3420
caacagggag aagatcgaga agatcctgac cttccgcatc ccgtactacg tgggcccgct   3480
ggccaggggc aacagcaggt tcgcctggat gaccaggaag agcgaggaga ccatcacccc   3540
gtggaacttc gaggaggtgg tggacaaggg cgccagcgcc cagagcttca tcgagaggat   3600
gaccaacttc gacaagaacc tgccgaacga gaaggtgctg ccgaagcaca gcctgctgta   3660
cgagtacttc accgtgtaca acgagctgac caaggtgaag tacgtgaccg agggcatgag   3720
gaagccggcc ttcctgagcg gcgagcagaa gaaggccatc gtggacctgc tgttcaagac   3780
caacaggaag gtgaccgtga agcagctgaa ggaggactac ttcaagaaga tcgagtgctt   3840
cgacagcgtg gagatcagcg gcgtggagga caggttcaac gccagcctgg gcacctacca   3900
cgacctgctg aagatcatca aggacaagga cttcctggac aacgaggaga acgaggacat   3960
cctggaggac atcgtgctga ccctgaccct gttcgaggac agggagatga tcgaggagag   4020
gctgaagacc tacgcccacc tgttcgacga caaggtgatg aagcagctga agaggaggag   4080
```

-continued

```
gtacaccggc tggggcaggc tgagcaggaa gctgatcaac ggcatcaggg acaagcagag   4140
cggcaagacc atcctggact tcctgaagag cgacggcttc gccaacagga acttcatgca   4200
gctgatccac gacgacagcc tgaccttcaa ggaggacatc cagaaggccc aggtgagcgg   4260
ccagggcgac agcctgcacg agcacatcgc caacctggcc ggcagcccgg ccatcaagaa   4320
gggcatcctg cagaccgtga aggtggtgga cgagctggtg aaggtgatgg gcaggcacaa   4380
gccggagaac atcgtgatcg agatggccag ggagaaccag accacccaga agggccagaa   4440
gaacagcagg gagaggatga agaggatcga ggagggcatc aaggagctgg gcagccagat   4500
cctgaaggag cacccggtgg agaacaccca gctgcagaac gagaagctgt acctgtacta   4560
cctgcagaac ggcagggaca tgtacgtgga ccaggagctg gacatcaaca ggctgagcga   4620
ctacgacgtg gaccacatcg tgccgcagag cttcctgaag gacgacagca tcgacaacaa   4680
ggtgctgacc aggagcgaca agaacagggg caagagcgac aacgtgccga gcgaggaggt   4740
ggtgaagaag atgaaaaact actggaggca gctgctgaac gccaagctga tcacccagag   4800
gaagttcgac aacctgacca aggccgagag gggcggcctg agcgagctgg acaaggccgg   4860
cttcattaaa aggcagctgg tggagaccag gcagatcacc aagcacgtgg cccagatcct   4920
ggacagcagg atgaacacca agtacgacga gaacgacaag ctgatcaggg aggtgaaggt   4980
gatcaccctg aagagcaagc tggtgagcga cttcaggaag gacttccagt tctacaaggt   5040
gagggagatc aataattacc accacgccca cgacgcctac ctgaacgccg tggtgggcac   5100
cgccctgatt aaaaagtacc cgaagctgga gagcgagttc gtgtacggcg actacaaggt   5160
gtacgacgtg aggaagatga tcgccaagag cgagcaggag atcggcaagg ccaccgccaa   5220
gtacttcttc tacagcaaca tcatgaactt cttcaagacc gagatcaccc tggccaacgg   5280
cgagatcagg aagaggccgc tgatcgagac caacggcgag accggcgaga tcgtgtggga   5340
caagggcagg gacttcgcca ccgtgaggaa ggtgctgtcc atgccgcagg tgaacatcgt   5400
gaagaagacc gaggtgcaga ccggcggctt cagcaaggag agcatcctgc cgaagaggaa   5460
cagcgacaag ctgatcgcca ggaagaagga ctgggacccg aagaagtacg gcggcttcga   5520
cagcccgacc gtggcctaca gcgtgctggt ggtggccaag gtggagaagg gcaagagcaa   5580
gaagctgaag agcgtgaagg agctggtggg catcaccatc atggagagga gcagcttcga   5640
gaagaaccca gtggacttcc tggaggccaa gggctacaag gaggtgaaga aggacctgat   5700
cattaaactg ccgaagtaca gcctgttcga gctggagaac ggcaggaaga ggatgctggc   5760
cagcgccggc gagctgcaga agggcaacga gctggccctg ccgagcaagt acgtgaactt   5820
cctgtacctg gccagccact acgagaagct gaagggcagc ccggaggaca acgagcagaa   5880
gcagctgttc gtggagcagc acaagcacta cctggacgag atcatcgagc agatcagcga   5940
gttcagcaag agggtgatcc tggccgacgc caacctggac aaggtgctga gcgcctacaa   6000
caagcacagg gacaagccga tcagggagca ggccgagaac atcatccacc tgttcaccct   6060
gaccaacctg ggcgccccgg ccgccttcaa gtacttcgac accaccatcg acaggaagag   6120
gtacaccagc accaaggagg tgctggacgc caccctgatc caccagagca tcaccggcct   6180
gtacgagacc aggatcgacc tgagccagct gggcggcgac agcagcccgc cgaagaagaa   6240
gaggaaggtg agctggaagg acgccagcgg ctggagcagg atgtgaagct tgatcgttca   6300
aacatttggc aataaagttt cttaagattg aatcctgttg ccggtcttgc gatgattatc   6360
atataatttc tgttgaatta cgttaagcat gtaataatta acatgtaatg catgacgtta   6420
```

-continued

```
tttatgagat gggtttttat gattagagtc ccgcaattat acatttaata cgcgatagaa   6480
aacaaaatat agcgcgcaaa ctaggataaa ttatcgcgcg cggtgtcatc tatgttacta   6540
gatcttcgaa gggatcttta aacatacgaa cagatcactt aaagttcttc tgaagcaact   6600
taaagttatc aggcatgcat ggatcttgga ggaatcagat gtgcagtcag ggaccatagc   6660
acaggacagg cgtcttctac tggtgctacc agcaaatgct ggaagccggg aacactgggt   6720
acgttggaaa ccacgtgatg tggagtaaga taaactgtag gagaaaagca tttcgtagtg   6780
ggccatgaag cctttcagga catgtattgc agtatgggcc ggcccattac gcaattggac   6840
gacaacaaag actagtatta gtaccacctc ggctatccac atagatcaaa gctggtttaa   6900
aagagttgtg cagatgatcc gtggcaaagc tcgcgccctg ctacccgttt tagagctaga   6960
aatagcaagt taaaataagg ctagtccgtt atcaacttga aaaagtggca ccgagtcggt   7020
gctttttttt tcggaccgcg cctgcagtgc agcgtgaccc ggtcgtgccc ctctctagag   7080
ataatgagca ttgcatgtct aagttataaa aaattaccac atattttttt tgtcacactt   7140
gtttgaagtg cagtttatct atctttatac atatatttaa actttactct acgaataata   7200
taatctatag tactacaata atatcagtgt tttagagaat catataaatg aacagttaga   7260
catggtctaa aggacaattg agtattttga caacaggact ctacagtttt atctttttag   7320
tgtgcatgtg ttctcctttt tttttgcaaa tagcttcacc tatataatac ttcatccatt   7380
ttattagtac atccatttag ggtttagggt taatggtttt tatagactaa tttttttagt   7440
acatctattt tattctattt tagcctctaa attaagaaaa ctaaaactct attttagttt   7500
ttttatttaa taatttagat ataaaataga ataaaataaa gtgactaaaa attaaacaaa   7560
taccctttaa gaaattaaaa aaactaagga aacatttttc ttgtttcgag tagataatgc   7620
cagcctgtta aacgccgtcg acgagtctaa cggacaccaa ccagcgaacc agcagcgtcg   7680
cgtcgggcca agcgaagcag acggcacggc atctctgtcg ctgcctctgg acccctctcg   7740
agagttccgc tccaccgttg gacttgctcc gctgtcggca tccagaaatt gcgtggcgga   7800
gcggcagacg tgagccggca cggcaggcgg cctcctcctc ctctcacggc accggcagct   7860
acgggggatt cctttcccac cgctccttcg ctttcccttc ctcgcccgcc gtaataaata   7920
gacacccct ccacaccctc tttccccaac ctcgtgttgt tcggagcgca cacacacaca   7980
accagatctc ccccaaatcc acccgtcggc acctccgctt caaggtacgc cgctcgtcct   8040
cccccccccc cctctctacc ttctctagat cggcgttccg gtccatggtt agggcccggt   8100
agttctactt ctgttcatgt ttgtgttaga tccgtgtttg tgttagatcc gtgctgctag   8160
cgttcgtaca cggatgcgac ctgtacgtca gacacgttct gattgctaac ttgccagtgt   8220
ttctctttgg ggaatcctgg gatggctcta gccgttccgc agacgggatc gatttcatga   8280
ttttttttgt ttcgttgcat agggtttggt ttgccctttt cctttatttc aatatatgcc   8340
gtgcacttgt ttgtcgggtc atcttttcat gctttttttt gtcttggttg tgatgatgtg   8400
gtctggttgg gcggtcgttc tagatcggag tagaattctg tttcaaacta cctggtggat   8460
ttattaattt tggatctgta tgtgtgtgcc atacatattc atagttacga attgaagatg   8520
atggatggaa atatcgatct aggataggta tacatgttga tgcgggtttt actgatgcat   8580
atacagagat gctttttgtt cgcttggttg tgatgatgtg gtgtggttgg gcggtcgttc   8640
attcgttcta gatcggagta gaatactgtt tcaaactacc tggtgtattt attaattttg   8700
gaactgtatg tgtgtgtcat acatcttcat agttacgagt ttaagatgga tggaaatatc   8760
gatctaggat aggtatacat gttgatgtgg gttttactga tgcatataca tgatggcata   8820
```

-continued

```
tgcagcatct attcatatgc tctaaccttg agtacctatc tattataata aacaagtatg   8880
ttttataatt attttgatct tgatatactt ggatgatggc atatgcagca gctatatgtg   8940
gattttttta gccctgcctt catacgctat ttatttgctt ggtactgttt cttttgtcga   9000
tgctcaccct gttgtttggt gttacttctg cagggatccg gcagcagcca tgcagaagct   9060
gatcaacagc gtgcagaact acgcctgggg cagcaagacc gccctgaccg agctgtacgg   9120
catggagaac cccagcagcc agcccatggc cgagctgtgg atgggcgccc accccaagag   9180
cagcagccgc gtgcagaacg ccgccggcga catcgtgagc ctgcgcgacg tgatcgagag   9240
cgacaagagc accctgctgg gcgaggccgt ggccaagcgc ttcggcgagc tgcccttcct   9300
gttcaaggtg ctgtgcgccg cccagcccct gagcatccag gtgcacccca acaagcacaa   9360
cagcgagatc ggcttcgcca aggagaacgc cgccggcatc cccatggacg ccgccgagcg   9420
caactacaag gaccccaacc acaagcccga gctggtgttc gccctgaccc ccttcctggc   9480
catgaacgcc ttccgcgagt tcagcgagat cgtgagcctg ctgcagcccg tggccggcgc   9540
ccaccccgcc atcgcccact tcctgcagca gcccgacgcc gagcgcctga gcgagctgtt   9600
cgccagcctg ctgaacatgc agggcgagga gaagagccgc gccctggcca tcctgaagag   9660
cgccctggac agccagcagg gcgagccctg gcagaccatc cgcctgatca gcgagttcta   9720
ccccgaggac agcggcctgt tcagccccct gctgctgaac gtggtgaagc tgaaccccgg   9780
cgaggccatg ttcctgttcg ccgagacccc ccacgcctac ctgcagggcg tggccctgga   9840
ggtgatggcc aacagcgaca acgtgctgcg cgccggcctg acccccaagt acatcgacat   9900
ccccgagctg gtggccaacg tgaagttcga ggccaagccc gccaaccagc tgctgaccca   9960
gcccgtgaag cagggcgccg agctggactt ccccatcccc gtggacgact tcgccttcag  10020
cctgcacgac ctgagcgaca aggagaccac catcagccag cagagcgccg ccatcctgtt  10080
ctgcgtggag ggcgacgcca ccctgtggaa gggcagccag cagctgcagc tgaagcccgg  10140
cgagagcgcc ttcatcgccg ccaacgagag ccccgtgacc gtgaagggcc acggccgcct  10200
ggcccgcgtg tacaacaagc tgtgatagga gctcgatccg tcgacctgca gatcgttcaa  10260
acatttggca ataaagtttc ttaagattga atcctgttgc cggtcttgcg atgattatca  10320
tataatttct gttgaattac gttaagcatg taataattaa catgtaatgc atgacgttat  10380
ttatgagatg ggtttttatg attagagtcc cgcaattata catttaatac gcgatagaaa  10440
acaaaatata gcgcgcaaac taggataaat tatcgcgcgc ggtgtcatct atgttactag  10500
atcggcgcgc cgcaattgaa gtttgggcgg ccagcatggc cgtatccgca atgtgttatt  10560
aagttgtcta agcgtcaatt tgtttacacc acaatatatc ctgccaccag ccagccaaca  10620
gctccccgac cggcagctcg gcacaaaatc accactcgat acaggcagcc catcagaatt  10680
aattctcatg tttgacagct tatcatcgac tgcacggtgc accaatgctt ctggcgtcag  10740
gcagccatcg gaagctgtgg tatggctgtg caggtcgtaa atcactgcat aattcgtgtc  10800
gctcaaggcg cactcccgtt ctggataatg ttttttgcgc cgacatcata acggttctgg  10860
caaatattct gaaatgagct gttgacaatt aatcatccgg ctcgtataat gtgtggaatt  10920
gtgagcggat aacaatttca cacaggaaac agaccatgag ggaagcgttg atcgccgaag  10980
tatcgactca actatcagag gtagttggcg tcatcgagcg ccatctcgaa ccgacgttgc  11040
tggccgtaca tttgtacggc tccgcagtgg atggcggcct gaagccacac agtgatattg  11100
atttgctggt tacggtgacc gtaaggcttg atgaaacaac gcggcgagct ttgatcaacg  11160
```

-continued

```
acttttgga aacttcggct tcccctggag agagcgagat tctccgcgct gtagaagtca  11220
ccattgttgt gcacgacgac atcattccgt ggcgttatcc agctaagcgc gaactgcaat  11280
ttggagaatg gcagcgcaat gacattcttg caggtatctt cgagccagcc acgatcgaca  11340
ttgatctggc tatcttgctg acaaaagcaa gagaacatag cgttgccttg gtaggtccag  11400
cggcggagga actctttgat ccggttcctg aacaggatct atttgaggcg ctaaatgaaa  11460
ccttaacgct atggaactcg ccgcccgact gggctggcga tgagcgaaat gtagtgctta  11520
cgttgtcccg catttggtac agcgcagtaa ccggcaaaat cgcgccgaag gatgtcgctg  11580
ccgactgggc aatggagcgc ctgccggccc agtatcagcc cgtcatactt gaagctaggc  11640
aggcttatct tggacaagaa gatcgcttgg cctcgcgcgc agatcagttg gaagaatttg  11700
ttcactacgt gaaaggcgag atcaccaaag tagtcggcaa ataaagctct agtggatctc  11760
cgtacccggg gatctggctc gcggcggacg cacgacgccg gggcgagacc ataggcgatc  11820
tcctaaatca atagtagctg taacctcgaa gcgtttcact tgtaacaacg attgagaatt  11880
tttgtcataa aattgaaata cttggttcgc atttttgtca tccgcggtca gccgcaattc  11940
tgacgaactg cccatttagc tggagatgat tgtacatcct tcacgtgaaa atttctcaag  12000
cgctgtgaac aagggttcag attttagatt gaaaggtgag ccgttgaaac acgttcttct  12060
tgtcgatgac gacgtcgcta tgcggcatct tattattgaa taccttacga tccacgcctt  12120
caaagtgacc gcggtagccg acagcaccca gttcacaaga gtactctctt ccgcgacggt  12180
cgatgtcgtg gttgttgatc tagatttagg tcgtgaagat gggctcgagc taggagcaag  12240
tgattttatc gctaagccgt tcagtatcag agagtttcta gcacgcattc gggttgcctt  12300
gcgcgtgcgc cccaacgttg tccgctccaa agaccgacgg tctttttgtt ttactgactg  12360
gacacttaat ctcaggcaac gtcgcttgat gtccgaagct ggcggtgagg tgaaacttac  12420
ggcaggtgag ttcaatcttc tcctcgcgtt tttagagaaa ccccgcgacg ttctatcgcg  12480
cgagcaactt ctcattgcca gtcgagtacg cgacgaggag gtttatgaca ggagtataga  12540
tgttctcatt ttgaggctgc gccgcaaact tgaggcagat ccgtcaagcc ctcaactgat  12600
aaaaacagca agaggtgccg gttatttctt tgacgcggac gtgcaggttt cgcacggggg  12660
gacgatggca gcctgagcca attcccagat ccccgaggaa tcggcgtgag cggtcgcaaa  12720
ccatccggcc cggtacaaat cggcgcggcg ctgggtgatg acctggtgga gaagttgaag  12780
gccgcgcagg ccgcccagcg gcaacgcatc gaggcagaag cacgccccgg tgaatcgtgg  12840
caagcggccg ctgatcgaat ccgcaaagaa tcccggcaac cgccggcagc cggtgcgccg  12900
tcgattagga agccgcccaa gggcgacgag caaccagatt ttttcgttcc gatgctctat  12960
gacgtgggca cccgcgatag tcgcagcatc atggacgtgg ccgttttccg tctgtcgaag  13020
cgtgaccgac gagctggcga ggtgatccgc tacgagcttc cagacgggca cgtagaggtt  13080
tccgcagggc cggccggcat ggccagtgtg tgggattacg acctggtact gatggcggtt  13140
tcccatctaa ccgaatccat gaaccgatac cgggaaggga agggagacaa gcccggccgc  13200
gtgttccgtc cacacgttgc ggacgtactc aagttctgcc ggcgagccga tggcggaaag  13260
cagaaagacg acctggtaga aacctgcatt cggttaaaca ccacgcacgt tgccatgcag  13320
cgtacgaaga aggccaagaa cggccgcctg gtgacggtat ccgagggtga agccttgatt  13380
agccgctaca agatcgtaaa gagcgaaacc gggcggccgg agtacatcga gatcgagcta  13440
gctgattgga tgtaccgcga gatcacagaa ggcaagaacc cggacgtgct gacggttcac  13500
cccgattact tttgatcga tcccggcatc ggccgttttc tctaccgcct ggcacgccgc  13560
```

-continued

```
gccgcaggca aggcagaagc cagatggttg ttcaagacga tctacgaacg cagtggcagc  13620
gccggagagt tcaagaagtt ctgtttcacc gtgcgcaagc tgatcgggtc aaatgacctg  13680
ccggagtacg atttgaagga ggaggcgggg caggctggcc cgatcctagt catgcgctac  13740
cgcaacctga tcgagggcga agcatccgcc ggttcctaat gtacggagca gatgctaggg  13800
caaattgccc tagcagggga aaaaggtcga aaaggtctct ttcctgtgga tagcacgtac  13860
attgggaacc caaagccgta cattgggaac cggaacccgt acattgggaa cccaaagccg  13920
tacattggga accggtcaca catgtaagtg actgatataa aagagaaaaa aggcgatttt  13980
tccgcctaaa actctttaaa acttattaaa actcttaaaa cccgcctggc ctgtgcataa  14040
ctgtctggcc agcgcacagc cgaagagctg caaaaagcgc ctacccttcg gtcgctgcgc  14100
tccctacgcc ccgccgcttc gcgtcggcct atcgcggccg ctggccgctc aaaaatggct  14160
ggcctacggc caggcaatct accagggcgc ggacaagccg cgccgtcgcc actcgaccgc  14220
cggcgctgag gtctgcctcg tgaagaaggt gttgctgact cataccaggc ctgaatcgcc  14280
ccatcatcca gccagaaagt gagggagcca cggttgatga gagctttgtt gtaggtggac  14340
cagttggtga ttttgaactt ttgctttgcc acggaacggt ctgcgttgtc gggaagatgc  14400
gtgatctgat ccttcaactc agcaaaagtt cgatttattc aacaaagccg ccgtcccgtc  14460
aagtcagcgt aatgctctgc cagtgttaca accaattaac caattctgat tagaaaaact  14520
catcgagcat caaatgaaac tgcaatttat tcatatcagg attatcaata ccatattttt  14580
gaaaaagccg tttctgtaat gaaggagaaa actcaccgag gcagttccat aggatggcaa  14640
gatcctggta tcggtctgcg attccgactc gtccaacatc aatacaacct attaatttcc  14700
cctcgtcaaa aataaggtta tcaagtgaga aatcaccatg agtgacgact gaatccggtg  14760
agaatggcaa aagctctgca ttaatgaatc ggccaacgcg cggggagagg cggtttgcgt  14820
attgggcgct cttccgcttc ctcgctcact gactcgctgc gctcggtcgt tcggctgcgg  14880
cgagcggtat cagctcactc aaaggcggta atacggttat ccacagaatc aggggataac  14940
gcaggaaaga acatgtgagc aaaaggccag caaaaggcca ggaaccgtaa aaaggccgcg  15000
ttgctggcgt ttttccatag gctccgcccc cctgacgagc atcacaaaaa tcgacgctca  15060
agtcagaggt ggcgaaaccc gacaggacta taaagatacc aggcgtttcc ccctggaagc  15120
tccctcgtgc gctctcctgt tccgaccctg ccgcttaccg gatacctgtc cgcctttctc  15180
ccttcgggaa gcgtggcgct ttctcatagc tcacgctgta ggtatctcag ttcggtgtag  15240
gtcgttcgct ccaagctggg ctgtgtgcac gaaccccccg ttcagcccga ccgctgcgcc  15300
ttatccggta actatcgtct tgagtccaac ccggtaagac acgacttatc gccactggca  15360
gcagccactg gtaacaggat tagcagagcg aggtatgtag gcggtgctac agagttcttg  15420
aagtggtggc ctaactacgg ctacactaga agaacagtat ttggtatctg cgctctgctg  15480
aagccagtta ccttcggaaa aagagttggt agctcttgat ccggcaaaca aaccaccgct  15540
ggtagcggtg gtttttttgt ttgcaagcag cagattacgc gcagaaaaaa aggatctcaa  15600
gaagatcctt tgatcttttc tacggggtct gacgctcagt ggaacgaaaa ctcacgttaa  15660
gggattttgg tcatgagatt atcaaaaagg atcttcacct agatcctttt gatccggaat  15720
ta                                                                 15722
```

<210> SEQ ID NO 4
<211> LENGTH: 20
<212> TYPE: DNA

<213> ORGANISM: Artificial Sequence
<220> FEATURE:
<223> OTHER INFORMATION: for editing GW2-2

<400> SEQUENCE: 4
aagctcgcgc cctgctaccc 20

<210> SEQ ID NO 5
<211> LENGTH: 19617
<212> TYPE: DNA
<213> ORGANISM: Artificial Sequence
<220> FEATURE:
<223> OTHER INFORMATION: vector 22808
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (304)..(2100)
<223> OTHER INFORMATION: prSoUbi4-04
<220> FEATURE:
<221> NAME/KEY: gene
<222> LOCATION: (2119)..(5193)
<223> OTHER INFORMATION: cTNPLAIIAFw-01
<220> FEATURE:
<221> NAME/KEY: terminator
<222> LOCATION: (5200)..(5452)
<223> OTHER INFORMATION: tNOS-05-01
<220> FEATURE:
<221> NAME/KEY: promoter
<222> LOCATION: (5486)..(7478)
<223> OTHER INFORMATION: prUbi1-10
<220> FEATURE:
<221> NAME/KEY: gene
<222> LOCATION: (7492)..(10566)
<223> OTHER INFORMATION: cTNPLAIIARv-01
<220> FEATURE:
<221> NAME/KEY: terminator
<222> LOCATION: (10573)..(10825)
<223> OTHER INFORMATION: tNOS-05-01
<220> FEATURE:
<221> NAME/KEY: promoter
<222> LOCATION: (10844)..(12835)
<223> OTHER INFORMATION: prUbi1-04
<220> FEATURE:
<221> NAME/KEY: gene
<222> LOCATION: (12852)..(14030)
<223> OTHER INFORMATION: cPMI-09
<220> FEATURE:
<221> NAME/KEY: terminator
<222> LOCATION: (14053)..(14305)
<223> OTHER INFORMATION: tNOS-05-01
<220> FEATURE:
<221> NAME/KEY: misc_feature
<222> LOCATION: (14349)..(14478)
<223> OTHER INFORMATION: bNLB-03
<220> FEATURE:
<221> NAME/KEY: gene
<222> LOCATION: (14758)..(15546)
<223> OTHER INFORMATION: cSpec-03
<220> FEATURE:
<221> NAME/KEY: promoter
<222> LOCATION: (15641)..(15771)
<223> OTHER INFORMATION: prVirG-01
<220> FEATURE:
<221> NAME/KEY: gene
<222> LOCATION: (15846)..(16571)
<223> OTHER INFORMATION: cVirG-01
<220> FEATURE:
<221> NAME/KEY: gene
<222> LOCATION: (16601)..(17674)
<223> OTHER INFORMATION: cRepA-01
<220> FEATURE:
<221> NAME/KEY: misc_feature
<222> LOCATION: (17717)..(18121)
<223> OTHER INFORMATION: oVS1-02

<220> FEATURE:
<221> NAME/KEY: misc_feature
<222> LOCATION: (18799)..(19605)
<223> OTHER INFORMATION: oCOLE-06

<400> SEQUENCE: 5
attcctgtgg ttggcatgca catacaaatg gacgaacgga taaacctttt cacgcccttt 60
taaatatccg attattctaa taaacgctct tttctcttag gtttacccgc caatatatcc 120
tgtcaaacac tgatagttta aactgaaggc gggaaacgac aatctgatca tgagcggaga 180
attaagggag tcacgttatg acccccgccg atgacgcggg acaagccgtt ttacgtttgg 240
aactgacaga accgcaacgc tgcaggaatt ggccgcagcg gccatttaaa caaagcttgg 300
taccattatg tggtctaggt aggttctata tataagaaaa cttgaaatgt tctaaaaaaa 360
aattcaagcc catgcatgat tgaagcaaac ggtatagcaa cggtgttaac ctgatctagt 420
gatctcttgc aatccttaac ggccacctac cgcaggtagc aaacggcgtc cccctcctcg 480
atatctccgc ggcgacctct ggctttttcc gcggaattgc gcggtgggga cggattccac 540
gagaccgcga cgcaaccgcc tctcgccgct gggccccaca ccgctcggtg ccgtagcctc 600
acgggactct ttctccctcc tcccccgtta taaattggct tcatcccctc cttgcctcat 660
ccatccaaat cccagtcccc aatcccatcc cttcgtagga gaaattcatc gaagctaagc 720
gaatcctcgc gatcctctca aggtactgcg agttttcgat ccccctctcg acccctcgta 780
tgtttgtgtt tgtcgtagcg tttgattagg tatgctttcc ctgtttgtgt tcgtcgtagc 840
gtttgattag gtatgctttc cctgttcgtg ttcatcgtag tgtttgatta ggtcgtgtga 900
ggcgatggcc tgctcgcgtc cttcgatctg tagtcgattt gcgggtcgtg gtgtagatct 960
gcgggctgtg atgaagttat ttggtgtgat ctgctcgcct gattctgcgg gttggctcga 1020
gtagatatga tggttggacc ggttggttcg tttaccgcgc tagggttggg ctgggatgat 1080
gttgcatgcg ccgttgcgcg tgatcccgca gcaggacttg cgtttgattg ccagatctcg 1140
ttacgattat gtgatttggt ttggactttt tagatctgta gcttctgctt atgtgccaga 1200
tgcgcctact gctcatatgc ctgatgataa tcataaatgg ctgtggaact aactagttga 1260
ttgcggagtc atgtatcagc tacaggtgta gggactagct acaggtgtag ggacttgcgt 1320
ctaattgttt ggtcctttac tcatgttgca attatgcaat ttagtttaga ttgtttgttc 1380
cactcatcta ggctgtaaaa gggacactgc ttagattgct gtttaatctt tttagtagat 1440
tatattatat tggtaactta ttacccctat tacatgccat acgtgacttc tgctcatgcc 1500
tgatgataat catagatcac tgtggaatta attagttgat tgttgaatca tgtttcatgt 1560
acataccacg gcacaattgc ttagttcctt aacaaatgca aattttactg atccatgtat 1620
gatttgcgtg gttctctaat gtgaaatact atagctactt gttagtaaga atcaggttcg 1680
tatgcttaat gctgtatgtg ccttctgctc atgcctgatg ataatcatat atcactggaa 1740
ttaattagtt gatcgtttaa tcatatatca agtacatacc atgccacaat tttagtcac 1800 ttaacccatg cagattgaac tggtccctgc atgttttgct aaattgttct attctgatta 1860
gaccatatat catgtatttt tttttggtaa tggttctctt attttaaatg ctatatagtt 1920
ctggtacttg ttagaaagat ctgcttcata gtttagttgc ctatccctcg aattaggatg 1980
ctgagcagct gatcctatag ctttgtttca tgtatcaatt cttttgtgtt caacagtcag 2040
tttttgttag attcattgta acttatggtc gcttactctt ctggtcctca atgcttgcag 2100
gatcgcggcc gcgccaccat gggaaaacct attcctaatc ctctgctggg cctggattct 2160

-continued

```
accggaggca tggcccctaa gaaaaagcgg aaggtggacg gcggagtgga cctgagaaca   2220
ctgggatatt ctcagcagca gcaggagaag atcaagccca aggtgagatc tacagtggcc   2280
cagcaccacg aagccctggt gggacacgga tttacacacg cccacattgt ggccctgtct   2340
cagcaccctg ccgccctggg aacagtggcc gtgaaatatc aggatatgat tgccgccctg   2400
cctgaggcca cacacgaagc cattgtggga gtgggaaaac agtggtctgg agccagagcc   2460
ctggaagccc tgctgacagt ggccggagaa ctgagaggac ctcctctgca gctggataca   2520
ggacagctgc tgaagattgc caaaaggggc ggagtgaccg cggtggaagc cgtgcacgcc   2580
tggagaaatg ccctgacagg agcccctctg aacctgaccc ccgaacaggt ggtggccatt   2640
gccagccacg acggcggcaa gcaggccctg gaaaccgtgc agagactgct gcccgtgctg   2700
tgccaggccc atggcctgac acctgaacag gtggtggcta tcgcctctca cgacggagga   2760
aaacaggctc tggaaacagt gcagcggctg ctgcctgtgc tgtgtcaggc tcacggcttg   2820
actccagaac aggtggtggc tattgcttcc aatattgggg ggaaacaggc cctggaaact   2880
gtgcagcgcc tgctgccagt gctgtgccag gctcacggac tgacccccga acaggtggtg   2940
gccattgcca gcaacaacgg cggcaagcag gccctggaaa ccgtgcagag actgctgccc   3000
gtgctgtgcc aggcccatgg cctgacacct gaacaggtgg tggctatcgc ctctaacaac   3060
ggaggaaaac aggctctgga aacagtgcag cggctgctgc ctgtgctgtg tcaggctcac   3120
ggcttgactc cagaacaggt ggtggctatt gcttccaaca acggggggaa acaggccctg   3180
gaaactgtgc agcgcctgct gccagtgctg tgccaggctc acgggctgac ccccgaacag   3240
gtggtggcca ttgccagcaa cggcggcggc aagcaggccc tggaaaccgt gcagagactg   3300
ctgcccgtgc tgtgccaggc ccatggcctg acacctgaac aggtggtggc tatcgcctct   3360
cacgacggag gaaaacaggc tctggaaaca gtgcagcggc tgctgcctgt gctgtgtcag   3420
gctcacggct tgactccaga acaggtggtg gctattgctt ccaatattgg ggggaaacag   3480
gccctggaaa ctgtgcagcg cctgctgcca gtgctgtgcc aggctcacgg cctcactccc   3540
gaacaggtgg tggccattgc cagcaacatc ggcggcaagc aggccctgga aaccgtgcag   3600
agactgctgc ccgtgctgtg ccaggcccat ggcctgacac ctgaacaggt ggtggctatc   3660
gcctctcacg acggaggaaa acaggctctg gaaacagtgc agcggctgct gcctgtgctg   3720
tgtcaggctc acggcttgac tccagaacag gtggtggcta ttgcttccaa caacgggggg   3780
aaacaggccc tggaaactgt gcagcgcctg ctgccagtgc tgtgccaggc tcacggactg   3840
acccccgaac aggtggtggc cattgccagc aacggcggcg gcaagcaggc cctggaaacc   3900
gtgcagagac tgctgcccgt gctgtgccag gcccatggcc tgacacctga acaggtggtg   3960
gctatcgcct ctaacaacgg aggaaaacaa gcactcgaga cagtgcagcg gctgctgcct   4020
gtgctgtgtc aggctcacgg cttgactcca gaacaggtgg tggctattgc ttccaacaac   4080
ggggggaaac aggccctgga aactgtgcag cgcctgctgc cagtgctgtg ccaggctcac   4140
gggctgaccc ccgaacaggt ggtggccatt gccagcaaca tcggcggcaa gcaggccctg   4200
gaaaccgtgc agagactgct gcccgtgctg tgccaggccc atggcctgac acctgaacag   4260
gtggtggcta tcgcctctaa caacggagga aaacaggctc tggaaacagt gcagcggctg   4320
ctgcctgtgc tgtgtcaggc tcacggcttg actccacagc aggtcgtggc aattgctagc   4380
aatatcggcg gacggcccgc cctggagagc attgtggccc agctgtctag acctgatcct   4440
gccctggccg ccctgacaaa tgatcacctg gtggccctgg cctgtctggg aggcagacct   4500
gccctggatg ccgtgaaaaa aggactgcct cacgcccctg ccctgattaa aagaacaaat   4560
```

-continued

```
agaagaatcc ccgagcggac ctctcacaga gtggccggat cccagctggt gaaatctgag   4620

ctggaggaga agaagtctga gctgagacac aagctgaagt acgtgcctca cgagtacatc   4680

gagctgatcg agatcgccag aaatagcacc caggatagaa tcctggagat gaaggtgatg   4740

gagttcttca tgaaagtgta cggctacaga ggaaagcatc tgggaggaag cagaaaacct   4800

gacggagcca tttatacagt gggcagccct atcgattatg gcgtgatcgt ggatacaaag   4860

gcctacagcg gaggctacaa tctgcctatt ggacaggccg atgagatgca gagatacgtg   4920

gaggagaacc aaaccaggaa caagcatatc aaccctaacg agtggtggaa ggtgtaccct   4980

tctagcgtga ccgagttcaa gttcctgttt gtgagcggcc acttcaaggg caattataag   5040

gcccagctga ccaggctgaa ccacatcaca aattgtaatg gcgccgtgct gtctgtggag   5100

gaactgctga ttggaggaga gatgattaag gccggaacac tgacactgga ggaggtgaga   5160

agaaagttca acaacggcga gatcaacttc tgaaagcttg atcgttcaaa catttggcaa   5220

taaagtttct taagattgaa tcctgttgcc ggtcttgcga tgattatcat ataatttctg   5280

ttgaattacg ttaagcatgt aataattaac atgtaatgca tgacgttatt tatgagatgg   5340

gtttttatga ttagagtccc gcaattatac atttaatacg cgatagaaaa caaaatatag   5400

cgcgcaaact aggataaatt atcgcgcgcg gtgtcatcta tgttactaga tcttcgaacc   5460

ctagtcgaag acaaccggtg catgcctgca gtgcagcgtg acccggtcgt gcccctctct   5520

agagataatg agcattgcat gtctaagtta taaaaaatta ccacatattt tttttgtcac   5580

acttgtttga agtgcagttt atctatcttt atacatatat ttaaacttta ctctacgaat   5640

aatataatct atagtactac aataatatca gtgttttaga gaatcatata aatgaacagt   5700

tagacatggt ctaaaggaca attgagtatt ttgacaacag gactctacag ttttatcttt   5760

ttagtgtgca tgtgttctcc tttttttttg caaatagctt cacctatata atacttcatc   5820

cattttatta gtacatccat ttagggttta gggttaatgg tttttataga ctaatttttt   5880

tagtacatct attttattct attttagcct ctaaattaag aaaactaaaa ctctatttta   5940

gtttttttat ttaataattt agatataaaa tagaataaaa taaagtgact aaaaattaaa   6000

caaataccct ttaagaaatt aaaaaaacta aggaaacatt tttcttgttt cgagtagata   6060

atgccagcct gttaaacgcc gtcgacgagt ctaacggaca ccaaccagcg aaccagcagc   6120

gtcgcgtcgg gccaagcgaa gcagacggca cggcatctct gtcgctgcct ctggacccct   6180

ctcgagagtt ccgctccacc gttggacttg ctccgctgtc ggcatccaga aattgcgtgg   6240

cggagcggca gacgtgagcc ggcacggcag gcggcctcct cctcctctca cggcaccggc   6300

agctacgggg gattcctttc ccaccgctcc ttcgctttcc cttcctcgcc cgccgtaata   6360

aatagacacc ccctccacac cctctttccc caacctcgtg ttgttcggag cgcacacaca   6420

cacaaccaga tctcccccaa atccacccgt cggcacctcc gcttcaaggt acgccgctcg   6480

tcctcccccc ccccccctct ctaccttctc tagatcggcg ttccggtcca tggttagggc   6540

ccggtagttc tacttctgtt catgtttgtg ttagatccgt gtttgtgtta gatccgtgct   6600

gctagcgttc gtacacggat gcgacctgta cgtcagacac gttctgattg ctaacttgcc   6660

agtgtttctc tttggggaat cctgggatgg ctctagccgt tccgcagacg ggatcgattt   6720

catgattttt tttgtttcgt tgcatagggt ttggtttgcc cttttccttt atttcaatat   6780

atgccgtgca cttgtttgtc gggtcatctt ttcatgcttt tttttgtctt ggttgtgatg   6840

atgtggtctg gttgggcggt cgttctagat cggagtagaa ttctgtttca aactacctgg   6900
```

-continued

```
tggatttatt aattttggat ctgtatgtgt gtgccataca tattcatagt tacgaattga   6960

agatgatgga tggaaatatc gatctaggat aggtatacat gttgatgcgg gttttactga   7020

tgcatataca gagatgcttt ttgttcgctt ggttgtgatg atgtggtgtg gttgggcggt   7080

cgttcattcg ttctagatcg gagtagaata ctgtttcaaa ctacctggtg tatttattaa   7140

ttttggaact gtatgtgtgt gtcatacatc ttcatagtta cgagtttaag atggatggaa   7200

atatcgatct aggataggta tacatgttga tgtgggtttt actgatgcat atacatgatg   7260

gcatatgcag catctattca tatgctctaa ccttgagtac ctatctatta taataaacaa   7320

gtatgtttta taattatttt gatcttgata tacttggatg atggcatatg cagcagctat   7380

atgtggattt ttttagccct gccttcatac gctatttatt tgcttggtac tgtttctttt   7440

gtcgatgctc accctgttgt ttggtgttac ttctgcagcg gccgcgccac catgggaaaa   7500

cctattccta atcctctgct gggcctggat tctaccggag gcatggcccc taagaaaaag   7560

cggaaggtgg acggcggagt ggacctgaga acactgggat attctcagca gcagcaggag   7620

aagatcaagc ccaaggtgag atctacagtg gcccagcacc acgaagccct ggtgggacac   7680

ggatttacac acgcccacat tgtggccctg tctcagcacc ctgccgccct gggaacagtg   7740

gccgtgaaat atcaggatat gattgccgcc ctgcctgagg ccacacacga agccattgtg   7800

ggagtgggaa aacagtggtc tggagccaga gccctggaag ccctgctgac agtggccgga   7860

gaactgagag gacctcctct gcagctggat acaggacagc tgctgaagat tgccaaaagg   7920

ggcggagtga ccgcggtgga agccgtgcac gcctggagaa atgccctgac aggagcccct   7980

ctgaacctga cccccgaaca ggtggtggcc attgccagca acaacggcgg caagcaggcc   8040

ctggaaaccg tgcagagact gctgcccgtg ctgtgccagg cccatggcct gacacctgaa   8100

caggtggtgg ctatcgcctc tcacgacgga ggaaaacagg ctctggaaac agtgcagcgg   8160

ctgctgcctg tgctgtgtca ggctcacggc ttgactccag aacaggtggt ggctattgct   8220

tccaacggcg gggggaaaca ggccctggaa actgtgcagc gcctgctgcc agtgctgtgc   8280

caggctcacg gactgacccc cgaacaggtg gtggccattg ccagcaacgg cggcggcaag   8340

caggccctgg aaaccgtgca gagactgctg cccgtgctgt gccaggccca tggcctgaca   8400

cctgaacagg tggtggctat cgcctctcac gacggaggaa aacaggctct ggaaacagtg   8460

cagcggctgc tgcctgtgct gtgtcaggct cacggcttga ctccagaaca ggtggtggct   8520

attgcttccc acgacggggg gaaacaggcc ctggaaactg tgcagcgcct gctgccagtg   8580

ctgtgccagg ctcacgggct gacccccgaa caggtggtgg ccattgccag caacggcggc   8640

ggcaagcagg ccctggaaac cgtgcagaga ctgctgcccg tgctgtgcca ggcccatggc   8700

ctgacacctg aacaggtggt ggctatcgcc tctaacggcg gaggaaaaca ggctctggaa   8760

acagtgcagc ggctgctgcc tgtgctgtgt caggctcacg gcttgactcc agaacaggtg   8820

gtggctattg cttcccacga cggggggaaa caggccctgg aaactgtgca gcgcctgctg   8880

ccagtgctgt gccaggctca cggcctcact cccgaacagg tggtggccat tgccagcaac   8940

aacggcggca agcaggccct ggaaaccgtg cagagactgc tgcccgtgct gtgccaggcc   9000

catggcctga cacctgaaca ggtggtggct atcgcctctc acgacggagg aaaacaggct   9060

ctggaaacag tgcagcggct gctgcctgtg ctgtgtcagg ctcacggctt gactccagaa   9120

caggtggtgg ctattgcttc ccacgacggg gggaaacagg ccctggaaac tgtgcagcgc   9180

ctgctgccag tgctgtgcca ggctcacgga ctgacccccg aacaggtggt ggccattgcc   9240

agcaacatcg gcggcaagca ggccctggaa accgtgcaga gactgctgcc cgtgctgtgc   9300
```

```
caggcccatg gcctgacacc tgaacaggtg gtggctatcg cctctaacaa cggaggaaaa   9360
caagcactcg agacagtgca gcggctgctg cctgtgctgt gtcaggctca cggcttgact   9420
ccagaacagg tggtggctat tgcttccaac ggcgggggga aacaggccct ggaaactgtg   9480
cagcgcctgc tgccagtgct gtgccaggct cacgggctga cccccgaaca ggtggtggcc   9540
attgccagcc acgacggcgg caagcaggcc ctggaaaccg tgcagagact gctgcccgtg   9600
ctgtgccagg cccatggcct gacacctgaa caggtggtgg ctatcgcctc taatatcgga   9660
ggaaaacagg ctctggaaac agtgcagcgg ctgctgcctg tgctgtgtca ggctcacggc   9720
ttgactccac agcaggtcgt ggcaattgct agccacgacg gcggacggcc cgccctggag   9780
agcattgtgg cccagctgtc tagacctgat cctgccctgg ccgccctgac aaatgatcac   9840
ctggtggccc tggcctgtct gggaggcaga cctgccctgg atgccgtgaa aaaaggactg   9900
cctcacgccc ctgccctgat taaaagaaca aatagaagaa tccccgagcg gacctctcac   9960
agagtggccg gatcccagct ggtgaaatct gagctggagg agaagaagtc tgagctgaga  10020
cacaagctga agtacgtgcc tcacgagtac atcgagctga tcgagatcgc cagaaatagc  10080
acccaggata gaatcctgga gatgaaggtg atggagttct tcatgaaagt gtacggctac  10140
agaggaaagc atctgggagg aagcagaaaa cctgacggag ccatttatac agtgggcagc  10200
cctatcgatt atggcgtgat cgtggataca aaggcctaca gcggaggcta caatctgcct  10260
attggacagg ccgatgagat gcagagatac gtggaggaga accaaaccag gaacaagcat  10320
atcaacccta acgagtggtg gaaggtgtac ccttctagcg tgaccgagtt caagttcctg  10380
tttgtgagcg gccacttcaa gggcaattat aaggcccagc tgaccaggct gaaccacatc  10440
acaaattgta atggcgccgt gctgtctgtg gaggaactgc tgattggagg agagatgatt  10500
aaggccggaa cactgacact ggaggaggtg agaagaaagt tcaacaacgg cgagatcaac  10560
ttctgaaagc ttgatcgttc aaacatttgg caataaagtt tcttaagatt gaatcctgtt  10620
gccggtcttg cgatgattat catataattt ctgttgaatt acgttaagca tgtaataatt  10680
aacatgtaat gcatgacgtt atttatgaga tgggttttta tgattagagt cccgcaatta  10740
tacatttaat acgcgataga aaacaaaata tagcgcgcaa actaggataa attatcgcgc  10800
gcggtgtcat ctatgttact agatcttcga agacggaccg cgcctgcagt gcagcgtgac  10860
ccggtcgtgc ccctctctag agataatgag cattgcatgt ctaagttata aaaaattacc  10920
acatattttt tttgtcacac ttgtttgaag tgcagtttat ctatctttat acatatattt  10980
aaactttact ctacgaataa tataatctat agtactacaa taatatcagt gttttagaga  11040
atcatataaa tgaacagtta gacatggtct aaaggacaat tgagtatttt gacaacagga  11100
ctctacagtt ttatcttttt agtgtgcatg tgttctcctt tttttttgca aatagcttca  11160
cctatataat acttcatcca ttttattagt acatccattt agggtttagg gttaatggtt  11220
tttatagact aatttttttta gtacatctat tttattctat tttagcctct aaattaagaa  11280
aactaaaact ctattttagt ttttttattt aataatttag atataaaata gaataaaata  11340
aagtgactaa aaattaaaca aataccottt aagaaattaa aaaaactaag gaaacatttt  11400
tcttgtttcg agtagataat gccagcctgt taaacgccgt cgacgagtct aacggacacc  11460
aaccagcgaa ccagcagcgt cgcgtcgggc caagcgaagc agacggcacg gcatctctgt  11520
cgctgcctct ggacccctct cgagagttcc gctccaccgt tggacttgct ccgctgtcgg  11580
catccagaaa ttgcgtggcg gagcggcaga cgtgagccgg cacggcaggc ggcctcctcc  11640
```

```
tcctctcacg gcaccggcag ctacggggga ttcctttccc accgctcctt cgctttccct  11700
tcctcgcccg ccgtaataaa tagacacccc ctccacaccc tctttcccca acctcgtgtt  11760
gttcggagcg cacacacaca caaccagatc tcccccaaat ccacccgtcg gcacctccgc  11820
ttcaaggtac gccgctcgtc ctcccccccc cccctctcta ccttctctag atcggcgttc  11880
cggtccatgg ttagggcccg gtagttctac ttctgttcat gtttgtgtta gatccgtgtt  11940
tgtgttagat ccgtgctgct agcgttcgta cacggatgcg acctgtacgt cagacacgtt  12000
ctgattgcta acttgccagt gtttctcttt ggggaatcct gggatggctc tagccgttcc  12060
gcagacggga tcgatttcat gatttttttt gtttcgttgc atagggtttg gtttgccctt  12120
ttcctttatt tcaatatatg ccgtgcactt gtttgtcggg tcatcttttc atgctttttt  12180
ttgtcttggt tgtgatgatg tggtctggtt gggcggtcgt tctagatcgg agtagaattc  12240
tgtttcaaac tacctggtgg atttattaat tttggatctg tatgtgtgtg ccatacatat  12300
tcatagttac gaattgaaga tgatggatgg aaatatcgat ctaggatagg tatacatgtt  12360
gatgcgggtt ttactgatgc atatacagag atgctttttg ttcgcttggt tgtgatgatg  12420
tggtgtggtt gggcggtcgt tcattcgttc tagatcggag tagaatactg tttcaaacta  12480
cctggtgtat ttattaattt tggaactgta tgtgtgtgtc atacatcttc atagttacga  12540
gtttaagatg gatggaaata tcgatctagg ataggtatac atgttgatgt gggttttact  12600
gatgcatata catgatggca tatgcagcat ctattcatat gctctaacct tgagtaccta  12660
tctattataa taaacaagta tgttttataa ttattttgat cttgatatac ttggatgatg  12720
gcatatgcag cagctatatg tggatttttt tagccctgcc ttcatacgct atttatttgc  12780
ttggtactgt ttcttttgtc gatgctcacc ctgttgtttg gtgttacttc tgcagggatc  12840
cggcagcagc catgcagaag ctgatcaaca gcgtgcagaa ctacgcctgg ggcagcaaga  12900
ccgccctgac cgagctgtac ggcatggaga accccagcag ccagcccatg gccgagctgt  12960
ggatgggcgc ccaccccaag agcagcagcc gcgtgcagaa cgccgccggc gacatcgtga  13020
gcctgcgcga cgtgatcgag agcgacaaga gcaccctgct gggcgaggcc gtggccaagc  13080
gcttcggcga gctgcccttc ctgttcaagg tgctgtgcgc cgcccagccc ctgagcatcc  13140
aggtgcaccc caacaagcac aacagcgaga tcggcttcgc caaggagaac gccgccggca  13200
tccccatgga cgccgccgag cgcaactaca aggaccccaa ccacaagccc gagctggtgt  13260
tcgccctgac cccctttcctg gccatgaacg ccttccgcga gttcagcgag atcgtgagcc  13320
tgctgcagcc cgtggccggc gcccaccccg ccatcgccca cttcctgcag cagcccgacg  13380
ccgagcgcct gagcgagctg ttcgccagcc tgctgaacat gcagggcgag gagaagagcc  13440
gcgccctggc catcctgaag agcgccctgg acagccagca gggcgagccc tggcagacca  13500
tccgcctgat cagcgagttc taccccgagg acagcggcct gttcagcccc ctgctgctga  13560
acgtggtgaa gctgaacccc ggcgaggcca tgttcctgtt cgccgagacc ccccacgcct  13620
acctgcaggg cgtggccctg gaggtgatgg ccaacagcga caacgtgctg cgcgccggcc  13680
tgacccccaa gtacatcgac atccccgagc tggtggccaa cgtgaagttc gaggccaagc  13740
ccgccaacca gctgctgacc cagcccgtga agcagggcgc cgagctggac ttccccatcc  13800
ccgtggacga cttcgccttc agcctgcacg acctgagcga caaggagacc accatcagcc  13860
agcagagcgc cgccatcctg ttctgcgtgg agggcgacgc caccctgtgg aagggcagcc  13920
agcagctgca gctgaagccc ggcgagagcg ccttcatcgc cgccaacgag agccccgtga  13980
ccgtgaaggg ccacggccgc ctggcccgcg tgtacaacaa gctgtgatag gagctcgatc  14040
```

cgtcgacctg cagatcgttc aaacatttgg caataaagtt tcttaagatt gaatcctgtt 14100
gccggtcttg cgatgattat catataattt ctgttgaatt acgttaagca tgtaataatt 14160
aacatgtaat gcatgacgtt atttatgaga tgggttttta tgattagagt cccgcaatta 14220
tacatttaat acgcgataga aaacaaaata tagcgcgcaa actaggataa attatcgcgc 14280
gcggtgtcat ctatgttact agatcggcgc gccgcaattg aagtttgggc ggccagcatg 14340
gccgtatccg caatgtgtta ttaagttgtc taagcgtcaa tttgtttaca ccacaatata 14400
tcctgccacc agccagccaa cagctccccg accggcagct cggcacaaaa tcaccactcg 14460
atacaggcag cccatcagaa ttaattctca tgtttgacag cttatcatcg actgcacggt 14520
gcaccaatgc ttctggcgtc aggcagccat cggaagctgt ggtatggctg tgcaggtcgt 14580
aaatcactgc ataattcgtg tcgctcaagg cgcactcccg ttctggataa tgttttttgc 14640
gccgacatca taacggttct ggcaaatatt ctgaaatgag ctgttgacaa ttaatcatcc 14700
ggctcgtata atgtgtggaa ttgtgagcgg ataacaattt cacacaggaa acagaccatg 14760
agggaagcgt tgatcgccga agtatcgact caactatcag aggtagttgg cgtcatcgag 14820
cgccatctcg aaccgacgtt gctggccgta catttgtacg gctccgcagt ggatggcggc 14880
ctgaagccac acagtgatat tgatttgctg gttacggtga ccgtaaggct tgatgaaaca 14940
acgcggcgag ctttgatcaa cgaccttttg gaaacttcgg cttcccctgg agagagcgag 15000
attctccgcg ctgtagaagt caccattgtt gtgcacgacg acatcattcc gtggcgttat 15060
ccagctaagc gcgaactgca atttggagaa tggcagcgca atgacattct tgcaggtatc 15120
ttcgagccag ccacgatcga cattgatctg gctatcttgc tgacaaaagc aagagaacat 15180
agcgttgcct tggtaggtcc agcggcggag gaactctttg atccggttcc tgaacaggat 15240
ctatttgagg cgctaaatga aaccttaacg ctatggaact cgccgcccga ctgggctggc 15300
gatgagcgaa atgtagtgct tacgttgtcc cgcatttggt acagcgcagt aaccggcaaa 15360
atcgcgccga aggatgtcgc tgccgactgg gcaatggagc gcctgccggc ccagtatcag 15420
cccgtcatac ttgaagctag gcaggcttat cttggacaag aagatcgctt ggcctcgcgc 15480
gcagatcagt tggaagaatt tgttcactac gtgaaaggcg agatcaccaa agtagtcggc 15540
aaataaagct ctagtggatc tccgtacccg ggatctggc tcgcggcgga cgcacgacgc 15600
cggggcgaga ccataggcga tctcctaaat caatagtagc tgtaacctcg aagcgtttca 15660
cttgtaacaa cgattgagaa tttttgtcat aaaattgaaa tacttggttc gcatttttgt 15720
catccgcggt cagccgcaat tctgacgaac tgcccattta gctggagatg attgtacatc 15780
cttcacgtga aaatttctca agcgctgtga acaagggttc agattttaga ttgaaaggtg 15840
agccgttgaa acacgttctt cttgtcgatg acgacgtcgc tatgcggcat cttattattg 15900
aataccttac gatccacgcc ttcaaagtga ccgcggtagc cgacagcacc cagttcacaa 15960
gagtactctc ttccgcgacg gtcgatgtcg tggttgttga tctagattta ggtcgtgaag 16020
atgggctcga gatcgttcgt aatctggcgg caaagtctga tattccaatc ataattatca 16080
gtggcgaccg ccttgaggag acggataaag ttgttgcact cgagctagga gcaagtgatt 16140
ttatcgctaa gccgttcagt atcagagagt ttctagcacg cattcgggtt gccttgcgcg 16200
tgcgccccaa cgttgtccgc tccaaagacc gacggtcttt ttgttttact gactggacac 16260
ttaatctcag gcaacgtcgc ttgatgtccg aagctggcgg tgaggtgaaa cttacggcag 16320
gtgagttcaa tcttctcctc gcgtttttag agaaaccccg cgacgttcta tcgcgcgagc 16380

-continued

```
aacttctcat tgccagtcga gtacgcgacg aggaggttta tgacaggagt atagatgttc  16440
tcattttgag gctgcgccgc aaacttgagg cagatccgtc aagccctcaa ctgataaaaa  16500
cagcaagagg tgccggttat ttctttgacg cggacgtgca ggtttcgcac ggggggacga  16560
tggcagcctg agccaattcc cagatccccg aggaatcggc gtgagcggtc gcaaaccatc  16620
cggcccggta caaatcggcg cggcgctggg tgatgacctg gtggagaagt tgaaggccgc  16680
gcaggccgcc cagcggcaac gcatcgaggc agaagcacgc cccggtgaat cgtggcaagc  16740
ggccgctgat cgaatccgca aagaatcccg gcaaccgccg gcagccggtg cgccgtcgat  16800
taggaagccg cccaagggcg acgagcaacc agattttttc gttccgatgc tctatgacgt  16860
gggcacccgc gatagtcgca gcatcatgga cgtggccgtt ttccgtctgt cgaagcgtga  16920
ccgacgagct ggcgaggtga tccgctacga gcttccagac gggcacgtag aggtttccgc  16980
agggccggcc ggcatggcca gtgtgtggga ttacgacctg gtactgatgg cggtttccca  17040
tctaaccgaa tccatgaacc gataccggga agggaaggga gacaagcccg gccgcgtgtt  17100
ccgtccacac gttgcggacg tactcaagtt ctgccggcga gccgatggcg gaaagcagaa  17160
agacgacctg gtagaaacct gcattcggtt aaacaccacg cacgttgcca tgcagcgtac  17220
gaagaaggcc aagaacggcc gcctggtgac ggtatccgag ggtgaagcct tgattagccg  17280
ctacaagatc gtaaagagcg aaaccgggcg gccggagtac atcgagatcg agctagctga  17340
ttggatgtac cgcgagatca cagaaggcaa gaacccggac gtgctgacgg ttcaccccga  17400
ttactttttg atcgatcccg gcatcggccg ttttctctac cgcctggcac gccgcgccgc  17460
aggcaaggca gaagccagat ggttgttcaa gacgatctac gaacgcagtg gcagcgccgg  17520
agagttcaag aagttctgtt tcaccgtgcg caagctgatc gggtcaaatg acctgccgga  17580
gtacgatttg aaggaggagg cggggcaggc tggcccgatc ctagtcatgc gctaccgcaa  17640
cctgatcgag ggcgaagcat ccgccggttc ctaatgtacg gagcagatgc tagggcaaat  17700
tgccctagca ggggaaaaag gtcgaaaagg tctctttcct gtggatagca cgtacattgg  17760
gaacccaaag ccgtacattg ggaaccggaa cccgtacatt gggaacccaa agccgtacat  17820
tgggaaccgg tcacacatgt aagtgactga tataaaagag aaaaaaggcg atttttccgc  17880
ctaaaactct ttaaaactta ttaaaactct taaaacccgc ctggcctgtg cataactgtc  17940
tggccagcgc acagccgaag agctgcaaaa agcgcctacc cttcggtcgc tgcgctccct  18000
acgccccgcc gcttcgcgtc ggcctatcgc ggccgctggc cgctcaaaaa tggctggcct  18060
acggccaggc aatctaccag ggcgcggaca agccgcgccg tcgccactcg accgccggcg  18120
ctgaggtctg cctcgtgaag aaggtgttgc tgactcatac caggcctgaa tcgccccatc  18180
atccagccag aaagtgaggg agccacggtt gatgagagct ttgttgtagg tggaccagtt  18240
ggtgattttg aacttttgct ttgccacgga acggtctgcg ttgtcgggaa gatgcgtgat  18300
ctgatccttc aactcagcaa aagttcgatt tattcaacaa agccgccgtc ccgtcaagtc  18360
agcgtaatgc tctgccagtg ttacaaccaa ttaaccaatt ctgattagaa aaactcatcg  18420
agcatcaaat gaaactgcaa tttattcata tcaggattat caataccata tttttgaaaa  18480
agccgtttct gtaatgaagg agaaaactca ccgaggcagt tccataggat ggcaagatcc  18540
tggtatcggt ctgcgattcc gactcgtcca acatcaatac aacctattaa tttcccctcg  18600
tcaaaaataa ggttatcaag tgagaaatca ccatgagtga cgactgaatc cggtgagaat  18660
ggcaaaagct ctgcattaat gaatcggcca acgcgcgggg agaggcggtt tgcgtattgg  18720
gcgctcttcc gcttcctcgc tcactgactc gctgcgctcg gtcgttcggc tgcggcgagc  18780
```

```
ggtatcagct cactcaaagg cggtaatacg gttatccaca gaatcagggg ataacgcagg  18840

aaagaacatg tgagcaaaag gccagcaaaa ggccaggaac cgtaaaaagg ccgcgttgct  18900

ggcgtttttc cataggctcc gcccccctga cgagcatcac aaaaatcgac gctcaagtca  18960

gaggtggcga aacccgacag gactataaag ataccaggcg tttccccctg gaagctccct  19020

cgtgcgctct cctgttccga ccctgccgct taccggatac ctgtccgcct ttctcccttc  19080

gggaagcgtg gcgctttctc atagctcacg ctgtaggtat ctcagttcgg tgtaggtcgt  19140

tcgctccaag ctgggctgtg tgcacgaacc ccccgttcag cccgaccgct gcgccttatc  19200

cggtaactat cgtcttgagt ccaacccggt aagacacgac ttatcgccac tggcagcagc  19260

cactggtaac aggattagca gagcgaggta tgtaggcggt gctacagagt tcttgaagtg  19320

gtggcctaac tacggctaca ctagaagaac agtatttggt atctgcgctc tgctgaagcc  19380

agttaccttc ggaaaaagag ttggtagctc ttgatccggc aaacaaacca ccgctggtag  19440

cggtggtttt tttgtttgca agcagcagat tacgcgcaga aaaaaaggat ctcaagaaga  19500

tcctttgatc ttttctacgg ggtctgacgc tcagtggaac gaaaactcac gttaagggat  19560

tttggtcatg agattatcaa aaaggatctt cacctagatc cttttgatcc ggaatta     19617
```

<210> SEQ ID NO 6
<211> LENGTH: 55
<212> TYPE: DNA
<213> ORGANISM: Artificial Sequence
<220> FEATURE:
<223> OTHER INFORMATION: target sequence for the TALEN of 22808

<400> SEQUENCE: 6

```
tccagggtca acgtggagac agggaggtac gaaccggtga ctggcgaagg aagca          55
```

<210> SEQ ID NO 7
<211> LENGTH: 15722
<212> TYPE: DNA
<213> ORGANISM: Artificial Sequence
<220> FEATURE:
<223> OTHER INFORMATION: vector 23123
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (304)..(2100)
<223> OTHER INFORMATION: prSoUbi4-04
<220> FEATURE:
<221> NAME/KEY: gene
<222> LOCATION: (2117)..(6286)
<223> OTHER INFORMATION: cCas9-01
<220> FEATURE:
<221> NAME/KEY: mutation
<222> LOCATION: (5606)..(5608)
<223> OTHER INFORMATION: L to V mutation
<220> FEATURE:
<221> NAME/KEY: mutation
<222> LOCATION: (5651)..(5653)
<223> OTHER INFORMATION: I to V mutation
<220> FEATURE:
<221> NAME/KEY: terminator
<222> LOCATION: (6292)..(6544)
<223> OTHER INFORMATION: tNOS-05-01
<220> FEATURE:
<221> NAME/KEY: promoter
<222> LOCATION: (6551)..(6925)
<223> OTHER INFORMATION: prOsU3-01
<220> FEATURE:
<221> NAME/KEY: misc_feature
<222> LOCATION: (6927)..(6946)

<223> OTHER INFORMATION: xZmPLAIIA
<220> FEATURE:
<221> NAME/KEY: misc_feature
<222> LOCATION: (6927)..(7031)
<223> OTHER INFORMATION: rsgRNAZmPLAIIA02
<220> FEATURE:
<221> NAME/KEY: promoter
<222> LOCATION: (7042)..(9033)
<223> OTHER INFORMATION: prUbi1-04
<220> FEATURE:
<221> NAME/KEY: gene
<222> LOCATION: (9050)..(10228)
<223> OTHER INFORMATION: cPMI-09
<220> FEATURE:
<221> NAME/KEY: terminator
<222> LOCATION: (10251)..(10503)
<223> OTHER INFORMATION: tNOS-05-01
<220> FEATURE:
<221> NAME/KEY: misc_feature
<222> LOCATION: (10547)..(10676)
<223> OTHER INFORMATION: bNLB-03
<220> FEATURE:
<221> NAME/KEY: gene
<222> LOCATION: (10956)..(11744)
<223> OTHER INFORMATION: cSpec-03
<220> FEATURE:
<221> NAME/KEY: promoter
<222> LOCATION: (11839)..(11969)
<223> OTHER INFORMATION: prVirG-01
<220> FEATURE:
<221> NAME/KEY: gene
<222> LOCATION: (12706)..(13779)
<223> OTHER INFORMATION: cRepA-01
<220> FEATURE:
<221> NAME/KEY: misc_feature
<222> LOCATION: (13822)..(14226)
<223> OTHER INFORMATION: oVS1-02
<220> FEATURE:
<221> NAME/KEY: misc_feature
<222> LOCATION: (14904)..(15710)
<223> OTHER INFORMATION: oCOLE-06

<400> SEQUENCE: 7
attcctgtgg ttggcatgca catacaaatg gacgaacgga taaacctttt cacgcccttt 60
taaatatccg attattctaa taaacgctct tttctcttag gtttacccgc caatatatcc 120
tgtcaaacac tgatagttta aactgaaggc gggaaacgac aatctgatca tgagcggaga 180
attaagggag tcacgttatg acccccgccg atgacgcggg acaagccgtt ttacgtttgg 240
aactgacaga accgcaacgc tgcaggaatt ggccgcagcg gccatttaaa caaagcttgg 300
taccattatg tggtctaggt aggttctata tataagaaaa cttgaaatgt tctaaaaaaa 360
aattcaagcc catgcatgat tgaagcaaac ggtatagcaa cggtgttaac ctgatctagt 420
gatctcttgc aatccttaac ggccacctac cgcaggtagc aaacggcgtc cccctcctcg 480
atatctccgc ggcgacctct ggctttttcc gcggaattgc gcggtgggga cggattccac 540
gagaccgcga cgcaaccgcc tctcgccgct gggccccaca ccgctcggtg ccgtagcctc 600
acgggactct ttctccctcc tcccccgtta taaattggct tcatcccctc cttgcctcat 660
ccatccaaat cccagtcccc aatcccatcc cttcgtagga gaaattcatc gaagctaagc 720
gaatcctcgc gatcctctca aggtactgcg agttttcgat ccccctctcg acccctcgta 780
tgtttgtgtt tgtcgtagcg tttgattagg tatgctttcc ctgtttgtgt tcgtcgtagc 840
gtttgattag gtatgctttc cctgttcgtg ttcatcgtag tgtttgatta ggtcgtgtga 900
ggcgatggcc tgctcgcgtc cttcgatctg tagtcgattt gcgggtcgtg gtgtagatct 960
gcgggctgtg atgaagttat ttggtgtgat ctgctcgcct gattctgcgg gttggctcga 1020
gtagatatga tggttggacc ggttggttcg tttaccgcgc tagggttggg ctgggatgat 1080

```
gttgcatgcg ccgttgcgcg tgatcccgca gcaggacttg cgtttgattg ccagatctcg   1140
ttacgattat gtgatttggt ttggactttt tagatctgta gcttctgctt atgtgccaga   1200
tgcgcctact gctcatatgc ctgatgataa tcataaatgg ctgtggaact aactagttga   1260
ttgcggagtc atgtatcagc tacaggtgta gggactagct acaggtgtag ggacttgcgt   1320
ctaattgttt ggtcctttac tcatgttgca attatgcaat ttagtttaga ttgtttgttc   1380
cactcatcta ggctgtaaaa gggacactgc ttagattgct gtttaatctt tttagtagat   1440
tatattatat tggtaactta ttacccctat tacatgccat acgtgacttc tgctcatgcc   1500
tgatgataat catagatcac tgtggaatta attagttgat tgttgaatca tgtttcatgt   1560
acataccacg gcacaattgc ttagttcctt aacaaatgca aattttactg atccatgtat   1620
gatttgcgtg gttctctaat gtgaaatact atagctactt gttagtaaga atcaggttcg   1680
tatgcttaat gctgtatgtg ccttctgctc atgcctgatg ataatcatat atcactggaa   1740
ttaattagtt gatcgtttaa tcatatatca agtacatacc atgccacaat ttttagtcac   1800
ttaacccatg cagattgaac tggtccctgc atgttttgct aaattgttct attctgatta   1860
gaccatatat catgtatttt tttttggtaa tggttctctt attttaaatg ctatatagtt   1920
ctggtacttg ttagaaagat ctgcttcata gtttagttgc ctatccctcg aattaggatg   1980
ctgagcagct gatcctatag ctttgtttca tgtatcaatt cttttgtgtt caacagtcag   2040
tttttgttag attcattgta acttatggtc gcttactctt ctggtcctca atgcttgcag   2100
gatcgcggcc gctcatatgg acaagaagta cagcatcggc ctggacatcg gcaccaacag   2160
cgtgggctgg gccgtgatca ccgacgagta caaggtgccg agcaagaagt tcaaggtgct   2220
gggcaacacc gacaggcaca gcatcaagaa gaacctgatc ggcgccctgc tgttcgacag   2280
cggcgagacc gccgaggcca ccaggctgaa gaggaccgcc aggaggaggt acaccaggag   2340
gaagaacagg atctgctacc tgcaggagat cttcagcaac gagatggcca aggtggacga   2400
cagcttcttc cacaggctgg aggagagctt cctggtggag gaggacaaga agcacgagag   2460
gcacccgatc ttcggcaaca tcgtggacga ggtggcctac cacgagaagt acccgaccat   2520
ctaccacctg aggaagaagc tggtggacag caccgacaag gccgacctga ggctgatcta   2580
cctggccctg gcccacatga tcaagttcag gggccacttc ctgatcgagg gcgacctgaa   2640
cccggacaac agcgacgtgg acaagctgtt catccagctg gtgcagacct acaaccagct   2700
gttcgaggag aacccgatca acgccagcgg cgtggacgcc aaggccatcc tgagcgccag   2760
gctgagcaag agcaggaggc tggagaacct gatcgcccag ctgccgggcg agaagaagaa   2820
cggcctgttc ggcaacctga tcgccctgag cctgggcctg accccgaact tcaagagcaa   2880
cttcgacctg gccgaggacg ccaagctgca gctgagcaag gacacctacg acgacgacct   2940
ggacaacctg ctggcccaga tcggcgacca gtacgccgac ctgttcctgg ccgccaagaa   3000
cctgagcgac gccatcctgc tgagcgacat cctgagggtg aacaccgaga tcaccaaggc   3060
cccgctgagc gccagcatga tcaagaggta cgacgagcac caccaggacc tgaccctgct   3120
gaaggccctg gtgaggcagc agctgccgga gaagtacaag gagatcttct tcgaccagag   3180
caagaacggc tacgccggct acatcgacgg cggcgccagc caggaggagt tctacaagtt   3240
catcaagccg atcctggaga agatggacgg caccgaggag ctgctggtga agctgaacag   3300
ggaggacctg ctgaggaagc agaggacctt cgacaacggc agcatcccgc accagatcca   3360
cctgggcgag ctgcacgcca tcctgaggag gcaggaggac ttctacccgt tcctgaagga   3420
```

-continued

```
caacagggag aagatcgaga agatcctgac cttccgcatc ccgtactacg tgggcccgct   3480
ggccaggggc aacagcaggt tcgcctggat gaccaggaag agcgaggaga ccatcacccc   3540
gtggaacttc gaggaggtgg tggacaaggg cgccagcgcc cagagcttca tcgagaggat   3600
gaccaacttc gacaagaacc tgccgaacga gaaggtgctg ccgaagcaca gcctgctgta   3660
cgagtacttc accgtgtaca acgagctgac caaggtgaag tacgtgaccg agggcatgag   3720
gaagccggcc ttcctgagcg gcgagcagaa gaaggccatc gtggacctgc tgttcaagac   3780
caacaggaag gtgaccgtga agcagctgaa ggaggactac ttcaagaaga tcgagtgctt   3840
cgacagcgtg gagatcagcg gcgtggagga caggttcaac gccagcctgg gcacctacca   3900
cgacctgctg aagatcatca aggacaagga cttcctggac aacgaggaga acgaggacat   3960
cctggaggac atcgtgctga ccctgaccct gttcgaggac agggagatga tcgaggagag   4020
gctgaagacc tacgcccacc tgttcgacga caaggtgatg aagcagctga agaggaggag   4080
gtacaccggc tggggcaggc tgagcaggaa gctgatcaac ggcatcaggg acaagcagag   4140
cggcaagacc atcctggact tcctgaagag cgacggcttc gccaacagga acttcatgca   4200
gctgatccac gacgacagcc tgaccttcaa ggaggacatc cagaaggccc aggtgagcgg   4260
ccagggcgac agcctgcacg agcacatcgc caacctggcc ggcagcccgg ccatcaagaa   4320
gggcatcctg cagaccgtga aggtggtgga cgagctggtg aaggtgatgg gcaggcacaa   4380
gccggagaac atcgtgatcg agatggccag ggagaaccag accacccaga agggccagaa   4440
gaacagcagg gagaggatga agaggatcga ggagggcatc aaggagctgg gcagccagat   4500
cctgaaggag cacccggtgg agaacaccca gctgcagaac gagaagctgt acctgtacta   4560
cctgcagaac ggcagggaca tgtacgtgga ccaggagctg gacatcaaca ggctgagcga   4620
ctacgacgtg gaccacatcg tgccgcagag cttcctgaag gacgacagca tcgacaacaa   4680
ggtgctgacc aggagcgaca agaacagggg caagagcgac aacgtgccga gcgaggaggt   4740
ggtgaagaag atgaaaaact actggaggca gctgctgaac gccaagctga tcacccagag   4800
gaagttcgac aacctgacca aggccgagag gggcggcctg agcgagctgg acaaggccgg   4860
cttcattaaa aggcagctgg tggagaccag gcagatcacc aagcacgtgg cccagatcct   4920
ggacagcagg atgaacacca agtacgacga gaacgacaag ctgatcaggg aggtgaaggt   4980
gatcaccctg aagagcaagc tggtgagcga cttcaggaag gacttccagt tctacaaggt   5040
gagggagatc aataattacc accacgccca cgacgcctac ctgaacgccg tggtgggcac   5100
cgccctgatt aaaaagtacc cgaagctgga gagcgagttc gtgtacggcg actacaaggt   5160
gtacgacgtg aggaagatga tcgccaagag cgagcaggag atcggcaagg ccaccgccaa   5220
gtacttcttc tacagcaaca tcatgaactt cttcaagacc gagatcaccc tggccaacgg   5280
cgagatcagg aagaggccgc tgatcgagac caacggcgag accggcgaga tcgtgtggga   5340
caagggcagg gacttcgcca ccgtgaggaa ggtgctgtcc atgccgcagg tgaacatcgt   5400
gaagaagacc gaggtgcaga ccggcggctt cagcaaggag agcatcctgc cgaagaggaa   5460
cagcgacaag ctgatcgcca ggaagaagga ctgggacccg aagaagtacg gcggcttcga   5520
cagcccgacc gtggcctaca gcgtgctggt ggtggccaag gtggagaagg gcaagagcaa   5580
gaagctgaag agcgtgaagg agctggtggg catcaccatc atggagagga gcagcttcga   5640
gaagaaccca gtggacttcc tggaggccaa gggctacaag gaggtgaaga aggacctgat   5700
cattaaactg ccgaagtaca gcctgttcga gctggagaac ggcaggaaga ggatgctggc   5760
cagcgccggc gagctgcaga agggcaacga gctggccctg ccgagcaagt acgtgaactt   5820
```

-continued

```
cctgtacctg gccagccact acgagaagct gaagggcagc ccggaggaca acgagcagaa   5880
gcagctgttc gtggagcagc acaagcacta cctggacgag atcatcgagc agatcagcga   5940
gttcagcaag agggtgatcc tggccgacgc caacctggac aaggtgctga gcgcctacaa   6000
caagcacagg gacaagccga tcagggagca ggccgagaac atcatccacc tgttcaccct   6060
gaccaacctg ggcgccccgg ccgccttcaa gtacttcgac accaccatcg acaggaagag   6120
gtacaccagc accaaggagg tgctggacgc caccctgatc caccagagca tcaccggcct   6180
gtacgagacc aggatcgacc tgagccagct gggcggcgac agcagcccgc cgaagaagaa   6240
gaggaaggtg agctggaagg acgccagcgg ctggagcagg atgtgaagct tgatcgttca   6300
aacatttggc aataaagttt cttaagattg aatcctgttg ccggtcttgc gatgattatc   6360
atataatttc tgttgaatta cgttaagcat gtaataatta acatgtaatg catgacgtta   6420
tttatgagat gggtttttat gattagagtc ccgcaattat acatttaata cgcgatagaa   6480
aacaaaatat agcgcgcaaa ctaggataaa ttatcgcgcg cggtgtcatc tatgttacta   6540
gatcttcgaa gggatcttta aacatacgaa cagatcactt aaagttcttc tgaagcaact   6600
taaagttatc aggcatgcat ggatcttgga ggaatcagat gtgcagtcag ggaccatagc   6660
acaggacagg cgtcttctac tggtgctacc agcaaatgct ggaagccggg aacactgggt   6720
acgttggaaa ccacgtgatg tggagtaaga taaactgtag gagaaaagca tttcgtagtg   6780
ggccatgaag cctttcagga catgtattgc agtatgggcc ggcccattac gcaattggac   6840
gacaacaaag actagtatta gtaccacctc ggctatccac atagatcaaa gctggtttaa   6900
aagagttgtg cagatgatcc gtggcagggt caacgtggag acaggggttt tagagctaga   6960
aatagcaagt taaaataagg ctagtccgtt atcaacttga aaaagtggca ccgagtcggt   7020
gctttttttt tcggaccgcg cctgcagtgc agcgtgaccc ggtcgtgccc ctctctagag   7080
ataatgagca ttgcatgtct aagttataaa aaattaccac atattttttt tgtcacactt   7140
gtttgaagtg cagtttatct atctttatac atatatttaa actttactct acgaataata   7200
taatctatag tactacaata atatcagtgt tttagagaat catataaatg aacagttaga   7260
catggtctaa aggacaattg agtattttga caacaggact ctacagtttt atctttttag   7320
tgtgcatgtg ttctcctttt tttttgcaaa tagcttcacc tatataatac ttcatccatt   7380
ttattagtac atccatttag ggtttagggt taatggtttt tatagactaa tttttttagt   7440
acatctattt tattctattt tagcctctaa attaagaaaa ctaaaactct attttagttt   7500
ttttatttaa taatttagat ataaaataga ataaaataaa gtgactaaaa attaaacaaa   7560
taccctttaa gaaattaaaa aaactaagga aacatttttc ttgtttcgag tagataatgc   7620
cagcctgtta aacgccgtcg acgagtctaa cggacaccaa ccagcgaacc agcagcgtcg   7680
cgtcgggcca agcgaagcag acggcacggc atctctgtcg ctgcctctgg acccctctcg   7740
agagttccgc tccaccgttg gacttgctcc gctgtcggca tccagaaatt gcgtggcgga   7800
gcggcagacg tgagccggca cggcaggcgg cctcctcctc ctctcacggc accggcagct   7860
acgggggatt cctttcccac cgctccttcg ctttcccttc ctcgcccgcc gtaataaata   7920
gacacccccct ccacaccctc tttccccaac ctcgtgttgt tcggagcgca cacacacaca   7980
accagatctc ccccaaatcc acccgtcggc acctccgctt caaggtacgc cgctcgtcct   8040
cccccccccc cctctctacc ttctctagat cggcgttccg gtccatggtt agggcccggt   8100
agttctactt ctgttcatgt ttgtgttaga tccgtgtttg tgttagatcc gtgctgctag   8160
```

-continued

```
cgttcgtaca cggatgcgac ctgtacgtca gacacgttct gattgctaac ttgccagtgt   8220
ttctctttgg ggaatcctgg gatggctcta gccgttccgc agacgggatc gatttcatga   8280
ttttttttgt ttcgttgcat agggtttggt ttgccctttt cctttatttc aatatatgcc   8340
gtgcacttgt ttgtcgggtc atcttttcat gctttttttt gtcttggttg tgatgatgtg   8400
gtctggttgg gcggtcgttc tagatcggag tagaattctg tttcaaacta cctggtggat   8460
ttattaattt tggatctgta tgtgtgtgcc atacatattc atagttacga attgaagatg   8520
atggatggaa atatcgatct aggataggta tacatgttga tgcgggtttt actgatgcat   8580
atacagagat gctttttgtt cgcttggttg tgatgatgtg gtgtggttgg gcggtcgttc   8640
attcgttcta gatcggagta gaatactgtt tcaaactacc tggtgtattt attaattttg   8700
gaactgtatg tgtgtgtcat acatcttcat agttacgagt ttaagatgga tggaaatatc   8760
gatctaggat aggtatacat gttgatgtgg gttttactga tgcatataca tgatggcata   8820
tgcagcatct attcatatgc tctaaccttg agtacctatc tattataata aacaagtatg   8880
ttttataatt attttgatct tgatatactt ggatgatggc atatgcagca gctatatgtg   8940
gattttttta gccctgcctt catacgctat ttatttgctt ggtactgttt cttttgtcga   9000
tgctcaccct gttgtttggt gttacttctg cagggatccg gcagcagcca tgcagaagct   9060
gatcaacagc gtgcagaact acgcctgggg cagcaagacc gccctgaccg agctgtacgg   9120
catggagaac cccagcagcc agcccatggc cgagctgtgg atgggcgccc accccaagag   9180
cagcagccgc gtgcagaacg ccgccggcga catcgtgagc ctgcgcgacg tgatcgagag   9240
cgacaagagc accctgctgg gcgaggccgt ggccaagcgc ttcggcgagc tgcccttcct   9300
gttcaaggtg ctgtgcgccg cccagcccct gagcatccag gtgcacccca acaagcacaa   9360
cagcgagatc ggcttcgcca aggagaacgc cgccggcatc cccatggacg ccgccgagcg   9420
caactacaag gaccccaacc acaagcccga gctggtgttc gccctgaccc ccttcctggc   9480
catgaacgcc ttccgcgagt tcagcgagat cgtgagcctg ctgcagcccg tggccggcgc   9540
ccaccccgcc atcgcccact tcctgcagca gcccgacgcc gagcgcctga gcgagctgtt   9600
cgccagcctg ctgaacatgc agggcgagga gaagagccgc gccctggcca tcctgaagag   9660
cgccctggac agccagcagg gcgagccctg gcagaccatc cgcctgatca gcgagttcta   9720
ccccgaggac agcggcctgt tcagccccct gctgctgaac gtggtgaagc tgaaccccgg   9780
cgaggccatg ttcctgttcg ccgagacccc ccacgcctac ctgcagggcg tggccctgga   9840
ggtgatggcc aacagcgaca acgtgctgcg cgccggcctg acccccaagt acatcgacat   9900
ccccgagctg gtggccaacg tgaagttcga ggccaagccc gccaaccagc tgctgaccca   9960
gcccgtgaag cagggcgccg agctggactt ccccatcccc gtggacgact tcgccttcag  10020
cctgcacgac ctgagcgaca aggagaccac catcagccag cagagcgccg ccatcctgtt  10080
ctgcgtggag ggcgacgcca ccctgtggaa gggcagccag cagctgcagc tgaagcccgg  10140
cgagagcgcc ttcatcgccg ccaacgagag ccccgtgacc gtgaagggcc acggccgcct  10200
ggcccgcgtg tacaacaagc tgtgatagga gctcgatccg tcgacctgca gatcgttcaa  10260
acatttggca ataaagtttc ttaagattga atcctgttgc cggtcttgcg atgattatca  10320
tataatttct gttgaattac gttaagcatg taataattaa catgtaatgc atgacgttat  10380
ttatgagatg ggtttttatg attagagtcc cgcaattata catttaatac gcgatagaaa  10440
acaaaatata gcgcgcaaac taggataaat tatcgcgcgc ggtgtcatct atgttactag  10500
atcggcgcgc cgcaattgaa gtttgggcgg ccagcatggc cgtatccgca atgtgttatt  10560
```

aagttgtcta agcgtcaatt tgtttacacc acaatatatc ctgccaccag ccagccaaca 10620
gctccccgac cggcagctcg gcacaaaatc accactcgat acaggcagcc catcagaatt 10680
aattctcatg tttgacagct tatcatcgac tgcacggtgc accaatgctt ctggcgtcag 10740
gcagccatcg gaagctgtgg tatggctgtg caggtcgtaa atcactgcat aattcgtgtc 10800
gctcaaggcg cactcccgtt ctggataatg ttttttgcgc cgacatcata acggttctgg 10860
caaatattct gaaatgagct gttgacaatt aatcatccgg ctcgtataat gtgtggaatt 10920
gtgagcggat aacaatttca cacaggaaac agaccatgag ggaagcgttg atcgccgaag 10980
tatcgactca actatcagag gtagttggcg tcatcgagcg ccatctcgaa ccgacgttgc 11040
tggccgtaca tttgtacggc tccgcagtgg atggcggcct gaagccacac agtgatattg 11100
atttgctggt tacggtgacc gtaaggcttg atgaaacaac gcggcgagct ttgatcaacg 11160
accttttgga aacttcggct tcccctggag agagcgagat tctccgcgct gtagaagtca 11220
ccattgttgt gcacgacgac atcattccgt ggcgttatcc agctaagcgc gaactgcaat 11280
ttggagaatg gcagcgcaat gacattcttg caggtatctt cgagccagcc acgatcgaca 11340
ttgatctggc tatcttgctg acaaaagcaa gagaacatag cgttgccttg gtaggtccag 11400
cggcggagga actctttgat ccggttcctg aacaggatct atttgaggcg ctaaatgaaa 11460
ccttaacgct atggaactcg ccgcccgact gggctggcga tgagcgaaat gtagtgctta 11520
cgttgtcccg catttggtac agcgcagtaa ccggcaaaat cgcgccgaag gatgtcgctg 11580
ccgactgggc aatggagcgc ctgccggccc agtatcagcc cgtcatactt gaagctaggc 11640
aggcttatct tggacaagaa gatcgcttgg cctcgcgcgc agatcagttg gaagaatttg 11700
ttcactacgt gaaaggcgag atcaccaaag tagtcggcaa ataaagctct agtggatctc 11760
cgtacccggg gatctggctc gcggcggacg cacgacgccg gggcgagacc ataggcgatc 11820
tcctaaatca atagtagctg taacctcgaa gcgtttcact tgtaacaacg attgagaatt 11880
tttgtcataa aattgaaata cttggttcgc atttttgtca tccgcggtca gccgcaattc 11940
tgacgaactg cccatttagc tggagatgat tgtacatcct tcacgtgaaa atttctcaag 12000
cgctgtgaac aagggttcag attttagatt gaaaggtgag ccgttgaaac acgttcttct 12060
tgtcgatgac gacgtcgcta tgcggcatct tattattgaa taccttacga tccacgcctt 12120
caaagtgacc gcggtagccg acagcaccca gttcacaaga gtactctctt ccgcgacggt 12180
cgatgtcgtg gttgttgatc tagatttagg tcgtgaagat gggctcgagc taggagcaag 12240
tgattttatc gctaagccgt tcagtatcag agagtttcta gcacgcattc gggttgcctt 12300
gcgcgtgcgc cccaacgttg tccgctccaa agaccgacgg tctttttgtt ttactgactg 12360
gacacttaat ctcaggcaac gtcgcttgat gtccgaagct ggcggtgagg tgaaacttac 12420
ggcaggtgag ttcaatcttc tcctcgcgtt tttagagaaa ccccgcgacg ttctatcgcg 12480
cgagcaactt ctcattgcca gtcgagtacg cgacgaggag gtttatgaca ggagtataga 12540
tgttctcatt ttgaggctgc gccgcaaact tgaggcagat ccgtcaagcc ctcaactgat 12600
aaaaacagca agaggtgccg gttatttctt tgacgcggac gtgcaggttt cgcacggggg 12660
gacgatggca gcctgagcca attcccagat ccccgaggaa tcggcgtgag cggtcgcaaa 12720
ccatccggcc cggtacaaat cggcgcggcg ctgggtgatg acctggtgga gaagttgaag 12780
gccgcgcagg ccgcccagcg gcaacgcatc gaggcagaag cacgccccgg tgaatcgtgg 12840
caagcggccg ctgatcgaat ccgcaaagaa tcccggcaac cgccggcagc cggtgcgccg 12900
tcgattagga agccgcccaa gggcgacgag caaccagatt ttttcgttcc gatgctctat 12960
gacgtgggca cccgcgatag tcgcagcatc atggacgtgg ccgttttccg tctgtcgaag 13020
cgtgaccgac gagctggcga ggtgatccgc tacgagcttc cagacgggca cgtagaggtt 13080
tccgcagggc cggccggcat ggccagtgtg tgggattacg acctggtact gatggcggtt 13140
tcccatctaa ccgaatccat gaaccgatac cgggaaggga agggagacaa gcccggccgc 13200
gtgttccgtc cacacgttgc ggacgtactc aagttctgcc ggcgagccga tggcggaaag 13260
cagaaagacg acctggtaga aacctgcatt cggttaaaca ccacgcacgt tgccatgcag 13320
cgtacgaaga aggccaagaa cggccgcctg gtgacggtat ccgagggtga agccttgatt 13380
agccgctaca agatcgtaaa gagcgaaacc gggcggccgg agtacatcga gatcgagcta 13440
gctgattgga tgtaccgcga gatcacagaa ggcaagaacc cggacgtgct gacggttcac 13500
cccgattact ttttgatcga tcccggcatc ggccgttttc tctaccgcct ggcacgccgc 13560
gccgcaggca aggcagaagc cagatggttg ttcaagacga tctacgaacg cagtggcagc 13620
gccggagagt tcaagaagtt ctgtttcacc gtgcgcaagc tgatcgggtc aaatgacctg 13680
ccggagtacg atttgaagga ggaggcgggg caggctggcc cgatcctagt catgcgctac 13740
cgcaacctga tcgagggcga agcatccgcc ggttcctaat gtacggagca gatgctaggg 13800
caaattgccc tagcagggga aaaaggtcga aaaggtctct ttcctgtgga tagcacgtac 13860
attgggaacc caaagccgta cattgggaac cggaacccgt acattgggaa cccaaagccg 13920
tacattggga accggtcaca catgtaagtg actgatataa aagagaaaaa aggcgatttt 13980
tccgcctaaa actctttaaa acttattaaa actcttaaaa cccgcctggc ctgtgcataa 14040
ctgtctggcc agcgcacagc cgaagagctg caaaaagcgc ctacccttcg gtcgctgcgc 14100
tccctacgcc ccgccgcttc gcgtcggcct atcgcggccg ctggccgctc aaaaatggct 14160
ggcctacggc caggcaatct accagggcgc ggacaagccg cgccgtcgcc actcgaccgc 14220
cggcgctgag gtctgcctcg tgaagaaggt gttgctgact cataccaggc ctgaatcgcc 14280
ccatcatcca gccagaaagt gagggagcca cggttgatga gagctttgtt gtaggtggac 14340
cagttggtga ttttgaactt ttgctttgcc acggaacggt ctgcgttgtc gggaagatgc 14400
gtgatctgat ccttcaactc agcaaaagtt cgatttattc aacaaagccg ccgtcccgtc 14460
aagtcagcgt aatgctctgc cagtgttaca accaattaac caattctgat tagaaaaact 14520
catcgagcat caaatgaaac tgcaatttat tcatatcagg attatcaata ccatattttt 14580
gaaaaagccg tttctgtaat gaaggagaaa actcaccgag gcagttccat aggatggcaa 14640
gatcctggta tcggtctgcg attccgactc gtccaacatc aatacaacct attaatttcc 14700
cctcgtcaaa aataaggtta tcaagtgaga aatcaccatg agtgacgact gaatccggtg 14760
agaatggcaa aagctctgca ttaatgaatc ggccaacgcg cggggagagg cggtttgcgt 14820
attgggcgct cttccgcttc ctcgctcact gactcgctgc gctcggtcgt tcggctgcgg 14880
cgagcggtat cagctcactc aaaggcggta atacggttat ccacagaatc aggggataac 14940
gcaggaaaga acatgtgagc aaaaggccag caaaaggcca ggaaccgtaa aaaggccgcg 15000
ttgctggcgt ttttccatag gctccgcccc cctgacgagc atcacaaaaa tcgacgctca 15060
agtcagaggt ggcgaaaccc gacaggacta taaagatacc aggcgtttcc ccctggaagc 15120
tccctcgtgc gctctcctgt tccgaccctg ccgcttaccg gatacctgtc cgcctttctc 15180
ccttcgggaa gcgtggcgct ttctcatagc tcacgctgta ggtatctcag ttcggtgtag 15240
gtcgttcgct ccaagctggg ctgtgtgcac gaaccccccg ttcagcccga ccgctgcgcc 15300
ttatccggta actatcgtct tgagtccaac ccggtaagac acgacttatc gccactggca 15360
gcagccactg gtaacaggat tagcagagcg aggtatgtag gcggtgctac agagttcttg 15420
aagtggtggc ctaactacgg ctacactaga agaacagtat ttggtatctg cgctctgctg 15480
aagccagtta ccttcggaaa aagagttggt agctcttgat ccggcaaaca aaccaccgct 15540
ggtagcggtg gtttttttgt ttgcaagcag cagattacgc gcagaaaaaa aggatctcaa 15600
gaagatcctt tgatcttttc tacggggtct gacgctcagt ggaacgaaaa ctcacgttaa 15660
gggattttgg tcatgagatt atcaaaaagg atcttcacct agatcctttt gatccggaat 15720
ta 15722

<210> SEQ ID NO 8
<211> LENGTH: 20
<212> TYPE: DNA
<213> ORGANISM: Artificial Sequence
<220> FEATURE:
<223> OTHER INFORMATION: for editing MTL

<400> SEQUENCE: 8
gggtcaacgt ggagacaggg 20

<210> SEQ ID NO 9
<211> LENGTH: 41
<212> TYPE: DNA
<213> ORGANISM: Zea mays

<400> SEQUENCE: 9
agggtcaacg tggagacagg gaggtacgaa ccggtgactg g 41

<210> SEQ ID NO 10
<211> LENGTH: 45
<212> TYPE: DNA
<213> ORGANISM: Zea mays

<400> SEQUENCE: 10
agggtcaacg tggagacagg cgaggaggta cgaaccggtg actgg 45

<210> SEQ ID NO 11
<211> LENGTH: 42
<212> TYPE: DNA
<213> ORGANISM: Artificial Sequence
<220> FEATURE:
<223> OTHER INFORMATION: mutated MTL

<400> SEQUENCE: 11
agggtcaacg tggagacaag ggaggtacga accggtgact gg 42

<210> SEQ ID NO 12
<211> LENGTH: 28
<212> TYPE: DNA
<213> ORGANISM: Artificial Sequence
<220> FEATURE:
<223> OTHER INFORMATION: mutated MTL portion

<400> SEQUENCE: 12
agggtcaacg tggagaaccg gtgactgg 28

<210> SEQ ID NO 13
<211> LENGTH: 40
<212> TYPE: DNA
<213> ORGANISM: Artificial Sequence
<220> FEATURE:

<223> OTHER INFORMATION: mutated MTL portion

<400> SEQUENCE: 13
agggtcaacg tggagacggg aggtacgaac cggtgactgg 40

<210> SEQ ID NO 14
<211> LENGTH: 28
<212> TYPE: DNA
<213> ORGANISM: Artificial Sequence
<220> FEATURE:
<223> OTHER INFORMATION: mutated MTL portion

<400> SEQUENCE: 14
agggtcaacg tggagaaccg gtgactgg 28

<210> SEQ ID NO 15
<211> LENGTH: 42
<212> TYPE: DNA
<213> ORGANISM: Artificial Sequence
<220> FEATURE:
<223> OTHER INFORMATION: mutated MTL portion

<400> SEQUENCE: 15
agggtcaacg tggagacaag ggaggtacga accggtgact gg 42

<210> SEQ ID NO 16
<211> LENGTH: 40
<212> TYPE: DNA
<213> ORGANISM: Artificial Sequence
<220> FEATURE:
<223> OTHER INFORMATION: mutated MTL portion

<400> SEQUENCE: 16
agggtcaacg tggagacggg aggtacgaac cggtgactgg 40

<210> SEQ ID NO 17
<211> LENGTH: 41
<212> TYPE: DNA
<213> ORGANISM: Artificial Sequence
<220> FEATURE:
<223> OTHER INFORMATION: unmutated MTL portion

<400> SEQUENCE: 17
agggtcaacg tggagacagg gaggtacgaa ccggtgactg g 41

<210> SEQ ID NO 18
<211> LENGTH: 28
<212> TYPE: DNA
<213> ORGANISM: Artificial Sequence
<220> FEATURE:
<223> OTHER INFORMATION: mutated MTL portion

<400> SEQUENCE: 18
agggtcaacg tggagaaccg gtgactgg 28

<210> SEQ ID NO 19
<211> LENGTH: 1371
<212> TYPE: DNA
<213> ORGANISM: Zea mays

<400> SEQUENCE: 19
agttcatcac taatcacact tattgttccc tcgacgagta tctagctagc tcattaatcg 60
atcaatcggg gtgtgcggtc gaaggcggca atggcgagct actcgtcgcg gcgtccatgc 120
aatacctgta gcacgaaggc gatggccggg agcgtggtcg gcgagcccgt cgtgctgggg 180

```
cagagggtga cggtgctgac ggtggacggc ggcggcgtcc ggggtctcat cccgggaacc    240

atcctcgcct tcctcgaggc caggctgcag gagctggacg gaccggaggc gaggctggcg    300

gactacttcg actacatcgc cggaaccagc accggcggtc tcatcaccgc catgctcacc    360

gcgcccggca aggacaagcg gcctctctac gctgccaagg acatcaacca cttttacatg    420

gagaactgcc cgcgcatctt ccctcagaag agcaggcttg cggccgccat gtccgcgctg    480

aggaagccaa agtacaacgg caagtgcatg cgcagcctga ttaggagcat cctcggcgag    540

acgagggcca agagcacgcc tctgaagaac gctctgctct cggacgtgtg cattggcacg    600

tccgccgcgc cgacctacct cccggcgcac tacttccaga ctgaagacgc caacggcaag    660

gagcgcgaat acaacctcat cgacggcggt gtggcggcca acaacccgac gatggttgcg    720

atgacgcaga tcaccaaaaa gatgcttgcc agcaaggaca aggccgagga gctgtaccca    780

gtgaagccgt cgaactgccg caggttcctg gtgctgtcca tcgggacggg gtcgacgtcc    840

gagcagggcc tctacacggc gcggcagtgc tcccggtggg gtatctgccg gtggctccgc    900

aacaacggca tggcccccat catcgacatc ttcatggcgg ccagctcgga cctggtggac    960

atccacgtcg ccgcgatgtt ccagtcgctc cacagcgacg gcgactacct gcgcatccag   1020

gacaactcgc tccgtggcgc cgcggccacc gtggacgcgg cgacgccgga gaacatgcgg   1080

acgctcgtcg ggatcgggga gcggatgctg gcacagaggg tgtccagggt caacgtggag   1140

acagggaggt acgaaccggt gactggcgaa ggaagcaatg ccgatgccct cggtgggctc   1200

gctaggcagc tctccgagga gaggagaaca aggctcgcgc gccgcgtgtc tgccatcaac   1260

ccaagaggct ctagatgtgc gtcgtacgat atctaagaca agtggcttta ctgtcagtca   1320

catgcttgta aataagtaga ctttatttta ataaaacata aaaatatata t            1371
```

```
<210> SEQ ID NO 20
<211> LENGTH: 15722
<212> TYPE: DNA
<213> ORGANISM: Artificial Sequence
<220> FEATURE:
<223> OTHER INFORMATION: vector 23397
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (304)..(2100)
<223> OTHER INFORMATION: prSoUbi4-04
<220> FEATURE:
<221> NAME/KEY: gene
<222> LOCATION: (2117)..(6286)
<223> OTHER INFORMATION: cCas9-01
<220> FEATURE:
<221> NAME/KEY: mutation
<222> LOCATION: (5606)..(5608)
<223> OTHER INFORMATION: L to V mutation
<220> FEATURE:
<221> NAME/KEY: mutation
<222> LOCATION: (5651)..(5653)
<223> OTHER INFORMATION: I to V mutation
<220> FEATURE:
<221> NAME/KEY: terminator
<222> LOCATION: (6292)..(6544)
<223> OTHER INFORMATION: tNOS-05-01
<220> FEATURE:
<221> NAME/KEY: promoter
<222> LOCATION: (6551)..(6925)
<223> OTHER INFORMATION: prOsU3-01
<220> FEATURE:
<221> NAME/KEY: misc_feature
<222> LOCATION: (6927)..(6946)
```

<223> OTHER INFORMATION: xZmVLHP
<220> FEATURE:
<221> NAME/KEY: misc_feature
<222> LOCATION: (6927)..(7031)
<223> OTHER INFORMATION: rsgRNAZmVLHP-02
<220> FEATURE:
<221> NAME/KEY: promoter
<222> LOCATION: (7042)..(9033)
<223> OTHER INFORMATION: prUbi1-04
<220> FEATURE:
<221> NAME/KEY: gene
<222> LOCATION: (9050)..(10228)
<223> OTHER INFORMATION: cPMI-09
<220> FEATURE:
<221> NAME/KEY: terminator
<222> LOCATION: (10251)..(10503)
<223> OTHER INFORMATION: tNOS-05-01
<220> FEATURE:
<221> NAME/KEY: misc_feature
<222> LOCATION: (10547)..(10676)
<223> OTHER INFORMATION: bNLB-03
<220> FEATURE:
<221> NAME/KEY: gene
<222> LOCATION: (10956)..(11744)
<223> OTHER INFORMATION: cSpec-03
<220> FEATURE:
<221> NAME/KEY: promoter
<222> LOCATION: (11839)..(11969)
<223> OTHER INFORMATION: prVirG-01
<220> FEATURE:
<221> NAME/KEY: gene
<222> LOCATION: (12706)..(13779)
<223> OTHER INFORMATION: cRepA-01
<220> FEATURE:
<221> NAME/KEY: misc_feature
<222> LOCATION: (13822)..(14226)
<223> OTHER INFORMATION: oVS1-02
<220> FEATURE:
<221> NAME/KEY: misc_feature
<222> LOCATION: (14904)..(15710)
<223> OTHER INFORMATION: oCOLE-06

<400> SEQUENCE: 20
attcctgtgg ttggcatgca catacaaatg gacgaacgga taaacctttt cacgcccttt 60
taaatatccg attattctaa taaacgctct tttctcttag gtttacccgc caatatatcc 120
tgtcaaacac tgatagttta aactgaaggc gggaaacgac aatctgatca tgagcggaga 180
attaagggag tcacgttatg acccccgccg atgacgcggg acaagccgtt ttacgtttgg 240
aactgacaga accgcaacgc tgcaggaatt ggccgcagcg gccatttaaa caaagcttgg 300
taccattatg tggtctaggt aggttctata tataagaaaa cttgaaatgt tctaaaaaaa 360
aattcaagcc catgcatgat tgaagcaaac ggtatagcaa cggtgttaac ctgatctagt 420
gatctcttgc aatccttaac ggccacctac cgcaggtagc aaacggcgtc cccctcctcg 480
atatctccgc ggcgacctct ggctttttcc gcggaattgc gcggtgggga cggattccac 540
gagaccgcga cgcaaccgcc tctcgccgct gggccccaca ccgctcggtg ccgtagcctc 600
acgggactct ttctccctcc tcccccgtta taaattggct tcatcccctc cttgcctcat 660
ccatccaaat cccagtcccc aatcccatcc cttcgtagga gaaattcatc gaagctaagc 720
gaatcctcgc gatcctctca aggtactgcg agttttcgat ccccctctcg acccctcgta 780
tgtttgtgtt tgtcgtagcg tttgattagg tatgctttcc ctgtttgtgt tcgtcgtagc 840
gtttgattag gtatgctttc cctgttcgtg ttcatcgtag tgtttgatta ggtcgtgtga 900
ggcgatggcc tgctcgcgtc cttcgatctg tagtcgattt gcgggtcgtg gtgtagatct 960
gcgggctgtg atgaagttat ttggtgtgat ctgctcgcct gattctgcgg gttggctcga 1020
gtagatatga tggttggacc ggttggttcg tttaccgcgc tagggttggg ctgggatgat 1080

-continued

```
gttgcatgcg ccgttgcgcg tgatcccgca gcaggacttg cgtttgattg ccagatctcg   1140
ttacgattat gtgatttggt ttggactttt tagatctgta gcttctgctt atgtgccaga   1200
tgcgcctact gctcatatgc ctgatgataa tcataaatgg ctgtggaact aactagttga   1260
ttgcggagtc atgtatcagc tacaggtgta gggactagct acaggtgtag ggacttgcgt   1320
ctaattgttt ggtcctttac tcatgttgca attatgcaat ttagtttaga ttgtttgttc   1380
cactcatcta ggctgtaaaa gggacactgc ttagattgct gtttaatctt tttagtagat   1440
tatattatat tggtaactta ttacccctat tacatgccat acgtgacttc tgctcatgcc   1500
tgatgataat catagatcac tgtggaatta attagttgat tgttgaatca tgtttcatgt   1560
acataccacg gcacaattgc ttagttcctt aacaaatgca aattttactg atccatgtat   1620
gatttgcgtg gttctctaat gtgaaatact atagctactt gttagtaaga atcaggttcg   1680
tatgcttaat gctgtatgtg ccttctgctc atgcctgatg ataatcatat atcactggaa   1740
ttaattagtt gatcgtttaa tcatatatca agtacatacc atgccacaat ttttagtcac   1800
ttaacccatg cagattgaac tggtccctgc atgttttgct aaattgttct attctgatta   1860
gaccatatat catgtatttt tttttggtaa tggttctctt attttaaatg ctatatagtt   1920
ctggtacttg ttagaaagat ctgcttcata gtttagttgc ctatccctcg aattaggatg   1980
ctgagcagct gatcctatag ctttgtttca tgtatcaatt cttttgtgtt caacagtcag   2040
tttttgttag attcattgta acttatggtc gcttactctt ctggtcctca atgcttgcag   2100
gatcgcggcc gctcatatgg acaagaagta cagcatcggc ctggacatcg gcaccaacag   2160
cgtgggctgg gccgtgatca ccgacgagta caaggtgccg agcaagaagt tcaaggtgct   2220
gggcaacacc gacaggcaca gcatcaagaa gaacctgatc ggcgccctgc tgttcgacag   2280
cggcgagacc gccgaggcca ccaggctgaa gaggaccgcc aggaggaggt acaccaggag   2340
gaagaacagg atctgctacc tgcaggagat cttcagcaac gagatggcca aggtggacga   2400
cagcttcttc cacaggctgg aggagagctt cctggtggag gaggacaaga agcacgagag   2460
gcacccgatc ttcggcaaca tcgtggacga ggtggcctac cacgagaagt acccgaccat   2520
ctaccacctg aggaagaagc tggtggacag caccgacaag gccgacctga ggctgatcta   2580
cctggccctg gcccacatga tcaagttcag gggccacttc ctgatcgagg gcgacctgaa   2640
cccggacaac agcgacgtgg acaagctgtt catccagctg gtgcagacct acaaccagct   2700
gttcgaggag aacccgatca acgccagcgg cgtggacgcc aaggccatcc tgagcgccag   2760
gctgagcaag agcaggaggc tggagaacct gatcgcccag ctgccgggcg agaagaagaa   2820
cggcctgttc ggcaacctga tcgccctgag cctgggcctg accccgaact tcaagagcaa   2880
cttcgacctg gccgaggacg ccaagctgca gctgagcaag gacacctacg acgacgacct   2940
ggacaacctg ctggcccaga tcggcgacca gtacgccgac ctgttcctgg ccgccaagaa   3000
cctgagcgac gccatcctgc tgagcgacat cctgagggtg aacaccgaga tcaccaaggc   3060
cccgctgagc gccagcatga tcaagaggta cgacgagcac caccaggacc tgaccctgct   3120
gaaggccctg gtgaggcagc agctgccgga gaagtacaag gagatcttct tcgaccagag   3180
caagaacggc tacgccggct acatcgacgg cggcgccagc caggaggagt tctacaagtt   3240
catcaagccg atcctggaga agatggacgg caccgaggag ctgctggtga agctgaacag   3300
ggaggacctg ctgaggaagc agaggacctt cgacaacggc agcatcccgc accagatcca   3360
cctgggcgag ctgcacgcca tcctgaggag gcaggaggac ttctacccgt tcctgaagga   3420
```

caacagggag aagatcgaga agatcctgac cttccgcatc ccgtactacg tgggcccgct 3480
ggccaggggc aacagcaggt tcgcctggat gaccaggaag agcgaggaga ccatcacccc 3540
gtggaacttc gaggaggtgg tggacaaggg cgccagcgcc cagagcttca tcgagaggat 3600
gaccaacttc gacaagaacc tgccgaacga gaaggtgctg ccgaagcaca gcctgctgta 3660
cgagtacttc accgtgtaca acgagctgac caaggtgaag tacgtgaccg agggcatgag 3720
gaagccggcc ttcctgagcg gcgagcagaa gaaggccatc gtggacctgc tgttcaagac 3780
caacaggaag gtgaccgtga agcagctgaa ggaggactac ttcaagaaga tcgagtgctt 3840
cgacagcgtg gagatcagcg gcgtggagga caggttcaac gccagcctgg gcacctacca 3900
cgacctgctg aagatcatca aggacaagga cttcctggac aacgaggaga acgaggacat 3960
cctggaggac atcgtgctga ccctgaccct gttcgaggac agggagatga tcgaggagag 4020
gctgaagacc tacgcccacc tgttcgacga caaggtgatg aagcagctga agaggaggag 4080
gtacaccggc tggggcaggc tgagcaggaa gctgatcaac ggcatcaggg acaagcagag 4140
cggcaagacc atcctggact tcctgaagag cgacggcttc gccaacagga acttcatgca 4200
gctgatccac gacgacagcc tgaccttcaa ggaggacatc cagaaggccc aggtgagcgg 4260
ccagggcgac agcctgcacg agcacatcgc caacctggcc ggcagcccgg ccatcaagaa 4320
gggcatcctg cagaccgtga aggtggtgga cgagctggtg aaggtgatgg gcaggcacaa 4380
gccggagaac atcgtgatcg agatggccag ggagaaccag accacccaga agggccagaa 4440
gaacagcagg gagaggatga agaggatcga ggagggcatc aaggagctgg gcagccagat 4500
cctgaaggag cacccggtgg agaacaccca gctgcagaac gagaagctgt acctgtacta 4560
cctgcagaac ggcagggaca tgtacgtgga ccaggagctg gacatcaaca ggctgagcga 4620
ctacgacgtg gaccacatcg tgccgcagag cttcctgaag gacgacagca tcgacaacaa 4680
ggtgctgacc aggagcgaca agaacagggg caagagcgac aacgtgccga gcgaggaggt 4740
ggtgaagaag atgaaaaact actggaggca gctgctgaac gccaagctga tcacccagag 4800
gaagttcgac aacctgacca aggccgagag gggcggcctg agcgagctgg acaaggccgg 4860
cttcattaaa aggcagctgg tggagaccag gcagatcacc aagcacgtgg cccagatcct 4920
ggacagcagg atgaacacca agtacgacga gaacgacaag ctgatcaggg aggtgaaggt 4980
gatcaccctg aagagcaagc tggtgagcga cttcaggaag gacttccagt tctacaaggt 5040
gagggagatc aataattacc accacgccca cgacgcctac ctgaacgccg tggtgggcac 5100
cgccctgatt aaaaagtacc cgaagctgga gagcgagttc gtgtacggcg actacaaggt 5160
gtacgacgtg aggaagatga tcgccaagag cgagcaggag atcggcaagg ccaccgccaa 5220
gtacttcttc tacagcaaca tcatgaactt cttcaagacc gagatcaccc tggccaacgg 5280
cgagatcagg aagaggccgc tgatcgagac caacggcgag accggcgaga tcgtgtggga 5340
caagggcagg gacttcgcca ccgtgaggaa ggtgctgtcc atgccgcagg tgaacatcgt 5400
gaagaagacc gaggtgcaga ccggcggctt cagcaaggag agcatcctgc cgaagaggaa 5460
cagcgacaag ctgatcgcca ggaagaagga ctgggacccg aagaagtacg gcggcttcga 5520
cagcccgacc gtggcctaca gcgtgctggt ggtggccaag gtggagaagg gcaagagcaa 5580
gaagctgaag agcgtgaagg agctggtggg catcaccatc atggagagga gcagcttcga 5640
gaagaaccca gtggacttcc tggaggccaa gggctacaag gaggtgaaga aggacctgat 5700
cattaaactg ccgaagtaca gcctgttcga gctggagaac ggcaggaaga ggatgctggc 5760
cagcgccggc gagctgcaga agggcaacga gctggccctg ccgagcaagt acgtgaactt 5820

-continued

```
cctgtacctg gccagccact acgagaagct gaagggcagc ccggaggaca acgagcagaa   5880
gcagctgttc gtggagcagc acaagcacta cctggacgag atcatcgagc agatcagcga   5940
gttcagcaag agggtgatcc tggccgacgc caacctggac aaggtgctga gcgcctacaa   6000
caagcacagg gacaagccga tcagggagca ggccgagaac atcatccacc tgttcaccct   6060
gaccaacctg ggcgccccgg ccgccttcaa gtacttcgac accaccatcg acaggaagag   6120
gtacaccagc accaaggagg tgctggacgc caccctgatc caccagagca tcaccggcct   6180
gtacgagacc aggatcgacc tgagccagct gggcggcgac agcagcccgc cgaagaagaa   6240
gaggaaggtg agctggaagg acgccagcgg ctggagcagg atgtgaagct tgatcgttca   6300
aacatttggc aataaagttt cttaagattg aatcctgttg ccggtcttgc gatgattatc   6360
atataatttc tgttgaatta cgttaagcat gtaataatta acatgtaatg catgacgtta   6420
tttatgagat gggtttttat gattagagtc ccgcaattat acatttaata cgcgatagaa   6480
aacaaaatat agcgcgcaaa ctaggataaa ttatcgcgcg cggtgtcatc tatgttacta   6540
gatcttcgaa gggatcttta aacatacgaa cagatcactt aaagttcttc tgaagcaact   6600
taaagttatc aggcatgcat ggatcttgga ggaatcagat gtgcagtcag ggaccatagc   6660
acaggacagg cgtcttctac tggtgctacc agcaaatgct ggaagccggg aacactgggt   6720
acgttggaaa ccacgtgatg tggagtaaga taaactgtag gagaaaagca tttcgtagtg   6780
ggccatgaag cctttcagga catgtattgc agtatgggcc ggcccattac gcaattggac   6840
gacaacaaag actagtatta gtaccacctc ggctatccac atagatcaaa gctggtttaa   6900
aagagttgtg cagatgatcc gtggcagctg gagctgagct tccggggttt tagagctaga   6960
aatagcaagt taaaataagg ctagtccgtt atcaacttga aaaagtggca ccgagtcggt   7020
gctttttttt tcggaccgcg cctgcagtgc agcgtgaccc ggtcgtgccc ctctctagag   7080
ataatgagca ttgcatgtct aagttataaa aaattaccac atattttttt tgtcacactt   7140
gtttgaagtg cagtttatct atctttatac atatatttaa actttactct acgaataata   7200
taatctatag tactacaata atatcagtgt tttagagaat catataaatg aacagttaga   7260
catggtctaa aggacaattg agtattttga caacaggact ctacagtttt atctttttag   7320
tgtgcatgtg ttctcctttt tttttgcaaa tagcttcacc tatataatac ttcatccatt   7380
ttattagtac atccatttag ggtttagggt taatggtttt tatagactaa tttttttagt   7440
acatctattt tattctattt tagcctctaa attaagaaaa ctaaaactct attttagttt   7500
ttttatttaa taatttagat ataaaataga ataaaataaa gtgactaaaa attaaacaaa   7560
taccctttaa gaaattaaaa aaactaagga aacatttttc ttgtttcgag tagataatgc   7620
cagcctgtta aacgccgtcg acgagtctaa cggacaccaa ccagcgaacc agcagcgtcg   7680
cgtcgggcca agcgaagcag acggcacggc atctctgtcg ctgcctctgg accccctctcg  7740
agagttccgc tccaccgttg gacttgctcc gctgtcggca tccagaaatt gcgtggcgga   7800
gcggcagacg tgagccggca cggcaggcgg cctcctcctc ctctcacggc accggcagct   7860
acgggggatt cctttcccac cgctccttcg ctttcccttc ctcgcccgcc gtaataaata   7920
gacacccccct ccacaccctc tttccccaac ctcgtgttgt tcggagcgca cacacacaca  7980
accagatctc ccccaaatcc acccgtcggc acctccgctt caaggtacgc cgctcgtcct   8040
cccccccccc cctctctacc ttctctagat cggcgttccg gtccatggtt agggcccggt   8100
agttctactt ctgttcatgt ttgtgttaga tccgtgtttg tgttagatcc gtgctgctag   8160
```

-continued

```
cgttcgtaca cggatgcgac ctgtacgtca gacacgttct gattgctaac ttgccagtgt   8220
ttctctttgg ggaatcctgg gatggctcta gccgttccgc agacgggatc gatttcatga   8280
ttttttttgt ttcgttgcat agggtttggt ttgccctttt cctttatttc aatatatgcc   8340
gtgcacttgt ttgtcgggtc atcttttcat gctttttttt gtcttggttg tgatgatgtg   8400
gtctggttgg gcggtcgttc tagatcggag tagaattctg tttcaaacta cctggtggat   8460
ttattaattt tggatctgta tgtgtgtgcc atacatattc atagttacga attgaagatg   8520
atggatggaa atatcgatct aggataggta tacatgttga tgcgggtttt actgatgcat   8580
atacagagat gctttttgtt cgcttggttg tgatgatgtg gtgtggttgg gcggtcgttc   8640
attcgttcta gatcggagta gaatactgtt tcaaactacc tggtgtattt attaattttg   8700
gaactgtatg tgtgtgtcat acatcttcat agttacgagt ttaagatgga tggaaatatc   8760
gatctaggat aggtatacat gttgatgtgg gttttactga tgcatataca tgatggcata   8820
tgcagcatct attcatatgc tctaaccttg agtacctatc tattataata aacaagtatg   8880
ttttataatt attttgatct tgatatactt ggatgatggc atatgcagca gctatatgtg   8940
gattttttta gccctgcctt catacgctat ttatttgctt ggtactgttt cttttgtcga   9000
tgctcaccct gttgtttggt gttacttctg cagggatccg gcagcagcca tgcagaagct   9060
gatcaacagc gtgcagaact acgcctgggg cagcaagacc gccctgaccg agctgtacgg   9120
catggagaac cccagcagcc agcccatggc cgagctgtgg atgggcgccc accccaagag   9180
cagcagccgc gtgcagaacg ccgccggcga catcgtgagc ctgcgcgacg tgatcgagag   9240
cgacaagagc accctgctgg gcgaggccgt ggccaagcgc ttcggcgagc tgcccttcct   9300
gttcaaggtg ctgtgcgccg cccagcccct gagcatccag gtgcacccca acaagcacaa   9360
cagcgagatc ggcttcgcca aggagaacgc cgccggcatc cccatggacg ccgccgagcg   9420
caactacaag gaccccaacc acaagcccga gctggtgttc gccctgaccc ccttcctggc   9480
catgaacgcc ttccgcgagt tcagcgagat cgtgagcctg ctgcagcccg tggccggcgc   9540
ccaccccgcc atcgcccact tcctgcagca gcccgacgcc gagcgcctga gcgagctgtt   9600
cgccagcctg ctgaacatgc agggcgagga gaagagccgc gccctggcca tcctgaagag   9660
cgccctggac agccagcagg gcgagccctg gcagaccatc cgcctgatca gcgagttcta   9720
ccccgaggac agcggcctgt tcagcccct gctgctgaac gtggtgaagc tgaaccccgg   9780
cgaggccatg ttcctgttcg ccgagacccc ccacgcctac ctgcagggcg tggccctgga   9840
ggtgatggcc aacagcgaca acgtgctgcg cgccggcctg acccccaagt acatcgacat   9900
ccccgagctg gtggccaacg tgaagttcga ggccaagccc gccaaccagc tgctgaccca   9960
gcccgtgaag cagggcgccg agctggactt ccccatcccc gtggacgact tcgccttcag  10020
cctgcacgac ctgagcgaca aggagaccac catcagccag cagagcgccg ccatcctgtt  10080
ctgcgtggag ggcgacgcca ccctgtggaa gggcagccag cagctgcagc tgaagcccgg  10140
cgagagcgcc ttcatcgccg ccaacgagag ccccgtgacc gtgaagggcc acggccgcct  10200
ggcccgcgtg tacaacaagc tgtgatagga gctcgatccg tcgacctgca gatcgttcaa  10260
acatttggca ataaagtttc ttaagattga atcctgttgc cggtcttgcg atgattatca  10320
tataatttct gttgaattac gttaagcatg taataattaa catgtaatgc atgacgttat  10380
ttatgagatg ggtttttatg attagagtcc cgcaattata catttaatac gcgatagaaa  10440
acaaaatata gcgcgcaaac taggataaat tatcgcgcgc ggtgtcatct atgttactag  10500
atcggcgcgc cgcaattgaa gtttgggcgg ccagcatggc cgtatccgca atgtgttatt  10560
```

```
aagttgtcta agcgtcaatt tgtttacacc acaatatatc ctgccaccag ccagccaaca  10620
gctccccgac cggcagctcg gcacaaaatc accactcgat acaggcagcc catcagaatt  10680
aattctcatg tttgacagct tatcatcgac tgcacggtgc accaatgctt ctggcgtcag  10740
gcagccatcg gaagctgtgg tatggctgtg caggtcgtaa atcactgcat aattcgtgtc  10800
gctcaaggcg cactcccgtt ctggataatg ttttttgcgc cgacatcata acggttctgg  10860
caaatattct gaaatgagct gttgacaatt aatcatccgg ctcgtataat gtgtggaatt  10920
gtgagcggat aacaatttca cacaggaaac agaccatgag ggaagcgttg atcgccgaag  10980
tatcgactca actatcagag gtagttggcg tcatcgagcg ccatctcgaa ccgacgttgc  11040
tggccgtaca tttgtacggc tccgcagtgg atggcggcct gaagccacac agtgatattg  11100
atttgctggt tacggtgacc gtaaggcttg atgaaacaac gcggcgagct ttgatcaacg  11160
accttttgga aacttcggct tcccctggag agagcgagat tctccgcgct gtagaagtca  11220
ccattgttgt gcacgacgac atcattccgt ggcgttatcc agctaagcgc gaactgcaat  11280
ttggagaatg gcagcgcaat gacattcttg caggtatctt cgagccagcc acgatcgaca  11340
ttgatctggc tatcttgctg acaaaagcaa gagaacatag cgttgccttg gtaggtccag  11400
cggcggagga actctttgat ccggttcctg aacaggatct atttgaggcg ctaaatgaaa  11460
ccttaacgct atggaactcg ccgcccgact gggctggcga tgagcgaaat gtagtgctta  11520
cgttgtcccg catttggtac agcgcagtaa ccggcaaaat cgcgccgaag gatgtcgctg  11580
ccgactgggc aatggagcgc ctgccggccc agtatcagcc cgtcatactt gaagctaggc  11640
aggcttatct tggacaagaa gatcgcttgg cctcgcgcgc agatcagttg gaagaatttg  11700
ttcactacgt gaaaggcgag atcaccaaag tagtcggcaa ataaagctct agtggatctc  11760
cgtacccggg gatctggctc gcggcggacg cacgacgccg gggcgagacc ataggcgatc  11820
tcctaaatca atagtagctg taacctcgaa gcgtttcact tgtaacaacg attgagaatt  11880
tttgtcataa aattgaaata cttggttcgc atttttgtca tccgcggtca gccgcaattc  11940
tgacgaactg cccatttagc tggagatgat tgtacatcct tcacgtgaaa atttctcaag  12000
cgctgtgaac aagggttcag attttagatt gaaaggtgag ccgttgaaac acgttcttct  12060
tgtcgatgac gacgtcgcta tgcggcatct tattattgaa taccttacga tccacgcctt  12120
caaagtgacc gcggtagccg acagcaccca gttcacaaga gtactctctt ccgcgacggt  12180
cgatgtcgtg gttgttgatc tagatttagg tcgtgaagat gggctcgagc taggagcaag  12240
tgattttatc gctaagccgt tcagtatcag agagtttcta gcacgcattc gggttgcctt  12300
gcgcgtgcgc cccaacgttg tccgctccaa agaccgacgg tctttttgtt ttactgactg  12360
gacacttaat ctcaggcaac gtcgcttgat gtccgaagct ggcggtgagg tgaaacttac  12420
ggcaggtgag ttcaatcttc tcctcgcgtt tttagagaaa ccccgcgacg ttctatcgcg  12480
cgagcaactt ctcattgcca gtcgagtacg cgacgaggag gtttatgaca ggagtataga  12540
tgttctcatt ttgaggctgc gccgcaaact tgaggcagat ccgtcaagcc ctcaactgat  12600
aaaaacagca agaggtgccg gttatttctt tgacgcggac gtgcaggttt cgcacggggg  12660
gacgatggca gcctgagcca attcccagat ccccgaggaa tcggcgtgag cggtcgcaaa  12720
ccatccggcc cggtacaaat cggcgcggcg ctgggtgatg acctggtgga gaagttgaag  12780
gccgcgcagg ccgcccagcg gcaacgcatc gaggcagaag cacgccccgg tgaatcgtgg  12840
caagcggccg ctgatcgaat ccgcaaagaa tcccggcaac cgccggcagc cggtgcgccg  12900
```

-continued tcgattagga agccgcccaa gggcgacgag caaccagatt ttttcgttcc gatgctctat 12960
gacgtgggca cccgcgatag tcgcagcatc atggacgtgg ccgttttccg tctgtcgaag 13020
cgtgaccgac gagctggcga ggtgatccgc tacgagcttc cagacgggca cgtagaggtt 13080
tccgcagggc cggccggcat ggccagtgtg tgggattacg acctggtact gatggcggtt 13140
tcccatctaa ccgaatccat gaaccgatac cgggaaggga agggagacaa gcccggccgc 13200
gtgttccgtc cacacgttgc ggacgtactc aagttctgcc ggcgagccga tggcggaaag 13260
cagaaagacg acctggtaga aacctgcatt cggttaaaca ccacgcacgt tgccatgcag 13320
cgtacgaaga aggccaagaa cggccgcctg gtgacggtat ccgagggtga agccttgatt 13380
agccgctaca agatcgtaaa gagcgaaacc gggcggccgg agtacatcga gatcgagcta 13440
gctgattgga tgtaccgcga gatcacagaa ggcaagaacc cggacgtgct gacggttcac 13500
cccgattact ttttgatcga tcccggcatc ggccgttttc tctaccgcct ggcacgccgc 13560
gccgcaggca aggcagaagc cagatggttg ttcaagacga tctacgaacg cagtggcagc 13620
gccggagagt tcaagaagtt ctgtttcacc gtgcgcaagc tgatcgggtc aaatgacctg 13680
ccggagtacg atttgaagga ggaggcgggg caggctggcc cgatcctagt catgcgctac 13740
cgcaacctga tcgagggcga agcatccgcc ggttcctaat gtacggagca gatgctaggg 13800
caaattgccc tagcagggga aaaaggtcga aaaggtctct ttcctgtgga tagcacgtac 13860
attgggaacc caaagccgta cattgggaac cggaacccgt acattgggaa cccaaagccg 13920
tacattggga accggtcaca catgtaagtg actgatataa aagagaaaaa aggcgatttt 13980
tccgcctaaa actctttaaa acttattaaa actcttaaaa cccgcctggc ctgtgcataa 14040
ctgtctggcc agcgcacagc cgaagagctg caaaaagcgc ctacccttcg gtcgctgcgc 14100
tccctacgcc ccgccgcttc gcgtcggcct atcgcggccg ctggccgctc aaaaatggct 14160
ggcctacggc caggcaatct accagggcgc ggacaagccg cgccgtcgcc actcgaccgc 14220
cggcgctgag gtctgcctcg tgaagaaggt gttgctgact cataccaggc ctgaatcgcc 14280
ccatcatcca gccagaaagt gagggagcca cggttgatga gagctttgtt gtaggtggac 14340
cagttggtga ttttgaactt ttgctttgcc acggaacggt ctgcgttgtc gggaagatgc 14400
gtgatctgat ccttcaactc agcaaaagtt cgatttattc aacaaagccg ccgtcccgtc 14460
aagtcagcgt aatgctctgc cagtgttaca accaattaac caattctgat tagaaaaact 14520
catcgagcat caaatgaaac tgcaatttat tcatatcagg attatcaata ccatattttt 14580
gaaaaagccg tttctgtaat gaaggagaaa actcaccgag gcagttccat aggatggcaa 14640
gatcctggta tcggtctgcg attccgactc gtccaacatc aatacaacct attaatttcc 14700
cctcgtcaaa aataaggtta tcaagtgaga aatcaccatg agtgacgact gaatccggtg 14760
agaatggcaa aagctctgca ttaatgaatc ggccaacgcg cggggagagg cggtttgcgt 14820
attgggcgct cttccgcttc ctcgctcact gactcgctgc gctcggtcgt tcggctgcgg 14880
cgagcggtat cagctcactc aaaggcggta atacggttat ccacagaatc aggggataac 14940
gcaggaaaga acatgtgagc aaaaggccag caaaaggcca ggaaccgtaa aaaggccgcg 15000
ttgctggcgt ttttccatag gctccgcccc cctgacgagc atcacaaaaa tcgacgctca 15060
agtcagaggt ggcgaaaccc gacaggacta taaagatacc aggcgtttcc ccctggaagc 15120
tccctcgtgc gctctcctgt tccgaccctg ccgcttaccg gatacctgtc cgcctttctc 15180
ccttcgggaa gcgtggcgct ttctcatagc tcacgctgta ggtatctcag ttcggtgtag 15240
gtcgttcgct ccaagctggg ctgtgtgcac gaaccccccg ttcagcccga ccgctgcgcc 15300
ttatccggta actatcgtct tgagtccaac ccggtaagac acgacttatc gccactggca 15360
gcagccactg gtaacaggat tagcagagcg aggtatgtag gcggtgctac agagttcttg 15420
aagtggtggc ctaactacgg ctacactaga agaacagtat ttggtatctg cgctctgctg 15480
aagccagtta ccttcggaaa aagagttggt agctcttgat ccggcaaaca aaccaccgct 15540
ggtagcggtg gtttttttgt ttgcaagcag cagattacgc gcagaaaaaa aggatctcaa 15600
gaagatcctt tgatcttttc tacggggtct gacgctcagt ggaacgaaaa ctcacgttaa 15660
gggattttgg tcatgagatt atcaaaaagg atcttcacct agatcctttt gatccggaat 15720
ta 15722

<210> SEQ ID NO 21
<211> LENGTH: 20
<212> TYPE: DNA
<213> ORGANISM: Artificial Sequence
<220> FEATURE:
<223> OTHER INFORMATION: for editing VLHP2

<400> SEQUENCE: 21
gctggagctg agcttccggg 20

<210> SEQ ID NO 22
<211> LENGTH: 15722
<212> TYPE: DNA
<213> ORGANISM: Artificial Sequence
<220> FEATURE:
<223> OTHER INFORMATION: vector 23398
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (304)..(2100)
<223> OTHER INFORMATION: prSoUbi4-04
<220> FEATURE:
<221> NAME/KEY: gene
<222> LOCATION: (2117)..(6286)
<223> OTHER INFORMATION: cCas9-01
<220> FEATURE:
<221> NAME/KEY: misc_feature
<222> LOCATION: (5606)..(5608)
<223> OTHER INFORMATION: L to V mutation
<220> FEATURE:
<221> NAME/KEY: misc_feature
<222> LOCATION: (5651)..(5653)
<223> OTHER INFORMATION: I to V mutation
<220> FEATURE:
<221> NAME/KEY: terminator
<222> LOCATION: (6292)..(6544)
<223> OTHER INFORMATION: tNOS-05-01
<220> FEATURE:
<221> NAME/KEY: promoter
<222> LOCATION: (6551)..(6925)
<223> OTHER INFORMATION: prOsU3-01
<220> FEATURE:
<221> NAME/KEY: misc_feature
<222> LOCATION: (6927)..(6946)
<223> OTHER INFORMATION: xZmGW2
<220> FEATURE:
<221> NAME/KEY: misc_feature
<222> LOCATION: (6927)..(7031)
<223> OTHER INFORMATION: rsgRNAZmGW2-01
<220> FEATURE:
<221> NAME/KEY: promoter
<222> LOCATION: (7042)..(9033)
<223> OTHER INFORMATION: prUbi1-04
<220> FEATURE:
<221> NAME/KEY: gene
<222> LOCATION: (9050)..(10228)

<223> OTHER INFORMATION: cPMI-09
<220> FEATURE:
<221> NAME/KEY: terminator
<222> LOCATION: (10251)..(10503)
<223> OTHER INFORMATION: tNOS-05-01
<220> FEATURE:
<221> NAME/KEY: misc_feature
<222> LOCATION: (10547)..(10676)
<223> OTHER INFORMATION: bNLB-03
<220> FEATURE:
<221> NAME/KEY: gene
<222> LOCATION: (10956)..(11744)
<223> OTHER INFORMATION: cSpec-03
<220> FEATURE:
<221> NAME/KEY: promoter
<222> LOCATION: (11839)..(11969)
<223> OTHER INFORMATION: prVirG-01
<220> FEATURE:
<221> NAME/KEY: gene
<222> LOCATION: (12706)..(13779)
<223> OTHER INFORMATION: cRepA-01
<220> FEATURE:
<221> NAME/KEY: misc_feature
<222> LOCATION: (13822)..(14226)
<223> OTHER INFORMATION: oVS1-02
<220> FEATURE:
<221> NAME/KEY: misc_feature
<222> LOCATION: (14904)..(15710)
<223> OTHER INFORMATION: oCOLE-06

<400> SEQUENCE: 22
attcctgtgg ttggcatgca catacaaatg gacgaacgga taaacctttt cacgcccttt 60
taaatatccg attattctaa taaacgctct tttctcttag gtttacccgc caatatatcc 120
tgtcaaacac tgatagttta aactgaaggc gggaaacgac aatctgatca tgagcggaga 180
attaagggag tcacgttatg acccccgccg atgacgcggg acaagccgtt ttacgtttgg 240
aactgacaga accgcaacgc tgcaggaatt ggccgcagcg gccatttaaa caaagcttgg 300
taccattatg tggtctaggt aggttctata tataagaaaa cttgaaatgt tctaaaaaaa 360
aattcaagcc catgcatgat tgaagcaaac ggtatagcaa cggtgttaac ctgatctagt 420
gatctcttgc aatccttaac ggccacctac cgcaggtagc aaacggcgtc cccctcctcg 480
atatctccgc ggcgacctct ggctttttcc gcggaattgc gcggtgggga cggattccac 540
gagaccgcga cgcaaccgcc tctcgccgct gggccccaca ccgctcggtg ccgtagcctc 600
acgggactct ttctccctcc tcccccgtta taaattggct tcatcccctc cttgcctcat 660
ccatccaaat cccagtcccc aatcccatcc cttcgtagga gaaattcatc gaagctaagc 720
gaatcctcgc gatcctctca aggtactgcg agttttcgat ccccctctcg acccctcgta 780
tgtttgtgtt tgtcgtagcg tttgattagg tatgctttcc ctgtttgtgt tcgtcgtagc 840
gtttgattag gtatgctttc cctgttcgtg ttcatcgtag tgtttgatta ggtcgtgtga 900
ggcgatggcc tgctcgcgtc cttcgatctg tagtcgattt gcgggtcgtg gtgtagatct 960
gcgggctgtg atgaagttat ttggtgtgat ctgctcgcct gattctgcgg gttggctcga 1020
gtagatatga tggttggacc ggttggttcg tttaccgcgc tagggttggg ctgggatgat 1080
gttgcatgcg ccgttgcgcg tgatcccgca gcaggacttg cgtttgattg ccagatctcg 1140
ttacgattat gtgatttggt ttggactttt tagatctgta gcttctgctt atgtgccaga 1200
tgcgcctact gctcatatgc ctgatgataa tcataaatgg ctgtggaact aactagttga 1260
ttgcggagtc atgtatcagc tacaggtgta gggactagct acaggtgtag ggacttgcgt 1320
ctaattgttt ggtcctttac tcatgttgca attatgcaat ttagtttaga ttgtttgttc 1380
cactcatcta ggctgtaaaa gggacactgc ttagattgct gtttaatctt tttagtagat 1440

-continued

```
tatattatat tggtaactta ttacccctat tacatgccat acgtgacttc tgctcatgcc   1500
tgatgataat catagatcac tgtggaatta attagttgat tgttgaatca tgtttcatgt   1560
acataccacg gcacaattgc ttagttcctt aacaaatgca aattttactg atccatgtat   1620
gatttgcgtg gttctctaat gtgaaatact atagctactt gttagtaaga atcaggttcg   1680
tatgcttaat gctgtatgtg ccttctgctc atgcctgatg ataatcatat atcactggaa   1740
ttaattagtt gatcgtttaa tcatatatca agtacatacc atgccacaat tttagtcac   1800
ttaacccatg cagattgaac tggtccctgc atgttttgct aaattgttct attctgatta   1860
gaccatatat catgtatttt tttttggtaa tggttctctt attttaaatg ctatatagtt   1920
ctggtacttg ttagaaagat ctgcttcata gtttagttgc ctatccctcg aattaggatg   1980
ctgagcagct gatcctatag ctttgtttca tgtatcaatt cttttgtgtt caacagtcag   2040
tttttgttag attcattgta acttatggtc gcttactctt ctggtcctca atgcttgcag   2100
gatcgcggcc gctcatatgg acaagaagta cagcatcggc ctggacatcg gcaccaacag   2160
cgtgggctgg gccgtgatca ccgacgagta caaggtgccg agcaagaagt tcaaggtgct   2220
gggcaacacc gacaggcaca gcatcaagaa gaacctgatc ggcgccctgc tgttcgacag   2280
cggcgagacc gccgaggcca ccaggctgaa gaggaccgcc aggaggaggt acaccaggag   2340
gaagaacagg atctgctacc tgcaggagat cttcagcaac gagatggcca aggtggacga   2400
cagcttcttc cacaggctgg aggagagctt cctggtggag gaggacaaga agcacgagag   2460
gcacccgatc ttcggcaaca tcgtggacga ggtggcctac cacgagaagt acccgaccat   2520
ctaccacctg aggaagaagc tggtggacag caccgacaag gccgacctga ggctgatcta   2580
cctggccctg gcccacatga tcaagttcag gggccacttc ctgatcgagg gcgacctgaa   2640
cccggacaac agcgacgtgg acaagctgtt catccagctg gtgcagacct acaaccagct   2700
gttcgaggag aacccgatca acgccagcgg cgtggacgcc aaggccatcc tgagcgccag   2760
gctgagcaag agcaggaggc tggagaacct gatcgcccag ctgccgggcg agaagaagaa   2820
cggcctgttc ggcaacctga tcgccctgag cctgggcctg accccgaact tcaagagcaa   2880
cttcgacctg gccgaggacg ccaagctgca gctgagcaag gacacctacg acgacgacct   2940
ggacaacctg ctggcccaga tcggcgacca gtacgccgac ctgttcctgg ccgccaagaa   3000
cctgagcgac gccatcctgc tgagcgacat cctgagggtg aacaccgaga tcaccaaggc   3060
cccgctgagc gccagcatga tcaagaggta cgacgagcac caccaggacc tgaccctgct   3120
gaaggccctg gtgaggcagc agctgccgga gaagtacaag gagatcttct tcgaccagag   3180
caagaacggc tacgccggct acatcgacgg cggcgccagc caggaggagt tctacaagtt   3240
catcaagccg atcctggaga agatggacgg caccgaggag ctgctggtga agctgaacag   3300
ggaggacctg ctgaggaagc agaggacctt cgacaacggc agcatcccgc accagatcca   3360
cctgggcgag ctgcacgcca tcctgaggag gcaggaggac ttctacccgt tcctgaagga   3420
caacagggag aagatcgaga agatcctgac cttccgcatc ccgtactacg tgggcccgct   3480
ggccaggggc aacagcaggt tcgcctggat gaccaggaag agcgaggaga ccatcacccc   3540
gtggaacttc gaggaggtgg tggacaaggg cgccagcgcc cagagcttca tcgagaggat   3600
gaccaacttc gacaagaacc tgccgaacga gaaggtgctg ccgaagcaca gcctgctgta   3660
cgagtacttc accgtgtaca acgagctgac caaggtgaag tacgtgaccg agggcatgag   3720
gaagccggcc ttcctgagcg gcgagcagaa gaaggccatc gtggacctgc tgttcaagac   3780
```

-continued caacaggaag gtgaccgtga agcagctgaa ggaggactac ttcaagaaga tcgagtgctt 3840
cgacagcgtg gagatcagcg gcgtggagga caggttcaac gccagcctgg gcacctacca 3900
cgacctgctg aagatcatca aggacaagga cttcctggac aacgaggaga acgaggacat 3960
cctggaggac atcgtgctga ccctgaccct gttcgaggac agggagatga tcgaggagag 4020
gctgaagacc tacgcccacc tgttcgacga caaggtgatg aagcagctga agaggaggag 4080
gtacaccggc tggggcaggc tgagcaggaa gctgatcaac ggcatcaggg acaagcagag 4140
cggcaagacc atcctggact tcctgaagag cgacggcttc gccaacagga acttcatgca 4200
gctgatccac gacgacagcc tgaccttcaa ggaggacatc cagaaggccc aggtgagcgg 4260
ccagggcgac agcctgcacg agcacatcgc caacctggcc ggcagcccgg ccatcaagaa 4320
gggcatcctg cagaccgtga aggtggtgga cgagctggtg aaggtgatgg gcaggcacaa 4380
gccggagaac atcgtgatcg agatggccag ggagaaccag accacccaga agggccagaa 4440
gaacagcagg gagaggatga agaggatcga ggagggcatc aaggagctgg gcagccagat 4500
cctgaaggag cacccggtgg agaacaccca gctgcagaac gagaagctgt acctgtacta 4560
cctgcagaac ggcagggaca tgtacgtgga ccaggagctg gacatcaaca ggctgagcga 4620
ctacgacgtg gaccacatcg tgccgcagag cttcctgaag gacgacagca tcgacaacaa 4680
ggtgctgacc aggagcgaca agaacagggg caagagcgac aacgtgccga gcgaggaggt 4740
ggtgaagaag atgaaaaact actggaggca gctgctgaac gccaagctga tcacccagag 4800
gaagttcgac aacctgacca aggccgagag gggcggcctg agcgagctgg acaaggccgg 4860
cttcattaaa aggcagctgg tggagaccag gcagatcacc aagcacgtgg cccagatcct 4920
ggacagcagg atgaacacca agtacgacga gaacgacaag ctgatcaggg aggtgaaggt 4980
gatcaccctg aagagcaagc tggtgagcga cttcaggaag gacttccagt tctacaaggt 5040
gagggagatc aataattacc accacgccca cgacgcctac ctgaacgccg tggtgggcac 5100
cgccctgatt aaaaagtacc cgaagctgga gagcgagttc gtgtacggcg actacaaggt 5160
gtacgacgtg aggaagatga tcgccaagag cgagcaggag atcggcaagg ccaccgccaa 5220
gtacttcttc tacagcaaca tcatgaactt cttcaagacc gagatcaccc tggccaacgg 5280
cgagatcagg aagaggccgc tgatcgagac caacggcgag accggcgaga tcgtgtggga 5340
caagggcagg gacttcgcca ccgtgaggaa ggtgctgtcc atgccgcagg tgaacatcgt 5400
gaagaagacc gaggtgcaga ccggcggctt cagcaaggag agcatcctgc cgaagaggaa 5460
cagcgacaag ctgatcgcca ggaagaagga ctgggacccg aagaagtacg gcggcttcga 5520
cagcccgacc gtggcctaca gcgtgctggt ggtggccaag gtggagaagg gcaagagcaa 5580
gaagctgaag agcgtgaagg agctggtggg catcaccatc atggagagga gcagcttcga 5640
gaagaaccca gtggacttcc tggaggccaa gggctacaag gaggtgaaga aggacctgat 5700
cattaaactg ccgaagtaca gcctgttcga gctggagaac ggcaggaaga ggatgctggc 5760
cagcgccggc gagctgcaga agggcaacga gctggccctg ccgagcaagt acgtgaactt 5820
cctgtacctg gccagccact acgagaagct gaagggcagc ccggaggaca acgagcagaa 5880
gcagctgttc gtggagcagc acaagcacta cctggacgag atcatcgagc agatcagcga 5940
gttcagcaag agggtgatcc tggccgacgc caacctggac aaggtgctga gcgcctacaa 6000
caagcacagg gacaagccga tcagggagca ggccgagaac atcatccacc tgttcaccct 6060
gaccaacctg ggcgccccgg ccgccttcaa gtacttcgac accaccatcg acaggaagag 6120
gtacaccagc accaaggagg tgctggacgc caccctgatc caccagagca tcaccggcct 6180

```
gtacgagacc aggatcgacc tgagccagct gggcggcgac agcagcccgc cgaagaagaa   6240
gaggaaggtg agctggaagg acgccagcgg ctggagcagg atgtgaagct tgatcgttca   6300
aacatttggc aataaagttt cttaagattg aatcctgttg ccggtcttgc gatgattatc   6360
atataatttc tgttgaatta cgttaagcat gtaataatta acatgtaatg catgacgtta   6420
tttatgagat gggtttttat gattagagtc ccgcaattat acatttaata cgcgatagaa   6480
aacaaaatat agcgcgcaaa ctaggataaa ttatcgcgcg cggtgtcatc tatgttacta   6540
gatcttcgaa gggatcttta aacatacgaa cagatcactt aaagttcttc tgaagcaact   6600
taaagttatc aggcatgcat ggatcttgga ggaatcagat gtgcagtcag ggaccatagc   6660
acaggacagg cgtcttctac tggtgctacc agcaaatgct ggaagccggg aacactgggt   6720
acgttggaaa ccacgtgatg tggagtaaga taaactgtag gagaaaagca tttcgtagtg   6780
ggccatgaag cctttcagga catgtattgc agtatgggcc ggcccattac gcaattggac   6840
gacaacaaag actagtatta gtaccacctc ggctatccac atagatcaaa gctggtttaa   6900
aagagttgtg cagatgatcc gtggcagagc ggttcacgcg gccgcagttt tagagctaga   6960
aatagcaagt taaaataagg ctagtccgtt atcaacttga aaaagtggca ccgagtcggt   7020
gctttttttt tcggaccgcg cctgcagtgc agcgtgaccc ggtcgtgccc ctctctagag   7080
ataatgagca ttgcatgtct aagttataaa aaattaccac atattttttt tgtcacactt   7140
gtttgaagtg cagtttatct atctttatac atatatttaa actttactct acgaataata   7200
taatctatag tactacaata atatcagtgt tttagagaat catataaatg aacagttaga   7260
catggtctaa aggacaattg agtattttga caacaggact ctacagtttt atctttttag   7320
tgtgcatgtg ttctcctttt tttttgcaaa tagcttcacc tatataatac ttcatccatt   7380
ttattagtac atccatttag ggtttagggt taatggtttt tatagactaa tttttttagt   7440
acatctattt tattctattt tagcctctaa attaagaaaa ctaaaactct attttagttt   7500
ttttatttaa taatttagat ataaaataga ataaaataaa gtgactaaaa attaaacaaa   7560
taccctttaa gaaattaaaa aaactaagga aacatttttc ttgtttcgag tagataatgc   7620
cagcctgtta aacgccgtcg acgagtctaa cggacaccaa ccagcgaacc agcagcgtcg   7680
cgtcgggcca agcgaagcag acggcacggc atctctgtcg ctgcctctgg acccctctcg   7740
agagttccgc tccaccgttg gacttgctcc gctgtcggca tccagaaatt gcgtggcgga   7800
gcggcagacg tgagccggca cggcaggcgg cctcctcctc ctctcacggc accggcagct   7860
acgggggatt cctttcccac cgctccttcg ctttcccttc ctcgcccgcc gtaataaata   7920
gacacccct ccacaccctc tttccccaac ctcgtgttgt tcggagcgca cacacacaca   7980
accagatctc ccccaaatcc acccgtcggc acctccgctt caaggtacgc cgctcgtcct   8040
cccccccccc cctctctacc ttctctagat cggcgttccg gtccatggtt agggcccggt   8100
agttctactt ctgttcatgt ttgtgttaga tccgtgtttg tgttagatcc gtgctgctag   8160
cgttcgtaca cggatgcgac ctgtacgtca gacacgttct gattgctaac ttgccagtgt   8220
ttctctttgg ggaatcctgg gatggctcta gccgttccgc agacgggatc gatttcatga   8280
tttttttgt ttcgttgcat agggtttggt ttgccctttt cctttatttc aatatatgcc   8340
gtgcacttgt ttgtcgggtc atcttttcat gcttttttt gtcttggttg tgatgatgtg   8400
gtctggttgg gcggtcgttc tagatcggag tagaattctg tttcaaacta cctggtggat   8460
ttattaattt tggatctgta tgtgtgtgcc atacatattc atagttacga attgaagatg   8520
```

-continued

```
atggatggaa atatcgatct aggataggta tacatgttga tgcgggtttt actgatgcat   8580
atacagagat gctttttgtt cgcttggttg tgatgatgtg gtgtggttgg gcggtcgttc   8640
attcgttcta gatcggagta gaatactgtt tcaaactacc tggtgtattt attaattttg   8700
gaactgtatg tgtgtgtcat acatcttcat agttacgagt ttaagatgga tggaaatatc   8760
gatctaggat aggtatacat gttgatgtgg gttttactga tgcatataca tgatggcata   8820
tgcagcatct attcatatgc tctaaccttg agtacctatc tattataata aacaagtatg   8880
ttttataatt attttgatct tgatatactt ggatgatggc atatgcagca gctatatgtg   8940
gattttttta gccctgcctt catacgctat ttatttgctt ggtactgttt cttttgtcga   9000
tgctcaccct gttgtttggt gttacttctg cagggatccg gcagcagcca tgcagaagct   9060
gatcaacagc gtgcagaact acgcctgggg cagcaagacc gccctgaccg agctgtacgg   9120
catggagaac cccagcagcc agcccatggc cgagctgtgg atgggcgccc accccaagag   9180
cagcagccgc gtgcagaacg ccgccggcga catcgtgagc ctgcgcgacg tgatcgagag   9240
cgacaagagc accctgctgg gcgaggccgt ggccaagcgc ttcggcgagc tgcccttcct   9300
gttcaaggtg ctgtgcgccg cccagcccct gagcatccag gtgcacccca acaagcacaa   9360
cagcgagatc ggcttcgcca aggagaacgc cgccggcatc cccatggacg ccgccgagcg   9420
caactacaag gaccccaacc acaagcccga gctggtgttc gccctgaccc ccttcctggc   9480
catgaacgcc ttccgcgagt tcagcgagat cgtgagcctg ctgcagcccg tggccggcgc   9540
ccaccccgcc atcgcccact tcctgcagca gcccgacgcc gagcgcctga gcgagctgtt   9600
cgccagcctg ctgaacatgc agggcgagga gaagagccgc gccctggcca tcctgaagag   9660
cgccctggac agccagcagg gcgagccctg gcagaccatc cgcctgatca gcgagttcta   9720
ccccgaggac agcggcctgt tcagcccccct gctgctgaac gtggtgaagc tgaaccccgg   9780
cgaggccatg ttcctgttcg ccgagacccc ccacgcctac ctgcagggcg tggccctgga   9840
ggtgatggcc aacagcgaca acgtgctgcg cgccggcctg acccccaagt acatcgacat   9900
ccccgagctg gtggccaacg tgaagttcga ggccaagccc gccaaccagc tgctgaccca   9960
gcccgtgaag cagggcgccg agctggactt ccccatcccc gtggacgact tcgccttcag  10020
cctgcacgac ctgagcgaca aggagaccac catcagccag cagagcgccg ccatcctgtt  10080
ctgcgtggag ggcgacgcca ccctgtggaa gggcagccag cagctgcagc tgaagcccgg  10140
cgagagcgcc ttcatcgccg ccaacgagag ccccgtgacc gtgaagggcc acggccgcct  10200
ggcccgcgtg tacaacaagc tgtgatagga gctcgatccg tcgacctgca gatcgttcaa  10260
acatttggca ataaagtttc ttaagattga atcctgttgc cggtcttgcg atgattatca  10320
tataatttct gttgaattac gttaagcatg taataattaa catgtaatgc atgacgttat  10380
ttatgagatg ggtttttatg attagagtcc cgcaattata catttaatac gcgatagaaa  10440
acaaaatata gcgcgcaaac taggataaat tatcgcgcgc ggtgtcatct atgttactag  10500
atcggcgcgc cgcaattgaa gtttgggcgg ccagcatggc cgtatccgca atgtgttatt  10560
aagttgtcta agcgtcaatt tgtttacacc acaatatatc ctgccaccag ccagccaaca  10620
gctccccgac cggcagctcg gcacaaaatc accactcgat acaggcagcc catcagaatt  10680
aattctcatg tttgacagct tatcatcgac tgcacggtgc accaatgctt ctggcgtcag  10740
gcagccatcg gaagctgtgg tatggctgtg caggtcgtaa atcactgcat aattcgtgtc  10800
gctcaaggcg cactcccgtt ctggataatg ttttttgcgc cgacatcata acggttctgg  10860
caaatattct gaaatgagct gttgacaatt aatcatccgg ctcgtataat gtgtggaatt  10920
```

```
gtgagcggat aacaatttca cacaggaaac agaccatgag ggaagcgttg atcgccgaag  10980
tatcgactca actatcagag gtagttggcg tcatcgagcg ccatctcgaa ccgacgttgc  11040
tggccgtaca tttgtacggc tccgcagtgg atggcggcct gaagccacac agtgatattg  11100
atttgctggt tacggtgacc gtaaggcttg atgaaacaac gcggcgagct ttgatcaacg  11160
acctttttgga aacttcggct tcccctggag agagcgagat tctccgcgct gtagaagtca  11220
ccattgttgt gcacgacgac atcattccgt ggcgttatcc agctaagcgc gaactgcaat  11280
ttggagaatg gcagcgcaat gacattcttg caggtatctt cgagccagcc acgatcgaca  11340
ttgatctggc tatcttgctg acaaaagcaa gagaacatag cgttgccttg gtaggtccag  11400
cggcggagga actctttgat ccggttcctg aacaggatct atttgaggcg ctaaatgaaa  11460
ccttaacgct atggaactcg ccgcccgact gggctggcga tgagcgaaat gtagtgctta  11520
cgttgtcccg catttggtac agcgcagtaa ccggcaaaat cgcgccgaag gatgtcgctg  11580
ccgactgggc aatggagcgc ctgccggccc agtatcagcc cgtcatactt gaagctaggc  11640
aggcttatct tggacaagaa gatcgcttgg cctcgcgcgc agatcagttg gaagaatttg  11700
ttcactacgt gaaaggcgag atcaccaaag tagtcggcaa ataaagctct agtggatctc  11760
cgtacccggg gatctggctc gcggcggacg cacgacgccg gggcgagacc ataggcgatc  11820
tcctaaatca atagtagctg taacctcgaa gcgtttcact tgtaacaacg attgagaatt  11880
tttgtcataa aattgaaata cttggttcgc atttttgtca tccgcggtca gccgcaattc  11940
tgacgaactg cccatttagc tggagatgat tgtacatcct tcacgtgaaa atttctcaag  12000
cgctgtgaac aagggttcag attttagatt gaaaggtgag ccgttgaaac acgttcttct  12060
tgtcgatgac gacgtcgcta tgcggcatct tattattgaa taccttacga tccacgcctt  12120
caaagtgacc gcggtagccg acagcaccca gttcacaaga gtactctctt ccgcgacggt  12180
cgatgtcgtg gttgttgatc tagatttagg tcgtgaagat gggctcgagc taggagcaag  12240
tgattttatc gctaagccgt tcagtatcag agagtttcta gcacgcattc gggttgcctt  12300
gcgcgtgcgc cccaacgttg tccgctccaa agaccgacgg tctttttgtt ttactgactg  12360
gacacttaat ctcaggcaac gtcgcttgat gtccgaagct ggcggtgagg tgaaacttac  12420
ggcaggtgag ttcaatcttc tcctcgcgtt tttagagaaa ccccgcgacg ttctatcgcg  12480
cgagcaactt ctcattgcca gtcgagtacg cgacgaggag gtttatgaca ggagtataga  12540
tgttctcatt ttgaggctgc gccgcaaact tgaggcagat ccgtcaagcc ctcaactgat  12600
aaaaacagca agaggtgccg gttatttctt tgacgcggac gtgcaggttt cgcacggggg  12660
gacgatggca gcctgagcca attcccagat ccccgaggaa tcggcgtgag cggtcgcaaa  12720
ccatccggcc cggtacaaat cggcgcggcg ctgggtgatg acctggtgga gaagttgaag  12780
gccgcgcagg ccgcccagcg gcaacgcatc gaggcagaag cacgccccgg tgaatcgtgg  12840
caagcggccg ctgatcgaat ccgcaaagaa tcccggcaac cgccggcagc cggtgcgccg  12900
tcgattagga agccgcccaa gggcgacgag caaccagatt ttttcgttcc gatgctctat  12960
gacgtgggca cccgcgatag tcgcagcatc atggacgtgg ccgttttccg tctgtcgaag  13020
cgtgaccgac gagctggcga ggtgatccgc tacgagcttc cagacgggca cgtagaggtt  13080
tccgcagggc cggccggcat ggccagtgtg tgggattacg acctggtact gatggcggtt  13140
tcccatctaa ccgaatccat gaaccgatac cgggaaggga agggagacaa gcccggccgc  13200
gtgttccgtc cacacgttgc ggacgtactc aagttctgcc ggcgagccga tggcggaaag  13260
```

-continued

```
cagaaagacg acctggtaga aacctgcatt cggttaaaca ccacgcacgt tgccatgcag  13320
cgtacgaaga aggccaagaa cggccgcctg gtgacggtat ccgagggtga agccttgatt  13380
agccgctaca agatcgtaaa gagcgaaacc gggcggccgg agtacatcga gatcgagcta  13440
gctgattgga tgtaccgcga gatcacagaa ggcaagaacc cggacgtgct gacggttcac  13500
cccgattact tttgatcga tcccggcatc ggccgttttc tctaccgcct ggcacgccgc  13560
gccgcaggca aggcagaagc cagatggttg ttcaagacga tctacgaacg cagtggcagc  13620
gccggagagt tcaagaagtt ctgtttcacc gtgcgcaagc tgatcgggtc aaatgacctg  13680
ccggagtacg atttgaagga ggaggcgggg caggctggcc cgatcctagt catgcgctac  13740
cgcaacctga tcgagggcga agcatccgcc ggttcctaat gtacggagca gatgctaggg  13800
caaattgccc tagcagggga aaaaggtcga aaaggtctct ttcctgtgga tagcacgtac  13860
attgggaacc caaagccgta cattgggaac cggaacccgt acattgggaa cccaaagccg  13920
tacattggga accggtcaca catgtaagtg actgatataa aagagaaaaa aggcgatttt  13980
tccgcctaaa actctttaaa acttattaaa actcttaaaa cccgcctggc ctgtgcataa  14040
ctgtctggcc agcgcacagc cgaagagctg caaaaagcgc ctacccttcg gtcgctgcgc  14100
tccctacgcc ccgccgcttc gcgtcggcct atcgcggccg ctggccgctc aaaaatggct  14160
ggcctacggc caggcaatct accagggcgc ggacaagccg cgccgtcgcc actcgaccgc  14220
cggcgctgag gtctgcctcg tgaagaaggt gttgctgact cataccaggc ctgaatcgcc  14280
ccatcatcca gccagaaagt gagggagcca cggttgatga gagctttgtt gtaggtggac  14340
cagttggtga ttttgaactt ttgctttgcc acggaacggt ctgcgttgtc gggaagatgc  14400
gtgatctgat ccttcaactc agcaaaagtt cgatttattc aacaaagccg ccgtcccgtc  14460
aagtcagcgt aatgctctgc cagtgttaca accaattaac caattctgat tagaaaaact  14520
catcgagcat caaatgaaac tgcaatttat tcatatcagg attatcaata ccatattttt  14580
gaaaaagccg tttctgtaat gaaggagaaa actcaccgag gcagttccat aggatggcaa  14640
gatcctggta tcggtctgcg attccgactc gtccaacatc aatacaacct attaatttcc  14700
cctcgtcaaa aataaggtta tcaagtgaga aatcaccatg agtgacgact gaatccggtg  14760
agaatggcaa aagctctgca ttaatgaatc ggccaacgcg cggggagagg cggtttgcgt  14820
attgggcgct cttccgcttc ctcgctcact gactcgctgc gctcggtcgt tcggctgcgg  14880
cgagcggtat cagctcactc aaaggcggta atacggttat ccacagaatc aggggataac  14940
gcaggaaaga acatgtgagc aaaaggccag caaaaggcca ggaaccgtaa aaaggccgcg  15000
ttgctggcgt ttttccatag gctccgcccc cctgacgagc atcacaaaaa tcgacgctca  15060
agtcagaggt ggcgaaaccc gacaggacta taaagatacc aggcgtttcc ccctggaagc  15120
tccctcgtgc gctctcctgt tccgaccctg ccgcttaccg gatacctgtc cgcctttctc  15180
ccttcgggaa gcgtggcgct ttctcatagc tcacgctgta ggtatctcag ttcggtgtag  15240
gtcgttcgct ccaagctggg ctgtgtgcac gaaccccccg ttcagcccga ccgctgcgcc  15300
ttatccggta actatcgtct tgagtccaac ccggtaagac acgacttatc gccactggca  15360
gcagccactg gtaacaggat tagcagagcg aggtatgtag gcggtgctac agagttcttg  15420
aagtggtggc ctaactacgg ctacactaga agaacagtat ttggtatctg cgctctgctg  15480
aagccagtta ccttcggaaa aagagttggt agctcttgat ccggcaaaca aaccaccgct  15540
ggtagcggtg gtttttttgt ttgcaagcag cagattacgc gcagaaaaaa aggatctcaa  15600
gaagatcctt tgatcttttc tacggggtct gacgctcagt ggaacgaaaa ctcacgttaa  15660
```

gggattttgg tcatgagatt atcaaaaagg atcttcacct agatcctttt gatccggaat 15720
ta 15722

<210> SEQ ID NO 23
<211> LENGTH: 20
<212> TYPE: DNA
<213> ORGANISM: Artificial Sequence
<220> FEATURE:
<223> OTHER INFORMATION: for editing GW2-1

<400> SEQUENCE: 23
gagcggttca cgcggccgca 20

<210> SEQ ID NO 24
<211> LENGTH: 15721
<212> TYPE: DNA
<213> ORGANISM: Artificial Sequence
<220> FEATURE:
<223> OTHER INFORMATION: vector 23763
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (304)..(2100)
<223> OTHER INFORMATION: prSoUbi4-04
<220> FEATURE:
<221> NAME/KEY: gene
<222> LOCATION: (2117)..(6286)
<223> OTHER INFORMATION: cCas9-01
<220> FEATURE:
<221> NAME/KEY: mutation
<222> LOCATION: (5606)..(5608)
<223> OTHER INFORMATION: L to V mutation
<220> FEATURE:
<221> NAME/KEY: mutation
<222> LOCATION: (5651)..(5653)
<223> OTHER INFORMATION: I to V mutation
<220> FEATURE:
<221> NAME/KEY: misc_feature
<222> LOCATION: (6221)..(6283)
<223> OTHER INFORMATION: xSV40NLS-03
<220> FEATURE:
<221> NAME/KEY: terminator
<222> LOCATION: (6292)..(6544)
<223> OTHER INFORMATION: tNOS-05-01
<220> FEATURE:
<221> NAME/KEY: promoter
<222> LOCATION: (6551)..(6925)
<223> OTHER INFORMATION: prOsU3-01
<220> FEATURE:
<221> NAME/KEY: misc_feature
<222> LOCATION: (6927)..(6945)
<223> OTHER INFORMATION: xTaVLHP1
<220> FEATURE:
<221> NAME/KEY: misc_feature
<222> LOCATION: (6927)..(7030)
<223> OTHER INFORMATION: rsgRNA TaVLHP1-01
<220> FEATURE:
<221> NAME/KEY: promoter
<222> LOCATION: (7041)..(9032)
<223> OTHER INFORMATION: prUbi1-04
<220> FEATURE:
<221> NAME/KEY: gene
<222> LOCATION: (9049)..(10227)
<223> OTHER INFORMATION: cPMI-09
<220> FEATURE:
<221> NAME/KEY: terminator
<222> LOCATION: (10250)..(10502)
<223> OTHER INFORMATION: tNOS-05-01
<220> FEATURE:
<221> NAME/KEY: misc_feature
<222> LOCATION: (10546)..(10675)

<223> OTHER INFORMATION: bNLB-03
<220> FEATURE:
<221> NAME/KEY: gene
<222> LOCATION: (10955)..(11743)
<223> OTHER INFORMATION: cSpec-03
<220> FEATURE:
<221> NAME/KEY: promoter
<222> LOCATION: (11838)..(11968)
<223> OTHER INFORMATION: prVirG-01
<220> FEATURE:
<221> NAME/KEY: gene
<222> LOCATION: (12705)..(13778)
<223> OTHER INFORMATION: cRepA-01
<220> FEATURE:
<221> NAME/KEY: misc_feature
<222> LOCATION: (13821)..(14225)
<223> OTHER INFORMATION: oVS1-02
<220> FEATURE:
<221> NAME/KEY: misc_feature
<222> LOCATION: (14903)..(15709)
<223> OTHER INFORMATION: oCOLE-06

<400> SEQUENCE: 24

```
attcctgtgg ttggcatgca catacaaatg gacgaacgga taaacctttt cacgcccttt     60

taaatatccg attattctaa taaacgctct tttctcttag gtttacccgc caatatatcc    120

tgtcaaacac tgatagttta aactgaaggc gggaaacgac aatctgatca tgagcggaga    180

attaagggag tcacgttatg acccccgccg atgacgcggg acaagccgtt ttacgtttgg    240

aactgacaga accgcaacgc tgcaggaatt ggccgcagcg gccatttaaa caaagcttgg    300

taccattatg tggtctaggt aggttctata tataagaaaa cttgaaatgt tctaaaaaaa    360

aattcaagcc catgcatgat tgaagcaaac ggtatagcaa cggtgttaac ctgatctagt    420

gatctcttgc aatccttaac ggccacctac cgcaggtagc aaacggcgtc cccctcctcg    480

atatctccgc ggcgacctct ggctttttcc gcggaattgc gcggtgggga cggattccac    540

gagaccgcga cgcaaccgcc tctcgccgct gggccccaca ccgctcggtg ccgtagcctc    600

acgggactct ttctccctcc tcccccgtta taaattggct tcatcccctc cttgcctcat    660

ccatccaaat cccagtcccc aatcccatcc cttcgtagga gaaattcatc gaagctaagc    720

gaatcctcgc gatcctctca aggtactgcg agttttcgat ccccctctcg acccctcgta    780

tgtttgtgtt tgtcgtagcg tttgattagg tatgctttcc ctgtttgtgt tcgtcgtagc    840

gtttgattag gtatgctttc cctgttcgtg ttcatcgtag tgtttgatta ggtcgtgtga    900

ggcgatggcc tgctcgcgtc cttcgatctg tagtcgattt gcgggtcgtg gtgtagatct    960

gcgggctgtg atgaagttat ttggtgtgat ctgctcgcct gattctgcgg gttggctcga   1020

gtagatatga tggttggacc ggttggttcg tttaccgcgc tagggttggg ctgggatgat   1080

gttgcatgcg ccgttgcgcg tgatcccgca gcaggacttg cgtttgattg ccagatctcg   1140

ttacgattat gtgatttggt ttggactttt tagatctgta gcttctgctt atgtgccaga   1200

tgcgcctact gctcatatgc ctgatgataa tcataaatgg ctgtggaact aactagttga   1260

ttgcggagtc atgtatcagc tacaggtgta gggactagct acaggtgtag ggacttgcgt   1320

ctaattgttt ggtcctttac tcatgttgca attatgcaat ttagtttaga ttgtttgttc   1380

cactcatcta ggctgtaaaa gggacactgc ttagattgct gtttaatctt tttagtagat   1440

tatattatat tggtaactta ttacccctat tacatgccat acgtgacttc tgctcatgcc   1500

tgatgataat catagatcac tgtggaatta attagttgat tgttgaatca tgtttcatgt   1560

acataccacg gcacaattgc ttagttcctt aacaaatgca aattttactg atccatgtat   1620

gatttgcgtg gttctctaat gtgaaatact atagctactt gttagtaaga atcaggttcg   1680
```

```
tatgcttaat gctgtatgtg ccttctgctc atgcctgatg ataatcatat atcactggaa   1740
ttaattagtt gatcgtttaa tcatatatca agtacatacc atgccacaat ttttagtcac   1800
ttaacccatg cagattgaac tggtccctgc atgttttgct aaattgttct attctgatta   1860
gaccatatat catgtatttt tttttggtaa tggttctctt attttaaatg ctatatagtt   1920
ctggtacttg ttagaaagat ctgcttcata gtttagttgc ctatccctcg aattaggatg   1980
ctgagcagct gatcctatag ctttgtttca tgtatcaatt cttttgtgtt caacagtcag   2040
tttttgttag attcattgta acttatggtc gcttactctt ctggtcctca atgcttgcag   2100
gatcgcggcc gctcatatgg acaagaagta cagcatcggc ctggacatcg gcaccaacag   2160
cgtgggctgg gccgtgatca ccgacgagta caaggtgccg agcaagaagt tcaaggtgct   2220
gggcaacacc gacaggcaca gcatcaagaa gaacctgatc ggcgccctgc tgttcgacag   2280
cggcgagacc gccgaggcca ccaggctgaa gaggaccgcc aggaggaggt acaccaggag   2340
gaagaacagg atctgctacc tgcaggagat cttcagcaac gagatggcca aggtggacga   2400
cagcttcttc cacaggctgg aggagagctt cctggtggag gaggacaaga agcacgagag   2460
gcacccgatc ttcggcaaca tcgtggacga ggtggcctac cacgagaagt acccgaccat   2520
ctaccacctg aggaagaagc tggtggacag caccgacaag gccgacctga ggctgatcta   2580
cctggccctg gcccacatga tcaagttcag gggccacttc ctgatcgagg gcgacctgaa   2640
cccggacaac agcgacgtgg acaagctgtt catccagctg gtgcagacct acaaccagct   2700
gttcgaggag aacccgatca acgccagcgg cgtggacgcc aaggccatcc tgagcgccag   2760
gctgagcaag agcaggaggc tggagaacct gatcgcccag ctgccgggcg agaagaagaa   2820
cggcctgttc ggcaacctga tcgccctgag cctgggcctg accccgaact tcaagagcaa   2880
cttcgacctg gccgaggacg ccaagctgca gctgagcaag gacacctacg acgacgacct   2940
ggacaacctg ctggcccaga tcggcgacca gtacgccgac ctgttcctgg ccgccaagaa   3000
cctgagcgac gccatcctgc tgagcgacat cctgagggtg aacaccgaga tcaccaaggc   3060
cccgctgagc gccagcatga tcaagaggta cgacgagcac caccaggacc tgaccctgct   3120
gaaggccctg gtgaggcagc agctgccgga gaagtacaag gagatcttct tcgaccagag   3180
caagaacggc tacgccggct acatcgacgg cggcgccagc caggaggagt tctacaagtt   3240
catcaagccg atcctggaga agatggacgg caccgaggag ctgctggtga agctgaacag   3300
ggaggacctg ctgaggaagc agaggacctt cgacaacggc agcatcccgc accagatcca   3360
cctgggcgag ctgcacgcca tcctgaggag gcaggaggac ttctacccgt tcctgaagga   3420
caacagggag aagatcgaga agatcctgac cttccgcatc ccgtactacg tgggcccgct   3480
ggccaggggc aacagcaggt tcgcctggat gaccaggaag agcgaggaga ccatcacccc   3540
gtggaacttc gaggaggtgg tggacaaggg cgccagcgcc cagagcttca tcgagaggat   3600
gaccaacttc gacaagaacc tgccgaacga gaaggtgctg ccgaagcaca gcctgctgta   3660
cgagtacttc accgtgtaca acgagctgac caaggtgaag tacgtgaccg agggcatgag   3720
gaagccggcc ttcctgagcg gcgagcagaa gaaggccatc gtggacctgc tgttcaagac   3780
caacaggaag gtgaccgtga agcagctgaa ggaggactac ttcaagaaga tcgagtgctt   3840
cgacagcgtg gagatcagcg gcgtggagga caggttcaac gccagcctgg gcacctacca   3900
cgacctgctg aagatcatca aggacaagga cttcctggac aacgaggaga acgaggacat   3960
cctggaggac atcgtgctga ccctgaccct gttcgaggac agggagatga tcgaggagag   4020
```

-continued

```
gctgaagacc tacgcccacc tgttcgacga caaggtgatg aagcagctga agaggaggag   4080
gtacaccggc tggggcaggc tgagcaggaa gctgatcaac ggcatcaggg acaagcagag   4140
cggcaagacc atcctggact tcctgaagag cgacggcttc gccaacagga acttcatgca   4200
gctgatccac gacgacagcc tgaccttcaa ggaggacatc cagaaggccc aggtgagcgg   4260
ccagggcgac agcctgcacg agcacatcgc caacctggcc ggcagcccgg ccatcaagaa   4320
gggcatcctg cagaccgtga aggtggtgga cgagctggtg aaggtgatgg gcaggcacaa   4380
gccggagaac atcgtgatcg agatggccag ggagaaccag accacccaga agggccagaa   4440
gaacagcagg gagaggatga agaggatcga ggagggcatc aaggagctgg gcagccagat   4500
cctgaaggag cacccggtgg agaacaccca gctgcagaac gagaagctgt acctgtacta   4560
cctgcagaac ggcagggaca tgtacgtgga ccaggagctg gacatcaaca ggctgagcga   4620
ctacgacgtg gaccacatcg tgccgcagag cttcctgaag gacgacagca tcgacaacaa   4680
ggtgctgacc aggagcgaca agaacagggg caagagcgac aacgtgccga gcgaggaggt   4740
ggtgaagaag atgaaaaact actggaggca gctgctgaac gccaagctga tcacccagag   4800
gaagttcgac aacctgacca aggccgagag gggcggcctg agcgagctgg acaaggccgg   4860
cttcattaaa aggcagctgg tggagaccag gcagatcacc aagcacgtgg cccagatcct   4920
ggacagcagg atgaacacca agtacgacga gaacgacaag ctgatcaggg aggtgaaggt   4980
gatcaccctg aagagcaagc tggtgagcga cttcaggaag gacttccagt tctacaaggt   5040
gagggagatc aataattacc accacgccca cgacgcctac ctgaacgccg tggtgggcac   5100
cgccctgatt aaaaagtacc cgaagctgga gagcgagttc gtgtacggcg actacaaggt   5160
gtacgacgtg aggaagatga tcgccaagag cgagcaggag atcggcaagg ccaccgccaa   5220
gtacttcttc tacagcaaca tcatgaactt cttcaagacc gagatcaccc tggccaacgg   5280
cgagatcagg aagaggccgc tgatcgagac caacggcgag accggcgaga tcgtgtggga   5340
caagggcagg gacttcgcca ccgtgaggaa ggtgctgtcc atgccgcagg tgaacatcgt   5400
gaagaagacc gaggtgcaga ccggcggctt cagcaaggag agcatcctgc cgaagaggaa   5460
cagcgacaag ctgatcgcca ggaagaagga ctgggacccg aagaagtacg gcggcttcga   5520
cagcccgacc gtggcctaca gcgtgctggt ggtggccaag gtggagaagg gcaagagcaa   5580
gaagctgaag agcgtgaagg agctggtggg catcaccatc atggagagga gcagcttcga   5640
gaagaaccca gtggacttcc tggaggccaa gggctacaag gaggtgaaga aggacctgat   5700
cattaaactg ccgaagtaca gcctgttcga gctggagaac ggcaggaaga ggatgctggc   5760
cagcgccggc gagctgcaga agggcaacga gctggccctg ccgagcaagt acgtgaactt   5820
cctgtacctg gccagccact acgagaagct gaagggcagc ccggaggaca acgagcagaa   5880
gcagctgttc gtggagcagc acaagcacta cctggacgag atcatcgagc agatcagcga   5940
gttcagcaag agggtgatcc tggccgacgc caacctggac aaggtgctga gcgcctacaa   6000
caagcacagg gacaagccga tcagggagca ggccgagaac atcatccacc tgttcaccct   6060
gaccaacctg ggcgccccgg ccgccttcaa gtacttcgac accaccatcg acaggaagag   6120
gtacaccagc accaaggagg tgctggacgc caccctgatc caccagagca tcaccggcct   6180
gtacgagacc aggatcgacc tgagccagct gggcggcgac agcagcccgc cgaagaagaa   6240
gaggaaggtg agctggaagg acgccagcgg ctggagcagg atgtgaagct tgatcgttca   6300
aacatttggc aataaagttt cttaagattg aatcctgttg ccggtcttgc gatgattatc   6360
atataatttc tgttgaatta cgttaagcat gtaataatta acatgtaatg catgacgtta   6420
```

-continued

```
tttatgagat gggtttttat gattagagtc ccgcaattat acatttaata cgcgatagaa   6480
aacaaaatat agcgcgcaaa ctaggataaa ttatcgcgcg cggtgtcatc tatgttacta   6540
gatcttcgaa gggatcttta aacatacgaa cagatcactt aaagttcttc tgaagcaact   6600
taaagttatc aggcatgcat ggatcttgga ggaatcagat gtgcagtcag ggaccatagc   6660
acaggacagg cgtcttctac tggtgctacc agcaaatgct ggaagccggg aacactgggt   6720
acgttggaaa ccacgtgatg tggagtaaga taaactgtag gagaaaagca tttcgtagtg   6780
ggccatgaag cctttcagga catgtattgc agtatgggcc ggcccattac gcaattggac   6840
gacaacaaag actagtatta gtaccacctc ggctatccac atagatcaaa gctggtttaa   6900
aagagttgtg cagatgatcc gtggcagacg agcaggcgca gttccgtttt agagctagaa   6960
atagcaagtt aaaataaggc tagtccgtta tcaacttgaa aaagtggcac cgagtcggtg   7020
cttttttttt cggaccgcgc ctgcagtgca gcgtgacccg gtcgtgcccc tctctagaga   7080
taatgagcat tgcatgtcta agttataaaa aattaccaca tatttttttt gtcacacttg   7140
tttgaagtgc agtttatcta tctttataca tatatttaaa ctttactcta cgaataatat   7200
aatctatagt actacaataa tatcagtgtt ttagagaatc atataaatga acagttagac   7260
atggtctaaa ggacaattga gtattttgac aacaggactc tacagtttta tctttttagt   7320
gtgcatgtgt tctccttttt ttttgcaaat agcttcacct atataatact tcatccattt   7380
tattagtaca tccatttagg gtttagggtt aatggttttt atagactaat ttttttagta   7440
catctatttt attctatttt agcctctaaa ttaagaaaac taaaactcta ttttagtttt   7500
tttatttaat aatttagata taaaatagaa taaaataaag tgactaaaaa ttaaacaaat   7560
accctttaag aaattaaaaa aactaaggaa acatttttct tgtttcgagt agataatgcc   7620
agcctgttaa acgccgtcga cgagtctaac ggacaccaac cagcgaacca gcagcgtcgc   7680
gtcgggccaa gcgaagcaga cggcacggca tctctgtcgc tgcctctgga cccctctcga   7740
gagttccgct ccaccgttgg acttgctccg ctgtcggcat ccagaaattg cgtggcggag   7800
cggcagacgt gagccggcac ggcaggcggc ctcctcctcc tctcacggca ccggcagcta   7860
cgggggattc ctttcccacc gctccttcgc tttcccttcc tcgcccgccg taataaatag   7920
acaccccctc cacaccctct ttccccaacc tcgtgttgtt cggagcgcac acacacacaa   7980
ccagatctcc cccaaatcca cccgtcggca cctccgcttc aaggtacgcc gctcgtcctc   8040
cccccccccc ctctctacct tctctagatc ggcgttccgg tccatggtta gggcccggta   8100
gttctacttc tgttcatgtt tgtgttagat ccgtgtttgt gttagatccg tgctgctagc   8160
gttcgtacac ggatgcgacc tgtacgtcag acacgttctg attgctaact tgccagtgtt   8220
tctctttggg gaatcctggg atggctctag ccgttccgca gacgggatcg atttcatgat   8280
ttttttgtt tcgttgcata gggtttggtt tgccctttc ctttatttca atatatgccg   8340
tgcacttgtt tgtcgggtca tcttttcatg cttttttttg tcttggttgt gatgatgtgg   8400
tctggttggg cggtcgttct agatcggagt agaattctgt ttcaaactac ctggtggatt   8460
tattaatttt ggatctgtat gtgtgtgcca tacatattca tagttacgaa ttgaagatga   8520
tggatggaaa tatcgatcta ggataggtat acatgttgat gcgggtttta ctgatgcata   8580
tacagagatg ctttttgttc gcttggttgt gatgatgtgg tgtggttggg cggtcgttca   8640
ttcgttctag atcggagtag aatactgttt caaactacct ggtgtattta ttaattttgg   8700
aactgtatgt gtgtgtcata catcttcata gttacgagtt taagatggat ggaaatatcg   8760
```

-continued

```
atctaggata ggtatacatg ttgatgtggg ttttactgat gcatatacat gatggcatat   8820
gcagcatcta ttcatatgct ctaaccttga gtacctatct attataataa acaagtatgt   8880
tttataatta ttttgatctt gatatacttg gatgatggca tatgcagcag ctatatgtgg   8940
atttttttag ccctgccttc atacgctatt tatttgcttg gtactgtttc ttttgtcgat   9000
gctcaccctg ttgtttggtg ttacttctgc agggatccgg cagcagccat gcagaagctg   9060
atcaacagcg tgcagaacta cgcctggggc agcaagaccg ccctgaccga gctgtacggc   9120
atggagaacc ccagcagcca gcccatggcc gagctgtgga tgggcgccca ccccaagagc   9180
agcagccgcg tgcagaacgc cgccggcgac atcgtgagcc tgcgcgacgt gatcgagagc   9240
gacaagagca ccctgctggg cgaggccgtg gccaagcgct tcggcgagct gcccttcctg   9300
ttcaaggtgc tgtgcgccgc ccagcccctg agcatccagg tgcaccccaa caagcacaac   9360
agcgagatcg gcttcgccaa ggagaacgcc gccggcatcc ccatggacgc cgccgagcgc   9420
aactacaagg accccaacca caagcccgag ctggtgttcg ccctgacccc cttcctggcc   9480
atgaacgcct tccgcgagtt cagcgagatc gtgagcctgc tgcagcccgt ggccggcgcc   9540
caccccgcca tcgcccactt cctgcagcag cccgacgccg agcgcctgag cgagctgttc   9600
gccagcctgc tgaacatgca gggcgaggag aagagccgcg ccctggccat cctgaagagc   9660
gccctggaca gccagcaggg cgagccctgg cagaccatcc gcctgatcag cgagttctac   9720
cccgaggaca gcggcctgtt cagccccctg ctgctgaacg tggtgaagct gaaccccggc   9780
gaggccatgt tcctgttcgc cgagaccccc cacgcctacc tgcagggcgt ggccctggag   9840
gtgatggcca acagcgacaa cgtgctgcgc gccggcctga cccccaagta catcgacatc   9900
cccgagctgg tggccaacgt gaagttcgag gccaagcccg ccaaccagct gctgacccag   9960
cccgtgaagc agggcgccga gctggacttc cccatccccg tggacgactt cgccttcagc  10020
ctgcacgacc tgagcgacaa ggagaccacc atcagccagc agagcgccgc catcctgttc  10080
tgcgtggagg gcgacgccac cctgtggaag ggcagccagc agctgcagct gaagcccggc  10140
gagagcgcct tcatcgccgc caacgagagc cccgtgaccg tgaagggcca cggccgcctg  10200
gcccgcgtgt acaacaagct gtgataggag ctcgatccgt cgacctgcag atcgttcaaa  10260
catttggcaa taaagtttct taagattgaa tcctgttgcc ggtcttgcga tgattatcat  10320
ataatttctg ttgaattacg ttaagcatgt aataattaac atgtaatgca tgacgttatt  10380
tatgagatgg gtttttatga ttagagtccc gcaattatac atttaatacg cgatagaaaa  10440
caaaatatag cgcgcaaact aggataaatt atcgcgcgcg gtgtcatcta tgttactaga  10500
tcggcgcgcc gcaattgaag tttgggcggc cagcatggcc gtatccgcaa tgtgttatta  10560
agttgtctaa gcgtcaattt gtttacacca caatatatcc tgccaccagc cagccaacag  10620
ctccccgacc ggcagctcgg cacaaaatca ccactcgata caggcagccc atcagaatta  10680
attctcatgt ttgacagctt atcatcgact gcacggtgca ccaatgcttc tggcgtcagg  10740
cagccatcgg aagctgtggt atggctgtgc aggtcgtaaa tcactgcata attcgtgtcg  10800
ctcaaggcgc actcccgttc tggataatgt tttttgcgcc gacatcataa cggttctggc  10860
aaatattctg aaatgagctg ttgacaatta atcatccggc tcgtataatg tgtggaattg  10920
tgagcggata acaatttcac acaggaaaca gaccatgagg gaagcgttga tcgccgaagt  10980
atcgactcaa ctatcagagg tagttggcgt catcgagcgc catctcgaac cgacgttgct  11040
ggccgtacat ttgtacggct ccgcagtgga tggcggcctg aagccacaca gtgatattga  11100
tttgctggtt acggtgaccg taaggcttga tgaaacaacg cggcgagctt tgatcaacga  11160
```

```
ccttttggaa acttcggctt cccctggaga gagcgagatt ctccgcgctg tagaagtcac  11220
cattgttgtg cacgacgaca tcattccgtg gcgttatcca gctaagcgcg aactgcaatt  11280
tggagaatgg cagcgcaatg acattcttgc aggtatcttc gagccagcca cgatcgacat  11340
tgatctggct atcttgctga caaaagcaag agaacatagc gttgccttgg taggtccagc  11400
ggcggaggaa ctctttgatc cggttcctga acaggatcta tttgaggcgc taaatgaaac  11460
cttaacgcta tggaactcgc cgcccgactg ggctggcgat gagcgaaatg tagtgcttac  11520
gttgtcccgc atttggtaca gcgcagtaac cggcaaaatc gcgccgaagg atgtcgctgc  11580
cgactgggca atggagcgcc tgccggccca gtatcagccc gtcatacttg aagctaggca  11640
ggcttatctt ggacaagaag atcgcttggc ctcgcgcgca gatcagttgg aagaatttgt  11700
tcactacgtg aaaggcgaga tcaccaaagt agtcggcaaa taaagctcta gtggatctcc  11760
gtacccgggg atctggctcg cggcggacgc acgacgccgg ggcgagacca taggcgatct  11820
cctaaatcaa tagtagctgt aacctcgaag cgtttcactt gtaacaacga ttgagaattt  11880
ttgtcataaa attgaaatac ttggttcgca tttttgtcat ccgcggtcag ccgcaattct  11940
gacgaactgc ccatttagct ggagatgatt gtacatcctt cacgtgaaaa tttctcaagc  12000
gctgtgaaca agggttcaga ttttagattg aaaggtgagc cgttgaaaca cgttcttctt  12060
gtcgatgacg acgtcgctat gcggcatctt attattgaat accttacgat ccacgccttc  12120
aaagtgaccg cggtagccga cagcacccag ttcacaagag tactctcttc cgcgacggtc  12180
gatgtcgtgg ttgttgatct agatttaggt cgtgaagatg ggctcgagct aggagcaagt  12240
gattttatcg ctaagccgtt cagtatcaga gagtttctag cacgcattcg ggttgccttg  12300
cgcgtgcgcc ccaacgttgt ccgctccaaa gaccgacggt ctttttgttt tactgactgg  12360
acacttaatc tcaggcaacg tcgcttgatg tccgaagctg gcggtgaggt gaaacttacg  12420
gcaggtgagt tcaatcttct cctcgcgttt ttagagaaac cccgcgacgt tctatcgcgc  12480
gagcaacttc tcattgccag tcgagtacgc gacgaggagg tttatgacag gagtatagat  12540
gttctcattt tgaggctgcg ccgcaaactt gaggcagatc cgtcaagccc tcaactgata  12600
aaaacagcaa gaggtgccgg ttatttcttt gacgcggacg tgcaggtttc gcacgggggg  12660
acgatggcag cctgagccaa ttcccagatc cccgaggaat cggcgtgagc ggtcgcaaac  12720
catccggccc ggtacaaatc ggcgcggcgc tgggtgatga cctggtggag aagttgaagg  12780
ccgcgcaggc cgcccagcgg caacgcatcg aggcagaagc acgccccggt gaatcgtggc  12840
aagcggccgc tgatcgaatc cgcaaagaat cccggcaacc gccggcagcc ggtgcgccgt  12900
cgattaggaa gccgcccaag ggcgacgagc aaccagattt tttcgttccg atgctctatg  12960
acgtgggcac ccgcgatagt cgcagcatca tggacgtggc cgttttccgt ctgtcgaagc  13020
gtgaccgacg agctggcgag gtgatccgct acgagcttcc agacgggcac gtagaggttt  13080
ccgcagggcc ggccggcatg gccagtgtgt gggattacga cctggtactg atggcggttt  13140
cccatctaac cgaatccatg aaccgatacc gggaagggaa gggagacaag cccggccgcg  13200
tgttccgtcc acacgttgcg gacgtactca agttctgccg gcgagccgat ggcggaaagc  13260
agaaagacga cctggtagaa acctgcattc ggttaaacac cacgcacgtt gccatgcagc  13320
gtacgaagaa ggccaagaac ggccgcctgg tgacggtatc cgagggtgaa gccttgatta  13380
gccgctacaa gatcgtaaag agcgaaaccg ggcggccgga gtacatcgag atcgagctag  13440
ctgattggat gtaccgcgag atcacagaag gcaagaaccc ggacgtgctg acggttcacc  13500
```

```
ccgattactt tttgatcgat cccggcatcg gccgttttct ctaccgcctg gcacgccgcg  13560
ccgcaggcaa ggcagaagcc agatggttgt tcaagacgat ctacgaacgc agtggcagcg  13620
ccggagagtt caagaagttc tgtttcaccg tgcgcaagct gatcgggtca aatgacctgc  13680
cggagtacga tttgaaggag gaggcggggc aggctggccc gatcctagtc atgcgctacc  13740
gcaacctgat cgagggcgaa gcatccgccg gttcctaatg tacggagcag atgctagggc  13800
aaattgccct agcaggggaa aaaggtcgaa aaggtctctt tcctgtggat agcacgtaca  13860
ttgggaaccc aaagccgtac attgggaacc ggaacccgta cattgggaac ccaaagccgt  13920
acattgggaa ccggtcacac atgtaagtga ctgatataaa agagaaaaaa ggcgattttt  13980
ccgcctaaaa ctctttaaaa cttattaaaa ctcttaaaac ccgcctggcc tgtgcataac  14040
tgtctggcca gcgcacagcc gaagagctgc aaaaagcgcc tacccttcgg tcgctgcgct  14100
ccctacgccc cgccgcttcg cgtcggccta tcgcggccgc tggccgctca aaaatggctg  14160
gcctacggcc aggcaatcta ccagggcgcg gacaagccgc gccgtcgcca ctcgaccgcc  14220
ggcgctgagg tctgcctcgt gaagaaggtg ttgctgactc ataccaggcc tgaatcgccc  14280
catcatccag ccagaaagtg agggagccac ggttgatgag agctttgttg taggtggacc  14340
agttggtgat tttgaacttt tgctttgcca cggaacggtc tgcgttgtcg ggaagatgcg  14400
tgatctgatc cttcaactca gcaaaagttc gatttattca acaaagccgc cgtcccgtca  14460
agtcagcgta atgctctgcc agtgttacaa ccaattaacc aattctgatt agaaaaactc  14520
atcgagcatc aaatgaaact gcaatttatt catatcagga ttatcaatac catatttttg  14580
aaaaagccgt ttctgtaatg aaggagaaaa ctcaccgagg cagttccata ggatggcaag  14640
atcctggtat cggtctgcga ttccgactcg tccaacatca atacaaccta ttaatttccc  14700
ctcgtcaaaa ataaggttat caagtgagaa atcaccatga gtgacgactg aatccggtga  14760
gaatggcaaa agctctgcat taatgaatcg gccaacgcgc ggggagaggc ggtttgcgta  14820
ttgggcgctc ttccgcttcc tcgctcactg actcgctgcg ctcggtcgtt cggctgcggc  14880
gagcggtatc agctcactca aaggcggtaa tacggttatc cacagaatca ggggataacg  14940
caggaaagaa catgtgagca aaaggccagc aaaaggccag gaaccgtaaa aaggccgcgt  15000
tgctggcgtt tttccatagg ctccgccccc ctgacgagca tcacaaaaat cgacgctcaa  15060
gtcagaggtg gcgaaacccg acaggactat aaagatacca ggcgtttccc cctggaagct  15120
ccctcgtgcg ctctcctgtt ccgaccctgc cgcttaccgg atacctgtcc gcctttctcc  15180
cttcgggaag cgtggcgctt tctcatagct cacgctgtag gtatctcagt tcggtgtagg  15240
tcgttcgctc caagctgggc tgtgtgcacg aaccccccgt tcagcccgac cgctgcgcct  15300
tatccggtaa ctatcgtctt gagtccaacc cggtaagaca cgacttatcg ccactggcag  15360
cagccactgg taacaggatt agcagagcga ggtatgtagg cggtgctaca gagttcttga  15420
agtggtggcc taactacggc tacactagaa gaacagtatt tggtatctgc gctctgctga  15480
agccagttac cttcggaaaa agagttggta gctcttgatc cggcaaacaa accaccgctg  15540
gtagcggtgg tttttttgtt tgcaagcagc agattacgcg cagaaaaaaa ggatctcaag  15600
aagatccttt gatcttttct acggggtctg acgctcagtg gaacgaaaac tcacgttaag  15660
ggattttggt catgagatta tcaaaaagga tcttcaccta gatccttttg atccggaatt  15720
a                                                                  15721
```

<210> SEQ ID NO 25
<211> LENGTH: 19

<212> TYPE: DNA
<213> ORGANISM: Artificial Sequence
<220> FEATURE:
<223> OTHER INFORMATION: for editing VLHP1 in wheat

<400> SEQUENCE: 25
gacgagcagg cgcagttcc 19

<210> SEQ ID NO 26
<211> LENGTH: 20
<212> TYPE: DNA
<213> ORGANISM: Triticum aestivum

<400> SEQUENCE: 26
gctggagctg agcttccggg 20

<210> SEQ ID NO 27
<211> LENGTH: 20
<212> TYPE: DNA
<213> ORGANISM: Triticum aestivum

<400> SEQUENCE: 27
tctggagctg agcttccggg 20

<210> SEQ ID NO 28
<211> LENGTH: 20
<212> TYPE: DNA
<213> ORGANISM: Zea mays

<400> SEQUENCE: 28
aggcgtcgag cagcgaggtg 20

<210> SEQ ID NO 29
<211> LENGTH: 20
<212> TYPE: DNA
<213> ORGANISM: Artificial Sequence
<220> FEATURE:
<223> OTHER INFORMATION: edited ZmVLHP-03 portion

<400> SEQUENCE: 29
aggcgttgag cagcgaggtg 20

<210> SEQ ID NO 30
<211> LENGTH: 75
<212> TYPE: DNA
<213> ORGANISM: Artificial Sequence
<220> FEATURE:
<223> OTHER INFORMATION: repair donor template for creating E149L mutation in ZmPYL-D

<400> SEQUENCE: 30
ccttggtgtt gccgtcgggg acgtcgacga cgaatgacag gatgacgagc gtccctggcc 60
ggccgtcgat gacct 75

<210> SEQ ID NO 31
<211> LENGTH: 15722
<212> TYPE: DNA
<213> ORGANISM: Artificial Sequence
<220> FEATURE:
<223> OTHER INFORMATION: vector 23136
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (304)..(2100)
<223> OTHER INFORMATION: prSoUbi4-04
<220> FEATURE:
<221> NAME/KEY: gene
<222> LOCATION: (2117)..(6286)
<223> OTHER INFORMATION: cCas9-01
<220> FEATURE:
<221> NAME/KEY: mutation
<222> LOCATION: (5606)..(5608)
<223> OTHER INFORMATION: L to V mutation
<220> FEATURE:
<221> NAME/KEY: mutation
<222> LOCATION: (5651)..(5653)
<223> OTHER INFORMATION: I to V mutation
<220> FEATURE:
<221> NAME/KEY: terminator
<222> LOCATION: (6292)..(6544)
<223> OTHER INFORMATION: tNOS-05-01
<220> FEATURE:
<221> NAME/KEY: promoter
<222> LOCATION: (6551)..(6925)
<223> OTHER INFORMATION: prOsU3-01
<220> FEATURE:
<221> NAME/KEY: misc_feature
<222> LOCATION: (6927)..(6946)
<223> OTHER INFORMATION: xZmPYL-D
<220> FEATURE:
<221> NAME/KEY: misc_feature
<222> LOCATION: (6927)..(7031)
<223> OTHER INFORMATION: rsgRBAZmPYLd-02
<220> FEATURE:
<221> NAME/KEY: promoter
<222> LOCATION: (7042)..(9033)
<223> OTHER INFORMATION: prUbi1-04
<220> FEATURE:
<221> NAME/KEY: gene
<222> LOCATION: (9050)..(10228)
<223> OTHER INFORMATION: cPMI-09
<220> FEATURE:
<221> NAME/KEY: terminator
<222> LOCATION: (10251)..(10503)
<223> OTHER INFORMATION: tNOS-05-01
<220> FEATURE:
<221> NAME/KEY: misc_feature
<222> LOCATION: (10547)..(10676)
<223> OTHER INFORMATION: bNLB-03
<220> FEATURE:
<221> NAME/KEY: gene
<222> LOCATION: (10956)..(11744)
<223> OTHER INFORMATION: cSpec-03
<220> FEATURE:
<221> NAME/KEY: promoter
<222> LOCATION: (11839)..(11969)
<223> OTHER INFORMATION: prVirG-01
<220> FEATURE:
<221> NAME/KEY: gene
<222> LOCATION: (12706)..(13779)
<223> OTHER INFORMATION: cRepA-01
<220> FEATURE:
<221> NAME/KEY: misc_feature
<222> LOCATION: (13822)..(14226)
<223> OTHER INFORMATION: oVS1-02
<220> FEATURE:
<221> NAME/KEY: misc_feature
<222> LOCATION: (14904)..(15710)
<223> OTHER INFORMATION: oCOLE-06

<400> SEQUENCE: 31
attcctgtgg ttggcatgca catacaaatg gacgaacgga taaacctttt cacgcccttt 60
taaatatccg attattctaa taaacgctct tttctcttag gtttacccgc caatatatcc 120
tgtcaaacac tgatagttta aactgaaggc gggaaacgac aatctgatca tgagcggaga 180
attaagggag tcacgttatg acccccgccg atgacgcggg acaagccgtt ttacgtttgg 240
aactgacaga accgcaacgc tgcaggaatt ggccgcagcg gccatttaaa caaagcttgg 300

-continued

```
taccattatg tggtctaggt aggttctata tataagaaaa cttgaaatgt tctaaaaaaa    360
aattcaagcc catgcatgat tgaagcaaac ggtatagcaa cggtgttaac ctgatctagt    420
gatctcttgc aatccttaac ggccacctac cgcaggtagc aaacggcgtc cccctcctcg    480
atatctccgc ggcgacctct ggctttttcc gcggaattgc gcggtgggga cggattccac    540
gagaccgcga cgcaaccgcc tctcgccgct gggccccaca ccgctcggtg ccgtagcctc    600
acgggactct ttctccctcc tcccccgtta taaattggct tcatcccctc cttgcctcat    660
ccatccaaat cccagtcccc aatcccatcc cttcgtagga gaaattcatc gaagctaagc    720
gaatcctcgc gatcctctca aggtactgcg agttttcgat ccccctctcg acccctcgta    780
tgtttgtgtt tgtcgtagcg tttgattagg tatgctttcc ctgtttgtgt tcgtcgtagc    840
gtttgattag gtatgctttc cctgttcgtg ttcatcgtag tgtttgatta ggtcgtgtga    900
ggcgatggcc tgctcgcgtc cttcgatctg tagtcgattt gcgggtcgtg gtgtagatct    960
gcgggctgtg atgaagttat ttggtgtgat ctgctcgcct gattctgcgg gttggctcga   1020
gtagatatga tggttggacc ggttggttcg tttaccgcgc tagggttggg ctgggatgat   1080
gttgcatgcg ccgttgcgcg tgatcccgca gcaggacttg cgtttgattg ccagatctcg   1140
ttacgattat gtgatttggt ttggactttt tagatctgta gcttctgctt atgtgccaga   1200
tgcgcctact gctcatatgc ctgatgataa tcataaatgg ctgtggaact aactagttga   1260
ttgcggagtc atgtatcagc tacaggtgta gggactagct acaggtgtag ggacttgcgt   1320
ctaattgttt ggtcctttac tcatgttgca attatgcaat ttagtttaga ttgtttgttc   1380
cactcatcta ggctgtaaaa gggacactgc ttagattgct gtttaatctt tttagtagat   1440
tatattatat tggtaactta ttacccctat tacatgccat acgtgacttc tgctcatgcc   1500
tgatgataat catagatcac tgtggaatta attagttgat tgttgaatca tgtttcatgt   1560
acataccacg gcacaattgc ttagttcctt aacaaatgca aattttactg atccatgtat   1620
gatttgcgtg gttctctaat gtgaaatact atagctactt gttagtaaga atcaggttcg   1680
tatgcttaat gctgtatgtg ccttctgctc atgcctgatg ataatcatat atcactggaa   1740
ttaattagtt gatcgtttaa tcatatatca agtacatacc atgccacaat ttttagtcac   1800
ttaacccatg cagattgaac tggtccctgc atgttttgct aaattgttct attctgatta   1860
gaccatatat catgtatttt tttttggtaa tggttctctt attttaaatg ctatatagtt   1920
ctggtacttg ttagaaagat ctgcttcata gtttagttgc ctatccctcg aattaggatg   1980
ctgagcagct gatcctatag ctttgtttca tgtatcaatt cttttgtgtt caacagtcag   2040
tttttgttag attcattgta acttatggtc gcttactctt ctggtcctca atgcttgcag   2100
gatcgcggcc gctcatatgg acaagaagta cagcatcggc ctggacatcg gcaccaacag   2160
cgtgggctgg gccgtgatca ccgacgagta caaggtgccg agcaagaagt tcaaggtgct   2220
gggcaacacc gacaggcaca gcatcaagaa gaacctgatc ggcgccctgc tgttcgacag   2280
cggcgagacc gccgaggcca ccaggctgaa gaggaccgcc aggaggaggt acaccaggag   2340
gaagaacagg atctgctacc tgcaggagat cttcagcaac gagatggcca aggtggacga   2400
cagcttcttc cacaggctgg aggagagctt cctggtggag gaggacaaga agcacgagag   2460
gcacccgatc ttcggcaaca tcgtggacga ggtggcctac cacgagaagt acccgaccat   2520
ctaccacctg aggaagaagc tggtggacag caccgacaag gccgacctga ggctgatcta   2580
cctggccctg gcccacatga tcaagttcag gggccacttc ctgatcgagg gcgacctgaa   2640
cccggacaac agcgacgtgg acaagctgtt catccagctg gtgcagacct acaaccagct   2700
```

```
gttcgaggag aacccgatca acgccagcgg cgtggacgcc aaggccatcc tgagcgccag   2760
gctgagcaag agcaggaggc tggagaacct gatcgcccag ctgccgggcg agaagaagaa   2820
cggcctgttc ggcaacctga tcgccctgag cctgggcctg accccgaact tcaagagcaa   2880
cttcgacctg gccgaggacg ccaagctgca gctgagcaag gacacctacg acgacgacct   2940
ggacaacctg ctggcccaga tcggcgacca gtacgccgac ctgttcctgg ccgccaagaa   3000
cctgagcgac gccatcctgc tgagcgacat cctgagggtg aacaccgaga tcaccaaggc   3060
cccgctgagc gccagcatga tcaagaggta cgacgagcac caccaggacc tgaccctgct   3120
gaaggccctg gtgaggcagc agctgccgga gaagtacaag gagatcttct tcgaccagag   3180
caagaacggc tacgccggct acatcgacgg cggcgccagc caggaggagt tctacaagtt   3240
catcaagccg atcctggaga agatggacgg caccgaggag ctgctggtga agctgaacag   3300
ggaggacctg ctgaggaagc agaggacctt cgacaacggc agcatcccgc accagatcca   3360
cctgggcgag ctgcacgcca tcctgaggag gcaggaggac ttctacccgt tcctgaagga   3420
caacagggag aagatcgaga agatcctgac cttccgcatc ccgtactacg tgggcccgct   3480
ggccaggggc aacagcaggt tcgcctggat gaccaggaag agcgaggaga ccatcacccc   3540
gtggaacttc gaggaggtgg tggacaaggg cgccagcgcc cagagcttca tcgagaggat   3600
gaccaacttc gacaagaacc tgccgaacga gaaggtgctg ccgaagcaca gcctgctgta   3660
cgagtacttc accgtgtaca acgagctgac caaggtgaag tacgtgaccg agggcatgag   3720
gaagccggcc ttcctgagcg gcgagcagaa gaaggccatc gtggacctgc tgttcaagac   3780
caacaggaag gtgaccgtga agcagctgaa ggaggactac ttcaagaaga tcgagtgctt   3840
cgacagcgtg gagatcagcg gcgtggagga caggttcaac gccagcctgg gcacctacca   3900
cgacctgctg aagatcatca aggacaagga cttcctggac aacgaggaga acgaggacat   3960
cctggaggac atcgtgctga ccctgaccct gttcgaggac agggagatga tcgaggagag   4020
gctgaagacc tacgcccacc tgttcgacga caaggtgatg aagcagctga agaggaggag   4080
gtacaccggc tggggcaggc tgagcaggaa gctgatcaac ggcatcaggg acaagcagag   4140
cggcaagacc atcctggact tcctgaagag cgacggcttc gccaacagga acttcatgca   4200
gctgatccac gacgacagcc tgaccttcaa ggaggacatc cagaaggccc aggtgagcgg   4260
ccagggcgac agcctgcacg agcacatcgc caacctggcc ggcagcccgg ccatcaagaa   4320
gggcatcctg cagaccgtga aggtggtgga cgagctggtg aaggtgatgg gcaggcacaa   4380
gccggagaac atcgtgatcg agatggccag ggagaaccag accacccaga agggccagaa   4440
gaacagcagg gagaggatga agaggatcga ggagggcatc aaggagctgg gcagccagat   4500
cctgaaggag cacccggtgg agaacaccca gctgcagaac gagaagctgt acctgtacta   4560
cctgcagaac ggcagggaca tgtacgtgga ccaggagctg gacatcaaca ggctgagcga   4620
ctacgacgtg gaccacatcg tgccgcagag cttcctgaag gacgacagca tcgacaacaa   4680
ggtgctgacc aggagcgaca agaacagggg caagagcgac aacgtgccga gcgaggaggt   4740
ggtgaagaag atgaaaaact actggaggca gctgctgaac gccaagctga tcacccagag   4800
gaagttcgac aacctgacca aggccgagag gggcggcctg agcgagctgg acaaggccgg   4860
cttcattaaa aggcagctgg tggagaccag gcagatcacc aagcacgtgg cccagatcct   4920
ggacagcagg atgaacacca agtacgacga gaacgacaag ctgatcaggg aggtgaaggt   4980
gatcaccctg aagagcaagc tggtgagcga cttcaggaag gacttccagt tctacaaggt   5040
```

gagggagatc aataattacc accacgccca cgacgcctac ctgaacgccg tggtgggcac 5100
cgccctgatt aaaaagtacc cgaagctgga gagcgagttc gtgtacggcg actacaaggt 5160
gtacgacgtg aggaagatga tcgccaagag cgagcaggag atcggcaagg ccaccgccaa 5220
gtacttcttc tacagcaaca tcatgaactt cttcaagacc gagatcaccc tggccaacgg 5280
cgagatcagg aagaggccgc tgatcgagac caacggcgag accggcgaga tcgtgtggga 5340
caagggcagg gacttcgcca ccgtgaggaa ggtgctgtcc atgccgcagg tgaacatcgt 5400
gaagaagacc gaggtgcaga ccggcggctt cagcaaggag agcatcctgc cgaagaggaa 5460
cagcgacaag ctgatcgcca ggaagaagga ctgggacccg aagaagtacg gcggcttcga 5520
cagcccgacc gtggcctaca gcgtgctggt ggtggccaag gtggagaagg gcaagagcaa 5580
gaagctgaag agcgtgaagg agctggtggg catcaccatc atggagagga gcagcttcga 5640
gaagaaccca gtggacttcc tggaggccaa gggctacaag gaggtgaaga aggacctgat 5700
cattaaactg ccgaagtaca gcctgttcga gctggagaac ggcaggaaga ggatgctggc 5760
cagcgccggc gagctgcaga agggcaacga gctggccctg ccgagcaagt acgtgaactt 5820
cctgtacctg gccagccact acgagaagct gaagggcagc ccggaggaca acgagcagaa 5880
gcagctgttc gtggagcagc acaagcacta cctggacgag atcatcgagc agatcagcga 5940
gttcagcaag agggtgatcc tggccgacgc caacctggac aaggtgctga gcgcctacaa 6000
caagcacagg gacaagccga tcagggagca ggccgagaac atcatccacc tgttcaccct 6060
gaccaacctg ggcgccccgg ccgccttcaa gtacttcgac accaccatcg acaggaagag 6120
gtacaccagc accaaggagg tgctggacgc caccctgatc caccagagca tcaccggcct 6180
gtacgagacc aggatcgacc tgagccagct gggcggcgac agcagcccgc cgaagaagaa 6240
gaggaaggtg agctggaagg acgccagcgg ctggagcagg atgtgaagct tgatcgttca 6300
aacatttggc aataaagttt cttaagattg aatcctgttg ccggtcttgc gatgattatc 6360
atataatttc tgttgaatta cgttaagcat gtaataatta acatgtaatg catgacgtta 6420
tttatgagat gggtttttat gattagagtc ccgcaattat acatttaata cgcgatagaa 6480
aacaaaatat agcgcgcaaa ctaggataaa ttatcgcgcg cggtgtcatc tatgttacta 6540
gatcttcgaa gggatcttta aacatacgaa cagatcactt aaagttcttc tgaagcaact 6600
taaagttatc aggcatgcat ggatcttgga ggaatcagat gtgcagtcag ggaccatagc 6660
acaggacagg cgtcttctac tggtgctacc agcaaatgct ggaagccggg aacactgggt 6720
acgttggaaa ccacgtgatg tggagtaaga taaactgtag gagaaaagca tttcgtagtg 6780
ggccatgaag cctttcagga catgtattgc agtatgggcc ggcccattac gcaattggac 6840
gacaacaaag actagtatta gtaccacctc ggctatccac atagatcaaa gctggtttaa 6900
aagagttgtg cagatgatcc gtggcagtcg ggacgtcga cgacgagttt tagagctaga 6960
aatagcaagt taaaataagg ctagtccgtt atcaacttga aaaagtggca ccgagtcggt 7020
gctttttttt tcggaccgcg cctgcagtgc agcgtgaccc ggtcgtgccc ctctctagag 7080
ataatgagca ttgcatgtct aagttataaa aaattaccac atattttttt tgtcacactt 7140
gtttgaagtg cagtttatct atctttatac atatatttaa actttactct acgaataata 7200
taatctatag tactacaata atatcagtgt tttagagaat catataaatg aacagttaga 7260
catggtctaa aggacaattg agtattttga caacaggact ctacagtttt atctttttag 7320
tgtgcatgtg ttctcctttt tttttgcaaa tagcttcacc tatataatac ttcatccatt 7380
ttattagtac atccatttag ggtttagggt taatggtttt tatagactaa tttttttagt 7440

```
acatctattt tattctattt tagcctctaa attaagaaaa ctaaaactct attttagttt   7500
ttttatttaa taatttagat ataaaataga ataaaataaa gtgactaaaa attaaacaaa   7560
taccctttaa gaaattaaaa aaactaagga aacatttttc ttgtttcgag tagataatgc   7620
cagcctgtta aacgccgtcg acgagtctaa cggacaccaa ccagcgaacc agcagcgtcg   7680
cgtcgggcca agcgaagcag acggcacggc atctctgtcg ctgcctctgg acccctctcg   7740
agagttccgc tccaccgttg gacttgctcc gctgtcggca tccagaaatt gcgtggcgga   7800
gcggcagacg tgagccggca cggcaggcgg cctcctcctc ctctcacggc accggcagct   7860
acgggggatt cctttcccac cgctccttcg ctttcccttc ctcgcccgcc gtaataaata   7920
gacacccccct ccacaccctc tttccccaac ctcgtgttgt tcggagcgca cacacacaca   7980
accagatctc ccccaaatcc acccgtcggc acctccgctt caaggtacgc cgctcgtcct   8040
cccccccccc cctctctacc ttctctagat cggcgttccg gtccatggtt agggcccggt   8100
agttctactt ctgttcatgt ttgtgttaga tccgtgtttg tgttagatcc gtgctgctag   8160
cgttcgtaca cggatgcgac ctgtacgtca gacacgttct gattgctaac ttgccagtgt   8220
ttctctttgg ggaatcctgg gatggctcta gccgttccgc agacgggatc gatttcatga   8280
tttttttgt ttcgttgcat agggtttggt ttgccctttt cctttatttc aatatatgcc   8340
gtgcacttgt ttgtcgggtc atcttttcat gcttttttt gtcttggttg tgatgatgtg   8400
gtctggttgg gcggtcgttc tagatcggag tagaattctg tttcaaacta cctggtggat   8460
ttattaattt tggatctgta tgtgtgtgcc atacatattc atagttacga attgaagatg   8520
atggatggaa atatcgatct aggataggta tacatgttga tgcgggtttt actgatgcat   8580
atacagagat gctttttgtt cgcttggttg tgatgatgtg gtgtggttgg gcggtcgttc   8640
attcgttcta gatcggagta gaatactgtt tcaaactacc tggtgtattt attaattttg   8700
gaactgtatg tgtgtgtcat acatcttcat agttacgagt ttaagatgga tggaaatatc   8760
gatctaggat aggtatacat gttgatgtgg gttttactga tgcatataca tgatggcata   8820
tgcagcatct attcatatgc tctaaccttg agtacctatc tattataata aacaagtatg   8880
ttttataatt attttgatct tgatatactt ggatgatggc atatgcagca gctatatgtg   8940
gattttttta gccctgcctt catacgctat ttatttgctt ggtactgttt cttttgtcga   9000
tgctcaccct gttgtttggt gttacttctg cagggatccg gcagcagcca tgcagaagct   9060
gatcaacagc gtgcagaact acgcctgggg cagcaagacc gccctgaccg agctgtacgg   9120
catggagaac cccagcagcc agcccatggc cgagctgtgg atgggcgccc accccaagag   9180
cagcagccgc gtgcagaacg ccgccggcga catcgtgagc ctgcgcgacg tgatcgagag   9240
cgacaagagc accctgctgg gcgaggccgt ggccaagcgc ttcggcgagc tgcccttcct   9300
gttcaaggtg ctgtgcgccg cccagcccct gagcatccag gtgcaccccca acaagcacaa   9360
cagcgagatc ggcttcgcca aggagaacgc cgccggcatc cccatggacg ccgccgagcg   9420
caactacaag gaccccaacc acaagcccga gctggtgttc gccctgaccc ccttcctggc   9480
catgaacgcc ttccgcgagt tcagcgagat cgtgagcctg ctgcagcccg tggccggcgc   9540
ccaccccgcc atcgcccact tcctgcagca gcccgacgcc gagcgcctga gcgagctgtt   9600
cgccagcctg ctgaacatgc agggcgagga gaagagccgc gccctggcca tcctgaagag   9660
cgccctggac agccagcagg gcgagccctg gcagaccatc cgcctgatca gcgagttcta   9720
ccccgaggac agcggcctgt tcagcccccct gctgctgaac gtggtgaagc tgaaccccgg   9780
```

-continued

```
cgaggccatg ttcctgttcg ccgagacccc ccacgcctac ctgcagggcg tggccctgga   9840
ggtgatggcc aacagcgaca acgtgctgcg cgccggcctg acccccaagt acatcgacat   9900
ccccgagctg gtggccaacg tgaagttcga ggccaagccc gccaaccagc tgctgaccca   9960
gcccgtgaag cagggcgccg agctggactt ccccatcccc gtggacgact tcgccttcag  10020
cctgcacgac ctgagcgaca aggagaccac catcagccag cagagcgccg ccatcctgtt  10080
ctgcgtggag ggcgacgcca ccctgtggaa gggcagccag cagctgcagc tgaagcccgg  10140
cgagagcgcc ttcatcgccg ccaacgagag ccccgtgacc gtgaagggcc acggccgcct  10200
ggcccgcgtg tacaacaagc tgtgatagga gctcgatccg tcgacctgca gatcgttcaa  10260
acatttggca ataaagtttc ttaagattga atcctgttgc cggtcttgcg atgattatca  10320
tataatttct gttgaattac gttaagcatg taataattaa catgtaatgc atgacgttat  10380
ttatgagatg ggtttttatg attagagtcc cgcaattata catttaatac gcgatagaaa  10440
acaaaatata gcgcgcaaac taggataaat tatcgcgcgc ggtgtcatct atgttactag  10500
atcggcgcgc cgcaattgaa gtttgggcgg ccagcatggc cgtatccgca atgtgttatt  10560
aagttgtcta agcgtcaatt tgtttacacc acaatatatc ctgccaccag ccagccaaca  10620
gctccccgac cggcagctcg gcacaaaatc accactcgat acaggcagcc catcagaatt  10680
aattctcatg tttgacagct tatcatcgac tgcacggtgc accaatgctt ctggcgtcag  10740
gcagccatcg gaagctgtgg tatggctgtg caggtcgtaa atcactgcat aattcgtgtc  10800
gctcaaggcg cactcccgtt ctggataatg ttttttgcgc cgacatcata acggttctgg  10860
caaatattct gaaatgagct gttgacaatt aatcatccgg ctcgtataat gtgtggaatt  10920
gtgagcggat aacaatttca cacaggaaac agaccatgag ggaagcgttg atcgccgaag  10980
tatcgactca actatcagag gtagttggcg tcatcgagcg ccatctcgaa ccgacgttgc  11040
tggccgtaca tttgtacggc tccgcagtgg atggcggcct gaagccacac agtgatattg  11100
atttgctggt tacggtgacc gtaaggcttg atgaaacaac gcggcgagct ttgatcaacg  11160
accttttgga aacttcggct tcccctggag agagcgagat tctccgcgct gtagaagtca  11220
ccattgttgt gcacgacgac atcattccgt ggcgttatcc agctaagcgc gaactgcaat  11280
ttggagaatg gcagcgcaat gacattcttg caggtatctt cgagccagcc acgatcgaca  11340
ttgatctggc tatcttgctg acaaaagcaa gagaacatag cgttgccttg gtaggtccag  11400
cggcggagga actctttgat ccggttcctg aacaggatct atttgaggcg ctaaatgaaa  11460
ccttaacgct atggaactcg ccgcccgact gggctggcga tgagcgaaat gtagtgctta  11520
cgttgtcccg catttggtac agcgcagtaa ccggcaaaat cgcgccgaag gatgtcgctg  11580
ccgactgggc aatggagcgc ctgccggccc agtatcagcc cgtcatactt gaagctaggc  11640
aggcttatct tggacaagaa gatcgcttgg cctcgcgcgc agatcagttg gaagaatttg  11700
ttcactacgt gaaaggcgag atcaccaaag tagtcggcaa ataaagctct agtggatctc  11760
cgtacccggg gatctggctc gcggcggacg cacgacgccg ggcgagacc ataggcgatc  11820
tcctaaatca atagtagctg taacctcgaa gcgtttcact tgtaacaacg attgagaatt  11880
tttgtcataa aattgaaata cttggttcgc atttttgtca tccgcggtca gccgcaattc  11940
tgacgaactg cccatttagc tggagatgat tgtacatcct tcacgtgaaa atttctcaag  12000
cgctgtgaac aagggttcag attttagatt gaaaggtgag ccgttgaaac acgttcttct  12060
tgtcgatgac gacgtcgcta tgcggcatct tattattgaa taccttacga tccacgcctt  12120
caaagtgacc gcggtagccg acagcaccca gttcacaaga gtactctctt ccgcgacggt  12180
```

cgatgtcgtg gttgttgatc tagatttagg tcgtgaagat gggctcgagc taggagcaag 12240
tgattttatc gctaagccgt tcagtatcag agagtttcta gcacgcattc gggttgcctt 12300
gcgcgtgcgc cccaacgttg tccgctccaa agaccgacgg tctttttgtt ttactgactg 12360
gacacttaat ctcaggcaac gtcgcttgat gtccgaagct ggcggtgagg tgaaacttac 12420
ggcaggtgag ttcaatcttc tcctcgcgtt tttagagaaa ccccgcgacg ttctatcgcg 12480
cgagcaactt ctcattgcca gtcgagtacg cgacgaggag gtttatgaca ggagtataga 12540
tgttctcatt ttgaggctgc gccgcaaact tgaggcagat ccgtcaagcc ctcaactgat 12600
aaaaacagca agaggtgccg gttatttctt tgacgcggac gtgcaggttt cgcacggggg 12660
gacgatggca gcctgagcca attcccagat ccccgaggaa tcggcgtgag cggtcgcaaa 12720
ccatccggcc cggtacaaat cggcgcggcg ctgggtgatg acctggtgga gaagttgaag 12780
gccgcgcagg ccgcccagcg gcaacgcatc gaggcagaag cacgccccgg tgaatcgtgg 12840
caagcggccg ctgatcgaat ccgcaaagaa tcccggcaac cgccggcagc cggtgcgccg 12900
tcgattagga agccgcccaa gggcgacgag caaccagatt ttttcgttcc gatgctctat 12960
gacgtgggca cccgcgatag tcgcagcatc atggacgtgg ccgttttccg tctgtcgaag 13020
cgtgaccgac gagctggcga ggtgatccgc tacgagcttc cagacgggca cgtagaggtt 13080
tccgcagggc cggccggcat ggccagtgtg tgggattacg acctggtact gatggcggtt 13140
tcccatctaa ccgaatccat gaaccgatac cgggaaggga agggagacaa gcccggccgc 13200
gtgttccgtc cacacgttgc ggacgtactc aagttctgcc ggcgagccga tggcggaaag 13260
cagaaagacg acctggtaga aacctgcatt cggttaaaca ccacgcacgt tgccatgcag 13320
cgtacgaaga aggccaagaa cggccgcctg gtgacggtat ccgagggtga agccttgatt 13380
agccgctaca agatcgtaaa gagcgaaacc gggcggccgg agtacatcga gatcgagcta 13440
gctgattgga tgtaccgcga gatcacagaa ggcaagaacc cggacgtgct gacggttcac 13500
cccgattact ttttgatcga tcccggcatc ggccgttttc tctaccgcct ggcacgccgc 13560
gccgcaggca aggcagaagc cagatggttg ttcaagacga tctacgaacg cagtggcagc 13620
gccggagagt tcaagaagtt ctgtttcacc gtgcgcaagc tgatcgggtc aaatgacctg 13680
ccggagtacg atttgaagga ggaggcgggg caggctggcc cgatcctagt catgcgctac 13740
cgcaacctga tcgagggcga agcatccgcc ggttcctaat gtacggagca gatgctaggg 13800
caaattgccc tagcagggga aaaaggtcga aaaggtctct ttcctgtgga tagcacgtac 13860
attgggaacc caaagccgta cattgggaac cggaacccgt acattgggaa cccaaagccg 13920
tacattggga accggtcaca catgtaagtg actgatataa aagagaaaaa aggcgatttt 13980
tccgcctaaa actctttaaa acttattaaa actcttaaaa cccgcctggc ctgtgcataa 14040
ctgtctggcc agcgcacagc cgaagagctg caaaaagcgc ctacccttcg gtcgctgcgc 14100
tccctacgcc ccgccgcttc gcgtcggcct atcgcggccg ctggccgctc aaaaatggct 14160
ggcctacggc caggcaatct accagggcgc ggacaagccg cgccgtcgcc actcgaccgc 14220
cggcgctgag gtctgcctcg tgaagaaggt gttgctgact cataccaggc ctgaatcgcc 14280
ccatcatcca gccagaaagt gagggagcca cggttgatga gagctttgtt gtaggtggac 14340
cagttggtga ttttgaactt ttgctttgcc acggaacggt ctgcgttgtc gggaagatgc 14400
gtgatctgat ccttcaactc agcaaaagtt cgatttattc aacaaagccg ccgtcccgtc 14460
aagtcagcgt aatgctctgc cagtgttaca accaattaac caattctgat tagaaaaact 14520
catcgagcat caaatgaaac tgcaatttat tcatatcagg attatcaata ccatattttt 14580
gaaaaagccg tttctgtaat gaaggagaaa actcaccgag gcagttccat aggatggcaa 14640
gatcctggta tcggtctgcg attccgactc gtccaacatc aatacaacct attaatttcc 14700
cctcgtcaaa aataaggtta tcaagtgaga aatcaccatg agtgacgact gaatccggtg 14760
agaatggcaa aagctctgca ttaatgaatc ggccaacgcg cggggagagg cggtttgcgt 14820
attgggcgct cttccgcttc ctcgctcact gactcgctgc gctcggtcgt tcggctgcgg 14880
cgagcggtat cagctcactc aaaggcggta atacggttat ccacagaatc aggggataac 14940
gcaggaaaga acatgtgagc aaaaggccag caaaaggcca ggaaccgtaa aaaggccgcg 15000
ttgctggcgt ttttccatag gctccgcccc cctgacgagc atcacaaaaa tcgacgctca 15060
agtcagaggt ggcgaaaccc gacaggacta taaagatacc aggcgtttcc ccctggaagc 15120
tccctcgtgc gctctcctgt tccgaccctg ccgcttaccg gatacctgtc cgcctttctc 15180
ccttcgggaa gcgtggcgct ttctcatagc tcacgctgta ggtatctcag ttcggtgtag 15240
gtcgttcgct ccaagctggg ctgtgtgcac gaaccccccg ttcagcccga ccgctgcgcc 15300
ttatccggta actatcgtct tgagtccaac ccggtaagac acgacttatc gccactggca 15360
gcagccactg gtaacaggat tagcagagcg aggtatgtag gcggtgctac agagttcttg 15420
aagtggtggc ctaactacgg ctacactaga agaacagtat ttggtatctg cgctctgctg 15480
aagccagtta ccttcggaaa aagagttggt agctcttgat ccggcaaaca aaccaccgct 15540
ggtagcggtg gtttttttgt ttgcaagcag cagattacgc gcagaaaaaa aggatctcaa 15600
gaagatcctt tgatcttttc tacggggtct gacgctcagt ggaacgaaaa ctcacgttaa 15660
gggattttgg tcatgagatt atcaaaaagg atcttcacct agatcctttt gatccggaat 15720
ta 15722

<210> SEQ ID NO 32
<211> LENGTH: 20
<212> TYPE: DNA
<213> ORGANISM: Artificial Sequence
<220> FEATURE:
<223> OTHER INFORMATION: encoding gRNA for vector 23136

<400> SEQUENCE: 32
gtcggggacg tcgacgacga 20

<210> SEQ ID NO 33
<211> LENGTH: 1823
<212> TYPE: DNA
<213> ORGANISM: Oryza sativa

<400> SEQUENCE: 33
acagtgacta gtgacaaacg atcgatcgat ccctccatcc acaaaccctc ctcgatctca 60
tcttccttcg tctcgtcaat ggcggcgagc tactcgtgcc ggcggacatg cgaggcgtgc 120
agcacgaggg cgatggccgg gtgcgtggtg ggcgagccgg cgtcggcgcc ggggcagcgg 180
gtgacgttgc tggcgatcga cggcggcggc atcaggggcc tcatcccggg caccatcctc 240
gccttcctcg aggccaggct gcaggagctg gatggccccg acgcgcgcct cgccgattac 300
ttcgactgca tcgccgggac cagcaccggc ggcctcatca ccgccatgct cgccgcgccc 360
ggcgaccacg gccgcccgct cttcgccgcc agcgacatca accgcttcta cctcgacaac 420
ggcccactca tcttcccaca aaagtaactg atcacctcga attcgatctc ctctcttcga 480
tctctgcatt atttgatttg attggggatt gtgggcggcg tggcgtggcg tccaggaggt 540

-continued

```
gcggcatggc ggcggccatg gcggcgctga cgaggccgag gtacaacggc aagtacctgc      600

aggggaagat caggaagatg ctgggcgaga cgagggtgcg cgacacgctg acgaacgtcg      660

tcatccccac gttcgacgtc aggctgctcc agccaaccat cttctccaca tacgacgtgc      720

gtgcgttgat tccatccgca ttggcgttgg aatcagctga ttgtttgatt gatcgaacaa      780

ttgatcggtt aaaattttgc aggcgaagag catgccgctc aagaacgcgc tcctctccga      840

catctgcatc agcacatccg cggcgccgac ctacctcccc gcgcactgct tccagaccac      900

cgacgacgcc accggcaagg tccgcgagtt cgacctcatc gacggcggcg tcgccgccaa      960

caacccggta actaatcaat caagcaatcc atcaaacgaa gatccacatg tgcattcctg     1020

tggtacaaat gctgatcgat cgatggatgg atcgattttc gcgagaacgt acagacgatg     1080

gtggccatga cgcagatcac caagaagata atggtgaagg acaaggagga gctgtacccg     1140

gtaaagccgt cggactgcgg taagttcctg gtgctgtccg tgggcaccgg gtcgacgtcg     1200

gaccagggga tgtacacggc gaggcagtgc tcgcggtggg ggatcgtccg gtggctgcgc     1260

aacaagggga tggcgcccat catcgacatc ttcatggcgg ccagctccga cctcgtcgac     1320

atccacgccg ccgtcatgtt ccagtcgctg cacagcgacg gcgactacct ccgcatccag     1380

gacaacacgc tccacggcga cgccgccacg gtggacgccg ccaccaggga caacatgcgg     1440

gcgctcgtcg ggatcggcga gcggatgctg gcgcagcggg tgtcgagggt caacgtcgag     1500

accggcaggt acgtcgaggt gcccggcgcc ggcagcaacg ccgacgcgct gaggggcttc     1560

gccaggcagc tctccgagga gaggagggcg aggctaggtc ggcgaaacgc ctgcggcggc     1620

ggcggcgaag gagagcccag cggcgtggcg tgcaagcgtt agtaactgta cacgcatcat     1680

gctgacgcga tcttttttat ttttcttttt tttttttac ctttctagcg gacatgggga     1740

ataacaagac gtgacagtag tgcaatcggt ttgtaacgtg cgtataccaa cattgatcca     1800

tttcttcatc acagtttcag ttc                                            1823
```

```
<210> SEQ ID NO 34
<211> LENGTH: 15921
<212> TYPE: DNA
<213> ORGANISM: Artificial Sequence
<220> FEATURE:
<223> OTHER INFORMATION: Vector 24038
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (313)..(1149)
<223> OTHER INFORMATION: prZmGRMZM5G876285-01
<220> FEATURE:
<221> NAME/KEY: gene
<222> LOCATION: (1152)..(5412)
<223> OTHER INFORMATION: cCas9-12
<220> FEATURE:
<221> NAME/KEY: terminator
<222> LOCATION: (5419)..(6736)
<223> OTHER INFORMATION: tZmGRMZM5G876285-01
<220> FEATURE:
<221> NAME/KEY: promoter
<222> LOCATION: (6750)..(7124)
<223> OTHER INFORMATION: prOsU3-01
<220> FEATURE:
<221> NAME/KEY: misc_feature
<222> LOCATION: (7126)..(7145)
<223> OTHER INFORMATION: xZmVLHP2
<220> FEATURE:
<221> NAME/KEY: misc_feature
<222> LOCATION: (7126)..(7230)
```

<223> OTHER INFORMATION: rsgRNAZmVLHP-02
<220> FEATURE:
<221> NAME/KEY: misc_feature
<222> LOCATION: (7146)..(7157)
<223> OTHER INFORMATION: rCrRNA-01
<220> FEATURE:
<221> NAME/KEY: misc_feature
<222> LOCATION: (7146)..(7230)
<223> OTHER INFORMATION: rsgRNAbase-01
<220> FEATURE:
<221> NAME/KEY: misc_feature
<222> LOCATION: (7162)..(7230)
<223> OTHER INFORMATION: rTracrRNA-01
<220> FEATURE:
<221> NAME/KEY: promoter
<222> LOCATION: (7241)..(9232)
<223> OTHER INFORMATION: prUbi-04
<220> FEATURE:
<221> NAME/KEY: gene
<222> LOCATION: (9249)..(10427)
<223> OTHER INFORMATION: cPMI-09
<220> FEATURE:
<221> NAME/KEY: terminator
<222> LOCATION: (10450)..(10702)
<223> OTHER INFORMATION: tNOS-05-01
<220> FEATURE:
<221> NAME/KEY: misc_feature
<222> LOCATION: (10746)..(10875)
<223> OTHER INFORMATION: bNLB-03
<220> FEATURE:
<221> NAME/KEY: gene
<222> LOCATION: (11155)..(11943)
<223> OTHER INFORMATION: cSpec-03
<220> FEATURE:
<221> NAME/KEY: promoter
<222> LOCATION: (12038)..(12168)
<223> OTHER INFORMATION: prVirG-01
<220> FEATURE:
<221> NAME/KEY: gene
<222> LOCATION: (12243)..(12875)
<223> OTHER INFORMATION: cVirG-09
<220> FEATURE:
<221> NAME/KEY: gene
<222> LOCATION: (12905)..(13978)
<223> OTHER INFORMATION: cRepA-01
<220> FEATURE:
<221> NAME/KEY: misc_feature
<222> LOCATION: (14021)..(14425)
<223> OTHER INFORMATION: oVA1-02
<220> FEATURE:
<221> NAME/KEY: misc_feature
<222> LOCATION: (15103)..(15909)
<223> OTHER INFORMATION: oCOLE-06

<400> SEQUENCE: 34
attcctgtgg ttggcatgca catacaaatg gacgaacgga taaacctttt cacgcccttt 60
taaatatccg attattctaa taaacgctct tttctcttag gtttacccgc caatatatcc 120
tgtcaaacac tgatagttta aactgaaggc gggaaacgac aatctgatca tgagcggaga 180
attaagggag tcacgttatg acccccgccg atgacgcggg acaagccgtt ttacgtttgg 240
aactgacaga accgcaacgc tgcaggaatt ggccgcagcg gccatttaaa caaagcttgg 300
taccgggacc ctaagtaatc ttgtgctaca aatttatttt tcagacagaa aaatctattt 360
agctaactaa ttaatacaaa ttaataccaa gcaacgatag atgaacatct agttgtctaa 420
ttagctaact aattaataca aattaagtag aatccttacc gtggggagat ggggcgcgac 480
gaagtgctcg agcttggggc gcggcgaccg gcgacgtgaa gcttgggggc gcgggggccg 540
gacggcgctg cgggcggcat ggcgggcggc tgcgggcggc ggcgcgggcg caggaaacaa 600
acgacgggag tgggaggaag gagaaagcgg cgcgccggtt tagtcctagc tcggcgccaa 660
gatctgtggc gccgagctag gtgccacgat ggccgccgcg tcagcaaagc tcggcgccaa 720

```
ggcatgttgc gccgagccgt gttagctcgg cgtcatagct catggtgccg agttttgggt    780
ctaaaattgc gtttaagtat tctagggatc taaacgcaaa tatttttcga aaatagggcc    840
gaaaaacaaa aaaaaatcgg tcgtttcgtc gagcacatcg tccagcctat cttgcatgtc    900
catcctctct atggttcgcg agccgcgcgc atggcgctcc aaaggagggg cgaggttgaa    960
tatagacaga tggaatgggt ggttctctat ttatagcgca tgcagtcgtc ccctggcaca   1020
cctatttata tgtgagcgtt cctggcacta gagagatcga tcgatcgagc ttaattgcgc   1080
cactgctcgt tatcctcctc ttgcattgca ttgcaggtcg tagttgagca gcagcaacca   1140
ctgcacaggc catggacaag aagtacagca tcggcctgga catcggcacc aacagcgtgg   1200
gctgggccgt gatcaccgac gagtacaagg tgataccaat ttgcatgatc cttgttcgtt   1260
ctagctcttg catgccgatc agttgaatca cgcggtttcc ttctgcgcat ttgcatccag   1320
gtgccgagca agaagttcaa ggtgctgggc aacaccgaca ggcacagcat caagaagaac   1380
ctgatcggcg ccctgctgtt cgacagcggc gagaccgccg aggccaccag gctgaagagg   1440
accgccagga ggaggtacac caggaggaag aacaggatct gctacctgca ggagatcttc   1500
agcaacgaga tggccaaggt ggacgacagc ttcttccaca ggctggagga gagcttcctg   1560
gtggaggagg acaagaagca cgagaggcac ccgatcttcg gcaacatcgt ggacgaggtg   1620
gcctaccacg agaagtaccc gaccatctac cacctgagga agaagctggt ggacagcacc   1680
gacaaggccg acctgaggct gatctacctg gccctggccc acatgatcaa gttcaggggc   1740
cacttcctga tcgagggcga cctgaacccg gacaacagcg acgtggacaa gctgttcatc   1800
cagctggtgc agacctacaa ccagctgttc gaggagaacc cgatcaacgc cagcggcgtg   1860
gacgccaagg ccatcctgag cgccaggctg agcaagagca ggaggctgga gaacctgatc   1920
gcccagctgc cgggcgagaa gaagaacggc ctgttcggca acctgatcgc cctgagcctg   1980
ggcctgaccc cgaacttcaa gagcaacttc gacctggccg aggacgccaa gctgcagctg   2040
agcaaggaca cctacgacga cgacctggac aacctgctgg cccagatcgg cgaccagtac   2100
gccgacctgt tcctggccgc caagaacctg agcgacgcca tcctgctgag cgacatcctg   2160
agggtgaaca ccgagatcac caaggccccg ctgagcgcca gcatgatcaa gaggtacgac   2220
gagcaccacc aggacctgac cctgctgaag gccctggtga ggcagcagct gccggagaag   2280
tacaaggaga tcttcttcga ccagagcaag aacggctacg ccggctacat cgacggcggc   2340
gccagccagg aggagttcta caagttcatc aagccgatcc tggagaagat ggacggcacc   2400
gaggagctgc tggtgaagct gaacagggag gacctgctga ggaagcagag gaccttcgac   2460
aacggcagca tcccgcacca gatccacctg ggcgagctgc acgccatcct gaggaggcag   2520
gaggacttct acccgttcct gaaggacaac agggagaaga tcgagaagat cctgaccttc   2580
cgcatcccgt actacgtggg cccgctggcc aggggcaaca gcaggttcgc ctggatgacc   2640
aggaagagcg aggagaccat caccccgtgg aacttcgagg aggtggtgga caagggcgcc   2700
agcgcccaga gcttcatcga gaggatgacc aacttcgaca agaacctgcc gaacgagaag   2760
gtgctgccga agcacagcct gctgtacgag tacttcaccg tgtacaacga gctgaccaag   2820
gtgaagtacg tgaccgaggg catgaggaag ccggccttcc tgagcggcga gcagaagaag   2880
gccatcgtgg acctgctgtt caagaccaac aggaaggtga ccgtgaagca gctgaaggag   2940
gactacttca agaagatcga gtgcttcgac agcgtggaga tcagcggcgt ggaggacagg   3000
ttcaacgcca gcctgggcac ctaccacgac ctgctgaaga tcatcaagga caaggacttc   3060
```

-continued

```
ctggacaacg aggagaacga ggacatcctg gaggacatcg tgctgaccct gaccctgttc   3120
gaggacaggg agatgatcga ggagaggctg aagacctacg cccacctgtt cgacgacaag   3180
gtgatgaagc agctgaagag gaggaggtac accggctggg gcaggctgag caggaagctg   3240
atcaacggca tcagggacaa gcagagcggc aagaccatcc tggacttcct gaagagcgac   3300
ggcttcgcca acaggaactt catgcagctg atccacgacg acagcctgac cttcaaggag   3360
gacatccaga aggcccaggt gagcggccag ggcgacagcc tgcacgagca catcgccaac   3420
ctggccggca gcccggccat caagaagggc atcctgcaga ccgtgaaggt ggtggacgag   3480
ctggtgaagg tgatgggcag gcacaagccg gagaacatcg tgatcgagat ggccagggag   3540
aaccagacca cccagaaggg ccagaagaac agcagggaga ggatgaagag gatcgaggag   3600
ggcatcaagg agctgggcag ccagatcctg aaggagcacc cggtggagaa cacccagctg   3660
cagaacgaga agctgtacct gtactacctg cagaacggca gggacatgta cgtggaccag   3720
gagctggaca tcaacaggct gagcgactac gacgtggacc acatcgtgcc gcagagcttc   3780
ctgaaggacg acagcatcga caacaaggtg ctgaccagga gcgacaagaa caggggcaag   3840
agcgacaacg tgccgagcga ggaggtggtg aagaagatga aaaactactg gaggcagctg   3900
ctgaacgcca agctgatcac ccagaggaag ttcgacaacc tgaccaaggc cgagaggggc   3960
ggcctgagcg agctggacaa ggccggcttc attaaaaggc agctggtgga gaccaggcag   4020
atcaccaagc acgtggccca gatcctggac agcaggatga acaccaagta cgacgagaac   4080
gacaagctga tcagggaggt gaaggtgatc accctgaaga gcaagctggt gagcgacttc   4140
aggaaggact tccagttcta caaggtgagg gagatcaata attaccacca cgcccacgac   4200
gcctacctga acgccgtggt gggcaccgcc ctgattaaaa agtacccgaa gctggagagc   4260
gagttcgtgt acggcgacta caaggtgtac gacgtgagga agatgatcgc caagagcgag   4320
caggagatcg gcaaggccac cgccaagtac ttcttctaca gcaacatcat gaacttcttc   4380
aagaccgaga tcaccctggc caacggcgag atcaggaaga ggccgctgat cgagaccaac   4440
ggcgagaccg gcgagatcgt gtgggacaag ggcagggact tcgccaccgt gaggaaggtg   4500
ctgtccatgc cgcaggtgaa catcgtgaag aagaccgagg tgcagaccgg cggcttcagc   4560
aaggagagca tcctgccgaa gaggaacagc gacaagctga tcgccaggaa gaaggactgg   4620
gacccgaaga agtacggcgg cttcgacagc ccgaccgtgg cctacagcgt gctggtggtg   4680
gccaaggtgg agaagggcaa gagcaagaag ctgaagagcg tgaaggagct ggtgggcatc   4740
accatcatgg agaggagcag cttcgagaag aacccagtgg acttcctgga ggccaagggc   4800
tacaaggagg tgaagaagga cctgatcatt aaactgccga agtacagcct gttcgagctg   4860
gagaacggca ggaagaggat gctggccagc gccggcgagc tgcagaaggg caacgagctg   4920
gccctgccga gcaagtacgt gaacttcctg tacctggcca gccactacga gaagctgaag   4980
ggcagcccgg aggacaacga gcagaagcag ctgttcgtgg agcagcacaa gcactacctg   5040
gacgagatca tcgagcagat cagcgagttc agcaagaggg tgatcctggc cgacgccaac   5100
ctggacaagg tgctgagcgc ctacaacaag cacagggaca agccgatcag ggagcaggcc   5160
gagaacatca tccacctgtt caccctgacc aacctgggcg ccccggccgc cttcaagtac   5220
ttcgacacca ccatcgacag gaagaggtac accagcacca aggaggtgct ggacgccacc   5280
ctgatccacc agagcatcac cggcctgtac gagaccagga tcgacctgag ccagctgggc   5340
ggcgacagca gcccgccgaa gaagaagagg aaggtgagct ggaaggacgc cagcggctgg   5400
agcaggatgt gagctctaat gcatccaaac aacgacacca acgccaacat taattaatta   5460
```

-continued

```
gtagtctcca tgccctggga ttgtgcgtgg ccgctccgtt gaacaccacc catccttcgt   5520
tcggcatttt ttcccccctt gtttatataa ttttattgta tcgttttggc aaataatttt   5580
gtgattcgac cccaaagcaa gtttggttgt cttacgattt gtaaacctgg aacaatatat   5640
aatgtgattg aactgctttg tctattcttt ttgtagtacg ataatatgta tatgtattcc   5700
atgcgatctc ttctagggcg acgactaatg tgcaagtgtg tgtttgcatg cgctgagcac   5760
ggagtttgta ttcaggggtc aatatctttc gattccttta tctaaaaagg tgttgcatat   5820
atctaaaaaa aagaaaaaaa aggcttacaa ctgttgaaaa aataagcatt tttagtttta   5880
atttaattca gaaaatcata gtgatatatg tgacgatatg catgtgcata tgtatcacta   5940
ctcacataaa cagtaaacaa cagtaaaata tgtataaata caaaaataac aaagtgtacc   6000
ctgcggaggg accgatgttc aaggcatctg tggctccatt cacacgagac atctcgtgtg   6060
tatgttcgat gtagtcatac gcagtcgagg cagtcagatg tacgcagtgc agtccctcga   6120
tcggcgccgg cgacgaggaa cttgatcagt gctggtcgag cggacgaagc gagcagtcgc   6180
gagtacgctc ccgaaaaaca tgatcgctcg cacacccatg caagtgtcgc tctgcggacg   6240
acgatttcgg aagcctacgc gtatgagaat gtttgtatgt gtgttctctc gtaaccagaa   6300
gcctcatctc ctccgtatat atacacgcgc agagggaggc caacagatag taacggtgga   6360
aggaatactc ggaccaaggt ccgatctacc atggccacgg cccggcctgg ccagcggcgc   6420
gtgcgtgtgg cagtccttca tccttttatc agcttatcaa tagatgcacc aaagatccac   6480
ctatttaagt tgattgaatt gtctcttgta cttccggtat gttactaaag taataataca   6540
ccgtagcatt aaattgggcc tttagcattg gctattattg aatattaatt tgagccagac   6600
ccaccaccag atgctaagtc acaccaaaat gctctcatca tctcaaacat ttcatatact   6660
ggtgtttcga tggagactat taagttgaac atccacctag aatctagatt acacttgacc   6720
acaactacat aatggacgga ccgttcgaag ggatctttaa acatacgaac agatcactta   6780
aagttcttct gaagcaactt aaagttatca ggcatgcatg gatcttggag gaatcagatg   6840
tgcagtcagg gaccatagca caggacaggc gtcttctact ggtgctacca gcaaatgctg   6900
gaagccggga acactgggta cgttggaaac cacgtgatgt ggagtaagat aaactgtagg   6960
agaaaagcat ttcgtagtgg gccatgaagc ctttcaggac atgtattgca gtatgggccg   7020
gcccattacg caattggacg acaacaaaga ctagtattag taccacctcg gctatccaca   7080
tagatcaaag ctggtttaaa agagttgtgc agatgatccg tggcagctgg agctgagctt   7140
ccggggtttt agagctagaa atagcaagtt aaaataaggc tagtccgtta tcaacttgaa   7200
aaagtggcac cgagtcggtg cttttttttt cggaccgcgc ctgcagtgca gcgtgacccg   7260
gtcgtgcccc tctctagaga taatgagcat tgcatgtcta agttataaaa aattaccaca   7320
tatttttttt gtcacacttg tttgaagtgc agtttatcta tctttataca tatatttaaa   7380
ctttactcta cgaataatat aatctatagt actacaataa tatcagtgtt ttagagaatc   7440
atataaatga acagttagac atggtctaaa ggacaattga gtattttgac aacaggactc   7500
tacagtttta tctttttagt gtgcatgtgt tctccttttt ttttgcaaat agcttcacct   7560
atataatact tcatccattt tattagtaca tccatttagg gtttagggtt aatggttttt   7620
atagactaat ttttttagta catctatttt attctatttt agcctctaaa ttaagaaaac   7680
taaaactcta ttttagtttt tttatttaat aatttagata taaaatagaa taaaataaag   7740
tgactaaaaa ttaaacaaat accctttaag aaattaaaaa aactaaggaa acatttttct   7800
```

-continued

```
tgtttcgagt agataatgcc agcctgttaa acgccgtcga cgagtctaac ggacaccaac   7860
cagcgaacca gcagcgtcgc gtcgggccaa gcgaagcaga cggcacggca tctctgtcgc   7920
tgcctctgga cccctctcga gagttccgct ccaccgttgg acttgctccg ctgtcggcat   7980
ccagaaattg cgtggcggag cggcagacgt gagccggcac ggcaggcggc ctcctcctcc   8040
tctcacggca ccggcagcta cgggggattc ctttcccacc gctccttcgc tttcccttcc   8100
tcgcccgccg taataaatag acaccccctc cacaccctct ttccccaacc tcgtgttgtt   8160
cggagcgcac acacacacaa ccagatctcc cccaaatcca cccgtcggca cctccgcttc   8220
aaggtacgcc gctcgtcctc cccccccccc ctctctacct tctctagatc ggcgttccgg   8280
tccatggtta gggcccggta gttctacttc tgttcatgtt tgtgttagat ccgtgtttgt   8340
gttagatccg tgctgctagc gttcgtacac ggatgcgacc tgtacgtcag acacgttctg   8400
attgctaact tgccagtgtt tctctttggg gaatcctggg atggctctag ccgttccgca   8460
gacgggatcg atttcatgat ttttttgtt tcgttgcata gggtttggtt tgcccttttc   8520
ctttatttca atatatgccg tgcacttgtt tgtcgggtca tcttttcatg cttttttttg   8580
tcttggttgt gatgatgtgg tctggttggg cggtcgttct agatcggagt agaattctgt   8640
ttcaaactac ctggtggatt tattaatttt ggatctgtat gtgtgtgcca tacatattca   8700
tagttacgaa ttgaagatga tggatggaaa tatcgatcta ggataggtat acatgttgat   8760
gcgggtttta ctgatgcata tacagagatg ctttttgttc gcttggttgt gatgatgtgg   8820
tgtggttggg cggtcgttca ttcgttctag atcggagtag aatactgttt caaactacct   8880
ggtgtattta ttaatttgg aactgtatgt gtgtgtcata catcttcata gttacgagtt   8940
taagatggat ggaaatatcg atctaggata ggtatacatg ttgatgtggg ttttactgat   9000
gcatatacat gatggcatat gcagcatcta ttcatatgct ctaaccttga gtacctatct   9060
attataataa acaagtatgt tttataatta ttttgatctt gatatacttg gatgatggca   9120
tatgcagcag ctatatgtgg atttttttag ccctgccttc atacgctatt tatttgcttg   9180
gtactgtttc ttttgtcgat gctcaccctg ttgtttggtg ttacttctgc agggatccgg   9240
cagcagccat gcagaagctg atcaacagcg tgcagaacta cgcctggggc agcaagaccg   9300
ccctgaccga gctgtacggc atggagaacc ccagcagcca gcccatggcc gagctgtgga   9360
tgggcgccca ccccaagagc agcagccgcg tgcagaacgc cgccggcgac atcgtgagcc   9420
tgcgcgacgt gatcgagagc gacaagagca ccctgctggg cgaggccgtg gccaagcgct   9480
tcggcgagct gcccttcctg ttcaaggtgc tgtgcgccgc ccagcccctg agcatccagg   9540
tgcaccccaa caagcacaac agcgagatcg gcttcgccaa ggagaacgcc gccggcatcc   9600
ccatggacgc cgccgagcgc aactacaagg accccaacca caagcccgag ctggtgttcg   9660
ccctgacccc cttcctggcc atgaacgcct tccgcgagtt cagcgagatc gtgagcctgc   9720
tgcagcccgt ggccggcgcc caccccgcca tcgcccactt cctgcagcag cccgacgccg   9780
agcgcctgag cgagctgttc gccagcctgc tgaacatgca gggcgaggag aagagccgcg   9840
ccctggccat cctgaagagc gccctggaca gccagcaggg cgagccctgg cagaccatcc   9900
gcctgatcag cgagttctac cccgaggaca gcggcctgtt cagcccccctg ctgctgaacg   9960
tggtgaagct gaaccccggc gaggccatgt tcctgttcgc cgagaccccc cacgcctacc  10020
tgcagggcgt ggccctggag gtgatggcca acagcgacaa cgtgctgcgc gccggcctga  10080
cccccaagta catcgacatc cccgagctgg tggccaacgt gaagttcgag gccaagcccg  10140
ccaaccagct gctgacccag cccgtgaagc agggcgccga gctggacttc cccatccccg  10200
```

```
tggacgactt cgccttcagc ctgcacgacc tgagcgacaa ggagaccacc atcagccagc  10260
agagcgccgc catcctgttc tgcgtggagg gcgacgccac cctgtggaag ggcagccagc  10320
agctgcagct gaagcccggc gagagcgcct tcatcgccgc caacgagagc cccgtgaccg  10380
tgaagggcca cggccgcctg gcccgcgtgt acaacaagct gtgataggag ctcgatccgt  10440
cgacctgcag atcgttcaaa catttggcaa taaagtttct taagattgaa tcctgttgcc  10500
ggtcttgcga tgattatcat ataatttctg ttgaattacg ttaagcatgt aataattaac  10560
atgtaatgca tgacgttatt tatgagatgg gtttttatga ttagagtccc gcaattatac  10620
atttaatacg cgatagaaaa caaaatatag cgcgcaaact aggataaatt atcgcgcgcg  10680
gtgtcatcta tgttactaga tcggcgcgcc gcaattgaag tttgggcggc cagcatggcc  10740
gtatccgcaa tgtgttatta agttgtctaa gcgtcaattt gtttacacca caatatatcc  10800
tgccaccagc cagccaacag ctccccgacc ggcagctcgg cacaaaatca ccactcgata  10860
caggcagccc atcagaatta attctcatgt ttgacagctt atcatcgact gcacggtgca  10920
ccaatgcttc tggcgtcagg cagccatcgg aagctgtggt atggctgtgc aggtcgtaaa  10980
tcactgcata attcgtgtcg ctcaaggcgc actcccgttc tggataatgt tttttgcgcc  11040
gacatcataa cggttctggc aaatattctg aaatgagctg ttgacaatta atcatccggc  11100
tcgtataatg tgtggaattg tgagcggata acaatttcac acaggaaaca gaccatgagg  11160
gaagcgttga tcgccgaagt atcgactcaa ctatcagagg tagttggcgt catcgagcgc  11220
catctcgaac cgacgttgct ggccgtacat ttgtacggct ccgcagtgga tggcggcctg  11280
aagccacaca gtgatattga tttgctggtt acggtgaccg taaggcttga tgaaacaacg  11340
cggcgagctt tgatcaacga ccttttggaa acttcggctt cccctggaga gagcgagatt  11400
ctccgcgctg tagaagtcac cattgttgtg cacgacgaca tcattccgtg gcgttatcca  11460
gctaagcgcg aactgcaatt tggagaatgg cagcgcaatg acattcttgc aggtatcttc  11520
gagccagcca cgatcgacat tgatctggct atcttgctga caaaagcaag agaacatagc  11580
gttgccttgg taggtccagc ggcggaggaa ctctttgatc cggttcctga acaggatcta  11640
tttgaggcgc taaatgaaac cttaacgcta tggaactcgc cgcccgactg ggctggcgat  11700
gagcgaaatg tagtgcttac gttgtcccgc atttggtaca gcgcagtaac cggcaaaatc  11760
gcgccgaagg atgtcgctgc cgactgggca atggagcgcc tgccggccca gtatcagccc  11820
gtcatacttg aagctaggca ggcttatctt ggacaagaag atcgcttggc ctcgcgcgca  11880
gatcagttgg aagaatttgt tcactacgtg aaaggcgaga tcaccaaagt agtcggcaaa  11940
taaagctcta gtggatctcc gtacccgggg atctggctcg cggcggacgc acgacgccgg  12000
ggcgagacca taggcgatct cctaaatcaa tagtagctgt aacctcgaag cgtttcactt  12060
gtaacaacga ttgagaattt ttgtcataaa attgaaatac ttggttcgca tttttgtcat  12120
ccgcggtcag ccgcaattct gacgaactgc ccatttagct ggagatgatt gtacatcctt  12180
cacgtgaaaa tttctcaagc gctgtgaaca agggttcaga ttttagattg aaaggtgagc  12240
cgttgaaaca cgttcttctt gtcgatgacg acgtcgctat gcggcatctt attattgaat  12300
accttacgat ccacgccttc aaagtgaccg cggtagccga cagcacccag ttcacaagag  12360
tactctcttc cgcgacggtc gatgtcgtgg ttgttgatct agatttaggt cgtgaagatg  12420
ggctcgagct aggagcaagt gattttatcg ctaagccgtt cagtatcaga gagtttctag  12480
cacgcattcg ggttgccttg cgcgtgcgcc ccaacgttgt ccgctccaaa gaccgacggt  12540
```

-continued

```
cttttttgttt tactgactgg acacttaatc tcaggcaacg tcgcttgatg tccgaagctg  12600
gcggtgaggt gaaacttacg gcaggtgagt tcaatcttct cctcgcgttt ttagagaaac  12660
cccgcgacgt tctatcgcgc gagcaacttc tcattgccag tcgagtacgc gacgaggagg  12720
tttatgacag gagtatagat gttctcattt tgaggctgcg ccgcaaactt gaggcagatc  12780
cgtcaagccc tcaactgata aaaacagcaa gaggtgccgg ttatttcttt gacgcggacg  12840
tgcaggtttc gcacgggggg acgatggcag cctgagccaa ttcccagatc cccgaggaat  12900
cggcgtgagc ggtcgcaaac catccggccc ggtacaaatc ggcgcggcgc tgggtgatga  12960
cctggtggag aagttgaagg ccgcgcaggc cgcccagcgg caacgcatcg aggcagaagc  13020
acgccccggt gaatcgtggc aagcggccgc tgatcgaatc cgcaaagaat cccggcaacc  13080
gccggcagcc ggtgcgccgt cgattaggaa gccgcccaag ggcgacgagc aaccagattt  13140
tttcgttccg atgctctatg acgtgggcac ccgcgatagt cgcagcatca tggacgtggc  13200
cgttttccgt ctgtcgaagc gtgaccgacg agctggcgag gtgatccgct acgagcttcc  13260
agacgggcac gtagaggttt ccgcagggcc ggccggcatg gccagtgtgt gggattacga  13320
cctggtactg atggcggttt cccatctaac cgaatccatg aaccgatacc gggaagggaa  13380
gggagacaag cccggccgcg tgttccgtcc acacgttgcg gacgtactca agttctgccg  13440
gcgagccgat ggcggaaagc agaaagacga cctggtagaa acctgcattc ggttaaacac  13500
cacgcacgtt gccatgcagc gtacgaagaa ggccaagaac ggccgcctgg tgacggtatc  13560
cgagggtgaa gccttgatta gccgctacaa gatcgtaaag agcgaaaccg ggcggccgga  13620
gtacatcgag atcgagctag ctgattggat gtaccgcgag atcacagaag gcaagaaccc  13680
ggacgtgctg acggttcacc ccgattactt tttgatcgat cccggcatcg gccgttttct  13740
ctaccgcctg gcacgccgcg ccgcaggcaa ggcagaagcc agatggttgt tcaagacgat  13800
ctacgaacgc agtggcagcg ccggagagtt caagaagttc tgtttcaccg tgcgcaagct  13860
gatcgggtca aatgacctgc cggagtacga tttgaaggag gaggcggggc aggctggccc  13920
gatcctagtc atgcgctacc gcaacctgat cgagggcgaa gcatccgccg gttcctaatg  13980
tacggagcag atgctagggc aaattgccct agcaggggaa aaaggtcgaa aaggtctctt  14040
tcctgtggat agcacgtaca ttgggaaccc aaagccgtac attgggaacc ggaacccgta  14100
cattgggaac ccaaagccgt acattgggaa ccggtcacac atgtaagtga ctgatataaa  14160
agagaaaaaa ggcgattttt ccgcctaaaa ctctttaaaa cttattaaaa ctcttaaaac  14220
ccgcctggcc tgtgcataac tgtctggcca gcgcacagcc gaagagctgc aaaaagcgcc  14280
tacccttcgg tcgctgcgct ccctacgccc cgccgcttcg cgtcggccta tcgcggccgc  14340
tggccgctca aaaatggctg gcctacggcc aggcaatcta ccagggcgcg gacaagccgc  14400
gccgtcgcca ctcgaccgcc ggcgctgagg tctgcctcgt gaagaaggtg ttgctgactc  14460
ataccaggcc tgaatcgccc catcatccag ccagaaagtg agggagccac ggttgatgag  14520
agctttgttg taggtggacc agttggtgat tttgaacttt tgctttgcca cggaacggtc  14580
tgcgttgtcg ggaagatgcg tgatctgatc cttcaactca gcaaaagttc gatttattca  14640
acaaagccgc cgtcccgtca agtcagcgta atgctctgcc agtgttacaa ccaattaacc  14700
aattctgatt agaaaaactc atcgagcatc aaatgaaact gcaatttatt catatcagga  14760
ttatcaatac catatttttg aaaaagccgt ttctgtaatg aaggagaaaa ctcaccgagg  14820
cagttccata ggatggcaag atcctggtat cggtctgcga ttccgactcg tccaacatca  14880
atacaaccta ttaatttccc ctcgtcaaaa ataaggttat caagtgagaa atcaccatga  14940
```

gtgacgactg aatccggtga gaatggcaaa agctctgcat taatgaatcg gccaacgcgc 15000
ggggagaggc ggtttgcgta ttgggcgctc ttccgcttcc tcgctcactg actcgctgcg 15060
ctcggtcgtt cggctgcggc gagcggtatc agctcactca aaggcggtaa tacggttatc 15120
cacagaatca ggggataacg caggaaagaa catgtgagca aaaggccagc aaaaggccag 15180
gaaccgtaaa aaggccgcgt tgctggcgtt tttccatagg ctccgccccc ctgacgagca 15240
tcacaaaaat cgacgctcaa gtcagaggtg gcgaaacccg acaggactat aaagatacca 15300
ggcgtttccc cctggaagct ccctcgtgcg ctctcctgtt ccgaccctgc cgcttaccgg 15360
atacctgtcc gcctttctcc cttcgggaag cgtggcgctt tctcatagct cacgctgtag 15420
gtatctcagt tcggtgtagg tcgttcgctc caagctgggc tgtgtgcacg aaccccccgt 15480
tcagcccgac cgctgcgcct tatccggtaa ctatcgtctt gagtccaacc cggtaagaca 15540
cgacttatcg ccactggcag cagccactgg taacaggatt agcagagcga ggtatgtagg 15600
cggtgctaca gagttcttga agtggtggcc taactacggc tacactagaa gaacagtatt 15660
tggtatctgc gctctgctga agccagttac cttcggaaaa agagttggta gctcttgatc 15720
cggcaaacaa accaccgctg gtagcggtgg tttttttgtt tgcaagcagc agattacgcg 15780
cagaaaaaaa ggatctcaag aagatccttt gatcttttct acggggtctg acgctcagtg 15840
gaacgaaaac tcacgttaag ggattttggt catgagatta tcaaaaagga tcttcaccta 15900
gatccttttg atccggaatt a 15921

<210> SEQ ID NO 35
<211> LENGTH: 17954
<212> TYPE: DNA
<213> ORGANISM: artificial sequence
<220> FEATURE:
<223> OTHER INFORMATION: vector 24039
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (315)..(1729)
<223> OTHER INFORMATION: prZmGRMZM2G020852-01
<220> FEATURE:
<221> NAME/KEY: gene
<222> LOCATION: (1731)..(5979)
<223> OTHER INFORMATION: cCas9-13
<220> FEATURE:
<221> NAME/KEY: terminator
<222> LOCATION: (5989)..(8769)
<223> OTHER INFORMATION: tZmGRMZM2G020852-01
<220> FEATURE:
<221> NAME/KEY: promoter
<222> LOCATION: (8783)..(9157)
<223> OTHER INFORMATION: prOsU3-01
<220> FEATURE:
<221> NAME/KEY: misc_feature
<222> LOCATION: (9159)..(9178)
<223> OTHER INFORMATION: xZmVLHP2
<220> FEATURE:
<221> NAME/KEY: misc_feature
<222> LOCATION: (9159)..(9263)
<223> OTHER INFORMATION: rsgRNAZmVLHP-02
<220> FEATURE:
<221> NAME/KEY: misc_feature
<222> LOCATION: (9179)..(9190)
<223> OTHER INFORMATION: rCrRNA-01
<220> FEATURE:
<221> NAME/KEY: misc_feature
<222> LOCATION: (9195)..(9263)
<223> OTHER INFORMATION: rTracrRNA-01
<220> FEATURE:

<221> NAME/KEY: promoter
<222> LOCATION: (9274)..(11265)
<223> OTHER INFORMATION: prUbi1-04
<220> FEATURE:
<221> NAME/KEY: gene
<222> LOCATION: (11282)..(12460)
<223> OTHER INFORMATION: cPMI-09
<220> FEATURE:
<221> NAME/KEY: terminator
<222> LOCATION: (12483)..(12735)
<223> OTHER INFORMATION: tNOS-05-01
<220> FEATURE:
<221> NAME/KEY: misc_feature
<222> LOCATION: (12779)..(12908)
<223> OTHER INFORMATION: bNLB-03
<220> FEATURE:
<221> NAME/KEY: gene
<222> LOCATION: (13188)..(13976)
<223> OTHER INFORMATION: cSpec-03
<220> FEATURE:
<221> NAME/KEY: promoter
<222> LOCATION: (14071)..(14201)
<223> OTHER INFORMATION: prVirG-01
<220> FEATURE:
<221> NAME/KEY: gene
<222> LOCATION: (14276)..(14908)
<223> OTHER INFORMATION: cVirG-09
<220> FEATURE:
<221> NAME/KEY: gene
<222> LOCATION: (14938)..(16011)
<223> OTHER INFORMATION: cRepA-01
<220> FEATURE:
<221> NAME/KEY: misc_feature
<222> LOCATION: (16054)..(16458)
<223> OTHER INFORMATION: oVS1-02
<220> FEATURE:
<221> NAME/KEY: misc_feature
<222> LOCATION: (17136)..(17942)
<223> OTHER INFORMATION: oCOLE-o6

<400> SEQUENCE: 35
attcctgtgg ttggcatgca catacaaatg gacgaacgga taaacctttt cacgcccttt 60
taaatatccg attattctaa taaacgctct tttctcttag gtttacccgc caatatatcc 120
tgtcaaacac tgatagttta aactgaaggc gggaaacgac aatctgatca tgagcggaga 180
attaagggag tcacgttatg acccccgccg atgacgcggg acaagccgtt ttacgtttgg 240
aactgacaga accgcaacgc tgcaggaatt ggccgcagcg gccatttaaa caaagcttgg 300
taccggaccg ttataacagt gaatacaaaa atgacattcg tgttatttag cacaagttac 360
gatctatttc aggaacatgc cggaattttc gaacaccatt ctcacaaaac atgaccttga 420
acttgcgatc cagttgtttt aaaattatat aaaacaaaaa caaagtcaga aaatcatgaa 480
acttgtcgac atgtcatgat atcatatgta gagactctaa taaaaagttg agattgtttc 540
atgaaagttg tcacacacta tgtgtagaaa cttagcccgt ctacattgaa gttctatgat 600
ttcatgtgaa ggacacctag gcatcgatgt ttatgataat atcttatgtt tgtttggaca 660
aaatattaaa aacaaataaa aggggtccct gatcactttg acgagcattg cattcagcaa 720
agggtgcctt tgttgagtgc aatggtcata gaactcggta gaaaagacat acataaacat 780
cgggaaactt gctttaccgc acgctatggc caagacactc ggcaaactag gctcctttgt 840
tgagtgccat ctcaagcact cgacattgga actacgacta ggcctcacgg aagctttctt 900
tgccgagtgc cactaagcga ggaactcgga cactcagcaa cagctctgtc atcgtcacga 960
tgtcttttct ttgtcgtgta ccagttggca ctcggttaag actttactga gtgcccgata 1020
gaaagtactc ggcaaagaga ccgttgccga cgtttggttc actgagggct ctttgctgcc 1080
ttttggactt gacaaagaag tcatctccag tactgtctcc taggacgcag gatttatgtt 1140

-continued ttttcccgga gctcgatctg tgggacatca cagatggtcc aatctggtga tctaaaatgg 1200
acggtttgcc aagcccacag agaagtcttt aagatcttcc acgatgcacg catgctttaa 1260
ggttagatag tgtttggtcc aaaaaagcgt caacaatcag gaaattagaa ctaaaattat 1320
taaaggacag atcaaaaggc atgcatgttc ttcttctata gtgtgtgttg agcctgagtt 1380
ttgattttag gctttattag gggactcgca gtctagctaa ggagttgtat tgatgttctg 1440
acaaatatta tgttcgatcg tcacagtggt cttgtgcgga tcgattaggc ccgatcatgg 1500
tgaaataaac taaccaccgg taagcccggg cagccctaga gcatgcagcg gcctacgtga 1560
agcccgcgtg tcgcatcgtc gtccgtcaga cgctaacggc aggccgctgc atgcgttgcc 1620
ggcgaactct ctcctgagcc actcgtcatc catataagta gacatcccat cactgtcgtc 1680
tatcaacaac acacagagcg acatttcgaa taacacagtt gagcgcgacc atggacaaga 1740
agtacagcat cggcctggac atcggcacca acagcgtggg ctgggccgtg atcaccgacg 1800
agtacaaggt acgagcggga tacatgttta tactcctcct gtaggtcgct ccttcatgta 1860
atgtgttgcg attaaaacgg tgcgcaggtg ccgagcaaga agttcaaggt gctgggcaac 1920
accgacaggc acagcatcaa gaagaacctg atcggcgccc tgctgttcga cagcggcgag 1980
accgccgagg ccaccaggct gaagaggacc gccaggagga ggtacaccag gaggaagaac 2040
aggatctgct acctgcagga gatcttcagc aacgagatgg ccaaggtgga cgacagcttc 2100
ttccacaggc tggaggagag cttcctggtg gaggaggaca agaagcacga gaggcacccg 2160
atcttcggca acatcgtgga cgaggtggcc taccacgaga agtacccgac catctaccac 2220
ctgaggaaga agctggtgga cagcaccgac aaggccgacc tgaggctgat ctacctggcc 2280
ctggcccaca tgatcaagtt caggggccac ttcctgatcg agggcgacct gaacccggac 2340
aacagcgacg tggacaagct gttcatccag ctggtgcaga cctacaacca gctgttcgag 2400
gagaacccga tcaacgccag cggcgtggac gccaaggcca tcctgagcgc caggctgagc 2460
aagagcagga ggctggagaa cctgatcgcc cagctgccgg gcgagaagaa gaacggcctg 2520
ttcggcaacc tgatcgccct gagcctgggc ctgaccccga acttcaagag caacttcgac 2580
ctggccgagg acgccaagct gcagctgagc aaggacacct acgacgacga cctggacaac 2640
ctgctggccc agatcggcga ccagtacgcc gacctgttcc tggccgccaa gaacctgagc 2700
gacgccatcc tgctgagcga catcctgagg gtgaacaccg agatcaccaa ggccccgctg 2760
agcgccagca tgatcaagag gtacgacgag caccaccagg acctgaccct gctgaaggcc 2820
ctggtgaggc agcagctgcc ggagaagtac aaggagatct tcttcgacca gagcaagaac 2880
ggctacgccg gctacatcga cggcggcgcc agccaggagg agttctacaa gttcatcaag 2940
ccgatcctgg agaagatgga cggcaccgag gagctgctgg tgaagctgaa cagggaggac 3000
ctgctgagga agcagaggac cttcgacaac ggcagcatcc cgcaccagat ccacctgggc 3060
gagctgcacg ccatcctgag gaggcaggag gacttctacc cgttcctgaa ggacaacagg 3120
gagaagatcg agaagatcct gaccttccgc atcccgtact acgtgggccc gctggccagg 3180
ggcaacagca ggttcgcctg gatgaccagg aagagcgagg agaccatcac cccgtggaac 3240
ttcgaggagg tggtggacaa gggcgccagc gcccagagct tcatcgagag gatgaccaac 3300
ttcgacaaga acctgccgaa cgagaaggtg ctgccgaagc acagcctgct gtacgagtac 3360
ttcaccgtgt acaacgagct gaccaaggtg aagtacgtga ccgagggcat gaggaagccg 3420
gccttcctga gcggcgagca gaagaaggcc atcgtggacc tgctgttcaa gaccaacagg 3480

-continued

```
aaggtgaccg tgaagcagct gaaggaggac tacttcaaga agatcgagtg cttcgacagc   3540
gtggagatca gcggcgtgga ggacaggttc aacgccagcc tgggcaccta ccacgacctg   3600
ctgaagatca tcaaggacaa ggacttcctg gacaacgagg agaacgagga catcctggag   3660
gacatcgtgc tgaccctgac cctgttcgag gacagggaga tgatcgagga gaggctgaag   3720
acctacgccc acctgttcga cgacaaggtg atgaagcagc tgaagaggag gaggtacacc   3780
ggctggggca ggctgagcag gaagctgatc aacggcatca gggacaagca gagcggcaag   3840
accatcctgg acttcctgaa gagcgacggc ttcgccaaca ggaacttcat gcagctgatc   3900
cacgacgaca gcctgacctt caaggaggac atccagaagg cccaggtgag cggccagggc   3960
gacagcctgc acgagcacat cgccaacctg gccggcagcc cggccatcaa gaagggcatc   4020
ctgcagaccg tgaaggtggt ggacgagctg gtgaaggtga tgggcaggca caagccggag   4080
aacatcgtga tcgagatggc cagggagaac cagaccaccc agaagggcca gaagaacagc   4140
agggagagga tgaagaggat cgaggagggc atcaaggagc tgggcagcca gatcctgaag   4200
gagcacccgg tggagaacac ccagctgcag aacgagaagc tgtacctgta ctacctgcag   4260
aacggcaggg acatgtacgt ggaccaggag ctggacatca acaggctgag cgactacgac   4320
gtggaccaca tcgtgccgca gagcttcctg aaggacgaca gcatcgacaa caaggtgctg   4380
accaggagcg acaagaacag gggcaagagc gacaacgtgc cgagcgagga ggtggtgaag   4440
aagatgaaaa actactggag gcagctgctg aacgccaagc tgatcaccca gaggaagttc   4500
gacaacctga ccaaggccga gaggggcggc ctgagcgagc tggacaaggc cggcttcatt   4560
aaaaggcagc tggtggagac caggcagatc accaagcacg tggcccagat cctggacagc   4620
aggatgaaca ccaagtacga cgagaacgac aagctgatca gggaggtgaa ggtgatcacc   4680
ctgaagagca agctggtgag cgacttcagg aaggacttcc agttctacaa ggtgagggag   4740
atcaataatt accaccacgc ccacgacgcc tacctgaacg ccgtggtggg caccgccctg   4800
attaaaaagt acccgaagct ggagagcgag ttcgtgtacg gcgactacaa ggtgtacgac   4860
gtgaggaaga tgatcgccaa gagcgagcag gagatcggca aggccaccgc caagtacttc   4920
ttctacagca acatcatgaa cttcttcaag accgagatca ccctggccaa cggcgagatc   4980
aggaagaggc cgctgatcga gaccaacggc gagaccggcg agatcgtgtg ggacaagggc   5040
agggacttcg ccaccgtgag gaaggtgctg tccatgccgc aggtgaacat cgtgaagaag   5100
accgaggtgc agaccggcgg cttcagcaag gagagcatcc tgccgaagag gaacagcgac   5160
aagctgatcg ccaggaagaa ggactgggac ccgaagaagt acggcggctt cgacagcccg   5220
accgtggcct acagcgtgct ggtggtggcc aaggtggaga agggcaagag caagaagctg   5280
aagagcgtga aggagctggt gggcatcacc atcatggaga ggagcagctt cgagaagaac   5340
ccagtggact tcctggaggc caagggctac aaggaggtga agaaggacct gatcattaaa   5400
ctgccgaagt acagcctgtt cgagctggag aacggcagga agaggatgct ggccagcgcc   5460
ggcgagctgc agaagggcaa cgagctggcc ctgccgagca agtacgtgaa cttcctgtac   5520
ctggccagcc actacgagaa gctgaagggc agcccggagg acaacgagca gaagcagctg   5580
ttcgtggagc agcacaagca ctacctggac gagatcatcg agcagatcag cgagttcagc   5640
aagagggtga tcctggccga cgccaacctg gacaaggtgc tgagcgccta caacaagcac   5700
agggacaagc cgatcaggga gcaggccgag aacatcatcc acctgttcac cctgaccaac   5760
ctgggcgccc cggccgcctt caagtacttc gacaccacca tcgacaggaa gaggtacacc   5820
agcaccaagg aggtgctgga cgccaccctg atccaccaga gcatcaccgg cctgtacgag   5880
```

```
accaggatcg acctgagcca gctgggcggc gacagcagcc cgccgaagaa gaagaggaag   5940
gtgagctgga aggacgccag cggctggagc aggatgtgag ctcaattaac tttgaattcc   6000
cttcgattca tccggcgcgg tgggctatgg acctgcagca gcaagctaat taagtttata   6060
tatattgcat gagagagcat gcaccgctaa ccatatatac tactgagact tctgaattct   6120
agtatatgta atccttttgt ttgggtttag gaggcaattc taatcatgta tgccgaattc   6180
caaagagtgg aaaacaagca aaatgttaaa tatacatgcc attttcggag gcaatttttt   6240
tcatgagggc atgttgctat aattccgggg accttggact tcttggagca ccttcctgtg   6300
acttaggcat acatgattag attataatcc aattagttaa gtcatagaaa attacctcat   6360
tctcatctcc atctccattt ctctatttct tctcaatcaa ggaccaaaat agcacttttg   6420
ctaaaaaaca agttagattg caaaccaaag tgcacaatac atagtaaaag gtatatgcaa   6480
catatttgaa tactcaaacc tctcatactt acattttcca tcattttgtt ccatttagcc   6540
tgtttgagct cggggttgga ctccaaaacc tcatgtcaac ataacttgat ccttttagca   6600
aactatgagc tctaacacca tacaatggtc aacaagaact attccaaaca taggaatgac   6660
ccaaactaca agtcaaagta tacttagctc tttgggcact tacaggttct aactttgata   6720
attctgtact tcttgtgacc atgactctgc tcgagctagg atcttgagcc ttatgactta   6780
aacaattaaa ccacaaacat tacctcaatg gttgtaagcc acgtccatat atcacagact   6840
tcaatgcatt cagactattc acagcttgac caaccttgac ctcttgcaag aacctcttct   6900
tctttgtgac cttaggtact ttagtcttct tgaccttctc ccttgctctt cataccttga   6960
agtccttctt gccttcacct tagttcaatc agctatctcc aagtcatgca cattgagttc   7020
cacttagtca atgtccatcc ttcaacttga cttgtgatgt ccacaattca tagtcatctc   7080
agtctatggg tccatcatgc ttgactccat gtgatgaacc ttgtaaggtt ttcactaagt   7140
acatgctcag acctttaatt gtgttgccat ccaaaaaaac caaaacctag attggaccat   7200
tcattatatt catcaatcat tgtacttgca agagtgatca aggtcatatt atttctctca   7260
actactccat tttgttgagg ggtgtcagtt gtggagactt cttgtttgat cccaacctca   7320
tcacaatact catgaatata gttgttgtca aattcatttc cattgtcact tcttattttt   7380
cttgattttg caatcaaact cattttgtac tttcatggta aatttattca atgttgatgc   7440
aacttttgac ttttcttgaa gaaagaacac tcaattacat ctagagaaat catcaacaac   7500
gaccaaacaa tacaggtttc ccccaacact agcatattat gtaggaccaa ataaatccat   7560
gtgaagtaac tctagtggtc ttggtgttga cataaaagcg tttgtaggat gtgtattggc   7620
aacttgtttt ccagcttgac atgcactata aaagattttc ctttttcaaa cacaacatct   7680
ttcaaatctc taaccatttc tttctttgga agcttcttgt tggggaaatg atccccggac   7740
cctaggaccc accggtcaga gagcgcgagg aagagccccc ggtcgctggg acccgttggt   7800
ccgctggaaa atgtggttac gtcaaccctg aaagaacccg cccctggttg agccccgtgg   7860
caccgagcct agggtcgagc gcggtggaat ctgacaggag gggccagaca tgttggaggg   7920
gaaccactca agtggatccc gcgcctggcc ccagaatgac ccgtcattaa tacccaacca   7980
cattaaccat gcctggcacc gagccatagc acggacgtcg gtccacttcc cactcatgac   8040
ctacgaacca gttgggctgc atagcactca tgaccgatag gttgaaggct tggcttcgca   8100
gagtgaaagg cgctgcatac atgtgaaggc tcgacttctt tttcttttcc tttcttttct   8160
tttctatttt taggtttcca atttaaattc caattttttt gtggagttca tatttggatc   8220
```

```
aaatagacaa attcacctat cagtatgaat agatgcattt attttgttta tatctatttt   8280
cttcatattt atatagtatt tcccttattc tttatatcat tttcaatttg taattggtaa   8340
gtttggtctt aaattcccca tttgggcact aatatatttt tattaatatt attattatta   8400
ttattattat tatttataga tgcacaaaca cataaactcc gacatgatgc atagattatt   8460
ttagatgtca ctagttaatg gttcacttta aatatggtta ttcccatgtt ctaatgagta   8520
gagggcaaag catatattga ggtcaactct ttccttatta tttacaaatt ggggaaattc   8580
tattcataac tcttcttctc tctcccaagt agcttaatct tcaccatggt gatttcattg   8640
cactttgcac attttgatca ctttattcct tgtaacccga gtcaaagtgt caatgatctt   8700
gataggatac tccgtgcagg ttagatcacc ttgcacactg agttcttcca ttggtaactg   8760
ttcctctggc ggaccgttcg aagggatctt taaacatacg aacagatcac ttaaagttct   8820
tctgaagcaa cttaaagtta tcaggcatgc atggatcttg gaggaatcag atgtgcagtc   8880
agggaccata gcacaggaca ggcgtcttct actggtgcta ccagcaaatg ctggaagccg   8940
ggaacactgg gtacgttgga aaccacgtga tgtggagtaa gataaactgt aggagaaaag   9000
catttcgtag tgggccatga agcctttcag gacatgtatt gcagtatggg ccggcccatt   9060
acgcaattgg acgacaacaa agactagtat tagtaccacc tcggctatcc acatagatca   9120
aagctggttt aaaagagttg tgcagatgat ccgtggcagc tggagctgag cttccggggt   9180
tttagagcta gaaatagcaa gttaaaataa ggctagtccg ttatcaactt gaaaaagtgg   9240
caccgagtcg gtgctttttt tttcggaccg cgcctgcagt gcagcgtgac ccggtcgtgc   9300
ccctctctag agataatgag cattgcatgt ctaagttata aaaaattacc acatattttt   9360
tttgtcacac ttgtttgaag tgcagtttat ctatctttat acatatattt aaactttact   9420
ctacgaataa tataatctat agtactacaa taatatcagt gttttagaga atcatataaa   9480
tgaacagtta gacatggtct aaaggacaat tgagtatttt gacaacagga ctctacagtt   9540
ttatcttttt agtgtgcatg tgttctcctt tttttttgca aatagcttca cctatataat   9600
acttcatcca ttttattagt acatccattt agggtttagg gttaatggtt tttatagact   9660
aattttttta gtacatctat tttattctat tttagcctct aaattaagaa aactaaaact   9720
ctattttagt ttttttattt aataatttag atataaaata gaataaaata aagtgactaa   9780
aaattaaaca aataccettt aagaaattaa aaaaactaag gaaacatttt tcttgtttcg   9840
agtagataat gccagcctgt taaacgccgt cgacgagtct aacggacacc aaccagcgaa   9900
ccagcagcgt cgcgtcgggc caagcgaagc agacggcacg gcatctctgt cgctgcctct   9960
ggacccctct cgagagttcc gctccaccgt tggacttgct ccgctgtcgg catccagaaa  10020
ttgcgtggcg gagcggcaga cgtgagccgg cacggcaggc ggcctcctcc tcctctcacg  10080
gcaccggcag ctacggggga ttcctttccc accgctcctt cgctttccct tcctcgcccg  10140
ccgtaataaa tagacacccc ctccacaccc tctttcccca acctcgtgtt gttcggagcg  10200
cacacacaca caaccagatc tcccccaaat ccacccgtcg gcacctccgc ttcaaggtac  10260
gccgctcgtc ctcccccccc cccctctcta ccttctctag atcggcgttc cggtccatgg  10320
ttagggcccg gtagttctac ttctgttcat gtttgtgtta gatccgtgtt tgtgttagat  10380
ccgtgctgct agcgttcgta cacggatgcg acctgtacgt cagacacgtt ctgattgcta  10440
acttgccagt gtttctcttt ggggaatcct gggatggctc tagccgttcc gcagacggga  10500
tcgatttcat gatttttttt gtttcgttgc atagggtttg gtttgccctt ttcctttatt  10560
tcaatatatg ccgtgcactt gtttgtcggg tcatcttttc atgctttttt ttgtcttggt  10620
```

tgtgatgatg tggtctggtt gggcggtcgt tctagatcgg agtagaattc tgtttcaaac 10680
tacctggtgg atttattaat tttggatctg tatgtgtgtg ccatacatat tcatagttac 10740
gaattgaaga tgatggatgg aaatatcgat ctaggatagg tatacatgtt gatgcgggtt 10800
ttactgatgc atatacagag atgctttttg ttcgcttggt tgtgatgatg tggtgtggtt 10860
gggcggtcgt tcattcgttc tagatcggag tagaatactg tttcaaacta cctggtgtat 10920
ttattaattt tggaactgta tgtgtgtgtc atacatcttc atagttacga gtttaagatg 10980
gatggaaata tcgatctagg ataggtatac atgttgatgt gggttttact gatgcatata 11040
catgatggca tatgcagcat ctattcatat gctctaacct tgagtaccta tctattataa 11100
taaacaagta tgttttataa ttattttgat cttgatatac ttggatgatg gcatatgcag 11160
cagctatatg tggatttttt tagccctgcc ttcatacgct atttatttgc ttggtactgt 11220
ttcttttgtc gatgctcacc ctgttgtttg gtgttacttc tgcagggatc cggcagcagc 11280
catgcagaag ctgatcaaca gcgtgcagaa ctacgcctgg ggcagcaaga ccgccctgac 11340
cgagctgtac ggcatggaga accccagcag ccagcccatg gccgagctgt ggatgggcgc 11400
ccaccccaag agcagcagcc gcgtgcagaa cgccgccggc gacatcgtga gcctgcgcga 11460
cgtgatcgag agcgacaaga gcaccctgct gggcgaggcc gtggccaagc gcttcggcga 11520
gctgcccttc ctgttcaagg tgctgtgcgc cgcccagccc ctgagcatcc aggtgcaccc 11580
caacaagcac aacagcgaga tcggcttcgc caaggagaac gccgccggca tccccatgga 11640
cgccgccgag cgcaactaca aggaccccaa ccacaagccc gagctggtgt tcgccctgac 11700
ccccttcctg gccatgaacg ccttccgcga gttcagcgag atcgtgagcc tgctgcagcc 11760
cgtggccggc gcccaccccg ccatcgccca cttcctgcag cagcccgacg ccgagcgcct 11820
gagcgagctg ttcgccagcc tgctgaacat gcagggcgag gagaagagcc gcgccctggc 11880
catcctgaag agcgccctgg acagccagca gggcgagccc tggcagacca tccgcctgat 11940
cagcgagttc taccccgagg acagcggcct gttcagcccc ctgctgctga acgtggtgaa 12000
gctgaacccc ggcgaggcca tgttcctgtt cgccgagacc ccccacgcct acctgcaggg 12060
cgtggccctg gaggtgatgg ccaacagcga caacgtgctg cgcgccggcc tgacccccaa 12120
gtacatcgac atccccgagc tggtggccaa cgtgaagttc gaggccaagc ccgccaacca 12180
gctgctgacc cagcccgtga agcagggcgc cgagctggac ttccccatcc ccgtggacga 12240
cttcgccttc agcctgcacg acctgagcga caaggagacc accatcagcc agcagagcgc 12300
cgccatcctg ttctgcgtgg agggcgacgc caccctgtgg aagggcagcc agcagctgca 12360
gctgaagccc ggcgagagcg ccttcatcgc cgccaacgag agccccgtga ccgtgaaggg 12420
ccacggccgc ctggcccgcg tgtacaacaa gctgtgatag gagctcgatc cgtcgacctg 12480
cagatcgttc aaacatttgg caataaagtt tcttaagatt gaatcctgtt gccggtcttg 12540
cgatgattat catataattt ctgttgaatt acgttaagca tgtaataatt aacatgtaat 12600
gcatgacgtt atttatgaga tgggttttta tgattagagt cccgcaatta tacatttaat 12660
acgcgataga aaacaaaata tagcgcgcaa actaggataa attatcgcgc gcggtgtcat 12720
ctatgttact agatcggcgc gccgcaattg aagtttgggc ggccagcatg gccgtatccg 12780
caatgtgtta ttaagttgtc taagcgtcaa tttgtttaca ccacaatata tcctgccacc 12840
agccagccaa cagctccccg accggcagct cggcacaaaa tcaccactcg atacaggcag 12900
cccatcagaa ttaattctca tgtttgacag cttatcatcg actgcacggt gcaccaatgc 12960

-continued

```
ttctggcgtc aggcagccat cggaagctgt ggtatggctg tgcaggtcgt aaatcactgc  13020
ataattcgtg tcgctcaagg cgcactcccg ttctggataa tgttttttgc gccgacatca  13080
taacggttct ggcaaatatt ctgaaatgag ctgttgacaa ttaatcatcc ggctcgtata  13140
atgtgtggaa ttgtgagcgg ataacaattt cacacaggaa acagaccatg agggaagcgt  13200
tgatcgccga agtatcgact caactatcag aggtagttgg cgtcatcgag cgccatctcg  13260
aaccgacgtt gctggccgta catttgtacg gctccgcagt ggatggcggc ctgaagccac  13320
acagtgatat tgatttgctg gttacggtga ccgtaaggct tgatgaaaca acgcggcgag  13380
ctttgatcaa cgaccttttg gaaacttcgg cttcccctgg agagagcgag attctccgcg  13440
ctgtagaagt caccattgtt gtgcacgacg acatcattcc gtggcgttat ccagctaagc  13500
gcgaactgca atttggagaa tggcagcgca atgacattct tgcaggtatc ttcgagccag  13560
ccacgatcga cattgatctg gctatcttgc tgacaaaagc aagagaacat agcgttgcct  13620
tggtaggtcc agcggcggag gaactctttg atccggttcc tgaacaggat ctatttgagg  13680
cgctaaatga aaccttaacg ctatggaact cgccgcccga ctgggctggc gatgagcgaa  13740
atgtagtgct tacgttgtcc cgcatttggt acagcgcagt aaccggcaaa atcgcgccga  13800
aggatgtcgc tgccgactgg gcaatggagc gcctgccggc ccagtatcag cccgtcatac  13860
ttgaagctag gcaggcttat cttggacaag aagatcgctt ggcctcgcgc gcagatcagt  13920
tggaagaatt tgttcactac gtgaaaggcg agatcaccaa agtagtcggc aaataaagct  13980
ctagtggatc tccgtacccg gggatctggc tcgcggcgga cgcacgacgc cggggcgaga  14040
ccataggcga tctcctaaat caatagtagc tgtaacctcg aagcgtttca cttgtaacaa  14100
cgattgagaa tttttgtcat aaaattgaaa tacttggttc gcatttttgt catccgcggt  14160
cagccgcaat tctgacgaac tgcccattta gctggagatg attgtacatc cttcacgtga  14220
aaatttctca agcgctgtga acaagggttc agattttaga ttgaaaggtg agccgttgaa  14280
acacgttctt cttgtcgatg acgacgtcgc tatgcggcat cttattattg aataccttac  14340
gatccacgcc ttcaaagtga ccgcggtagc cgacagcacc cagttcacaa gagtactctc  14400
ttccgcgacg gtcgatgtcg tggttgttga tctagattta ggtcgtgaag atgggctcga  14460
gctaggagca agtgatttta tcgctaagcc gttcagtatc agagagtttc tagcacgcat  14520
tcgggttgcc ttgcgcgtgc gccccaacgt tgtccgctcc aaagaccgac ggtctttttg  14580
ttttactgac tggacactta atctcaggca acgtcgcttg atgtccgaag ctggcggtga  14640
ggtgaaactt acggcaggtg agttcaatct tctcctcgcg tttttagaga aaccccgcga  14700
cgttctatcg cgcgagcaac ttctcattgc cagtcgagta cgcgacgagg aggtttatga  14760
caggagtata gatgttctca ttttgaggct gcgccgcaaa cttgaggcag atccgtcaag  14820
ccctcaactg ataaaaacag caagaggtgc cggttatttc tttgacgcgg acgtgcaggt  14880
ttcgcacggg gggacgatgg cagcctgagc caattcccag atccccgagg aatcggcgtg  14940
agcggtcgca aaccatccgg cccggtacaa atcggcgcgg cgctgggtga tgacctggtg  15000
gagaagttga aggccgcgca ggccgcccag cggcaacgca tcgaggcaga agcacgcccc  15060
ggtgaatcgt ggcaagcggc cgctgatcga atccgcaaag aatcccggca accgccggca  15120
gccggtgcgc cgtcgattag gaagccgccc aagggcgacg agcaaccaga ttttttcgtt  15180
ccgatgctct atgacgtggg cacccgcgat agtcgcagca tcatggacgt ggccgttttc  15240
cgtctgtcga agcgtgaccg acgagctggc gaggtgatcc gctacgagct tccagacggg  15300
cacgtagagg tttccgcagg gccggccggc atggccagtg tgtgggatta cgacctggta  15360
```

```
ctgatggcgg tttcccatct aaccgaatcc atgaaccgat accgggaagg gaagggagac  15420
aagcccggcc gcgtgttccg tccacacgtt gcggacgtac tcaagttctg ccggcgagcc  15480
gatggcggaa agcagaaaga cgacctggta gaaacctgca ttcggttaaa caccacgcac  15540
gttgccatgc agcgtacgaa gaaggccaag aacggccgcc tggtgacggt atccgagggt  15600
gaagccttga ttagccgcta caagatcgta aagagcgaaa ccgggcggcc ggagtacatc  15660
gagatcgagc tagctgattg gatgtaccgc gagatcacag aaggcaagaa cccggacgtg  15720
ctgacggttc accccgatta ctttttgatc gatcccggca tcggccgttt tctctaccgc  15780
ctggcacgcc gcgccgcagg caaggcagaa gccagatggt tgttcaagac gatctacgaa  15840
cgcagtggca gcgccggaga gttcaagaag ttctgtttca ccgtgcgcaa gctgatcggg  15900
tcaaatgacc tgccggagta cgatttgaag gaggaggcgg ggcaggctgg cccgatccta  15960
gtcatgcgct accgcaacct gatcgagggc gaagcatccg ccggttccta atgtacggag  16020
cagatgctag ggcaaattgc cctagcaggg gaaaaaggtc gaaaaggtct ctttcctgtg  16080
gatagcacgt acattgggaa cccaaagccg tacattggga accggaaccc gtacattggg  16140
aacccaaagc cgtacattgg gaaccggtca cacatgtaag tgactgatat aaaagagaaa  16200
aaaggcgatt tttccgccta aaactcttta aaacttatta aaactcttaa aacccgcctg  16260
gcctgtgcat aactgtctgg ccagcgcaca gccgaagagc tgcaaaaagc gcctaccctt  16320
cggtcgctgc gctccctacg ccccgccgct tcgcgtcggc ctatcgcggc cgctggccgc  16380
tcaaaaatgg ctggcctacg gccaggcaat ctaccagggc gcggacaagc cgcgccgtcg  16440
ccactcgacc gccggcgctg aggtctgcct cgtgaagaag gtgttgctga ctcataccag  16500
gcctgaatcg ccccatcatc cagccagaaa gtgagggagc cacggttgat gagagctttg  16560
ttgtaggtgg accagttggt gattttgaac ttttgctttg ccacggaacg gtctgcgttg  16620
tcgggaagat gcgtgatctg atccttcaac tcagcaaaag ttcgatttat tcaacaaagc  16680
cgccgtcccg tcaagtcagc gtaatgctct gccagtgtta caaccaatta accaattctg  16740
attagaaaaa ctcatcgagc atcaaatgaa actgcaattt attcatatca ggattatcaa  16800
taccatattt ttgaaaaagc cgtttctgta atgaaggaga aaactcaccg aggcagttcc  16860
ataggatggc aagatcctgg tatcggtctg cgattccgac tcgtccaaca tcaatacaac  16920
ctattaattt cccctcgtca aaaataaggt tatcaagtga gaaatcacca tgagtgacga  16980
ctgaatccgg tgagaatggc aaaagctctg cattaatgaa tcggccaacg cgcggggaga  17040
ggcggtttgc gtattgggcg ctcttccgct tcctcgctca ctgactcgct gcgctcggtc  17100
gttcggctgc ggcgagcggt atcagctcac tcaaaggcgg taatacggtt atccacagaa  17160
tcaggggata acgcaggaaa gaacatgtga gcaaaaggcc agcaaaaggc caggaaccgt  17220
aaaaaggccg cgttgctggc gtttttccat aggctccgcc cccctgacga gcatcacaaa  17280
aatcgacgct caagtcagag gtggcgaaac ccgacaggac tataaagata ccaggcgttt  17340
ccccctggaa gctccctcgt gcgctctcct gttccgaccc tgccgcttac cggatacctg  17400
tccgcctttc tcccttcggg aagcgtggcg ctttctcata gctcacgctg taggtatctc  17460
agttcggtgt aggtcgttcg ctccaagctg ggctgtgtgc acgaaccccc cgttcagccc  17520
gaccgctgcg ccttatccgg taactatcgt cttgagtcca acccggtaag acacgactta  17580
tcgccactgg cagcagccac tggtaacagg attagcagag cgaggtatgt aggcggtgct  17640
acagagttct tgaagtggtg gcctaactac ggctacacta gaagaacagt atttggtatc  17700
```

```
tgcgctctgc tgaagccagt taccttcgga aaaagagttg gtagctcttg atccggcaaa  17760

caaaccaccg ctggtagcgg tggttttttt gtttgcaagc agcagattac gcgcagaaaa  17820

aaaggatctc aagaagatcc tttgatcttt tctacggggt ctgacgctca gtggaacgaa  17880

aactcacgtt aagggatttt ggtcatgaga ttatcaaaaa ggatcttcac ctagatcctt  17940

ttgatccgga atta                                                    17954


<210> SEQ ID NO 36
<211> LENGTH: 17045
<212> TYPE: DNA
<213> ORGANISM: Artificial Sequence
<220> FEATURE:
<223> OTHER INFORMATION: vector 24079
<220> FEATURE:
<221> NAME/KEY: misc_feature
<222> LOCATION: (4)..(259)
<220> FEATURE:
<221> NAME/KEY: promoter
<222> LOCATION: (312)..(2356)
<223> OTHER INFORMATION: prGRMZM2G146551-01
<220> FEATURE:
<221> NAME/KEY: gene
<222> LOCATION: (2358)..(6527)
<223> OTHER INFORMATION: cCas9-01
<220> FEATURE:
<221> NAME/KEY: mutation
<222> LOCATION: (5847)..(5849)
<223> OTHER INFORMATION: L to V mutation
<220> FEATURE:
<221> NAME/KEY: mutation
<222> LOCATION: (5892)..(5894)
<223> OTHER INFORMATION: I to V mutation
<220> FEATURE:
<221> NAME/KEY: terminator
<222> LOCATION: (6542)..(7860)
<223> OTHER INFORMATION: tGRMZM2G146551-01
<220> FEATURE:
<221> NAME/KEY: promoter
<222> LOCATION: (7874)..(8248)
<223> OTHER INFORMATION: prOsU3-01
<220> FEATURE:
<221> NAME/KEY: misc_feature
<222> LOCATION: (8249)..(8354)
<223> OTHER INFORMATION: rsgRNAZmVLHP-02
<220> FEATURE:
<221> NAME/KEY: misc_feature
<222> LOCATION: (8250)..(8269)
<223> OTHER INFORMATION: ZmVLHP2 target
<220> FEATURE:
<221> NAME/KEY: misc_feature
<222> LOCATION: (8270)..(8281)
<223> OTHER INFORMATION: rCrRNA-01
<220> FEATURE:
<221> NAME/KEY: misc_feature
<222> LOCATION: (8286)..(8354)
<223> OTHER INFORMATION: rTracrRNA-01
<220> FEATURE:
<221> NAME/KEY: promoter
<222> LOCATION: (8365)..(10356)
<223> OTHER INFORMATION: prUbi1-04
<220> FEATURE:
<221> NAME/KEY: gene
<222> LOCATION: (10373)..(11551)
<223> OTHER INFORMATION: cPMI-09
<220> FEATURE:
<221> NAME/KEY: terminator
<222> LOCATION: (11574)..(11826)
<223> OTHER INFORMATION: tNOS-05-01
<220> FEATURE:
<221> NAME/KEY: misc_feature
<222> LOCATION: (11870)..(11999)
<223> OTHER INFORMATION: bNLB-03
<220> FEATURE:
<221> NAME/KEY: gene
<222> LOCATION: (12279)..(13067)
```

<223> OTHER INFORMATION: cSpec-03
<220> FEATURE:
<221> NAME/KEY: promoter
<222> LOCATION: (13162)..(13292)
<223> OTHER INFORMATION: prVirG-01
<220> FEATURE:
<221> NAME/KEY: gene
<222> LOCATION: (13367)..(13999)
<223> OTHER INFORMATION: cVirG-09
<220> FEATURE:
<221> NAME/KEY: gene
<222> LOCATION: (14029)..(15102)
<223> OTHER INFORMATION: cRepA-01
<220> FEATURE:
<221> NAME/KEY: misc_feature
<222> LOCATION: (15145)..(15549)
<223> OTHER INFORMATION: oVS1-02
<220> FEATURE:
<221> NAME/KEY: misc_feature
<222> LOCATION: (16227)..(17033)
<223> OTHER INFORMATION: oCOLE-06

<400> SEQUENCE: 36
attcctgtgg ttggcatgca catacaaatg gacgaacgga taaacctttt cacgcccttt 60
taaatatccg attattctaa taaacgctct tttctcttag gtttacccgc caatatatcc 120
tgtcaaacac tgatagttta aactgaaggc gggaaacgac aatctgatca tgagcggaga 180
attaagggag tcacgttatg acccccgccg atgacgcggg acaagccgtt ttacgtttgg 240
aactgacaga accgcaacgc tgcaggaatt ggccgcagcg gccatttaaa caaagcttgg 300
taccgggacc catgtagtat cacatgagtg agtcaaggac taagtattat gcattttgtt 360
tctcactcac ggattagctc gcaatcatca tagtgaaatc tagctactgg cactatcgaa 420
atctagctct ttgccgagtg cactttatcg agcactcgac aaagcattct ttatcgagtg 480
ccagtcttgg cgaaataaga ctctcgacaa agaccttgtt taccgaggga gaaacactcg 540
gcgtaaaaag acactcggca aagaagactt tgctgagtgt caaaccctca gcgaaatgcg 600
accctcggca aaggaccgtc agcagccatc tatagttgat ggctattaac ttcgcgagtg 660
tcaggcgttg acacacgaca aaatatcttt tttgtcgagt gtcactgggc aaacacttgg 720
taaacctatg ttttgccgag tgtctttcct tgacactcga caaagtatat ttgtttttttc 780 tttttcccca aactttttgt ggtgtgtttc tacaatatat agacctattt gttcaatttt 840
ggcacaatta taaaagtgtt tgctataact atcagattta gtttgcttaa ttggatttct 900
ttggataatt cagatttgaa ctacaagcca cttgaaaaat ggaaaacagt gaatacaaaa 960
atgacattca tgttatttag cacaagttat gatctatttc aggaacatgc gagaattttc 1020
gaacaccatt ctcacaaaac atgattgcgg acttgtgatc aagttgtttt aaaattgtat 1080
aaaacaaaaa caaagtcaga aaatcatgaa acttgttgac atgtcatgat atcatatgta 1140
gagactctaa taaaaatttg agattgtttc atgaaagttg tcacgcgcta tgtgtagaaa 1200
cctagcccgt ctacattgag gttctatgat ttcatgtgaa ggacatctag gcatcaatgt 1260
ttatgataat atcttatgtt tgtttggacg aaatattaaa aacaaataaa aaggggtcct 1320
tgatcacttt gacgagcatt gcactcagca aagggtgcct ttgctgagtg caatggtcat 1380
agaactcggt agaaaaacat acatagacat agggaaactt gctttaccgc gtgctatggc 1440
caagacactc ggcaaactag gctcctttgt cgagttccat cccaagcact cgacattgga 1500
actgcgactg ggcctcacag aagctttctt tgccgagtgc cactaagcga ggaactcgga 1560
tgctcagcaa aggctctgtc atcgtcacga tgtcttttgt ttgtcgtgta ccagttggca 1620
ctcggtaaag actttactga gtgcccgata gaaagtactc gacaaagaga ccgttgccaa 1680

-continued

```
cgtttggttc actgagggct ctttgctgcc ttttggactt gacaaagaag ccgtctccag   1740
tagtgtctcc tgggaggcgg gatttatgtt ttttcccgga gctctgtggg acatcatgga   1800
cggtccagtc tggtgatcta aaatagacgg tttgccaagc tcacagagaa gtctttaaga   1860
tcttccacga tgcacgcatg ctttaaggtt agttagtgtt tggtctgaaa aagcgtcaac   1920
aattaggaaa caagaactaa aattattaaa ggacagatca ggaagcatgc atgttcttct   1980
tctatagtgt gtgttgagcc tgagtttggc cttttaggct ttattagggg gctcacagtc   2040
taactaagga gttgtattga tgtgctgaca aatattatgt tcgatcgtca cagtgttctt   2100
atgcggatcg attaggcccg atcatggtga aataaactaa ccaccggtaa gcccgggcag   2160
ccctagagca tgcagcggcc tacgtgaagc ccgcacatcg catcgtcgtc cgtcaggcgc   2220
taacggccgg ccgctgcatg cgtcgccggc gaactctctg ctgagccacc cgtcctccct   2280
ataagtagct atcccagcac cgtcgtctat caaccacaca cagagcggca tttcgaataa   2340
cacaggtgag cgcgaccatg gacaagaagt acagcatcgg cctggacatc ggcaccaaca   2400
gcgtgggctg ggccgtgatc accgacgagt acaaggtgcc gagcaagaag ttcaaggtgc   2460
tgggcaacac cgacaggcac agcatcaaga agaacctgat cggcgccctg ctgttcgaca   2520
gcggcgagac cgccgaggcc accaggctga agaggaccgc caggaggagg tacaccagga   2580
ggaagaacag gatctgctac ctgcaggaga tcttcagcaa cgagatggcc aaggtggacg   2640
acagcttctt ccacaggctg gaggagagct tcctggtgga ggaggacaag aagcacgaga   2700
ggcacccgat cttcggcaac atcgtggacg aggtggccta ccacgagaag tacccgacca   2760
tctaccacct gaggaagaag ctggtggaca gcaccgacaa ggccgacctg aggctgatct   2820
acctggccct ggcccacatg atcaagttca ggggccactt cctgatcgag ggcgacctga   2880
acccggacaa cagcgacgtg gacaagctgt tcatccagct ggtgcagacc tacaaccagc   2940
tgttcgagga gaacccgatc aacgccagcg gcgtggacgc caaggccatc ctgagcgcca   3000
ggctgagcaa gagcaggagg ctggagaacc tgatcgccca gctgccgggc gagaagaaga   3060
acggcctgtt cggcaacctg atcgccctga gcctgggcct gaccccgaac ttcaagagca   3120
acttcgacct ggccgaggac gccaagctgc agctgagcaa ggacacctac gacgacgacc   3180
tggacaacct gctggcccag atcggcgacc agtacgccga cctgttcctg gccgccaaga   3240
acctgagcga cgccatcctg ctgagcgaca tcctgagggt gaacaccgag atcaccaagg   3300
ccccgctgag cgccagcatg atcaagaggt acgacgagca ccaccaggac ctgaccctgc   3360
tgaaggccct ggtgaggcag cagctgccgg agaagtacaa ggagatcttc ttcgaccaga   3420
gcaagaacgg ctacgccggc tacatcgacg gcggcgccag ccaggaggag ttctacaagt   3480
tcatcaagcc gatcctggag aagatggacg gcaccgagga gctgctggtg aagctgaaca   3540
gggaggacct gctgaggaag cagaggacct tcgacaacgg cagcatcccg caccagatcc   3600
acctgggcga gctgcacgcc atcctgagga ggcaggagga cttctacccg ttcctgaagg   3660
acaacaggga gaagatcgag aagatcctga ccttccgcat cccgtactac gtgggcccgc   3720
tggccagggg caacagcagg ttcgcctgga tgaccaggaa gagcgaggag accatcaccc   3780
cgtggaactt cgaggaggtg gtggacaagg gcgccagcgc ccagagcttc atcgagagga   3840
tgaccaactt cgacaagaac ctgccgaacg agaaggtgct gccgaagcac agcctgctgt   3900
acgagtactt caccgtgtac aacgagctga ccaaggtgaa gtacgtgacc gagggcatga   3960
ggaagccggc cttcctgagc ggcgagcaga agaaggccat cgtggacctg ctgttcaaga   4020
```

```
ccaacaggaa ggtgaccgtg aagcagctga aggaggacta cttcaagaag atcgagtgct   4080
tcgacagcgt ggagatcagc ggcgtggagg acaggttcaa cgccagcctg ggcacctacc   4140
acgacctgct gaagatcatc aaggacaagg acttcctgga caacgaggag aacgaggaca   4200
tcctggagga catcgtgctg accctgaccc tgttcgagga cagggagatg atcgaggaga   4260
ggctgaagac ctacgcccac ctgttcgacg acaaggtgat gaagcagctg aagaggagga   4320
ggtacaccgg ctggggcagg ctgagcagga agctgatcaa cggcatcagg gacaagcaga   4380
gcggcaagac catcctggac ttcctgaaga gcgacggctt cgccaacagg aacttcatgc   4440
agctgatcca cgacgacagc ctgaccttca aggaggacat ccagaaggcc caggtgagcg   4500
gccagggcga cagcctgcac gagcacatcg ccaacctggc cggcagcccg gccatcaaga   4560
agggcatcct gcagaccgtg aaggtggtgg acgagctggt gaaggtgatg ggcaggcaca   4620
agccggagaa catcgtgatc gagatggcca gggagaacca gaccacccag aagggccaga   4680
agaacagcag ggagaggatg aagaggatcg aggagggcat caaggagctg ggcagccaga   4740
tcctgaagga gcacccggtg gagaacaccc agctgcagaa cgagaagctg tacctgtact   4800
acctgcagaa cggcagggac atgtacgtgg accaggagct ggacatcaac aggctgagcg   4860
actacgacgt ggaccacatc gtgccgcaga gcttcctgaa ggacgacagc atcgacaaca   4920
aggtgctgac caggagcgac aagaacaggg gcaagagcga caacgtgccg agcgaggagg   4980
tggtgaagaa gatgaaaaac tactggaggc agctgctgaa cgccaagctg atcacccaga   5040
ggaagttcga caacctgacc aaggccgaga ggggcggcct gagcgagctg gacaaggccg   5100
gcttcattaa aaggcagctg gtggagacca ggcagatcac caagcacgtg gcccagatcc   5160
tggacagcag gatgaacacc aagtacgacg agaacgacaa gctgatcagg gaggtgaagg   5220
tgatcaccct gaagagcaag ctggtgagcg acttcaggaa ggacttccag ttctacaagg   5280
tgagggagat caataattac caccacgccc acgacgccta cctgaacgcc gtggtgggca   5340
ccgccctgat taaaaagtac ccgaagctgg agagcgagtt cgtgtacggc gactacaagg   5400
tgtacgacgt gaggaagatg atcgccaaga gcgagcagga gatcggcaag gccaccgcca   5460
agtacttctt ctacagcaac atcatgaact tcttcaagac cgagatcacc ctggccaacg   5520
gcgagatcag gaagaggccg ctgatcgaga ccaacggcga gaccggcgag atcgtgtggg   5580
acaagggcag ggacttcgcc accgtgagga aggtgctgtc catgccgcag gtgaacatcg   5640
tgaagaagac cgaggtgcag accggcggct tcagcaagga gagcatcctg ccgaagagga   5700
acagcgacaa gctgatcgcc aggaagaagg actgggaccc gaagaagtac ggcggcttcg   5760
acagcccgac cgtggcctac agcgtgctgg tggtggccaa ggtggagaag ggcaagagca   5820
agaagctgaa gagcgtgaag gagctggtgg gcatcaccat catggagagg agcagcttcg   5880
agaagaaccc agtggacttc ctggaggcca agggctacaa ggaggtgaag aaggacctga   5940
tcattaaact gccgaagtac agcctgttcg agctggagaa cggcaggaag aggatgctgg   6000
ccagcgccgg cgagctgcag aagggcaacg agctggccct gccgagcaag tacgtgaact   6060
tcctgtacct ggccagccac tacgagaagc tgaagggcag cccggaggac aacgagcaga   6120
agcagctgtt cgtggagcag cacaagcact acctggacga gatcatcgag cagatcagcg   6180
agttcagcaa gagggtgatc ctggccgacg ccaacctgga caaggtgctg agcgcctaca   6240
acaagcacag ggacaagccg atcagggagc aggccgagaa catcatccac ctgttcaccc   6300
tgaccaacct gggcgccccg gccgccttca agtacttcga caccaccatc gacaggaaga   6360
ggtacaccag caccaaggag gtgctggacg ccaccctgat ccaccagagc atcaccggcc   6420
```

```
tgtacgagac caggatcgac ctgagccagc tgggcggcga cagcagcccg ccgaagaaga   6480
agaggaaggt gagctggaag gacgccagcg gctggagcag gatgtgacca tggagctcta   6540
aactttgaat tcccttcgat tcatccggca cagcgggcta tggaccttca gcagcaagct   6600
aattaagttg gcagcatgca ccgctaacct tatatactac tgagacttcc aaattctagt   6660
atatgtaatc cttttgttcg ggttcatgat cgaattccaa agagtggaaa acaagcaaaa   6720
ggttaaatat acatgccatt tttggaggca tttttttcat gagggcatgt ttcgatatat   6780
ggaccactaa atatacatat catttacttt cctacaaatt tgctacatcc ttggaaatgc   6840
atagtctgtc tccaagaaaa agatactctg attacatcac tagtacacac agcctctata   6900
gtggcggttc tagagacatt ttcactggcg cttttcagtg ccgccagtgt taggggccag   6960
tggaaatcgc catttccatt caataaccgc cagtggaaaa agcatttcca ctggcggttt   7020
tcttaagcaa ccgccagtgg aaatgtttcc cgtctttttt taaattttcg tactgaaatt   7080
tatatattta cacacacaaa catatatata tatatattga tattgataaa catgtagtat   7140
tgatactaaa agcaacatga aattaaattc tatcatacat ttatatacat caaagtcttg   7200
tttacaacca tgtatgcatc acacattata tacatcaaag ttttcactta agctctaata   7260
actatctcgg ctaagagata gtctactaat ttctgttagt attctaaact ctggcaaagc   7320
taatgttccg gaagcatcgt gatatttccc ttctgcggga atgacctctt tcaatatgaa   7380
tgtgcacagg tcctcaacta tgccatacaa tgcaccttca gtcaagttct ccgggcttcc   7440
tttttgaaat tgctgtaaag gaagtttata aacatcatct atttatactc aataataaca   7500
catttgcatc tttaatgaca taaatacata cgtgactatt actaataata ccttgccagg   7560
gttcgtgatg tatcgtccat tcattctcat aaactcgcac acgtagaacc cacataggac   7620
cgatccgggt ggttgcttgt ggcactacat aacgggagat tggttattta gttgcaacat   7680
tgtcctatgt acgtacatgt atgatatgta ttcataaatt cacatactta ctggccagtt   7740
ataatggatg tctagtggca cacctttttt ggacgtgtcg tactttccac catgtagctt   7800
ataaaaccta aatgccctgt gatctcaaat agaatcacca tgttattcta caattctcat   7860
gggacccttc gaagggatct ttaaacatac gaacagatca cttaaagttc ttctgaagca   7920
acttaaagtt atcaggcatg catggatctt ggaggaatca gatgtgcagt cagggaccat   7980
agcacaggac aggcgtcttc tactggtgct accagcaaat gctggaagcc gggaacactg   8040
ggtacgttgg aaaccacgtg atgtggagta agataaactg taggagaaaa gcatttcgta   8100
gtgggccatg aagcctttca ggacatgtat tgcagtatgg gccggcccat tacgcaattg   8160
gacgacaaca aagactagta ttagtaccac ctcggctatc cacatagatc aaagctggtt   8220
taaaagagtt gtgcagatga tccgtggcag ctggagctga gcttccgggg ttttagagct   8280
agaaatagca agttaaaata aggctagtcc gttatcaact tgaaaaagtg gcaccgagtc   8340
ggtgcttttt ttttcggacc gcgcctgcag tgcagcgtga cccggtcgtg cccctctcta   8400
gagataatga gcattgcatg tctaagttat aaaaaattac cacatatttt ttttgtcaca   8460
cttgtttgaa gtgcagttta tctatcttta tacatatatt taaactttac tctacgaata   8520
atataatcta tagtactaca ataatatcag tgttttagag aatcatataa atgaacagtt   8580
agacatggtc taaaggacaa ttgagtattt tgacaacagg actctacagt tttatctttt   8640
tagtgtgcat gtgttctcct ttttttttgc aaatagcttc acctatataa tacttcatcc   8700
attttattag tacatccatt tagggtttag ggttaatggt ttttatagac taattttttt   8760
```

-continued agtacatcta ttttattcta ttttagcctc taaattaaga aaactaaaac tctattttag 8820
tttttttatt taataattta gatataaaat agaataaaat aaagtgacta aaaattaaac 8880 aaatacccctt taagaaatta aaaaaactaa ggaaacattt ttcttgtttc gagtagataa 8940
tgccagcctg ttaaacgccg tcgacgagtc taacggacac caaccagcga accagcagcg 9000
tcgcgtcggg ccaagcgaag cagacggcac ggcatctctg tcgctgcctc tggacccctc 9060
tcgagagttc cgctccaccg ttggacttgc tccgctgtcg gcatccagaa attgcgtggc 9120
ggagcggcag acgtgagccg gcacggcagg cggcctcctc ctcctctcac ggcaccggca 9180
gctacggggg attcctttcc caccgctcct tcgctttccc ttcctcgccc gccgtaataa 9240
atagacaccc cctccacacc ctctttcccc aacctcgtgt tgttcggagc gcacacacac 9300
acaaccagat ctcccccaaa tccacccgtc ggcacctccg cttcaaggta cgccgctcgt 9360
cctccccccc cccccctctct accttctcta gatcggcgtt ccggtccatg gttagggccc 9420
ggtagttcta cttctgttca tgtttgtgtt agatccgtgt ttgtgttaga tccgtgctgc 9480
tagcgttcgt acacggatgc gacctgtacg tcagacacgt tctgattgct aacttgccag 9540
tgtttctctt tggggaatcc tgggatggct ctagccgttc cgcagacggg atcgatttca 9600
tgattttttt tgtttcgttg catagggttt ggtttgccct tttcctttat ttcaatatat 9660
gccgtgcact tgtttgtcgg gtcatctttt catgcttttt tttgtcttgg ttgtgatgat 9720
gtggtctggt tgggcggtcg ttctagatcg gagtagaatt ctgtttcaaa ctacctggtg 9780
gatttattaa ttttggatct gtatgtgtgt gccatacata ttcatagtta cgaattgaag 9840
atgatggatg gaaatatcga tctaggatag gtatacatgt tgatgcgggt tttactgatg 9900
catatacaga gatgcttttt gttcgcttgg ttgtgatgat gtggtgtggt tgggcggtcg 9960
ttcattcgtt ctagatcgga gtagaatact gtttcaaact acctggtgta tttattaatt 10020
ttggaactgt atgtgtgtgt catacatctt catagttacg agtttaagat ggatggaaat 10080
atcgatctag gataggtata catgttgatg tgggttttac tgatgcatat acatgatggc 10140
atatgcagca tctattcata tgctctaacc ttgagtacct atctattata ataaacaagt 10200
atgttttata attattttga tcttgatata cttggatgat ggcatatgca gcagctatat 10260
gtggattttt ttagccctgc cttcatacgc tatttatttg cttggtactg tttcttttgt 10320
cgatgctcac cctgttgttt ggtgttactt ctgcagggat ccggcagcag ccatgcagaa 10380
gctgatcaac agcgtgcaga actacgcctg ggcagcaag accgccctga ccgagctgta 10440
cggcatggag aaccccagca gccagcccat ggccgagctg tggatgggcg cccaccccaa 10500
gagcagcagc cgcgtgcaga acgccgccgg cgacatcgtg agcctgcgcg acgtgatcga 10560
gagcgacaag agcaccctgc tgggcgaggc cgtggccaag cgcttcggcg agctgccctt 10620
cctgttcaag gtgctgtgcg ccgcccagcc cctgagcatc caggtgcacc ccaacaagca 10680
caacagcgag atcggcttcg ccaaggagaa cgccgccggc atccccatgg acgccgccga 10740
gcgcaactac aaggacccca accacaagcc cgagctggtg ttcgccctga ccccttcct 10800 ggccatgaac gccttccgcg agttcagcga gatcgtgagc ctgctgcagc ccgtggccgg 10860
cgcccacccc gccatcgccc acttcctgca gcagcccgac gccgagcgcc tgagcgagct 10920
gttcgccagc ctgctgaaca tgcagggcga ggagaagagc cgcgccctgg ccatcctgaa 10980
gagcgccctg gacagccagc agggcgagcc ctggcagacc atccgcctga tcagcgagtt 11040
ctaccccgag gacagcggcc tgttcagccc cctgctgctg aacgtggtga agctgaaccc 11100
cggcgaggcc atgttcctgt tcgccgagac cccccacgcc tacctgcagg gcgtggccct 11160
ggaggtgatg gccaacagcg acaacgtgct gcgcgccggc ctgaccccca agtacatcga 11220
catccccgag ctggtggcca acgtgaagtt cgaggccaag cccgccaacc agctgctgac 11280
ccagcccgtg aagcagggcg ccgagctgga cttccccatc cccgtggacg acttcgcctt 11340
cagcctgcac gacctgagcg acaaggagac caccatcagc cagcagagcg ccgccatcct 11400
gttctgcgtg gagggcgacg ccaccctgtg gaagggcagc cagcagctgc agctgaagcc 11460
cggcgagagc gccttcatcg ccgccaacga gagccccgtg accgtgaagg gccacggccg 11520
cctggcccgc gtgtacaaca agctgtgata ggagctcgat ccgtcgacct gcagatcgtt 11580
caaacatttg gcaataaagt ttcttaagat tgaatcctgt tgccggtctt gcgatgatta 11640
tcatataatt tctgttgaat tacgttaagc atgtaataat taacatgtaa tgcatgacgt 11700
tatttatgag atgggttttt atgattagag tcccgcaatt atacatttaa tacgcgatag 11760
aaaacaaaat atagcgcgca aactaggata aattatcgcg cgcggtgtca tctatgttac 11820
tagatcggcg cgccgcaatt gaagtttggg cggccagcat ggccgtatcc gcaatgtgtt 11880
attaagttgt ctaagcgtca atttgtttac accacaatat atcctgccac cagccagcca 11940
acagctcccc gaccggcagc tcggcacaaa atcaccactc gatacaggca gcccatcaga 12000
attaattctc atgtttgaca gcttatcatc gactgcacgg tgcaccaatg cttctggcgt 12060
caggcagcca tcggaagctg tggtatggct gtgcaggtcg taaatcactg cataattcgt 12120
gtcgctcaag gcgcactccc gttctggata atgttttttg cgccgacatc ataacggttc 12180
tggcaaatat tctgaaatga gctgttgaca attaatcatc cggctcgtat aatgtgtgga 12240
attgtgagcg gataacaatt tcacacagga aacagaccat gagggaagcg ttgatcgccg 12300
aagtatcgac tcaactatca gaggtagttg gcgtcatcga gcgccatctc gaaccgacgt 12360
tgctggccgt acatttgtac ggctccgcag tggatggcgg cctgaagcca cacagtgata 12420
ttgatttgct ggttacggtg accgtaaggc ttgatgaaac aacgcggcga gctttgatca 12480
acgacctttt ggaaacttcg gcttcccctg gagagagcga gattctccgc gctgtagaag 12540
tcaccattgt tgtgcacgac gacatcattc cgtggcgtta tccagctaag cgcgaactgc 12600
aatttggaga atggcagcgc aatgacattc ttgcaggtat cttcgagcca gccacgatcg 12660
acattgatct ggctatcttg ctgacaaaag caagagaaca tagcgttgcc ttggtaggtc 12720
cagcggcgga ggaactcttt gatccggttc ctgaacagga tctatttgag gcgctaaatg 12780
aaaccttaac gctatggaac tcgccgcccg actgggctgg cgatgagcga aatgtagtgc 12840
ttacgttgtc ccgcatttgg tacagcgcag taaccggcaa aatcgcgccg aaggatgtcg 12900
ctgccgactg ggcaatggag cgcctgccgg cccagtatca gcccgtcata cttgaagcta 12960
ggcaggctta tcttggacaa gaagatcgct tggcctcgcg cgcagatcag ttggaagaat 13020
ttgttcacta cgtgaaaggc gagatcacca aagtagtcgg caaataaagc tctagtggat 13080
ctccgtaccc ggggatctgg ctcgcggcgg acgcacgacg ccggggcgag accataggcg 13140
atctcctaaa tcaatagtag ctgtaacctc gaagcgtttc acttgtaaca acgattgaga 13200
atttttgtca taaaattgaa atacttggtt cgcatttttg tcatccgcgg tcagccgcaa 13260
ttctgacgaa ctgcccattt agctggagat gattgtacat ccttcacgtg aaaatttctc 13320
aagcgctgtg aacaagggtt cagattttag attgaaaggt gagccgttga aacacgttct 13380
tcttgtcgat gacgacgtcg ctatgcggca tcttattatt gaatacctta cgatccacgc 13440
cttcaaagtg accgcggtag ccgacagcac ccagttcaca agagtactct cttccgcgac 13500

```
ggtcgatgtc gtggttgttg atctagattt aggtcgtgaa gatgggctcg agctaggagc  13560
aagtgatttt atcgctaagc cgttcagtat cagagagttt ctagcacgca ttcgggttgc  13620
cttgcgcgtg cgccccaacg ttgtccgctc caaagaccga cggtcttttt gttttactga  13680
ctggacactt aatctcaggc aacgtcgctt gatgtccgaa gctggcggtg aggtgaaact  13740
tacggcaggt gagttcaatc ttctcctcgc gtttttagag aaaccccgcg acgttctatc  13800
gcgcgagcaa cttctcattg ccagtcgagt acgcgacgag gaggtttatg acaggagtat  13860
agatgttctc attttgaggc tgcgccgcaa acttgaggca gatccgtcaa gccctcaact  13920
gataaaaaca gcaagaggtg ccggttattt ctttgacgcg gacgtgcagg tttcgcacgg  13980
ggggacgatg gcagcctgag ccaattccca gatccccgag gaatcggcgt gagcggtcgc  14040
aaaccatccg gcccggtaca aatcggcgcg gcgctgggtg atgacctggt ggagaagttg  14100
aaggccgcgc aggccgccca gcggcaacgc atcgaggcag aagcacgccc cggtgaatcg  14160
tggcaagcgg ccgctgatcg aatccgcaaa gaatcccggc aaccgccggc agccggtgcg  14220
ccgtcgatta ggaagccgcc caagggcgac gagcaaccag atttttttcgt tccgatgctc  14280
tatgacgtgg gcacccgcga tagtcgcagc atcatggacg tggccgtttt ccgtctgtcg  14340
aagcgtgacc gacgagctgg cgaggtgatc cgctacgagc ttccagacgg gcacgtagag  14400
gtttccgcag ggccggccgg catggccagt gtgtgggatt acgacctggt actgatggcg  14460
gtttcccatc taaccgaatc catgaaccga taccgggaag ggaagggaga caagcccggc  14520
cgcgtgttcc gtccacacgt tgcggacgta ctcaagttct gccggcgagc cgatggcgga  14580
aagcagaaag acgacctggt agaaacctgc attcggttaa acaccacgca cgttgccatg  14640
cagcgtacga agaaggccaa gaacggccgc ctggtgacgg tatccgaggg tgaagccttg  14700
attagccgct acaagatcgt aaagagcgaa accgggcggc cggagtacat cgagatcgag  14760
ctagctgatt ggatgtaccg cgagatcaca gaaggcaaga acccggacgt gctgacggtt  14820
caccccgatt actttttgat cgatcccggc atcggccgtt ttctctaccg cctggcacgc  14880
cgcgccgcag gcaaggcaga agccagatgg ttgttcaaga cgatctacga acgcagtggc  14940
agcgccggag agttcaagaa gttctgtttc accgtgcgca agctgatcgg gtcaaatgac  15000
ctgccggagt acgatttgaa ggaggaggcg gggcaggctg gcccgatcct agtcatgcgc  15060
taccgcaacc tgatcgaggg cgaagcatcc gccggttcct aatgtacgga gcagatgcta  15120
gggcaaattg ccctagcagg ggaaaaaggt cgaaaaggtc tctttcctgt ggatagcacg  15180
tacattggga acccaaagcc gtacattggg aaccggaacc cgtacattgg gaacccaaag  15240
ccgtacattg ggaaccggtc acacatgtaa gtgactgata taaaagagaa aaaaggcgat  15300
ttttccgcct aaaactcttt aaaacttatt aaaactctta aaacccgcct ggcctgtgca  15360
taactgtctg gccagcgcac agccgaagag ctgcaaaaag cgcctaccct tcggtcgctg  15420
cgctccctac gccccgccgc ttcgcgtcgg cctatcgcgg ccgctggccg ctcaaaaatg  15480
gctggcctac ggccaggcaa tctaccaggg cgcggacaag ccgcgccgtc gccactcgac  15540
cgccggcgct gaggtctgcc tcgtgaagaa ggtgttgctg actcatacca ggcctgaatc  15600
gccccatcat ccagccagaa agtgagggag ccacggttga tgagagcttt gttgtaggtg  15660
gaccagttgg tgattttgaa cttttgcttt gccacggaac ggtctgcgtt gtcgggaaga  15720
tgcgtgatct gatccttcaa ctcagcaaaa gttcgattta ttcaacaaag ccgccgtccc  15780
gtcaagtcag cgtaatgctc tgccagtgtt acaaccaatt aaccaattct gattagaaaa  15840
actcatcgag catcaaatga aactgcaatt tattcatatc aggattatca ataccatatt  15900
```

```
tttgaaaaag ccgtttctgt aatgaaggag aaaactcacc gaggcagttc cataggatgg  15960

caagatcctg gtatcggtct gcgattccga ctcgtccaac atcaatacaa cctattaatt  16020

tcccctcgtc aaaaataagg ttatcaagtg agaaatcacc atgagtgacg actgaatccg  16080

gtgagaatgg caaaagctct gcattaatga atcggccaac gcgcggggag aggcggtttg  16140

cgtattgggc gctcttccgc ttcctcgctc actgactcgc tgcgctcggt cgttcggctg  16200

cggcgagcgg tatcagctca ctcaaaggcg gtaatacggt tatccacaga atcaggggat  16260

aacgcaggaa agaacatgtg agcaaaaggc cagcaaaagg ccaggaaccg taaaaaggcc  16320

gcgttgctgg cgtttttcca taggctccgc ccccctgacg agcatcacaa aaatcgacgc  16380

tcaagtcaga ggtggcgaaa cccgacagga ctataaagat accaggcgtt tccccctgga  16440

agctccctcg tgcgctctcc tgttccgacc ctgccgctta ccggatacct gtccgccttt  16500

ctcccttcgg gaagcgtggc gctttctcat agctcacgct gtaggtatct cagttcggtg  16560

taggtcgttc gctccaagct gggctgtgtg cacgaacccc ccgttcagcc cgaccgctgc  16620

gccttatccg gtaactatcg tcttgagtcc aacccggtaa gacacgactt atcgccactg  16680

gcagcagcca ctggtaacag gattagcaga gcgaggtatg taggcggtgc tacagagttc  16740

ttgaagtggt ggcctaacta cggctacact agaagaacag tatttggtat ctgcgctctg  16800

ctgaagccag ttaccttcgg aaaaagagtt ggtagctctt gatccggcaa acaaaccacc  16860

gctggtagcg gtggtttttt tgtttgcaag cagcagatta cgcgcagaaa aaaaggatct  16920

caagaagatc ctttgatctt ttctacgggg tctgacgctc agtggaacga aaactcacgt  16980

taagggattt tggtcatgag attatcaaaa aggatcttca cctagatcct tttgatccgg  17040

aatta                                                              17045
```

<210> SEQ ID NO 37
<211> LENGTH: 16776
<212> TYPE: DNA
<213> ORGANISM: artificial sequence
<220> FEATURE:
<223> OTHER INFORMATION: vector 24091
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (330)..(2417)
<223> OTHER INFORMATION: prZmGRMZM2G471240-01
<220> FEATURE:
<221> NAME/KEY: gene
<222> LOCATION: (2420)..(6589)
<223> OTHER INFORMATION: cCas9-01
<220> FEATURE:
<221> NAME/KEY: mutation
<222> LOCATION: (5909)..(5911)
<223> OTHER INFORMATION: L to V mutation
<220> FEATURE:
<221> NAME/KEY: mutation
<222> LOCATION: (5954)..(5956)
<223> OTHER INFORMATION: I to V mutation
<220> FEATURE:
<221> NAME/KEY: terminator
<222> LOCATION: (6596)..(7591)
<223> OTHER INFORMATION: tZmGRMZM2G471240-01
<220> FEATURE:
<221> NAME/KEY: promoter
<222> LOCATION: (7605)..(7979)
<223> OTHER INFORMATION: prOsU3-01
<220> FEATURE:
<221> NAME/KEY: misc_feature
<222> LOCATION: (7981)..(8085)

<223> OTHER INFORMATION: rsgRNAZmVLHP-02
<220> FEATURE:
<221> NAME/KEY: misc_feature
<222> LOCATION: (7981)..(8000)
<223> OTHER INFORMATION: xZmVLHP2
<220> FEATURE:
<221> NAME/KEY: misc_feature
<222> LOCATION: (8001)..(8012)
<223> OTHER INFORMATION: rCrRNA-01
<220> FEATURE:
<221> NAME/KEY: misc_feature
<222> LOCATION: (8017)..(8085)
<223> OTHER INFORMATION: rTracrRNA-01
<220> FEATURE:
<221> NAME/KEY: promoter
<222> LOCATION: (8096)..(10087)
<223> OTHER INFORMATION: prUbi1-04
<220> FEATURE:
<221> NAME/KEY: gene
<222> LOCATION: (10104)..(11282)
<223> OTHER INFORMATION: cPMI-09
<220> FEATURE:
<221> NAME/KEY: terminator
<222> LOCATION: (11305)..(11557)
<223> OTHER INFORMATION: tNOS-05-01
<220> FEATURE:
<221> NAME/KEY: misc_feature
<222> LOCATION: (11601)..(11730)
<223> OTHER INFORMATION: bNLB-03
<220> FEATURE:
<221> NAME/KEY: gene
<222> LOCATION: (12010)..(12798)
<223> OTHER INFORMATION: cSpec-03
<220> FEATURE:
<221> NAME/KEY: promoter
<222> LOCATION: (12893)..(13023)
<223> OTHER INFORMATION: prVirG-01
<220> FEATURE:
<221> NAME/KEY: gene
<222> LOCATION: (13098)..(13730)
<223> OTHER INFORMATION: cVirG-09
<220> FEATURE:
<221> NAME/KEY: gene
<222> LOCATION: (13760)..(14833)
<223> OTHER INFORMATION: cRepA-01
<220> FEATURE:
<221> NAME/KEY: misc_feature
<222> LOCATION: (14876)..(15280)
<223> OTHER INFORMATION: oVS1-02
<220> FEATURE:
<221> NAME/KEY: misc_feature
<222> LOCATION: (15958)..(16764)
<223> OTHER INFORMATION: oCOLE-06

<400> SEQUENCE: 37
attcctgtgg ttggcatgca catacaaatg gacgaacgga taaacctttt cacgcccttt 60
taaatatccg attattctaa taaacgctct tttctcttag gtttacccgc caatatatcc 120
tgtcaaacac tgatagttta aactgaaggc gggaaacgac aatctgatca tgagcggaga 180
attaagggag tcacgttatg acccccgccg atgacgcggg acaagccgtt ttacgtttgg 240
aactgacaga accgcaacgc tgcaggaatt ggccgcagcg gccatttaaa caaagcttgg 300
tacctcgcga atgcatctag atgggaccct atttgtactc attccatgtc tcataaactt 360
tgggcaccat ccatccaaca catccaatct aaacacacca aacgatgggg aatggaaaga 420
gcagtattcg attcaacaat ggcaaacaaa tatcactgaa ttagaccaag aataaaccta 480
attagacaac gacctcccaa ccatcattcg tcaggctgta aagaagataa agctgccttg 540
gggcatggat caagcagaac accagagatg aatccaaaca cacagaaaat cacgcgcgct 600
gtctacaatg acaacaagcc ccacatttca ttgcagtaca ctgggctaca aaggcacgta 660
caacaaagag ctagggaaac attgcggagg gcacgagaga gcagctaact tgacaatata 720

```
gcagactgag cttgcactgt tagcaggcga ggaagggaat catggggacg gagaatgggg    780
tccatgcccg cgaaggagaa ggcggacgcc gccacggtgg caccggcgca cgcgcacaca    840
gggaacccgc acaggcagcc aaggatgctg cctcgccatt gcgccggtcg tctctgccac    900
gctcctctct ctctcccgct gcatcgccgt ggatggggca agcagagagc agggactgcg    960
acgatctggg cggaggactc gccttggaga gcgcggacgc agacgggatt ctagggagag   1020
agcgaagacg gggcgcgcgc ggcgctcgcg cggcgtggtg gcggcgagat tagcgggggt   1080
gggggggaggg cggagccgtg gtgagggtgt ggacgccctc cttaccctct taagtagtag   1140
tagagatata atccgttcca aaatatccat ccgttcaatt tatatttcgt ttgatctttt   1200
taccctaaat ttgattgact catcttatta aaaaagttca taactattat taatctttat   1260
tgagatatca tttagcatat aatatacttt aagtgtggtt ttagattttt tttaaaaaaa   1320
aaaattcgca aaaattaaat gaaacgaccc aatcaaactt gaaaagtaaa actaattata   1380
aatttgaacg gaaggagtaa gaggatgttt gaatgtacta gagctaatag ttggttgctt   1440
taaaatttgc tagtagaatt agctagctaa taaatatcta gataactatt agctaatttg   1500
ctaaaacagc taatagttga actattagct agattgtttg gatgtattcg gctaatttta   1560
atggctaact attagctata gtacaatatt caaacacctc ctaattaaaa tggacaaata   1620
tctcttcttt tggtcccttg cgttagattt ttcatatctc cttatttagt ataaaagaat   1680
catcaaaaag tggacaaccc ctagtggaac accattttag tagtggttgc atgaaacctt   1740
tcgcgcacca gtttctatgt gtcactctaa aaatgggaca gcatgtacgt agtgcctata   1800
tatatacaag tcatctatcg ttgcctcctc agttcatcac taatcacact tattgtgccc   1860
tcgacgagta tctatagcta gctcattaat cgattcgggg gtgtgttgtc gaaggcggca   1920
ttggcgagct actcgtcgcg gcgtccaagc aatacctgta gcacgaaggc gatcgccggg   1980
agcgtggtcg gcgagcccgt cgtgctgggg cagagggtga cggtgctgac ggtggacggc   2040
ggcggcgtcc ggggtctcat cccgggaacc atcctcgcct tcctggaggc caggctgcag   2100
gagctggacg caccggaggc gaggctggcg gactacttcg actacatcgc cggaaccagc   2160
accggcggtc tcatcaccgc cttgctgacc gcgcccggca aggacaagcg gcctctctag   2220
gctgccaagg acatcaacca cttttacatc cataactgcc cgcgcatctt tcctcagaag   2280
tgagtccgat gctgccgcca ttgttcttgc atccatccag catcgtacgt acgtcctcta   2340
tacatctgcg gatcatcatg tgcgcatgtt tgtggcatgc atgcatgcat gtgagcagga   2400
gcaggcttgc gaaaacccca tggacaagaa gtacagcatc ggcctggaca tcggcaccaa   2460
cagcgtgggc tgggccgtga tcaccgacga gtacaaggtg ccgagcaaga agttcaaggt   2520
gctgggcaac accgacaggc acagcatcaa gaagaacctg atcggcgccc tgctgttcga   2580
cagcggcgag accgccgagg ccaccaggct gaagaggacc gccaggagga ggtacaccag   2640
gaggaagaac aggatctgct acctgcagga gatcttcagc aacgagatgg ccaaggtgga   2700
cgacagcttc ttccacaggc tggaggagag cttcctggtg gaggaggaca agaagcacga   2760
gaggcacccg atcttcggca acatcgtgga cgaggtggcc taccacgaga agtacccgac   2820
catctaccac ctgaggaaga agctggtgga cagcaccgac aaggccgacc tgaggctgat   2880
ctacctggcc ctggcccaca tgatcaagtt caggggccac ttcctgatcg agggcgacct   2940
gaacccggac aacagcgacg tggacaagct gttcatccag ctggtgcaga cctacaacca   3000
gctgttcgag gagaacccga tcaacgccag cggcgtggac gccaaggcca tcctgagcgc   3060
```

caggctgagc aagagcagga ggctggagaa cctgatcgcc cagctgccgg gcgagaagaa 3120
gaacggcctg ttcggcaacc tgatcgccct gagcctgggc ctgaccccga acttcaagag 3180
caacttcgac ctggccgagg acgccaagct gcagctgagc aaggacacct acgacgacga 3240
cctggacaac ctgctggccc agatcggcga ccagtacgcc gacctgttcc tggccgccaa 3300
gaacctgagc gacgccatcc tgctgagcga catcctgagg gtgaacaccg agatcaccaa 3360
ggccccgctg agcgccagca tgatcaagag gtacgacgag caccaccagg acctgaccct 3420
gctgaaggcc ctggtgaggc agcagctgcc ggagaagtac aaggagatct tcttcgacca 3480
gagcaagaac ggctacgccg gctacatcga cggcggcgcc agccaggagg agttctacaa 3540
gttcatcaag ccgatcctgg agaagatgga cggcaccgag gagctgctgg tgaagctgaa 3600
cagggaggac ctgctgagga agcagaggac cttcgacaac ggcagcatcc cgcaccagat 3660
ccacctgggc gagctgcacg ccatcctgag gaggcaggag gacttctacc cgttcctgaa 3720
ggacaacagg gagaagatcg agaagatcct gaccttccgc atcccgtact acgtgggccc 3780
gctggccagg ggcaacagca ggttcgcctg gatgaccagg aagagcgagg agaccatcac 3840
cccgtggaac ttcgaggagg tggtggacaa gggcgccagc gcccagagct tcatcgagag 3900
gatgaccaac ttcgacaaga acctgccgaa cgagaaggtg ctgccgaagc acagcctgct 3960
gtacgagtac ttcaccgtgt acaacgagct gaccaaggtg aagtacgtga ccgagggcat 4020
gaggaagccg gccttcctga gcggcgagca gaagaaggcc atcgtggacc tgctgttcaa 4080
gaccaacagg aaggtgaccg tgaagcagct gaaggaggac tacttcaaga agatcgagtg 4140
cttcgacagc gtggagatca gcggcgtgga ggacaggttc aacgccagcc tgggcaccta 4200
ccacgacctg ctgaagatca tcaaggacaa ggacttcctg gacaacgagg agaacgagga 4260
catcctggag gacatcgtgc tgaccctgac cctgttcgag gacagggaga tgatcgagga 4320
gaggctgaag acctacgccc acctgttcga cgacaaggtg atgaagcagc tgaagaggag 4380
gaggtacacc ggctggggca ggctgagcag gaagctgatc aacggcatca gggacaagca 4440
gagcggcaag accatcctgg acttcctgaa gagcgacggc ttcgccaaca ggaacttcat 4500
gcagctgatc cacgacgaca gcctgacctt caaggaggac atccagaagg cccaggtgag 4560
cggccagggc gacagcctgc acgagcacat cgccaacctg gccggcagcc cggccatcaa 4620
gaagggcatc ctgcagaccg tgaaggtggt ggacgagctg gtgaaggtga tgggcaggca 4680
caagccggag aacatcgtga tcgagatggc cagggagaac cagaccaccc agaagggcca 4740
gaagaacagc agggagagga tgaagaggat cgaggagggc atcaaggagc tgggcagcca 4800
gatcctgaag gagcacccgg tggagaacac ccagctgcag aacgagaagc tgtacctgta 4860
ctacctgcag aacggcaggg acatgtacgt ggaccaggag ctggacatca acaggctgag 4920
cgactacgac gtggaccaca tcgtgccgca gagcttcctg aaggacgaca gcatcgacaa 4980
caaggtgctg accaggagcg acaagaacag gggcaagagc gacaacgtgc cgagcgagga 5040
ggtggtgaag aagatgaaaa actactggag gcagctgctg aacgccaagc tgatcaccca 5100
gaggaagttc gacaacctga ccaaggccga gaggggcggc ctgagcgagc tggacaaggc 5160
cggcttcatt aaaaggcagc tggtggagac caggcagatc accaagcacg tggcccagat 5220
cctggacagc aggatgaaca ccaagtacga cgagaacgac aagctgatca gggaggtgaa 5280
ggtgatcacc ctgaagagca agctggtgag cgacttcagg aaggacttcc agttctacaa 5340
ggtgagggag atcaataatt accaccacgc ccacgacgcc tacctgaacg ccgtggtggg 5400
caccgccctg attaaaaagt acccgaagct ggagagcgag ttcgtgtacg gcgactacaa 5460

```
ggtgtacgac gtgaggaaga tgatcgccaa gagcgagcag gagatcggca aggccaccgc   5520
caagtacttc ttctacagca acatcatgaa cttcttcaag accgagatca ccctggccaa   5580
cggcgagatc aggaagaggc cgctgatcga gaccaacggc gagaccggcg agatcgtgtg   5640
ggacaagggc agggacttcg ccaccgtgag gaaggtgctg tccatgccgc aggtgaacat   5700
cgtgaagaag accgaggtgc agaccggcgg cttcagcaag gagagcatcc tgccgaagag   5760
gaacagcgac aagctgatcg ccaggaagaa ggactgggac ccgaagaagt acggcggctt   5820
cgacagcccg accgtggcct acagcgtgct ggtggtggcc aaggtggaga agggcaagag   5880
caagaagctg aagagcgtga aggagctggt gggcatcacc atcatggaga ggagcagctt   5940
cgagaagaac ccagtggact tcctggaggc caagggctac aaggaggtga agaaggacct   6000
gatcattaaa ctgccgaagt acagcctgtt cgagctggag aacggcagga agaggatgct   6060
ggccagcgcc ggcgagctgc agaagggcaa cgagctggcc ctgccgagca agtacgtgaa   6120
cttcctgtac ctggccagcc actacgagaa gctgaagggc agcccggagg acaacgagca   6180
gaagcagctg ttcgtggagc agcacaagca ctacctggac gagatcatcg agcagatcag   6240
cgagttcagc aagagggtga tcctggccga cgccaacctg gacaaggtgc tgagcgccta   6300
caacaagcac agggacaagc cgatcaggga gcaggccgag aacatcatcc acctgttcac   6360
cctgaccaac ctgggcgccc cggccgcctt caagtacttc gacaccacca tcgacaggaa   6420
gaggtacacc agcaccaagg aggtgctgga cgccaccctg atccaccaga gcatcaccgg   6480
cctgtacgag accaggatcg acctgagcca gctgggcggc gacagcagcc cgccgaagaa   6540
gaagaggaag gtgagctgga aggacgccag cggctggagc aggatgtgac catgggacaa   6600
gtggctttac tgtcagtcac atgcttgtaa ataagtagac tttattttaa taaaacataa   6660
aaatatatat atgttcttga atataaaatt gataaccaaa ttaaaattcg aaccatcact   6720
tatacataat tttactttat tttttataaa acgtgaacgg gaaggactac cgtgaatgac   6780
tatagaacca atcatactag tataaaatat atgatgacac tacgggagag acaaactttg   6840
tctggcgcta aatattttgc cgagtgtgaa ttcacgggca ctaggcaaag atcttctttg   6900
ccgagtgtta cgctgggcaa agtaagacac taggtaaatc agtcatttgc cgagtgtccg   6960
ccactaggca aagcaaaaca ctggcaaatc aaaagtttac ctagtgccag acactaggca   7020
aaaaaaaaac gctcggcaaa tcggaagttt ccctagtgcc agacactaga caaagaaaaa   7080
cacttgataa actagcgtcg tcagctaaca ccatccacca accgttaacg ttgccgagta   7140
tctgacttcg acactcggca aagaaggtct ctttgcctag tgtcggtctg gaacactagg   7200
caaagaggca ctttacctag tgtcgtattt tgacactcag taaaataatt ttttttcttt   7260
ctgcttccaa actttttatg atgtgttcct atagcaccta gaactacatg tcaagttttg   7320
gtaaaatttt tgaagttttt gctatattta cttaatttat tttatttaat tgaatttctt   7380
ttgataattc aaatttgaac tcggcaaggt aagaagcgag ggtagcctgg aaacacactt   7440
tgcctagtgt tacactcggt acaggagcct cccctgccta gtgctgcact cgacaaaaga   7500
ttcgcctttg cctagcgctg cactcggcac aggagtcgcc tttgcctagt gctgcactag   7560
gcaaagcctc cgttaccgtg ccttccatcg tcggaccctt cgaagggatc tttaaacata   7620
cgaacagatc acttaaagtt cttctgaagc aacttaaagt tatcaggcat gcatggatct   7680
tggaggaatc agatgtgcag tcagggacca tagcacagga caggcgtctt ctactggtgc   7740
taccagcaaa tgctggaagc cgggaacact gggtacgttg gaaaccacgt gatgtggagt   7800
```

-continued

```
aagataaact gtaggagaaa agcatttcgt agtgggccat gaagcctttc aggacatgta   7860
ttgcagtatg ggccggccca ttacgcaatt ggacgacaac aaagactagt attagtacca   7920
cctcggctat ccacatagat caaagctggt ttaaaagagt tgtgcagatg atccgtggca   7980
gctggagctg agcttccggg gttttagagc tagaaatagc aagttaaaat aaggctagtc   8040
cgttatcaac ttgaaaaagt ggcaccgagt cggtgctttt tttttcggac cgcgcctgca   8100
gtgcagcgtg acccggtcgt gcccctctct agagataatg agcattgcat gtctaagtta   8160
taaaaaatta ccacatattt tttttgtcac acttgtttga agtgcagttt atctatcttt   8220
atacatatat ttaaacttta ctctacgaat aatataatct atagtactac aataatatca   8280
gtgttttaga gaatcatata aatgaacagt tagacatggt ctaaaggaca attgagtatt   8340
ttgacaacag gactctacag ttttatcttt ttagtgtgca tgtgttctcc tttttttttg   8400
caaatagctt cacctatata atacttcatc cattttatta gtacatccat ttagggttta   8460
gggttaatgg tttttataga ctaatttttt tagtacatct attttattct attttagcct   8520
ctaaattaag aaaactaaaa ctctatttta gtttttttat ttaataattt agatataaaa   8580
tagaataaaa taaagtgact aaaaattaaa caaataccct ttaagaaatt aaaaaaacta   8640
aggaaacatt tttcttgttt cgagtagata atgccagcct gttaaacgcc gtcgacgagt   8700
ctaacggaca ccaaccagcg aaccagcagc gtcgcgtcgg gccaagcgaa gcagacggca   8760
cggcatctct gtcgctgcct ctggacccct ctcgagagtt ccgctccacc gttggacttg   8820
ctccgctgtc ggcatccaga aattgcgtgg cggagcggca gacgtgagcc ggcacggcag   8880
gcggcctcct cctcctctca cggcaccggc agctacgggg gattcctttc ccaccgctcc   8940
ttcgctttcc cttcctcgcc cgccgtaata aatagacacc ccctccacac cctctttccc   9000
caacctcgtg ttgttcggag cgcacacaca cacaaccaga tctcccccaa atccacccgt   9060
cggcacctcc gcttcaaggt acgccgctcg tcctcccccc cccccctctc taccttctct   9120
agatcggcgt tccggtccat ggttagggcc cggtagttct acttctgttc atgtttgtgt   9180
tagatccgtg tttgtgttag atccgtgctg ctagcgttcg tacacggatg cgacctgtac   9240
gtcagacacg ttctgattgc taacttgcca gtgtttctct ttggggaatc ctgggatggc   9300
tctagccgtt ccgcagacgg gatcgatttc atgatttttt ttgtttcgtt gcatagggtt   9360
tggtttgccc ttttccttta tttcaatata tgccgtgcac ttgtttgtcg ggtcatcttt   9420
tcatgctttt ttttgtcttg gttgtgatga tgtggtctgg ttgggcggtc gttctagatc   9480
ggagtagaat tctgtttcaa actacctggt ggatttatta attttggatc tgtatgtgtg   9540
tgccatacat attcatagtt acgaattgaa gatgatggat ggaaatatcg atctaggata   9600
ggtatacatg ttgatgcggg ttttactgat gcatatacag agatgctttt tgttcgcttg   9660
gttgtgatga tgtggtgtgg ttgggcggtc gttcattcgt tctagatcgg agtagaatac   9720
tgtttcaaac tacctggtgt atttattaat tttggaactg tatgtgtgtg tcatacatct   9780
tcatagttac gagtttaaga tggatggaaa tatcgatcta ggataggtat acatgttgat   9840
gtgggtttta ctgatgcata tacatgatgg catatgcagc atctattcat atgctctaac   9900
cttgagtacc tatctattat aataaacaag tatgttttat aattattttg atcttgatat   9960
acttggatga tggcatatgc agcagctata tgtggatttt tttagccctg ccttcatacg  10020
ctatttattt gcttggtact gtttcttttg tcgatgctca ccctgttgtt tggtgttact  10080
tctgcaggga tccggcagca gccatgcaga agctgatcaa cagcgtgcag aactacgcct  10140
ggggcagcaa gaccgccctg accgagctgt acggcatgga gaaccccagc agccagccca  10200
```

-continued

```
tggccgagct gtggatgggc gcccacccca agagcagcag ccgcgtgcag aacgccgccg  10260
gcgacatcgt gagcctgcgc gacgtgatcg agagcgacaa gagcaccctg ctgggcgagg  10320
ccgtggccaa gcgcttcggc gagctgccct tcctgttcaa ggtgctgtgc gccgcccagc  10380
ccctgagcat ccaggtgcac cccaacaagc acaacagcga gatcggcttc gccaaggaga  10440
acgccgccgg catccccatg gacgccgccg agcgcaacta caaggacccc aaccacaagc  10500
ccgagctggt gttcgccctg accccccttcc tggccatgaa cgccttccgc gagttcagcg  10560
agatcgtgag cctgctgcag cccgtggccg gcgcccaccc cgccatcgcc cacttcctgc  10620
agcagcccga cgccgagcgc ctgagcgagc tgttcgccag cctgctgaac atgcagggcg  10680
aggagaagag ccgcgccctg gccatcctga agagcgccct ggacagccag cagggcgagc  10740
cctggcagac catccgcctg atcagcgagt tctaccccga ggacagcggc ctgttcagcc  10800
ccctgctgct gaacgtggtg aagctgaacc ccggcgaggc catgttcctg ttcgccgaga  10860
ccccccacgc ctacctgcag ggcgtggccc tggaggtgat ggccaacagc gacaacgtgc  10920
tgcgcgccgg cctgaccccc aagtacatcg acatccccga gctggtggcc aacgtgaagt  10980
tcgaggccaa gcccgccaac cagctgctga cccagcccgt gaagcagggc gccgagctgg  11040
acttccccat ccccgtggac gacttcgcct tcagcctgca cgacctgagc gacaaggaga  11100
ccaccatcag ccagcagagc gccgccatcc tgttctgcgt ggagggcgac gccaccctgt  11160
ggaagggcag ccagcagctg cagctgaagc ccggcgagag cgccttcatc gccgccaacg  11220
agagccccgt gaccgtgaag ggccacggcc gcctggcccg cgtgtacaac aagctgtgat  11280
aggagctcga tccgtcgacc tgcagatcgt tcaaacattt ggcaataaag tttcttaaga  11340
ttgaatcctg ttgccggtct tgcgatgatt atcatataat ttctgttgaa ttacgttaag  11400
catgtaataa ttaacatgta atgcatgacg ttatttatga gatgggtttt tatgattaga  11460
gtcccgcaat tatacattta atacgcgata gaaaacaaaa tatagcgcgc aaactaggat  11520
aaattatcgc gcgcggtgtc atctatgtta ctagatcggc gcgccgcaat tgaagtttgg  11580
gcggccagca tggccgtatc cgcaatgtgt tattaagttg tctaagcgtc aatttgttta  11640
caccacaata tatcctgcca ccagccagcc aacagctccc cgaccggcag ctcggcacaa  11700
aatcaccact cgatacaggc agcccatcag aattaattct catgtttgac agcttatcat  11760
cgactgcacg gtgcaccaat gcttctggcg tcaggcagcc atcggaagct gtggtatggc  11820
tgtgcaggtc gtaaatcact gcataattcg tgtcgctcaa ggcgcactcc cgttctggat  11880
aatgtttttt gcgccgacat cataacggtt ctggcaaata ttctgaaatg agctgttgac  11940
aattaatcat ccggctcgta taatgtgtgg aattgtgagc ggataacaat ttcacacagg  12000
aaacagacca tgagggaagc gttgatcgcc gaagtatcga ctcaactatc agaggtagtt  12060
ggcgtcatcg agcgccatct cgaaccgacg ttgctggccg tacatttgta cggctccgca  12120
gtggatggcg gcctgaagcc acacagtgat attgatttgc tggttacggt gaccgtaagg  12180
cttgatgaaa caacgcggcg agctttgatc aacgaccttt tggaaacttc ggcttcccct  12240
ggagagagcg agattctccg cgctgtagaa gtcaccattg ttgtgcacga cgacatcatt  12300
ccgtggcgtt atccagctaa gcgcgaactg caatttggag aatggcagcg caatgacatt  12360
cttgcaggta tcttcgagcc agccacgatc gacattgatc tggctatctt gctgacaaaa  12420
gcaagagaac atagcgttgc cttggtaggt ccagcggcgg aggaactctt tgatccggtt  12480
cctgaacagg atctatttga ggcgctaaat gaaaccttaa cgctatggaa ctcgccgccc  12540
```

-continued

```
gactgggctg gcgatgagcg aaatgtagtg cttacgttgt cccgcatttg gtacagcgca  12600
gtaaccggca aaatcgcgcc gaaggatgtc gctgccgact gggcaatgga gcgcctgccg  12660
gcccagtatc agcccgtcat acttgaagct aggcaggctt atcttggaca agaagatcgc  12720
ttggcctcgc gcgcagatca gttggaagaa tttgttcact acgtgaaagg cgagatcacc  12780
aaagtagtcg gcaaataaag ctctagtgga tctccgtacc cggggatctg gctcgcggcg  12840
gacgcacgac gccggggcga gaccataggc gatctcctaa atcaatagta gctgtaacct  12900
cgaagcgttt cacttgtaac aacgattgag aatttttgtc ataaaattga aatacttggt  12960
tcgcattttt gtcatccgcg gtcagccgca attctgacga actgcccatt tagctggaga  13020
tgattgtaca tccttcacgt gaaaatttct caagcgctgt gaacaagggt tcagatttta  13080
gattgaaagg tgagccgttg aaacacgttc ttcttgtcga tgacgacgtc gctatgcggc  13140
atcttattat tgaatacctt acgatccacg ccttcaaagt gaccgcggta gccgacagca  13200
cccagttcac aagagtactc tcttccgcga cggtcgatgt cgtggttgtt gatctagatt  13260
taggtcgtga agatgggctc gagctaggag caagtgattt tatcgctaag ccgttcagta  13320
tcagagagtt tctagcacgc attcgggttg ccttgcgcgt gcgccccaac gttgtccgct  13380
ccaaagaccg acggtctttt tgttttactg actggacact taatctcagg caacgtcgct  13440
tgatgtccga agctggcggt gaggtgaaac ttacggcagg tgagttcaat cttctcctcg  13500
cgtttttaga gaaaccccgc gacgttctat cgcgcgagca acttctcatt gccagtcgag  13560
tacgcgacga ggaggtttat gacaggagta tagatgttct cattttgagg ctgcgccgca  13620
aacttgaggc agatccgtca agccctcaac tgataaaaac agcaagaggt gccggttatt  13680
tctttgacgc ggacgtgcag gtttcgcacg gggggacgat ggcagcctga gccaattccc  13740
agatccccga ggaatcggcg tgagcggtcg caaaccatcc ggcccggtac aaatcggcgc  13800
ggcgctgggt gatgacctgg tggagaagtt gaaggccgcg caggccgccc agcggcaacg  13860
catcgaggca gaagcacgcc ccggtgaatc gtggcaagcg gccgctgatc gaatccgcaa  13920
agaatcccgg caaccgccgg cagccggtgc gccgtcgatt aggaagccgc ccaagggcga  13980
cgagcaacca gattttttcg ttccgatgct ctatgacgtg ggcacccgcg atagtcgcag  14040
catcatggac gtggccgttt tccgtctgtc gaagcgtgac cgacgagctg gcgaggtgat  14100
ccgctacgag cttccagacg ggcacgtaga ggtttccgca gggccggccg gcatggccag  14160
tgtgtgggat tacgacctgg tactgatggc ggtttcccat ctaaccgaat ccatgaaccg  14220
ataccgggaa gggaagggag acaagcccgg ccgcgtgttc cgtccacacg ttgcggacgt  14280
actcaagttc tgccggcgag ccgatggcgg aaagcagaaa gacgacctgg tagaaacctg  14340
cattcggtta aacaccacgc acgttgccat gcagcgtacg aagaaggcca agaacggccg  14400
cctggtgacg gtatccgagg gtgaagcctt gattagccgc tacaagatcg taaagagcga  14460
aaccgggcgg ccggagtaca tcgagatcga gctagctgat tggatgtacc gcgagatcac  14520
agaaggcaag aacccggacg tgctgacggt tcaccccgat tactttttga tcgatcccgg  14580
catcggccgt tttctctacc gcctggcacg ccgcgccgca ggcaaggcag aagccagatg  14640
gttgttcaag acgatctacg aacgcagtgg cagcgccgga gagttcaaga agttctgttt  14700
caccgtgcgc aagctgatcg ggtcaaatga cctgccggag tacgatttga aggaggaggc  14760
ggggcaggct ggcccgatcc tagtcatgcg ctaccgcaac ctgatcgagg gcgaagcatc  14820
cgccggttcc taatgtacgg agcagatgct agggcaaatt gccctagcag gggaaaaagg  14880
tcgaaaaggt ctctttcctg tggatagcac gtacattggg aacccaaagc cgtacattgg  14940
```

gaaccggaac ccgtacattg ggaacccaaa gccgtacatt gggaaccggt cacacatgta 15000
agtgactgat ataaaagaga aaaaaggcga tttttccgcc taaaactctt taaaacttat 15060
taaaactctt aaaacccgcc tggcctgtgc ataactgtct ggccagcgca cagccgaaga 15120
gctgcaaaaa gcgcctaccc ttcggtcgct gcgctcccta cgccccgccg cttcgcgtcg 15180
gcctatcgcg gccgctggcc gctcaaaaat ggctggccta cggccaggca atctaccagg 15240
gcgcggacaa gccgcgccgt cgccactcga ccgccggcgc tgaggtctgc ctcgtgaaga 15300
aggtgttgct gactcatacc aggcctgaat cgccccatca tccagccaga aagtgaggga 15360
gccacggttg atgagagctt tgttgtaggt ggaccagttg gtgattttga acttttgctt 15420
tgccacggaa cggtctgcgt tgtcgggaag atgcgtgatc tgatccttca actcagcaaa 15480
agttcgattt attcaacaaa gccgccgtcc cgtcaagtca gcgtaatgct ctgccagtgt 15540
tacaaccaat taaccaattc tgattagaaa aactcatcga gcatcaaatg aaactgcaat 15600
ttattcatat caggattatc aataccatat ttttgaaaaa gccgtttctg taatgaagga 15660
gaaaactcac cgaggcagtt ccataggatg gcaagatcct ggtatcggtc tgcgattccg 15720
actcgtccaa catcaataca acctattaat ttcccctcgt caaaaataag gttatcaagt 15780
gagaaatcac catgagtgac gactgaatcc ggtgagaatg gcaaaagctc tgcattaatg 15840
aatcggccaa cgcgcgggga gaggcggttt gcgtattggg cgctcttccg cttcctcgct 15900
cactgactcg ctgcgctcgg tcgttcggct gcggcgagcg gtatcagctc actcaaaggc 15960
ggtaatacgg ttatccacag aatcagggga taacgcagga aagaacatgt gagcaaaagg 16020
ccagcaaaag gccaggaacc gtaaaaaggc cgcgttgctg gcgtttttcc ataggctccg 16080
cccccctgac gagcatcaca aaaatcgacg ctcaagtcag aggtggcgaa acccgacagg 16140
actataaaga taccaggcgt ttccccctgg aagctccctc gtgcgctctc ctgttccgac 16200
cctgccgctt accggatacc tgtccgcctt tctcccttcg ggaagcgtgg cgctttctca 16260
tagctcacgc tgtaggtatc tcagttcggt gtaggtcgtt cgctccaagc tgggctgtgt 16320
gcacgaaccc cccgttcagc ccgaccgctg cgccttatcc ggtaactatc gtcttgagtc 16380
caacccggta agacacgact tatcgccact ggcagcagcc actggtaaca ggattagcag 16440
agcgaggtat gtaggcggtg ctacagagtt cttgaagtgg tggcctaact acggctacac 16500
tagaagaaca gtatttggta tctgcgctct gctgaagcca gttaccttcg gaaaaagagt 16560
tggtagctct tgatccggca aacaaaccac cgctggtagc ggtggttttt ttgtttgcaa 16620
gcagcagatt acgcgcagaa aaaaaggatc tcaagaagat cctttgatct tttctacggg 16680
gtctgacgct cagtggaacg aaaactcacg ttaagggatt ttggtcatga gattatcaaa 16740
aaggatcttc acctagatcc ttttgatccg gaatta 16776

<210> SEQ ID NO 38
<211> LENGTH: 17475
<212> TYPE: DNA
<213> ORGANISM: Artificial Sequence
<220> FEATURE:
<223> OTHER INFORMATION: vector 24094
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (330)..(2417)
<223> OTHER INFORMATION: prZmGRMZM2G471240-01
<220> FEATURE:

<221> NAME/KEY: gene
<222> LOCATION: (2420)..(7288)
<223> OTHER INFORMATION: cAmCyanCas9-01
<220> FEATURE:
<221> NAME/KEY: terminator
<222> LOCATION: (7295)..(8290)
<223> OTHER INFORMATION: tZmGRMZM2G471240-01
<220> FEATURE:
<221> NAME/KEY: promoter
<222> LOCATION: (8304)..(8678)
<223> OTHER INFORMATION: prOsU3-01
<220> FEATURE:
<221> NAME/KEY: misc_feature
<222> LOCATION: (8679)..(8784)
<223> OTHER INFORMATION: rsgRNAZmVLHP-02
<220> FEATURE:
<221> NAME/KEY: misc_feature
<222> LOCATION: (8680)..(8699)
<223> OTHER INFORMATION: ZmVLHP2 target
<220> FEATURE:
<221> NAME/KEY: misc_feature
<222> LOCATION: (8700)..(8711)
<223> OTHER INFORMATION: rCrRNA-01
<220> FEATURE:
<221> NAME/KEY: misc_feature
<222> LOCATION: (8716)..(8784)
<223> OTHER INFORMATION: rTracrRNA-01
<220> FEATURE:
<221> NAME/KEY: promoter
<222> LOCATION: (8795)..(10786)
<223> OTHER INFORMATION: prUbi1-04
<220> FEATURE:
<221> NAME/KEY: gene
<222> LOCATION: (10803)..(11981)
<223> OTHER INFORMATION: cPMI-09
<220> FEATURE:
<221> NAME/KEY: terminator
<222> LOCATION: (12004)..(12256)
<223> OTHER INFORMATION: tNOS-05-01
<220> FEATURE:
<221> NAME/KEY: misc_feature
<222> LOCATION: (12300)..(12429)
<223> OTHER INFORMATION: bNLB-03
<220> FEATURE:
<221> NAME/KEY: gene
<222> LOCATION: (12709)..(13497)
<223> OTHER INFORMATION: cSpec-03
<220> FEATURE:
<221> NAME/KEY: promoter
<222> LOCATION: (13592)..(13722)
<223> OTHER INFORMATION: prVirG-01
<220> FEATURE:
<221> NAME/KEY: gene
<222> LOCATION: (13797)..(14429)
<223> OTHER INFORMATION: cVirG-09
<220> FEATURE:
<221> NAME/KEY: gene
<222> LOCATION: (14459)..(15532)
<223> OTHER INFORMATION: cRepA-01
<220> FEATURE:
<221> NAME/KEY: misc_feature
<222> LOCATION: (15575)..(15979)
<223> OTHER INFORMATION: oVS1-02
<220> FEATURE:
<221> NAME/KEY: misc_feature
<222> LOCATION: (16657)..(17463)
<223> OTHER INFORMATION: oCOLE-06

<400> SEQUENCE: 38
attcctgtgg ttggcatgca catacaaatg gacgaacgga taaacctttt cacgcccttt 60
taaatatccg attattctaa taaacgctct tttctcttag gtttacccgc caatatatcc 120
tgtcaaacac tgatagttta aactgaaggc gggaaacgac aatctgatca tgagcggaga 180
attaagggag tcacgttatg acccccgccg atgacgcggg acaagccgtt ttacgtttgg 240
aactgacaga accgcaacgc tgcaggaatt ggccgcagcg gccatttaaa caaagcttgg 300

```
tacctcgcga atgcatctag atgggaccct atttgtactc attccatgtc tcataaactt    360
tgggcaccat ccatccaaca catccaatct aaacacacca aacgatgggg aatggaaaga    420
gcagtattcg attcaacaat ggcaaacaaa tatcactgaa ttagaccaag aataaaccta    480
attagacaac gacctcccaa ccatcattcg tcaggctgta aagaagataa agctgccttg    540
gggcatggat caagcagaac accagagatg aatccaaaca cacagaaaat cacgcgcgct    600
gtctacaatg acaacaagcc ccacatttca ttgcagtaca ctgggctaca aaggcacgta    660
caacaaagag ctagggaaac attgcggagg gcacgagaga gcagctaact tgacaatata    720
gcagactgag cttgcactgt tagcaggcga ggaagggaat catggggacg gagaatgggg    780
tccatgcccg cgaaggagaa ggcggacgcc gccacggtgg caccggcgca cgcgcacaca    840
gggaacccgc acaggcagcc aaggatgctg cctcgccatt gcgccggtcg tctctgccac    900
gctcctctct ctctcccgct gcatcgccgt ggatggggca agcagagagc agggactgcg    960
acgatctggg cggaggactc gccttggaga gcgcggacgc agacgggatt ctagggagag   1020
agcgaagacg gggcgcgcgc ggcgctcgcg cggcgtggtg gcggcgagat tagcgggggt   1080
ggggggaggg cggagccgtg gtgagggtgt ggacgccctc cttaccctct taagtagtag   1140
tagagatata atccgttcca aaatatccat ccgttcaatt tatatttcgt ttgatctttt   1200
taccctaaat ttgattgact catcttatta aaaaagttca taactattat taatctttat   1260
tgagatatca tttagcatat aatatacttt aagtgtggtt ttagattttt tttaaaaaaa   1320
aaaattcgca aaaattaaat gaaacgaccc aatcaaactt gaaaagtaaa actaattata   1380
aatttgaacg gaaggagtaa gaggatgttt gaatgtacta gagctaatag ttggttgctt   1440
taaaatttgc tagtagaatt agctagctaa taaatatcta gataactatt agctaatttg   1500
ctaaaacagc taatagttga actattagct agattgtttg gatgtattcg gctaatttta   1560
atggctaact attagctata gtacaatatt caaacacctc ctaattaaaa tggacaaata   1620
tctcttcttt tggtcccttg cgttagattt ttcatatctc cttatttagt ataaaagaat   1680
catcaaaaag tggacaaccc ctagtggaac accattttag tagtggttgc atgaaacctt   1740
tcgcgcacca gtttctatgt gtcactctaa aaatgggaca gcatgtacgt agtgcctata   1800
tatatacaag tcatctatcg ttgcctcctc agttcatcac taatcacact tattgtgccc   1860
tcgacgagta tctatagcta gctcattaat cgattcgggg gtgtgttgtc gaaggcggca   1920
ttggcgagct actcgtcgcg gcgtccaagc aatacctgta gcacgaaggc gatcgccggg   1980
agcgtggtcg gcgagcccgt cgtgctgggg cagagggtga cggtgctgac ggtggacggc   2040
ggcggcgtcc ggggtctcat cccgggaacc atcctcgcct tcctggaggc caggctgcag   2100
gagctggacg caccggaggc gaggctggcg gactacttcg actacatcgc cggaaccagc   2160
accggcggtc tcatcaccgc cttgctgacc gcgcccggca aggacaagcg gcctctctag   2220
gctgccaagg acatcaacca cttttacatc cataactgcc cgcgcatctt tcctcagaag   2280
tgagtccgat gctgccgcca ttgttcttgc atccatccag catcgtacgt acgtcctcta   2340
tacatctgcg gatcatcatg tgcgcatgtt tgtggcatgc atgcatgcat gtgagcagga   2400
gcaggcttgc gaaaaccccca tggccctgtc caacaagttc atcggcgacg acatgaagat   2460
gacctaccac atggacggct gcgtgaacgg ccactacttc accgtgaagg gcgagggcag   2520
cggcaagccc tacgagggca cccagacctc caccttcaag gtgaccatgg ccaacggcgg   2580
ccccctggcc ttctccttcg acatcctgtc caccgtgttc atgtacggca accgctgctt   2640
```

-continued

```
caccgcctac cccaccagca tgcccgacta cttcaagcag gccttccccg acggcatgtc   2700
ctacgagaga accttcacct acgaggacgg cggcgtggcc accgccagct gggagatcag   2760
cctgaagggc aactgcttcg agcacaagtc caccttccac ggcgtgaact tccccgccga   2820
cggccccgtg atggccaaga agaccaccgg ctgggacccc tccttcgaga agatgaccgt   2880
gtgcgacggc atcttgaagg gcgacgtgac cgccttcctg atgctgcagg gcggcggcaa   2940
ctacagatgc cagttccaca cctcctacaa gaccaagaag cccgtgacca tgccccccaa   3000
ccacgtggtg gagcaccgca tcgccagaac cgacctggac aagggcggca acagcgtgca   3060
gctgaccgag cacgccgtgg cccacatcac ctccgtggtg cccttcggcg gcggcggatc   3120
cgacaagaag tacagcatcg gcctggacat cggcaccaac agcgtgggct gggccgtgat   3180
caccgacgag tacaaggtgc cgagcaagaa gttcaaggtg ctgggcaaca ccgacaggca   3240
cagcatcaag aagaacctga tcggcgccct gctgttcgac agcggcgaga ccgccgaggc   3300
caccaggctg aagaggaccg ccaggaggag gtacaccagg aggaagaaca ggatctgcta   3360
cctgcaggag atcttcagca acgagatggc caaggtggac gacagcttct tccacaggct   3420
ggaggagagc ttcctggtgg aggaggacaa gaagcacgag aggcacccga tcttcggcaa   3480
catcgtggac gaggtggcct accacgagaa gtacccgacc atctaccacc tgaggaagaa   3540
gctggtggac agcaccgaca aggccgacct gaggctgatc tacctggccc tggcccacat   3600
gatcaagttc aggggccact tcctgatcga gggcgacctg aacccggaca acagcgacgt   3660
ggacaagctg ttcatccagc tggtgcagac ctacaaccag ctgttcgagg agaacccgat   3720
caacgccagc ggcgtggacg ccaaggccat cctgagcgcc aggctgagca agagcaggag   3780
gctggagaac ctgatcgccc agctgccggg cgagaagaag aacggcctgt tcggcaacct   3840
gatcgccctg agcctgggcc tgaccccgaa cttcaagagc aacttcgacc tggccgagga   3900
cgccaagctg cagctgagca aggacaccta cgacgacgac ctggacaacc tgctggccca   3960
gatcggcgac cagtacgccg acctgttcct ggccgccaag aacctgagcg acgccatcct   4020
gctgagcgac atcctgaggg tgaacaccga gatcaccaag gccccgctga gcgccagcat   4080
gatcaagagg tacgacgagc accaccagga cctgaccctg ctgaaggccc tggtgaggca   4140
gcagctgccg gagaagtaca aggagatctt cttcgaccag agcaagaacg gctacgccgg   4200
ctacatcgac ggcggcgcca gccaggagga gttctacaag ttcatcaagc cgatcctgga   4260
gaagatggac ggcaccgagg agctgctggt gaagctgaac agggaggacc tgctgaggaa   4320
gcagaggacc ttcgacaacg gcagcatccc gcaccagatc cacctgggcg agctgcacgc   4380
catcctgagg aggcaggagg acttctaccc gttcctgaag gacaacaggg agaagatcga   4440
gaagatcctg accttccgca tcccgtacta cgtgggcccg ctggccaggg gcaacagcag   4500
gttcgcctgg atgaccagga agagcgagga gaccatcacc ccgtggaact tcgaggaggt   4560
ggtggacaag ggcgccagcg cccagagctt catcgagagg atgaccaact tcgacaagaa   4620
cctgccgaac gagaaggtgc tgccgaagca cagcctgctg tacgagtact tcaccgtgta   4680
caacgagctg accaaggtga agtacgtgac cgagggcatg aggaagccgg ccttcctgag   4740
cggcgagcag aagaaggcca tcgtggacct gctgttcaag accaacagga aggtgaccgt   4800
gaagcagctg aaggaggact acttcaagaa gatcgagtgc ttcgacagcg tggagatcag   4860
cggcgtggag gacaggttca acgccagcct gggcacctac cacgacctgc tgaagatcat   4920
caaggacaag gacttcctgg acaacgagga gaacgaggac atcctggagg acatcgtgct   4980
gaccctgacc ctgttcgagg acagggagat gatcgaggag aggctgaaga cctacgccca   5040
```

```
cctgttcgac gacaaggtga tgaagcagct gaagaggagg aggtacaccg gctggggcag   5100
gctgagcagg aagctgatca acggcatcag ggacaagcag agcggcaaga ccatcctgga   5160
cttcctgaag agcgacggct tcgccaacag gaacttcatg cagctgatcc acgacgacag   5220
cctgaccttc aaggaggaca tccagaaggc ccaggtgagc ggccagggcg acagcctgca   5280
cgagcacatc gccaacctgg ccggcagccc ggccatcaag aagggcatcc tgcagaccgt   5340
gaaggtggtg gacgagctgg tgaaggtgat gggcaggcac aagccggaga acatcgtgat   5400
cgagatggcc agggagaacc agaccaccca gaagggccag aagaacagca gggagaggat   5460
gaagaggatc gaggagggca tcaaggagct gggcagccag atcctgaagg agcacccggt   5520
ggagaacacc cagctgcaga acgagaagct gtacctgtac tacctgcaga acggcaggga   5580
catgtacgtg gaccaggagc tggacatcaa caggctgagc gactacgacg tggaccacat   5640
cgtgccgcag agcttcctga aggacgacag catcgacaac aaggtgctga ccaggagcga   5700
caagaacagg ggcaagagcg acaacgtgcc gagcgaggag gtggtgaaga agatgaaaaa   5760
ctactggagg cagctgctga acgccaagct gatcacccag aggaagttcg acaacctgac   5820
caaggccgag aggggcggcc tgagcgagct ggacaaggcc ggcttcatta aaaggcagct   5880
ggtggagacc aggcagatca ccaagcacgt ggcccagatc ctggacagca ggatgaacac   5940
caagtacgac gagaacgaca agctgatcag ggaggtgaag gtgatcaccc tgaagagcaa   6000
gctggtgagc gacttcagga aggacttcca gttctacaag gtgagggaga tcaataatta   6060
ccaccacgcc cacgacgcct acctgaacgc cgtggtgggc accgccctga ttaaaaagta   6120
cccgaagctg gagagcgagt tcgtgtacgg cgactacaag gtgtacgacg tgaggaagat   6180
gatcgccaag agcgagcagg agatcggcaa ggccaccgcc aagtacttct tctacagcaa   6240
catcatgaac ttcttcaaga ccgagatcac cctggccaac ggcgagatca ggaagaggcc   6300
gctgatcgag accaacggcg agaccggcga gatcgtgtgg gacaagggca gggacttcgc   6360
caccgtgagg aaggtgctgt ccatgccgca ggtgaacatc gtgaagaaga ccgaggtgca   6420
gaccggcggc ttcagcaagg agagcatcct gccgaagagg aacagcgaca agctgatcgc   6480
caggaagaag gactgggacc cgaagaagta cggcggcttc gacagcccga ccgtggccta   6540
cagcgtgctg gtggtggcca aggtggagaa gggcaagagc aagaagctga agagcgtgaa   6600
ggagctggtg ggcatcacca tcatggagag gagcagcttc gagaagaacc cagtggactt   6660
cctggaggcc aagggctaca aggaggtgaa gaaggacctg atcattaaac tgccgaagta   6720
cagcctgttc gagctggaga acggcaggaa gaggatgctg gccagcgccg gcgagctgca   6780
gaagggcaac gagctggccc tgccgagcaa gtacgtgaac ttcctgtacc tggccagcca   6840
ctacgagaag ctgaagggca gcccggagga caacgagcag aagcagctgt tcgtggagca   6900
gcacaagcac tacctggacg agatcatcga gcagatcagc gagttcagca agagggtgat   6960
cctggccgac gccaacctgg acaaggtgct gagcgcctac aacaagcaca gggacaagcc   7020
gatcagggag caggccgaga acatcatcca cctgttcacc ctgaccaacc tgggcgcccc   7080
ggccgccttc aagtacttcg acaccaccat cgacaggaag aggtacacca gcaccaagga   7140
ggtgctggac gccaccctga tccaccagag catcaccggc ctgtacgaga ccaggatcga   7200
cctgagccag ctgggcggcg acagcagccc gccgaagaag aagaggaagg tgagctggaa   7260
ggacgccagc ggctggagca ggatgtgacc atgggacaag tggctttact gtcagtcaca   7320
tgcttgtaaa taagtagact ttattttaat aaaacataaa aatatatata tgttcttgaa   7380
```

tataaaattg ataaccaaat taaaattcga accatcactt atacataatt ttactttatt 7440
ttttataaaa cgtgaacggg aaggactacc gtgaatgact atagaaccaa tcatactagt 7500
ataaaatata tgatgacact acgggagaga caaactttgt ctggcgctaa atattttgcc 7560
gagtgtgaat tcacgggcac taggcaaaga tcttctttgc cgagtgttac gctgggcaaa 7620
gtaagacact aggtaaatca gtcatttgcc gagtgtccgc cactaggcaa agcaaaacac 7680
tggcaaatca aaagtttacc tagtgccaga cactaggcaa aaaaaaaacg ctcggcaaat 7740
cggaagtttc cctagtgcca gacactagac aaagaaaaac acttgataaa ctagcgtcgt 7800
cagctaacac catccaccaa ccgttaacgt tgccgagtat ctgacttcga cactcggcaa 7860
agaaggtctc tttgcctagt gtcggtctgg aacactaggc aaagaggcac tttacctagt 7920
gtcgtatttt gacactcagt aaaataattt tttttcttc tgcttccaaa ctttttatga 7980
tgtgttccta tagcacctag aactacatgt caagttttgg taaaattttt gaagtttttg 8040
ctatatttac ttaatttatt ttatttaatt gaatttcttt tgataattca aatttgaact 8100
cggcaaggta agaagcgagg gtagcctgga aacacacttt gcctagtgtt acactcggta 8160
caggagcctc ccctgcctag tgctgcactc gacaaaagat tcgcctttgc ctagcgctgc 8220
actcggcaca ggagtcgcct ttgcctagtg ctgcactagg caaagcctcc gttaccgtgc 8280
cttccatcgt cggacccttc gaagggatct ttaaacatac gaacagatca cttaaagttc 8340
ttctgaagca acttaaagtt atcaggcatg catggatctt ggaggaatca gatgtgcagt 8400
cagggaccat agcacaggac aggcgtcttc tactggtgct accagcaaat gctggaagcc 8460
gggaacactg ggtacgttgg aaaccacgtg atgtggagta agataaactg taggagaaaa 8520
gcatttcgta gtgggccatg aagcctttca ggacatgtat tgcagtatgg gccggcccat 8580
tacgcaattg gacgacaaca aagactagta ttagtaccac ctcggctatc cacatagatc 8640
aaagctggtt taaaagagtt gtgcagatga tccgtggcag ctggagctga gcttccgggg 8700
ttttagagct agaaatagca agttaaaata aggctagtcc gttatcaact tgaaaaagtg 8760
gcaccgagtc ggtgcttttt ttttcggacc gcgcctgcag tgcagcgtga cccggtcgtg 8820
cccctctcta gagataatga gcattgcatg tctaagttat aaaaaattac cacatatttt 8880
ttttgtcaca cttgtttgaa gtgcagttta tctatcttta tacatatatt taaactttac 8940
tctacgaata atataatcta tagtactaca ataatatcag tgttttagag aatcatataa 9000
atgaacagtt agacatggtc taaaggacaa ttgagtattt tgacaacagg actctacagt 9060
tttatctttt tagtgtgcat gtgttctcct ttttttttgc aaatagcttc acctatataa 9120
tacttcatcc attttattag tacatccatt tagggtttag ggttaatggt ttttatagac 9180
taattttttt agtacatcta ttttattcta ttttagcctc taaattaaga aaactaaaac 9240
tctattttag tttttttatt taataattta gatataaaat agaataaaat aaagtgacta 9300
aaaattaaac aaataccctt taagaaatta aaaaaactaa ggaaacattt ttcttgtttc 9360
gagtagataa tgccagcctg ttaaacgccg tcgacgagtc taacggacac caaccagcga 9420
accagcagcg tcgcgtcggg ccaagcgaag cagacggcac ggcatctctg tcgctgcctc 9480
tggacccctc tcgagagttc cgctccaccg ttggacttgc tccgctgtcg gcatccagaa 9540
attgcgtggc ggagcggcag acgtgagccg gcacggcagg cggcctcctc ctcctctcac 9600
ggcaccggca gctacggggg attcctttcc caccgctcct tcgctttccc ttcctcgccc 9660
gccgtaataa atagacaccc cctccacacc ctctttcccc aacctcgtgt tgttcggagc 9720
gcacacacac acaaccagat ctcccccaaa tccacccgtc ggcacctccg cttcaaggta 9780

-continued

```
cgccgctcgt cctccccccc cccctctct accttctcta gatcggcgtt ccggtccatg   9840
gttagggccc ggtagttcta cttctgttca tgtttgtgtt agatccgtgt ttgtgttaga   9900
tccgtgctgc tagcgttcgt acacggatgc gacctgtacg tcagacacgt tctgattgct   9960
aacttgccag tgtttctctt tggggaatcc tgggatggct ctagccgttc cgcagacggg  10020
atcgatttca tgattttttt tgtttcgttg catagggttt ggtttgccct tttcctttat  10080
ttcaatatat gccgtgcact tgtttgtcgg gtcatctttt catgcttttt tttgtcttgg  10140
ttgtgatgat gtggtctggt tgggcggtcg ttctagatcg gagtagaatt ctgtttcaaa  10200
ctacctggtg gatttattaa ttttggatct gtatgtgtgt gccatacata ttcatagtta  10260
cgaattgaag atgatggatg gaaatatcga tctaggatag gtatacatgt tgatgcgggt  10320
tttactgatg catatacaga gatgcttttt gttcgcttgg ttgtgatgat gtggtgtggt  10380
tgggcggtcg ttcattcgtt ctagatcgga gtagaatact gtttcaaact acctggtgta  10440
tttattaatt ttggaactgt atgtgtgtgt catacatctt catagttacg agtttaagat  10500
ggatggaaat atcgatctag gataggtata catgttgatg tgggttttac tgatgcatat  10560
acatgatggc atatgcagca tctattcata tgctctaacc ttgagtacct atctattata  10620
ataaacaagt atgttttata attattttga tcttgatata cttggatgat ggcatatgca  10680
gcagctatat gtggattttt ttagccctgc cttcatacgc tatttatttg cttggtactg  10740
tttcttttgt cgatgctcac cctgttgttt ggtgttactt ctgcagggat ccggcagcag  10800
ccatgcagaa gctgatcaac agcgtgcaga actacgcctg ggcagcaag accgccctga  10860
ccgagctgta cggcatggag aaccccagca gccagcccat ggccgagctg tggatgggcg  10920
cccaccccaa gagcagcagc cgcgtgcaga acgccgccgg cgacatcgtg agcctgcgcg  10980
acgtgatcga gagcgacaag agcaccctgc tgggcgaggc cgtggccaag cgcttcggcg  11040
agctgccctt cctgttcaag gtgctgtgcg ccgcccagcc cctgagcatc caggtgcacc  11100
ccaacaagca caacagcgag atcggcttcg ccaaggagaa cgccgccggc atccccatgg  11160
acgccgccga gcgcaactac aaggacccca accacaagcc cgagctggtg ttcgccctga  11220
ccccccttcct ggccatgaac gccttccgcg agttcagcga gatcgtgagc ctgctgcagc  11280
ccgtggccgg cgcccacccc gccatcgccc acttcctgca gcagcccgac gccgagcgcc  11340
tgagcgagct gttcgccagc ctgctgaaca tgcagggcga ggagaagagc cgcgccctgg  11400
ccatcctgaa gagcgccctg gacagccagc agggcgagcc ctggcagacc atccgcctga  11460
tcagcgagtt ctaccccgag gacagcggcc tgttcagccc cctgctgctg aacgtggtga  11520
agctgaaccc cggcgaggcc atgttcctgt tcgccgagac cccccacgcc tacctgcagg  11580
gcgtggccct ggaggtgatg gccaacagcg acaacgtgct gcgcgccggc ctgacccccca  11640
agtacatcga catccccgag ctggtggcca acgtgaagtt cgaggccaag cccgccaacc  11700
agctgctgac ccagcccgtg aagcagggcg ccgagctgga cttccccatc cccgtggacg  11760
acttcgcctt cagcctgcac gacctgagcg acaaggagac caccatcagc cagcagagcg  11820
ccgccatcct gttctgcgtg gagggcgacg ccaccctgtg gaagggcagc cagcagctgc  11880
agctgaagcc cggcgagagc gccttcatcg ccgccaacga gagcccccgtg accgtgaagg  11940
gccacggccg cctggcccgc gtgtacaaca agctgtgata ggagctcgat ccgtcgacct  12000
gcagatcgtt caaacatttg gcaataaagt ttcttaagat tgaatcctgt tgccggtctt  12060
gcgatgatta tcatataatt tctgttgaat tacgttaagc atgtaataat taacatgtaa  12120
```

-continued tgcatgacgt tatttatgag atgggttttt atgattagag tcccgcaatt atacatttaa 12180
tacgcgatag aaaacaaaat atagcgcgca aactaggata aattatcgcg cgcggtgtca 12240
tctatgttac tagatcggcg cgccgcaatt gaagtttggg cggccagcat ggccgtatcc 12300
gcaatgtgtt attaagttgt ctaagcgtca atttgtttac accacaatat atcctgccac 12360
cagccagcca acagctcccc gaccggcagc tcggcacaaa atcaccactc gatacaggca 12420
gcccatcaga attaattctc atgtttgaca gcttatcatc gactgcacgg tgcaccaatg 12480
cttctggcgt caggcagcca tcggaagctg tggtatggct gtgcaggtcg taaatcactg 12540
cataattcgt gtcgctcaag gcgcactccc gttctggata atgttttttg cgccgacatc 12600
ataacggttc tggcaaatat tctgaaatga gctgttgaca attaatcatc cggctcgtat 12660
aatgtgtgga attgtgagcg gataacaatt tcacacagga aacagaccat gagggaagcg 12720
ttgatcgccg aagtatcgac tcaactatca gaggtagttg gcgtcatcga gcgccatctc 12780
gaaccgacgt tgctggccgt acatttgtac ggctccgcag tggatggcgg cctgaagcca 12840
cacagtgata ttgatttgct ggttacggtg accgtaaggc ttgatgaaac aacgcggcga 12900
gctttgatca acgacctttt ggaaacttcg gcttcccctg gagagagcga gattctccgc 12960
gctgtagaag tcaccattgt tgtgcacgac gacatcattc cgtggcgtta tccagctaag 13020
cgcgaactgc aatttggaga atggcagcgc aatgacattc ttgcaggtat cttcgagcca 13080
gccacgatcg acattgatct ggctatcttg ctgacaaaag caagagaaca tagcgttgcc 13140
ttggtaggtc cagcggcgga ggaactcttt gatccggttc ctgaacagga tctatttgag 13200
gcgctaaatg aaaccttaac gctatggaac tcgccgcccg actgggctgg cgatgagcga 13260
aatgtagtgc ttacgttgtc ccgcatttgg tacagcgcag taaccggcaa aatcgcgccg 13320
aaggatgtcg ctgccgactg ggcaatggag cgcctgccgg cccagtatca gcccgtcata 13380
cttgaagcta ggcaggctta tcttggacaa gaagatcgct tggcctcgcg cgcagatcag 13440
ttggaagaat ttgttcacta cgtgaaaggc gagatcacca aagtagtcgg caaataaagc 13500
tctagtggat ctccgtaccc ggggatctgg ctcgcggcgg acgcacgacg ccggggcgag 13560
accataggcg atctcctaaa tcaatagtag ctgtaacctc gaagcgtttc acttgtaaca 13620
acgattgaga atttttgtca taaaattgaa atacttggtt cgcatttttg tcatccgcgg 13680
tcagccgcaa ttctgacgaa ctgcccattt agctggagat gattgtacat ccttcacgtg 13740
aaaatttctc aagcgctgtg aacaagggtt cagattttag attgaaaggt gagccgttga 13800
aacacgttct tcttgtcgat gacgacgtcg ctatgcggca tcttattatt gaatacctta 13860
cgatccacgc cttcaaagtg accgcggtag ccgacagcac ccagttcaca agagtactct 13920
cttccgcgac ggtcgatgtc gtggttgttg atctagattt aggtcgtgaa gatgggctcg 13980
agctaggagc aagtgatttt atcgctaagc cgttcagtat cagagagttt ctagcacgca 14040
ttcgggttgc cttgcgcgtg cgccccaacg ttgtccgctc caaagaccga cggtcttttt 14100
gttttactga ctggacactt aatctcaggc aacgtcgctt gatgtccgaa gctggcggtg 14160
aggtgaaact tacggcaggt gagttcaatc ttctcctcgc gtttttagag aaaccccgcg 14220
acgttctatc gcgcgagcaa cttctcattg ccagtcgagt acgcgacgag gaggtttatg 14280
acaggagtat agatgttctc attttgaggc tgcgccgcaa acttgaggca gatccgtcaa 14340
gccctcaact gataaaaaca gcaagaggtg ccggttattt ctttgacgcg gacgtgcagg 14400
tttcgcacgg ggggacgatg gcagcctgag ccaattccca gatccccgag gaatcggcgt 14460
gagcggtcgc aaaccatccg gcccggtaca aatcggcgcg gcgctgggtg atgacctggt 14520
ggagaagttg aaggccgcgc aggccgccca gcggcaacgc atcgaggcag aagcacgccc 14580
cggtgaatcg tggcaagcgg ccgctgatcg aatccgcaaa gaatcccggc aaccgccggc 14640
agccggtgcg ccgtcgatta ggaagccgcc caagggcgac gagcaaccag atttttcgt 14700
tccgatgctc tatgacgtgg gcacccgcga tagtcgcagc atcatggacg tggccgtttt 14760
ccgtctgtcg aagcgtgacc gacgagctgg cgaggtgatc cgctacgagc ttccagacgg 14820
gcacgtagag gtttccgcag ggccggccgg catggccagt gtgtgggatt acgacctggt 14880
actgatggcg gtttcccatc taaccgaatc catgaaccga taccgggaag ggaagggaga 14940
caagcccggc cgcgtgttcc gtccacacgt tgcggacgta ctcaagttct gccggcgagc 15000
cgatggcgga aagcagaaag acgacctggt agaaacctgc attcggttaa acaccacgca 15060
cgttgccatg cagcgtacga agaaggccaa gaacggccgc ctggtgacgg tatccgaggg 15120
tgaagccttg attagccgct acaagatcgt aaagagcgaa accgggcggc cggagtacat 15180
cgagatcgag ctagctgatt ggatgtaccg cgagatcaca gaaggcaaga acccggacgt 15240
gctgacggtt caccccgatt actttttgat cgatcccggc atcggccgtt ttctctaccg 15300
cctggcacgc cgcgccgcag gcaaggcaga agccagatgg ttgttcaaga cgatctacga 15360
acgcagtggc agcgccggag agttcaagaa gttctgtttc accgtgcgca agctgatcgg 15420
gtcaaatgac ctgccggagt acgatttgaa ggaggaggcg gggcaggctg gcccgatcct 15480
agtcatgcgc taccgcaacc tgatcgaggg cgaagcatcc gccggttcct aatgtacgga 15540
gcagatgcta gggcaaattg ccctagcagg ggaaaaaggt cgaaaaggtc tctttcctgt 15600
ggatagcacg tacattggga acccaaagcc gtacattggg aaccggaacc cgtacattgg 15660
gaacccaaag ccgtacattg ggaaccggtc acacatgtaa gtgactgata taaaagagaa 15720
aaaaggcgat ttttccgcct aaaactcttt aaaacttatt aaaactctta aaacccgcct 15780
ggcctgtgca taactgtctg gccagcgcac agccgaagag ctgcaaaaag cgcctaccct 15840
tcggtcgctg cgctccctac gccccgccgc ttcgcgtcgg cctatcgcgg ccgctggccg 15900
ctcaaaaatg gctggcctac ggccaggcaa tctaccaggg cgcggacaag ccgcgccgtc 15960
gccactcgac cgccggcgct gaggtctgcc tcgtgaagaa ggtgttgctg actcatacca 16020
ggcctgaatc gccccatcat ccagccagaa agtgagggag ccacggttga tgagagcttt 16080
gttgtaggtg gaccagttgg tgattttgaa cttttgcttt gccacggaac ggtctgcgtt 16140
gtcgggaaga tgcgtgatct gatccttcaa ctcagcaaaa gttcgattta ttcaacaaag 16200
ccgccgtccc gtcaagtcag cgtaatgctc tgccagtgtt acaaccaatt aaccaattct 16260
gattagaaaa actcatcgag catcaaatga aactgcaatt tattcatatc aggattatca 16320
ataccatatt tttgaaaaag ccgtttctgt aatgaaggag aaaactcacc gaggcagttc 16380
cataggatgg caagatcctg gtatcggtct gcgattccga ctcgtccaac atcaatacaa 16440
cctattaatt tcccctcgtc aaaaataagg ttatcaagtg agaaatcacc atgagtgacg 16500
actgaatccg gtgagaatgg caaaagctct gcattaatga atcggccaac gcgcggggag 16560
aggcggtttg cgtattgggc gctcttccgc ttcctcgctc actgactcgc tgcgctcggt 16620
cgttcggctg cggcgagcgg tatcagctca ctcaaaggcg gtaatacggt tatccacaga 16680
atcaggggat aacgcaggaa agaacatgtg agcaaaaggc cagcaaaagg ccaggaaccg 16740
taaaaaggcc gcgttgctgg cgtttttcca taggctccgc ccccctgacg agcatcacaa 16800
aaatcgacgc tcaagtcaga ggtggcgaaa cccgacagga ctataaagat accaggcgtt 16860
tccccctgga agctccctcg tgcgctctcc tgttccgacc ctgccgctta ccggatacct 16920
gtccgccttt ctcccttcgg gaagcgtggc gctttctcat agctcacgct gtaggtatct 16980
cagttcggtg taggtcgttc gctccaagct gggctgtgtg cacgaacccc ccgttcagcc 17040
cgaccgctgc gccttatccg gtaactatcg tcttgagtcc aacccggtaa gacacgactt 17100
atcgccactg gcagcagcca ctggtaacag gattagcaga gcgaggtatg taggcggtgc 17160
tacagagttc ttgaagtggt ggcctaacta cggctacact agaagaacag tatttggtat 17220
ctgcgctctg ctgaagccag ttaccttcgg aaaaagagtt ggtagctctt gatccggcaa 17280
acaaaccacc gctggtagcg gtggtttttt tgtttgcaag cagcagatta cgcgcagaaa 17340
aaaaggatct caagaagatc ctttgatctt ttctacgggg tctgacgctc agtggaacga 17400
aaactcacgt taagggattt tggtcatgag attatcaaaa aggatcttca cctagatcct 17460
tttgatccgg aatta 17475

<210> SEQ ID NO 39
<211> LENGTH: 19
<212> TYPE: DNA
<213> ORGANISM: Artificial Sequence
<220> FEATURE:
<223> OTHER INFORMATION: primer

<400> SEQUENCE: 39
ttgtgctgct ccacgaaca 19

<210> SEQ ID NO 40
<211> LENGTH: 20
<212> TYPE: DNA
<213> ORGANISM: artificial sequence
<220> FEATURE:
<223> OTHER INFORMATION: primer

<400> SEQUENCE: 40
gccagccact acgagaagct 20

<210> SEQ ID NO 41
<211> LENGTH: 24
<212> TYPE: DNA
<213> ORGANISM: Artificial Sequence
<220> FEATURE:
<223> OTHER INFORMATION: probe

<400> SEQUENCE: 41
ctgcttctgc tcgttgtcct ccgg 24

<210> SEQ ID NO 42
<211> LENGTH: 17
<212> TYPE: DNA
<213> ORGANISM: Artificial Sequence
<220> FEATURE:
<223> OTHER INFORMATION: promer

<400> SEQUENCE: 42
gcggatgctg gcacagc 17

<210> SEQ ID NO 43
<211> LENGTH: 19
<212> TYPE: DNA
<213> ORGANISM: Artificial Sequence
<220> FEATURE:
<223> OTHER INFORMATION: primer

<400> SEQUENCE: 43
ggcattgctt ccttctccg 19

<210> SEQ ID NO 44
<211> LENGTH: 15
<212> TYPE: DNA
<213> ORGANISM: Artificial Sequence
<220> FEATURE:
<223> OTHER INFORMATION: probe

<400> SEQUENCE: 44
cagggagcga ggtac 15

<210> SEQ ID NO 45
<211> LENGTH: 20
<212> TYPE: DNA
<213> ORGANISM: Artificial Sequence
<220> FEATURE:
<223> OTHER INFORMATION: primer

<400> SEQUENCE: 45
ctggtggcca acgtgaagtt 20

<210> SEQ ID NO 46
<211> LENGTH: 17
<212> TYPE: DNA
<213> ORGANISM: Artificial Sequence
<220> FEATURE:
<223> OTHER INFORMATION: primer

<400> SEQUENCE: 46
gcttcacggg ctgggtc 17

<210> SEQ ID NO 47
<211> LENGTH: 20
<212> TYPE: DNA
<213> ORGANISM: Artificial Sequence
<220> FEATURE:
<223> OTHER INFORMATION: probe

<400> SEQUENCE: 47
aggccaagcc cgccaaccag 20

<210> SEQ ID NO 48
<211> LENGTH: 17
<212> TYPE: DNA
<213> ORGANISM: Artificial Sequence
<220> FEATURE:
<223> OTHER INFORMATION: primer

<400> SEQUENCE: 48
gcggatgctg gcacaga 17

<210> SEQ ID NO 49
<211> LENGTH: 18
<212> TYPE: DNA
<213> ORGANISM: Artificial Sequence
<220> FEATURE:
<223> OTHER INFORMATION: primer

<400> SEQUENCE: 49
gcattgcttc cttcgcca 18

<210> SEQ ID NO 50
<211> LENGTH: 16
<212> TYPE: DNA

<213> ORGANISM: Artificial Sequence
<220> FEATURE:
<223> OTHER INFORMATION: probe

<400> SEQUENCE: 50
cagggaggta cgaacc 16

<210> SEQ ID NO 51
<211> LENGTH: 16
<212> TYPE: DNA
<213> ORGANISM: Artificial Sequence
<220> FEATURE:
<223> OTHER INFORMATION: primer

<400> SEQUENCE: 51
gcggcgaaga agcgaa 16

<210> SEQ ID NO 52
<211> LENGTH: 17
<212> TYPE: DNA
<213> ORGANISM: Artificial Sequence
<220> FEATURE:
<223> OTHER INFORMATION: primer

<400> SEQUENCE: 52
gcggcgtctc cagcttc 17

<210> SEQ ID NO 53
<211> LENGTH: 12
<212> TYPE: DNA
<213> ORGANISM: Artificial Sequence
<220> FEATURE:
<223> OTHER INFORMATION: probe

<400> SEQUENCE: 53
ccaggaactg cg 12

<210> SEQ ID NO 54
<211> LENGTH: 18
<212> TYPE: DNA
<213> ORGANISM: Artificial Sequence
<220> FEATURE:
<223> OTHER INFORMATION: primer

<400> SEQUENCE: 54
aagaaacgcc ggctgagt 18

<210> SEQ ID NO 55
<211> LENGTH: 15
<212> TYPE: DNA
<213> ORGANISM: Artificial Sequence
<220> FEATURE:
<223> OTHER INFORMATION: primer

<400> SEQUENCE: 55
accttgcggg gcgtt 15

<210> SEQ ID NO 56
<211> LENGTH: 12
<212> TYPE: DNA
<213> ORGANISM: Artificial Sequence
<220> FEATURE:
<223> OTHER INFORMATION: probe

<400> SEQUENCE: 56
ccaggaactg cg 12

<210> SEQ ID NO 57
<211> LENGTH: 18
<212> TYPE: DNA
<213> ORGANISM: Artificial Sequence
<220> FEATURE:
<223> OTHER INFORMATION: primer

<400> SEQUENCE: 57
aagaaacgcc ggctgagt 18

<210> SEQ ID NO 58
<211> LENGTH: 14
<212> TYPE: DNA
<213> ORGANISM: Artificial Sequence
<220> FEATURE:
<223> OTHER INFORMATION: primer

<400> SEQUENCE: 58
ccttgcgcgg cgtc 14

<210> SEQ ID NO 59
<211> LENGTH: 12
<212> TYPE: DNA
<213> ORGANISM: Artificial Sequence
<220> FEATURE:
<223> OTHER INFORMATION: probe

<400> SEQUENCE: 59
ccaggaactg cg 12

<210> SEQ ID NO 60
<211> LENGTH: 19
<212> TYPE: DNA
<213> ORGANISM: Artificial Sequence
<220> FEATURE:
<223> OTHER INFORMATION: primer

<400> SEQUENCE: 60
tgatcctcga ggccaagct 19

<210> SEQ ID NO 61
<211> LENGTH: 18
<212> TYPE: DNA
<213> ORGANISM: Artificial Sequence
<220> FEATURE:
<223> OTHER INFORMATION: primer

<400> SEQUENCE: 61
aggtcgaggt cccctcca 18

<210> SEQ ID NO 62
<211> LENGTH: 14
<212> TYPE: DNA
<213> ORGANISM: Artificial Sequence
<220> FEATURE:
<223> OTHER INFORMATION: probe

<400> SEQUENCE: 62
cctgctaccc gggc 14

<210> SEQ ID NO 63
<211> LENGTH: 15
<212> TYPE: DNA
<213> ORGANISM: Artificial Sequence
<220> FEATURE:

<223> OTHER INFORMATION: primer

<400> SEQUENCE: 63
cgcgccctgc taccc 15

<210> SEQ ID NO 64
<211> LENGTH: 17
<212> TYPE: DNA
<213> ORGANISM: Artificial Sequence
<220> FEATURE:
<223> OTHER INFORMATION: primer

<400> SEQUENCE: 64
gcgcgtgctt accagga 17

<210> SEQ ID NO 65
<211> LENGTH: 13
<212> TYPE: DNA
<213> ORGANISM: Artificial Sequence
<220> FEATURE:
<223> OTHER INFORMATION: probe

<400> SEQUENCE: 65
tcgaggagtg ccc 13

<210> SEQ ID NO 66
<211> LENGTH: 16
<212> TYPE: DNA
<213> ORGANISM: Artificial Sequence
<220> FEATURE:
<223> OTHER INFORMATION: primer

<400> SEQUENCE: 66
caccgatgag caggcg 16

<210> SEQ ID NO 67
<211> LENGTH: 18
<212> TYPE: DNA
<213> ORGANISM: Artificial Sequence
<220> FEATURE:
<223> OTHER INFORMATION: primer

<400> SEQUENCE: 67
agatacacct tccggccg 18

<210> SEQ ID NO 68
<211> LENGTH: 14
<212> TYPE: DNA
<213> ORGANISM: Artificial Sequence
<220> FEATURE:
<223> OTHER INFORMATION: probe

<400> SEQUENCE: 68
ttcctcccgg aagc 14

<210> SEQ ID NO 69
<211> LENGTH: 16
<212> TYPE: DNA
<213> ORGANISM: Artificial Sequence
<220> FEATURE:
<223> OTHER INFORMATION: primer

<400> SEQUENCE: 69
caccgatgag caggcg 16

<210> SEQ ID NO 70
<211> LENGTH: 20
<212> TYPE: DNA
<213> ORGANISM: Artificial Sequence
<220> FEATURE:
<223> OTHER INFORMATION: primer

<400> SEQUENCE: 70
agatacacct tccggccagt 20

<210> SEQ ID NO 71
<211> LENGTH: 14
<212> TYPE: DNA
<213> ORGANISM: Artificial Sequence
<220> FEATURE:
<223> OTHER INFORMATION: probe

<400> SEQUENCE: 71
ctcctcccgg aagc 14

<210> SEQ ID NO 72
<211> LENGTH: 25
<212> TYPE: DNA
<213> ORGANISM: Artificial Sequence
<220> FEATURE:
<223> OTHER INFORMATION: primer

<400> SEQUENCE: 72
caagtttctg gacaaggaga ttctc 25

<210> SEQ ID NO 73
<211> LENGTH: 27
<212> TYPE: DNA
<213> ORGANISM: Artificial Sequence
<220> FEATURE:
<223> OTHER INFORMATION: primer

<400> SEQUENCE: 73
aagaattccc ttcttaatag ctggaga 27

<210> SEQ ID NO 74
<211> LENGTH: 26
<212> TYPE: DNA
<213> ORGANISM: Artificial Sequence
<220> FEATURE:
<223> OTHER INFORMATION: probe

<400> SEQUENCE: 74
cacgagcaca ttgctaacct tgctgg 26

<210> SEQ ID NO 75
<211> LENGTH: 17
<212> TYPE: DNA
<213> ORGANISM: Artificial Sequence
<220> FEATURE:
<223> OTHER INFORMATION: primer

<400> SEQUENCE: 75
tcaccgatga gcaggca 17

<210> SEQ ID NO 76
<211> LENGTH: 18
<212> TYPE: DNA
<213> ORGANISM: Artificial Sequence
<220> FEATURE:
<223> OTHER INFORMATION: primer

<400> SEQUENCE: 76
atacaccttc cggccagc 18

<210> SEQ ID NO 77
<211> LENGTH: 14
<212> TYPE: DNA
<213> ORGANISM: Artificial Sequence
<220> FEATURE:
<223> OTHER INFORMATION: probe

<400> SEQUENCE: 77
ttcctcccgg aagc 14

<210> SEQ ID NO 78
<211> LENGTH: 24
<212> TYPE: DNA
<213> ORGANISM: Artificial Sequence
<220> FEATURE:
<223> OTHER INFORMATION: primer

<400> SEQUENCE: 78
gatagggcta aagagatgtg ggaa 24

<210> SEQ ID NO 79
<211> LENGTH: 26
<212> TYPE: DNA
<213> ORGANISM: Artificial Sequence
<220> FEATURE:
<223> OTHER INFORMATION: primer

<400> SEQUENCE: 79
ctttgttcac attagggctc aaataa 26

<210> SEQ ID NO 80
<211> LENGTH: 16
<212> TYPE: DNA
<213> ORGANISM: Artificial Sequence
<220> FEATURE:
<223> OTHER INFORMATION: probe

<400> SEQUENCE: 80
tagactgaga tggatg 16

<210> SEQ ID NO 81
<211> LENGTH: 20
<212> TYPE: DNA
<213> ORGANISM: Artificial Sequence
<220> FEATURE:
<223> OTHER INFORMATION: primer

<400> SEQUENCE: 81
aaaaccaccg gagaagacga 20

<210> SEQ ID NO 82
<211> LENGTH: 17
<212> TYPE: DNA
<213> ORGANISM: Artificial Sequence
<220> FEATURE:
<223> OTHER INFORMATION: primer

<400> SEQUENCE: 82
aggtgtggcg gcagtga 17

<210> SEQ ID NO 83
<211> LENGTH: 14

<212> TYPE: DNA
<213> ORGANISM: Artificial Sequence
<220> FEATURE:
<223> OTHER INFORMATION: probe

<400> SEQUENCE: 83
caccgtcatt gttc 14

<210> SEQ ID NO 84
<211> LENGTH: 25
<212> TYPE: DNA
<213> ORGANISM: Artificial Sequence
<220> FEATURE:
<223> OTHER INFORMATION: primer

<400> SEQUENCE: 84
caagtttctg gacaaggaga ttctc 25

<210> SEQ ID NO 85
<211> LENGTH: 27
<212> TYPE: DNA
<213> ORGANISM: Artificial Sequence
<220> FEATURE:
<223> OTHER INFORMATION: primer

<400> SEQUENCE: 85
aagaattccc ttcttaatag ctggaga 27

<210> SEQ ID NO 86
<211> LENGTH: 26
<212> TYPE: DNA
<213> ORGANISM: Artificial Sequence
<220> FEATURE:
<223> OTHER INFORMATION: probe

<400> SEQUENCE: 86
cacgagcaca ttgctaacct tgctgg 26

<210> SEQ ID NO 87
<211> LENGTH: 15
<212> TYPE: DNA
<213> ORGANISM: Artificial Sequence
<220> FEATURE:
<223> OTHER INFORMATION: primer

<400> SEQUENCE: 87
gcgacgccgg aaagg 15

<210> SEQ ID NO 88
<211> LENGTH: 21
<212> TYPE: DNA
<213> ORGANISM: Artificial Sequence
<220> FEATURE:
<223> OTHER INFORMATION: primer

<400> SEQUENCE: 88
tggcgtggtt tcgtcttctt a 21

<210> SEQ ID NO 89
<211> LENGTH: 25
<212> TYPE: DNA
<213> ORGANISM: Artificial Sequence
<220> FEATURE:
<223> OTHER INFORMATION: probe

<400> SEQUENCE: 89
aagagcggcg tctggaggtg actca 25

<210> SEQ ID NO 90
<211> LENGTH: 20
<212> TYPE: DNA
<213> ORGANISM: Artificial Sequence
<220> FEATURE:
<223> OTHER INFORMATION: primer

<400> SEQUENCE: 90
aaccgcatcg tcagaaaaac 20

<210> SEQ ID NO 91
<211> LENGTH: 20
<212> TYPE: DNA
<213> ORGANISM: Artificial Sequence
<220> FEATURE:
<223> OTHER INFORMATION: primer

<400> SEQUENCE: 91
tcaacttaac cggccaaatc 20

<210> SEQ ID NO 92
<211> LENGTH: 21
<212> TYPE: DNA
<213> ORGANISM: Artificial Sequence
<220> FEATURE:
<223> OTHER INFORMATION: primer

<400> SEQUENCE: 92
catcccttct cttccctcct g 21

<210> SEQ ID NO 93
<211> LENGTH: 23
<212> TYPE: DNA
<213> ORGANISM: Artificial Sequence
<220> FEATURE:
<223> OTHER INFORMATION: primer

<400> SEQUENCE: 93
gccagtgtga gtgtgtatga gca 23

<210> SEQ ID NO 94
<211> LENGTH: 21
<212> TYPE: DNA
<213> ORGANISM: Artificial Sequence
<220> FEATURE:
<223> OTHER INFORMATION: primer

<400> SEQUENCE: 94
catcgttttc tcccctcctc a 21

<210> SEQ ID NO 95
<211> LENGTH: 19
<212> TYPE: DNA
<213> ORGANISM: Artificial Sequence
<220> FEATURE:
<223> OTHER INFORMATION: primer

<400> SEQUENCE: 95
actgatatgc acggcgcca 19

<210> SEQ ID NO 96
<211> LENGTH: 22
<212> TYPE: DNA
<213> ORGANISM: Artificial Sequence
<220> FEATURE:
<223> OTHER INFORMATION: primer

<400> SEQUENCE: 96
tgcagtagct tcattttcac cg 22

<210> SEQ ID NO 97
<211> LENGTH: 22
<212> TYPE: DNA
<213> ORGANISM: Artificial Sequence
<220> FEATURE:
<223> OTHER INFORMATION: primer

<400> SEQUENCE: 97
aggaattgat atgtacgccc gt 22

<210> SEQ ID NO 98
<211> LENGTH: 16279
<212> TYPE: DNA
<213> ORGANISM: Artificial Sequence
<220> FEATURE:
<223> OTHER INFORMATION: vector 24075
<220> FEATURE:
<221> NAME/KEY: misc_feature
<222> LOCATION: (1)..(517)
<223> OTHER INFORMATION: bNRB-07
<220> FEATURE:
<221> NAME/KEY: promoter
<222> LOCATION: (538)..(1697)
<223> OTHER INFORMATION: prAtEFaA1-02
<220> FEATURE:
<221> NAME/KEY: gene
<222> LOCATION: (1716)..(5885)
<223> OTHER INFORMATION: cCas9-05
<220> FEATURE:
<221> NAME/KEY: mutation
<222> LOCATION: (5205)..(5207)
<223> OTHER INFORMATION: L to V mutation
<220> FEATURE:
<221> NAME/KEY: mutation
<222> LOCATION: (5250)..(5252)
<223> OTHER INFORMATION: I to V mutation
<220> FEATURE:
<221> NAME/KEY: terminator
<222> LOCATION: (5894)..(6146)
<223> OTHER INFORMATION: tNOS-05-01
<220> FEATURE:
<221> NAME/KEY: promoter
<222> LOCATION: (6173)..(6620)
<223> OTHER INFORMATION: prAtU6-01
<220> FEATURE:
<221> NAME/KEY: misc_feature
<222> LOCATION: (6621)..(6640)
<223> OTHER INFORMATION: AtGL1 target1
<220> FEATURE:
<221> NAME/KEY: misc_feature
<222> LOCATION: (6621)..(6725)
<223> OTHER INFORMATION: rsgRNA AtGL1-01
<220> FEATURE:
<221> NAME/KEY: misc_feature
<222> LOCATION: (6641)..(6652)
<223> OTHER INFORMATION: rCrRNA-01
<220> FEATURE:
<221> NAME/KEY: misc_feature
<222> LOCATION: (6657)..(6725)
<223> OTHER INFORMATION: rTracrRNA-01
<220> FEATURE:
<221> NAME/KEY: promoter
<222> LOCATION: (6726)..(7173)
<223> OTHER INFORMATION: prAtU6-01
<220> FEATURE:
<221> NAME/KEY: misc_feature
<222> LOCATION: (7174)..(7193)
<223> OTHER INFORMATION: AtGl1 target 2
<220> FEATURE:

<221> NAME/KEY: misc_feature
<222> LOCATION: (7174)..(7278)
<223> OTHER INFORMATION: rsgRNA AtGL1-02
<220> FEATURE:
<221> NAME/KEY: misc_feature
<222> LOCATION: (7194)..(7205)
<223> OTHER INFORMATION: rCrRNA-01
<220> FEATURE:
<221> NAME/KEY: misc_feature
<222> LOCATION: (7210)..(7278)
<223> OTHER INFORMATION: rTracrRNA-01
<220> FEATURE:
<221> NAME/KEY: promoter
<222> LOCATION: (7295)..(7640)
<223> OTHER INFORMATION: prCMP-02
<220> FEATURE:
<221> NAME/KEY: gene
<222> LOCATION: (7653)..(8447)
<223> OTHER INFORMATION: cNpt2-10
<220> FEATURE:
<221> NAME/KEY: terminator
<222> LOCATION: (8476)..(8728)
<223> OTHER INFORMATION: tNOS-05-01
<220> FEATURE:
<221> NAME/KEY: promoter
<222> LOCATION: (8755)..(10752)
<223> OTHER INFORMATION: prGmUBI-01
<220> FEATURE:
<221> NAME/KEY: gene
<222> LOCATION: (10765)..(11454)
<223> OTHER INFORMATION: cAmCyan-06
<220> FEATURE:
<221> NAME/KEY: terminator
<222> LOCATION: (11477)..(12119)
<223> OTHER INFORMATION: tPsE9-01
<220> FEATURE:
<221> NAME/KEY: misc_feature
<222> LOCATION: (12193)..(12311)
<223> OTHER INFORMATION: bNLB-03
<220> FEATURE:
<221> NAME/KEY: gene
<222> LOCATION: (12928)..(13716)
<223> OTHER INFORMATION: cSpec-03
<220> FEATURE:
<221> NAME/KEY: gene
<222> LOCATION: (13751)..(14824)
<223> OTHER INFORMATION: cRepA-08
<220> FEATURE:
<221> NAME/KEY: misc_feature
<222> LOCATION: (14867)..(15271)
<223> OTHER INFORMATION: oVC1-04
<220> FEATURE:
<221> NAME/KEY: misc_feature
<222> LOCATION: (15441)..(16247)
<223> OTHER INFORMATION: oCOLE-06

<400> SEQUENCE: 98
gccaggacgt cggccgaaag agcgacaagc agatcacgct tttcgacagc gtcggatttg 60
cgatcgagga tttttcggcg ctgcgctacg tccgcgaccg cgttgaggga tcaagccaca 120
gcagcccact cgaccttcta gccgacccag acgagccaag ggatcttttt ggaatgctgc 180
tccgtcgtca ggctttccga cgtttgggtg gttgaacaga agtcattatc gcacggaatg 240
ccaagcactc ccgaggggaa ccctgtggtt ggcatgcaca tacaaatgga cgaacggata 300
aaccttttca cgccctttta aatatccgat tattctaata aacgctcttt tctcttaggt 360
ttacccgcca atatatcctg tcaaacactg atagtttaaa ctgaaggcgg gaaacgacaa 420
tctgatcatg agcggagaat taagggagtc acgttatgac ccccgccgat gacgcgggac 480
aagccgtttt acgtttggaa ctgacagaac cgcaacgttg aaggcgcgcc actcagcaag 540
cttgatatcg gaagtttctc tcttgaggga ggttgctcgt ggaatgggac acatatggtt 600
gttataataa accatttcca ttgtcatgag attttgaggt taatatatac tttacttgtt 660

```
cattatttta tttggtgttt gaataaatga tataaatggc tcttgataat ctgcattcat    720
tgagatatca aatatttact ctagagaaga gtgtcatata gattgatggt ccacaatcaa    780
tgaaattttt gggagacgaa catgtataac catttgcttg aataacctta attaaaaggt    840
gtgattaaat gatgtttgta acatgtagta ctaaacattc ataaaacaca accaacccaa    900
gaggtattga gtattcacgg ctaaacaggg gcataatggt aatttaaaga atgatattat    960
tttatgttaa accctaacat tggtttcgga ttcaacgcta taaataaaac cactctcgtt   1020
gctgattcca tttatcgttc ttattgaccc tagccgctac acacttttct gcgatatctc   1080
tgaggtaagc gttaacgtac ccttagatcg ttctttttct ttttcgtctg ctgatcgttg   1140
ctcatattat ttcgatgatt gttggattcg atgctctttg ttgattgatc gttctgaaaa   1200
ttctgatctg ttgtttagat tttatcgatt gttaatatca acgtttcact gcttctaaac   1260
gataatttat tcatgaaact attttcccat tctgatcgat cttgttttga gattttaatt   1320
tgttcgattg attgttggtt ggtggatcta tatacgagtg aacttgttga tttgcgtatt   1380
taagatgtat gtcgatttga attgtgattg ggtaattctg gagtagcata acaaatccag   1440
tgttcccttt ttctaagggt aattctcgga ttgtttgctt tatatctctt gaaattgccg   1500
atttgattga atttagctcg cttagctcag atgatagagc accacaattt ttgtggtaga   1560
aatcggtttg actccgatag cggcttttta ctatgattgt tttgtgttaa agatgatttt   1620
cataatggtt atatatgtct actgttttta ttgattcaat atttgattgt tctttttttt   1680
gcagatttgt tgaccaggga tccgcggccg ctaaaatgga taagaagtat tctattggac   1740
ttgatattgg aaccaactct gtgggatggg ctgttattac tgacgagtat aaggttccat   1800
ctaagaagtt caaggttctt ggaaacactg atagacactc tattaagaag aaccttattg   1860
gtgctcttct tttcgattct ggagagactg ctgaggctac tagacttaag agaactgcta   1920
gaagaagata tactagaaga aagaacagaa tttgctatct tcaagagatt ttctctaacg   1980
agatggctaa ggttgacgat tctttcttcc acagacttga ggagtctttc cttgttgagg   2040
aggataagaa gcacgagaga cacccaattt tcggaaacat tgttgacgag gttgcttatc   2100
acgagaagta tccaactatt tatcacctta gaaagaagct cgttgattct actgataagg   2160
ctgatcttag acttatttat cttgctcttg ctcacatgat taagttcaga ggacacttcc   2220
ttattgaggg agatcttaac ccagataact ctgacgttga taagctcttc attcaacttg   2280
ttcaaactta taaccaactt ttcgaggaga acccaattaa cgcttctgga gttgacgcta   2340
aggctattct ttctgctaga ctttctaagt ctagaaggct tgagaacctt attgctcaac   2400
ttccaggaga gaagaagaac ggacttttcg gaaaccttat tgctctttct cttggactta   2460
ctccaaactt caagtctaac ttcgatcttg ctgaggacgc taagctccaa ctttctaagg   2520
atacttacga cgatgatctt gataaccttc ttgctcaaat tggagatcaa tacgctgatc   2580
ttttccttgc tgctaagaac ctttctgacg ctattcttct ttctgatatt cttagagtta   2640
acactgagat tactaaggct ccactttctg cttctatgat taagagatac gacgagcacc   2700
accaagatct tactcttctt aaggctcttg ttagacaaca acttccagag aagtataagg   2760
agattttctt cgatcaatct aagaacggat acgctggata tattgacgga ggagcttctc   2820
aagaggagtt ctataagttc attaagccaa ttcttgagaa gatggacgga actgaggagc   2880
ttcttgttaa gctcaacaga gaggatcttc ttagaaagca aagaactttc gataacggat   2940
ctattccaca ccaaattcac cttggagagc ttcacgctat tcttagaagg caagaggatt   3000
```

-continued

```
tctatccatt ccttaaggat aacagagaga agattgagaa gattcttact ttccgtattc   3060
catattacgt tggaccactt gctagaggaa actctagatt cgcttggatg actagaaagt   3120
ctgaggagac tattactcct tggaacttcg aggaggttgt tgataaggga gcttctgctc   3180
aatctttcat tgagagaatg actaacttcg ataagaacct tccaaacgag aaggttcttc   3240
caaagcactc tcttctttac gagtatttca ctgtttataa cgagcttact aaggttaagt   3300
acgttactga gggaatgaga aagccagctt tcctttctgg agagcaaaag aaggctattg   3360
ttgatcttct tttcaagact aacagaaagg ttactgttaa gcaacttaag gaggattatt   3420
tcaagaagat tgagtgcttc gattctgttg agatttctgg agttgaggat agattcaacg   3480
cttctcttgg aacttatcac gatcttctta agattattaa ggataaggat ttccttgata   3540
acgaggagaa cgaggatatt cttgaggata ttgttcttac tcttactctt ttcgaggata   3600
gagagatgat tgaggagaga cttaagactt acgctcacct tttcgacgat aaggttatga   3660
agcaacttaa gagaagaaga tatactggat ggggtagact ttctagaaag ctcattaacg   3720
gaattagaga taagcaatct ggaaagacta ttcttgattt ccttaagtct gacggattcg   3780
ctaacagaaa cttcatgcaa cttattcacg acgattctct tactttcaag gaggatattc   3840
aaaaggctca agtttctgga caaggagatt ctcttcacga gcacattgct aaccttgctg   3900
gatctccagc tattaagaag ggaattcttc aaactgttaa ggttgttgac gagcttgtta   3960
aggttatggg tagacacaag ccagagaaca ttgttattga gatggctaga gagaaccaaa   4020
ctactcaaaa gggacaaaag aactctagag agagaatgaa gagaattgag gagggaatta   4080
aggagcttgg atctcaaatt cttaaggagc acccagttga gaacactcaa cttcaaaacg   4140
agaagctcta tctttattat cttcaaaacg gaagagatat gtacgttgat caagagcttg   4200
atattaacag actttctgat tacgacgttg atcacattgt tccacaatct ttccttaagg   4260
acgattctat tgataacaag gttcttacta gatctgataa gaacagagga aagtctgata   4320
acgttccatc tgaggaggtt gttaagaaga tgaagaacta ttggagacaa cttcttaacg   4380
ctaagctcat tactcaaaga aagttcgata accttactaa ggctgagaga ggaggacttt   4440
ctgagcttga taaggctgga ttcattaaga gacaacttgt tgagactaga caaattacta   4500
agcacgttgc tcaaattctt gattctagaa tgaacactaa gtacgacgag aacgataagc   4560
tcattagaga ggttaaggtt attactctta agtctaagct cgtttctgat ttcagaaagg   4620
atttccaatt ctataaggtt agagagatta acaactatca ccacgctcac gacgcttatc   4680
ttaacgctgt tgttggaact gctcttatta agaagtatcc aaaacttgag tctgagttcg   4740
tttacggaga ttataaggtt tacgacgtta gaaagatgat tgctaagtct gagcaagaga   4800
ttggaaaggc tactgctaag tatttcttct attctaacat tatgaacttc ttcaagactg   4860
agattactct tgctaacgga gagattagaa agaggccact tattgagact aacggagaga   4920
ctggagagat tgtttgggat aagggaagag atttcgctac tgttagaaag gttctttcta   4980
tgccacaagt taacattgtt aagaaaactg aggttcaaac tggaggattc tctaaggagt   5040
ctattcttcc aaagagaaac tctgataagc tcattgctag aaagaaggat tgggacccaa   5100
agaagtacgg aggattcgat tctccaactg ttgcttattc tgttcttgtt gttgctaagg   5160
ttgagaaggg aaagtctaag aagctcaagt ctgttaagga gcttgttgga attactatta   5220
tggagagatc ttctttcgag aagaacccag ttgatttcct tgaggctaag ggatataagg   5280
aggttaagaa ggatcttatt attaagctcc caaagtattc tcttttcgag cttgagaacg   5340
gaagaaagag aatgcttgct tctgctggag agcttcaaaa gggaaacgag cttgctcttc   5400
```

catctaagta cgttaacttc ctttatcttg cttctcacta cgagaagctc aagggatctc 5460
cagaggataa cgagcaaaag caacttttcg ttgagcaaca caagcactat cttgacgaga 5520
ttattgagca aatttctgag ttctctaaga gagttattct tgctgacgct aaccttgata 5580
aggttctttc tgcttataac aagcacagag ataagccaat tagagagcaa gctgagaaca 5640
ttattcacct tttcactctt actaaccttg gtgctccagc tgctttcaag tatttcgata 5700
ctactattga tagaaagaga tatacttcta ctaaggaggt tcttgacgct actcttattc 5760
accaatctat tactggactt tacgagacta gaattgatct ttctcaactt ggaggagatt 5820
cttctccacc aaagaagaag agaaaggttt cttggaagga cgcttctgga tggtctagaa 5880
tgtgacgtcg cgtgatcgtt caaacatttg gcaataaagt ttcttaagat tgaatcctgt 5940
tgccggtctt gcgatgatta tcatataatt tctgttgaat tacgttaagc atgtaataat 6000
taacatgtaa tgcatgacgt tatttatgag atgggttttt atgattagag tcccgcaatt 6060
atacatttaa tacgcgatag aaaacaaaat atagcgcgca aactaggata aattatcgcg 6120
cgcggtgtca tctatgttac tagatctgca gatcggaccc ctaattagct aaaagcttcg 6180
ttgaacaacg gaaactcgac ttgccttccg cacaatacat catttcttct tagctttttt 6240
tcttcttctt cgttcataca gttttttttt gtttatcagc ttacattttc ttgaaccgta 6300
gctttcgttt tcttcttttt aactttccat tcggagtttt tgtatcttgt ttcatagttt 6360
gtcccaggat tagaatgatt aggcatcgaa ccttcaagaa tttgattgaa taaaacatct 6420
tcattcttaa gatatgaaga taatcttcaa aaggcccctg ggaatctgaa agaagagaag 6480
caggcccatt tatatgggaa agaacaatag tatttcttat ataggcccat ttaagttgaa 6540
aacaatcttc aaaagtccca catcgcttag ataagaaaac gaagctgagt ttatatacag 6600
ctagagtcga agtagtgatt ggaaaagttg tagactgaga gttttagagc tagaaatagc 6660
aagttaaaat aaggctagtc cgttatcaac ttgaaaaagt ggcaccgagt cggtgctttt 6720
tttttaagct tcgttgaaca acggaaactc gacttgcctt ccgcacaata catcatttct 6780
tcttagcttt ttttcttctt cttcgttcat acagtttttt tttgtttatc agcttacatt 6840
ttcttgaacc gtagctttcg ttttcttctt tttaactttc cattcggagt ttttgtatct 6900
tgtttcatag tttgtcccag gattagaatg attaggcatc gaaccttcaa gaatttgatt 6960
gaataaaaca tcttcattct taagatatga agataatctt caaaaggccc ctgggaatct 7020
gaaagaagag aagcaggccc atttatatgg gaaagaacaa tagtatttct tatataggcc 7080
catttaagtt gaaaacaatc ttcaaaagtc ccacatcgct tagataagaa aacgaagctg 7140
agtttatata cagctagagt cgaagtagtg attgcagtga tgaacaatga cgggttttag 7200
agctagaaat agcaagttaa aataaggcta gtccgttatc aacttgaaaa agtggcaccg 7260
agtcggtgct ttttttttgg cgcgcctaaa gcttctggca gacaaagtgg cagacatact 7320
gtcccacaaa tgaagatgga atctgtaaaa gaaaacgcgt gaaataatgc gtctgacaaa 7380
ggttaggtcg gctgccttta atcaatacca aagtggtccc taccacgatg gaaaaactgt 7440
gcagtcggtt tggctttttc tgacgaacaa ataagattcg tggccgacag gtgggggtcc 7500
accatgtgaa ggcatcttca gactccaata atggagcaat gacgtaaggg cttacgaaat 7560
aagtaagggt agtttgggaa atgtccactc acccgtcagt ctataaatac ttagcccctc 7620
cctcattgtt aagggagcaa ggatcctaaa ccatgattga acaagatgga ttgcacgcag 7680
gttctccggc cgcttgggtg gagaggctat tcggctatga ctgggcacaa cagacaatcg 7740

```
gctgctctga tgccgccgtg ttccggctgt cagcgcaggg gcgcccggtt ctttttgtca   7800
agaccgacct gtccggtgcc ctgaatgaac tgcaggacga ggcagcgcgg ctatcgtggc   7860
tggccacgac gggcgttcct tgcgcagctg tgctcgacgt tgtcactgaa gcgggaaggg   7920
actggctgct attgggcgaa gtgccggggc aggatctcct gtcatctcac cttgctcctg   7980
ccgagaaagt atccatcatg gctgatgcaa tgcggcggct gcatacgctt gatccggcta   8040
cctgcccatt cgaccaccaa gcgaaacatc gcatcgagcg agcacgtact cggatggaag   8100
ccggtcttgt cgatcaggat gatctggacg aagagcatca ggggctcgcg ccagccgaac   8160
tgttcgccag gctcaaggcg cgcatgcccg acggcgagga tctcgtcgtg acccatggcg   8220
atgcctgctt gccgaatatc atggtggaaa atggccgctt ttctggattc atcgactgtg   8280
gccggctggg tgtggcggac cgctatcagg acatagcgtt ggctacccgt gatattgctg   8340
aagagcttgg cggcgaatgg gctgaccgct tcctcgtgct ttacggtatc gccgctcccg   8400
attcgcagcg catcgccttc tatcgccttc ttgacgagtt cttctgatga gagctctaga   8460
tccccgaatt tccccgatcg ttcaaacatt tggcaataaa gtttcttaag attgaatcct   8520
gttgccggtc ttgcgatgat tatcatataa tttctgttga attacgttaa gcatgtaata   8580
attaacatgt aatgcatgac gttatttatg agatgggttt ttatgattag agtcccgcaa   8640
ttatacattt aatacgcgat agaaaacaaa atatagcgcg caaactagga taaattatcg   8700
cgcgcggtgt catctatgtt actagatcgg gaattgggta ccctaattag ctaaattcca   8760
aaattttcag ttagtcctta ctaattatta aattatagta ttaatccaat gtgattgcgg   8820
ttacatcatg tacggaaaaa taattctaat ccttgattta aatttgatct tgactattta   8880
tttattcttt atttcatttt gtaaatcatt ttatgtatct cctggcaagc aattttatcc   8940
accttgcacc aacaccttcg ggttccataa tcaaaccacc ttaacttcac accatgctgt   9000
aactcacacc gcccagcatc tccaatgtga aagaagctaa aatttaataa acaatcatac   9060
gaagcagtga caaaatacca gatggtatta atgctttgat aaaattaatt ggaaagtata   9120
aaatggtaga aaataataaa ttataattaa tttaaataag ataaaaaata attaaaaact   9180
aaaatgttaa aattttaaaa aaattatttt aaataatatt taaaaacatt aaaaatcatt   9240
ttaaaaaatt tatttataga acaattaaat aaatatttca gctaataaaa aacaaaagct   9300
tacctagcct tagaagacaa cttgtccaac aattagatga tacccattgc ccttacgttt   9360
tctttaacat caattattgt tttgtcaac aagctatctt ttagttttat tttattggta   9420
aaaaatatgt cgccttcaag ttgcatcatt taacacatct cgtcattaga aaaataaaac   9480
tcttccctaa acgattagta gaaaaaatca ttcgataata aataagaaag aaaaattaga   9540
aaaaaataac ttcattttaa aaaaatcatt aaggctatat tttttaaatg actaatttta   9600
tatagactgt aactaaaagt atacaattta ttatgctatg tatcttaaag aattacttat   9660
aaaaatctac ggaagaatat cttacaaagt gaaaaacaaa tgagaaagaa tttagtggga   9720
tgattatgat tttatttgaa aattgaaaaa ataattatta aagactttag tggagtaaga   9780
aagctttcct attagtcttt tcttatccat aaaaaaaaaa aaaaatctag cgtgacagct   9840
tttccataga ttttaataat gtaaaatact ggtagcagcc gaccgttcag gtaatggaca   9900
ctgtggtcct aacttgcaac gggtgcgggc ccaatttaat aacgccgtgg taacggataa   9960
agccaagcgt gaagcggtga aggtacatct ctgactccgt caagattacg aaaccgtcaa  10020
ctacgaagga ctccccgaaa tatcatctgt gtcataaaca ccaagtcaca ccatacatgg  10080
gcacgcgtca caatatgatt ggagaacggt tccaccgcat atgctataaa atgcccccac  10140
```

acccctcgac cctaatcgca cttcaattgc aatcaaatta gttcattctc tttgcgcagt 10200
tccctacctc tcctttcaag gttcgtagat ttcttctgtt tttttttctt cttctttatt 10260
gtttgttcta catcagcatg atgttgattt gattgtgttt tctatcgttt catcgattat 10320
aaattttcat aatcagaaga ttcagctttt attaatgcaa gaacgtcctt aattgatgat 10380
tttataaccg taaattaggt ctaattagag tttttttcat aaagattttc agatccgttt 10440
acaacaagcc ttaattgttg attctgtagt cgtagattaa ggtttttttc atgaactact 10500
tcagatccgt taaacaacag ccttatttgt tgatacttca gtcgtttttc aagaaattgt 10560
tcagatccgt tgataaaagc cttattcgtt gattctgtat ggtatttcaa gagatattgc 10620
tcaggtcctt tagcaactac cttatttgtt gattctgtgg ccatagatta ggattttttt 10680
tcacgaaatt gcttcttgaa attacgtgat ggattttgat tctgatttat cttgtgattg 10740
ttgactctac agagatctaa aaaaatggcc ctgtccaaca agttcatcgg cgacgacatg 10800
aagatgacct accacatgga cggctgcgtg aacggccact acttcaccgt gaagggcgag 10860
ggcagcggca agccctacga gggcacccag acctccacct tcaaggtgac gatggccaac 10920
ggcggccccc tggccttctc cttcgacatc ctgtccaccg tgttcatgta cggcaaccgc 10980
tgcttcaccg cctaccccac cagcatgccc gactacttca agcaggcctt ccccgacggc 11040
atgtcctacg agagaacctt cacctacgag gacggcggcg tggccaccgc cagctgggag 11100
atcagcctga agggcaactg cttcgagcac aagtccacct tccacggcgt gaacttcccc 11160
gccgacggcc ccgtgatggc caagaagacc accggctggg atccctcctt cgagaagatg 11220
accgtgtgcg acggcatctt gaagggcgac gtgaccgcct tcctgatgct gcagggcggc 11280
ggcaactaca gatgccagtt ccacacctcc tacaagacca agaagcccgt gaccatgccc 11340
cccaaccacg tggtggagca ccgcatcgcc agaaccgacc tggacaaggg cggcaacagc 11400
gtgcagctga ccgagcacgc cgtggcccac atcacctccg tggtgccctt ctgatgaact 11460
agtgaattcg agctcaagct ttcgttcgta tcatcggttt cgacaacgtt cgtcaagttc 11520
aatgcatcag tttcattgcg cacacaccag aatcctactg agtttgagta ttatggcatt 11580
gggaaaactg tttttcttgt accatttgtt gtgcttgtaa tttactgtgt tttttattcg 11640
gttttcgcta tcgaactgtg aaatggaaat ggatggagaa gagttaatga atgatatggt 11700
ccttttgttc attctcaaat taatattatt tgtttttttct cttatttgtt gtgtgttgaa 11760
tttgaaatta taagagatat gcaaacattt tgttttgagt aaaaatgtgt caaatcgtgg 11820
cctctaatga ccgaagttaa tatgaggagt aaaacacttg tagttgtacc attatgctta 11880
ttcactaggc aacaaatata ttttcagacc tagaaaagct gcaaatgtta ctgaatacaa 11940
gtatgtcctc ttgtgtttta gacatttatg aactttcctt tatgtaattt tccagaatcc 12000
ttgtcagatt ctaatcattg ctttataatt atagttatac tcatggattt gtagttgagt 12060
atgaaaatat tttttaatgc attttatgac ttgccaattg attgacaaca tgcatcaatc 12120
ggaccgttaa ctagctagac ggccaggatc gccgcgtgag cctttagcaa ctagctagat 12180
taattaaacg tccgcaatgt gttattaagt tgtctaagcg tcaatttgtt tacaccacaa 12240
tatatcctgc caccagccag ccaacagctc cccgaccggc agctcggcac aaaatcacca 12300
ctcgatacag gcagcccatc agtccgggac ggcgtcagcg ggagagccgt tgtaaggcgg 12360
cagactttgc tcatgttacc gatgctattc ggaagaacgg caactaagct gccgggtttg 12420
aaacacggat gatctcgcgg agggtagcat gttgattgta acgatgacag agcgttgctg 12480

-continued

```
cctgtgatca aatatcatct ccctcgcaga gatccgaatt atcagccttc ttattcattt  12540
ctcgcttaac cgtgacaggc tgtcgatctt gagaactatg ccgacataat aggaaatcgc  12600
tggataaagc cgctgaggaa gctgagtggc gctatttctt tagaagtgaa cgtcgactca  12660
tgtttgacag cttatcatcg actgcacggt gcaccaatgc ttctggcgtc aggcagccat  12720
cggaagctgt ggtatggctg tgcaggtcgt aaatcactgc ataattcgtg tcgctcaagg  12780
cgcactcccg ttctggataa tgttttttgc gccgacatca taacggttct ggcaaatatt  12840
ctgaaatgag ctgttgacaa ttaatcatcc ggctcgtata atgtgtggaa ttgtgagcgg  12900
ataacaattt cacacaggaa acagaccatg agggaagcgt tgatcgccga agtatcgact  12960
caactatcag aggtagttgg cgtcatcgag cgccatctcg aaccgacgtt gctggccgta  13020
catttgtacg gctccgcagt ggatggcggc ctgaagccac acagtgatat tgatttgctg  13080
gttacggtga ccgtaaggct tgatgaaaca acgcggcgag ctttgatcaa cgaccttttg  13140
gaaacttcgg cttcccctgg agagagcgag attctccgcg ctgtagaagt caccattgtt  13200
gtgcacgacg acatcattcc gtggcgttat ccagctaagc gcgaactgca atttggagaa  13260
tggcagcgca atgacattct tgcaggtatc ttcgagccag ccacgatcga cattgatctg  13320
gctatcttgc tgacaaaagc aagagaacat agcgttgcct tggtaggtcc agcggcggag  13380
gaactctttg atccggttcc tgaacaggat ctatttgagg cgctaaatga aaccttaacg  13440
ctatggaact cgccgcccga ctgggctggc gatgagcgaa atgtagtgct tacgttgtcc  13500
cgcatttggt acagcgcagt aaccggcaaa atcgcgccga aggatgtcgc tgccgactgg  13560
gcaatggagc gcctgccggc ccagtatcag cccgtcatac ttgaagctag gcaggcttat  13620
cttggacaag aagatcgctt ggcctcgcgc gcagatcagt tggaagaatt tgttcactac  13680
gtgaaaggcg agatcaccaa agtagtcggc aaataaagct ctagtggatc tccgtacccg  13740
aggaatcggc gtgagcggtc gcaaaccatc cggcccggta caaatcggcg cggcgctggg  13800
tgatgacctg gtggagaagt tgaaggccgc gcaggccgcc cagcggcaac gcatcgaggc  13860
agaagcacgc cccggtgaat cgtggcaagc ggccgctgat cgaatccgca aagaatcccg  13920
gcaaccgccg gcagccggtg cgccgtcgat taggaagccg cccaagggcg acgagcaacc  13980
agattttttc gttccgatgc tctatgacgt gggcacccgc gatagtcgca gcatcatgga  14040
cgtggccgtt ttccgtctgt cgaagcgtga ccgacgagct ggcgaggtga tccgctacga  14100
gcttccagac gggcacgtag aggtttccgc agggccggcc ggcatggcca gtgtgtggga  14160
ttacgacctg gtactgatgg cggtttccca tctaaccgaa tccatgaacc gataccggga  14220
agggaaggga gacaagcccg gccgcgtgtt ccgtccacac gttgcggacg tactcaagtt  14280
ctgccggcga gccgatggcg gaaagcagaa agacgacctg gtagaaacct gcattcggtt  14340
aaacaccacg cacgttgcca tgcagcgtac caagaaggcc aagaacggcc gcctggtgac  14400
ggtatccgag ggtgaagcct tgattagccg ctacaagatc gtaaagagcg aaaccgggcg  14460
gccggagtac atcgagatcg agctggctga ttggatgtac cgcgagatca cagaaggcaa  14520
gaacccggac gtgctgacgg ttcaccccga ttactttttg atcgatcccg gcatcggccg  14580
ttttctctac cgcctggcac gccgcgccgc aggcaaggca gaagccagat ggttgttcaa  14640
gacgatctac gaacgcagtg gcagcgccgg agagttcaag aagttctgtt tcaccgtgcg  14700
caagctgatc gggtcaaatg acctgccgga gtacgatttg aaggaggagg cggggcaggc  14760
tggcccgatc ctagtcatgc gctaccgcaa cctgatcgag ggcgaagcat ccgccggttc  14820
ctaatgtacg gagcagatgc tagggcaaat tgccctagca ggggaaaaag gtcgaaaagg  14880
```

actctttcct gtggatagca cgtacattgg gaacccaaag ccgtacattg ggaaccggaa 14940
cccgtacatt gggaacccaa agccgtacat tgggaaccgg acacacatgt aagtgactga 15000
tataaaagag aaaaaaggcg atttttccgc ctaaaactct ttaaaactta ttaaaactct 15060
taaaacccgc ctggcctgtg cataactgtc tggccagcgc acagccgaag agctgcaaaa 15120
agcgcctacc cttcggtcgc tgcgctccct acgccccgcc gcttcgcgtc ggcctatcgc 15180
ggccgctggc cgctcaaaaa tggctggcct acggccaggc aatctaccag ggcgcggaca 15240
agccgcgccg tcgccactcg accgccggcg ctgaggtctg cctcgtgaag aaggtgttgc 15300
tgactcatac caggccatta atgaatcggc caacgcgcgg ggagaggcgg tttgcgtatt 15360
gggcgctctt ccgcttcctc gctcactgac tcgctgcgct cggtcgttcg gctgcggcga 15420
gcggtatcag ctcactcaaa ggcggtaata cggttatcca cagaatcagg ggataacgca 15480
ggaaagaaca tgtgagcaaa aggccagcaa aaggccagga accgtaaaaa ggccgcgttg 15540
ctggcgtttt tccataggct ccgcccccct gacgagcatc acaaaaatcg acgctcaagt 15600
cagaggtggc gaaacccgac aggactataa agataccagg cgtttccccc tggaagctcc 15660
ctcgtgcgct ctcctgttcc gaccctgccg cttaccggat acctgtccgc ctttctccct 15720
tcgggaagcg tggcgctttc tcatagctca cgctgtaggt atctcagttc ggtgtaggtc 15780
gttcgctcca agctgggctg tgtgcacgaa ccccccgttc agcccgaccg ctgcgcctta 15840
tccggtaact atcgtcttga gtccaacccg gtaagacacg acttatcgcc actggcagca 15900
gccactggta acaggattag cagagcgagg tatgtaggcg gtgctacaga gttcttgaag 15960
tggtggccta actacggcta cactagaaga acagtatttg gtatctgcgc tctgctgaag 16020
ccagttacct tcggaaaaag agttggtagc tcttgatccg gcaaacaaac caccgctggt 16080
agcggtggtt tttttgtttg caagcagcag attacgcgca gaaaaaaagg atctcaagaa 16140
gatcctttga tcttttctac ggggtctgac gctcagtgga acgaaaactc acgttaaggg 16200
attttggtca tgagattatc aaaaaggatc ttcacctaga tccttttgat ccggacaaac 16260
aaacaaatac agtaattta 16279

<210> SEQ ID NO 99
<211> LENGTH: 100
<212> TYPE: DNA
<213> ORGANISM: Zea mays

<400> SEQUENCE: 99
aagctgcgca agctcatcct cgaggccaag ctcgcgccct gctacccggg cgccgacgac 60
gccgcgcccg gcggagggga cctcgaggag tgccccatct 100

<210> SEQ ID NO 100
<211> LENGTH: 100
<212> TYPE: DNA
<213> ORGANISM: Zea mays

<400> SEQUENCE: 100
agatggggca ctcctcgagg tcccctccgc cgggcgcggc gtcgtcggcg cccgggtagc 60
agggcgcgag cttggcctcg aggatgagct tgcgcagctt 100

<210> SEQ ID NO 101
<211> LENGTH: 420
<212> TYPE: DNA
<213> ORGANISM: Triticum aestivum
<220> FEATURE:

<221> NAME/KEY: misc_feature
<222> LOCATION: (15)..(15)
<223> OTHER INFORMATION: n is a, c, g, or t

<400> SEQUENCE: 101
ctcatcgagt gttcnccgca atgcgctgtt gctgattctc aagtgcgtgt gggtgcaggt 60
ggagagcaga agaaggccgg ccggcagcgg cggaggagga gggcgaggca ggcagcggca 120
ggcgaaggcg cgggagggga cgatgcggcg aagaaacgcc ggctgagtga cgagcaggcg 180
cagttcctgg agatgagctt caggaaggaa cgtaaactgg aaacgccccg caaggtgcag 240
ctcgccgcgg agctgggcct ggacaccaag caggtcgcgg tgtggttcca gaaccgccgc 300
gcccgctaca agagcaagct catcgaggag gagttctcca agctccgcgc ggcacacgac 360
gccgtcgtcg tccacaactg ccacctcgag gccgaggtac agtgcaacag tccggctgcc 420

<210> SEQ ID NO 102
<211> LENGTH: 23
<212> TYPE: DNA
<213> ORGANISM: Artificial Sequence
<220> FEATURE:
<223> OTHER INFORMATION: gRNA target sequence

<400> SEQUENCE: 102
ggaaaagttg tagactgaga tgg 23

<210> SEQ ID NO 103
<211> LENGTH: 85
<212> TYPE: DNA
<213> ORGANISM: Arabidopsis thaliana

<400> SEQUENCE: 103
taaatttgat tcgttgatag ggctaaagag atgtgggaaa agttgtagac tgagatggat 60
gaattatttg agccctaatg tgaac 85

<210> SEQ ID NO 104
<211> LENGTH: 84
<212> TYPE: DNA
<213> ORGANISM: Arabidopsis thaliana

<400> SEQUENCE: 104
taaatttgat tcgttgatag ggctaaagag atgtgggaaa agttgtagac tagatggatg 60
aattatttga gccctaatgt gaac 84

<210> SEQ ID NO 105
<211> LENGTH: 86
<212> TYPE: DNA
<213> ORGANISM: Arabidopsis thaliana

<400> SEQUENCE: 105
taaatttgat tcgttgatag ggctaaagag atgtgggaaa agttgtagac tgtagatgga 60
tgaattattt gagccctaat gtgaac 86

<210> SEQ ID NO 106
<211> LENGTH: 85
<212> TYPE: DNA
<213> ORGANISM: Arabidopsis thaliana

<400> SEQUENCE: 106
taaatttgat tcgttgatag ggctaaagag atgtgggaaa agttgtagac tgagatggat 60
gaattatttg agccctaatg tgaac 85

<210> SEQ ID NO 107
<211> LENGTH: 86
<212> TYPE: DNA
<213> ORGANISM: Arabidopsis thaliana

<400> SEQUENCE: 107
taaatttgat tcgttgatag ggctaaagag atgtgggaaa agttgtagac tgaagatgga 60
tgaattattt gagccctaat gtgaac 86

<210> SEQ ID NO 108
<211> LENGTH: 86
<212> TYPE: DNA
<213> ORGANISM: Arabidopsis thaliana

<400> SEQUENCE: 108
taaatttgat tcgttgatag ggctaaagag atgtgggaaa agttgtagac tgtagatgga 60
tgaattattt gagccctaat gtgaac 86

<210> SEQ ID NO 109
<211> LENGTH: 82
<212> TYPE: DNA
<213> ORGANISM: Arabidopsis thaliana

<400> SEQUENCE: 109
taaatttgat tcgttgatag ggctaaagag atgtgggaaa agttgtagaa gatggatgaa 60
ttatttgagc cctaatgtga ac 82

<210> SEQ ID NO 110
<211> LENGTH: 86
<212> TYPE: DNA
<213> ORGANISM: Arabidopsis thaliana

<400> SEQUENCE: 110
taaatttgat tcgttgatag ggctaaagag atgtgggaaa agttgtagac tgaagatgga 60
tgaattattt gagccctaat gtgaac 86

<210> SEQ ID NO 111
<211> LENGTH: 84
<212> TYPE: DNA
<213> ORGANISM: Arabidopsis thaliana

<400> SEQUENCE: 111
taaatttgat tcgttgatag ggctaaagag atgtgggaaa agttgtagac tagatggatg 60
aattatttga gccctaatgt gaac 84

<210> SEQ ID NO 112
<211> LENGTH: 83
<212> TYPE: DNA
<213> ORGANISM: Arabidopsis thaliana

<400> SEQUENCE: 112
taaatttgat tcgttgatag ggctaaagag atgtgggaaa agttgtagac tgatggatga 60
attatttgag ccctaatgtg aac 83

<210> SEQ ID NO 113
<211> LENGTH: 83
<212> TYPE: DNA
<213> ORGANISM: Arabidopsis thaliana -continued

```
<400> SEQUENCE: 113

taaatttgat tcgttgatag ggctaaagag atgtgggaaa agttgtagac agatggatga     60

attatttgag ccctaatgtg aac                                             83


<210> SEQ ID NO 114
<211> LENGTH: 86
<212> TYPE: DNA
<213> ORGANISM: Arabidopsis thaliana

<400> SEQUENCE: 114

taaatttgat tcgttgatag ggctaaagag atgtgggaaa agttgtagac tgtagatgga     60

tgaattattt gagccctaat gtgaac                                          86


<210> SEQ ID NO 115
<211> LENGTH: 86
<212> TYPE: DNA
<213> ORGANISM: Arabidopsis thaliana

<400> SEQUENCE: 115

taaatttgat tcgttgatag ggctaaagag atgtgggaaa agttgtagac tgaagatgga     60

tgaattattt gagccctaat gtgaac                                          86


<210> SEQ ID NO 116
<211> LENGTH: 86
<212> TYPE: DNA
<213> ORGANISM: Arabidopsis thaliana

<400> SEQUENCE: 116

taaatttgat tcgttgatag ggctaaagag atgtgggaaa agttgtagac tgtagatgga     60

tgaattattt gagccctaat gtgaac                                          86


<210> SEQ ID NO 117
<211> LENGTH: 78
<212> TYPE: DNA
<213> ORGANISM: Arabidopsis thaliana

<400> SEQUENCE: 117

taaatttgat tcgttgatag ggctaaagag atgtgggcta aacatagatg gatgaattat     60

ttgagcccta atgtgaac                                                   78
```